(12) United States Patent
Schwartz

(10) Patent No.: US 11,806,275 B2
(45) Date of Patent: Nov. 7, 2023

(54) PENILE CONDOM CATHETER FOR FACILITATING URINE COLLECTION AND EGRESS OF URINARY FLUIDS AWAY FROM THE BODY TORSO

(71) Applicant: Alan N. Schwartz, Edmonds, WA (US)

(72) Inventor: Alan N. Schwartz, Edmonds, WA (US)

( * ) Notice: Subject to any disclaimer, the term of this patent is extended or adjusted under 35 U.S.C. 154(b) by 1334 days.

(21) Appl. No.: 16/243,010

(22) Filed: Jan. 8, 2019

(65) Prior Publication Data
US 2019/0142627 A1     May 16, 2019

Related U.S. Application Data

(63) Continuation of application No. 14/663,348, filed on Mar. 19, 2015, now abandoned, which is a
(Continued)

(51) Int. Cl.
*A61F 6/20*     (2006.01)
*A61F 5/00*     (2006.01)
(Continued)

(52) U.S. Cl.
CPC ............... *A61F 6/20* (2013.01); *A61F 5/00* (2013.01); *A61F 5/451* (2013.01); *A61F 5/453* (2013.01);
(Continued)

(58) Field of Classification Search
CPC ................................ A61F 5/451; A61F 5/453
See application file for complete search history.

(56) References Cited

U.S. PATENT DOCUMENTS 3,394,703 A * 7/1968 Orgel ..................... A61F 5/453
                                                          604/353
3,563,235 A   2/1971 Zipper
(Continued)

FOREIGN PATENT DOCUMENTS

DE     10241071     1/2010
JP     4716119      7/2011
(Continued)

OTHER PUBLICATIONS

Ganguly, Rumpa, "Accuracy of linear measurement in Galileos cone beam CT under simulated clinical condition," MS (Master of Science) thesis, Universtiy of Iowa, (2009).
(Continued)

*Primary Examiner* — Sarah Al Hashimi
*Assistant Examiner* — Nhu Q. Tran
(74) *Attorney, Agent, or Firm* — Patrick J. S. Inouye; Leonid Kisselev

(57) ABSTRACT

A penile condom catheter facilitates urine collection and egress of urinary fluids away from the body torso. A circumferential anchoring structure includes a web of flexible strands sized and arranged to at least partially contact a portion of the penis. The anchoring structure provides a flexible yet secure hold against the penis when flaccid and provides an increase in the hold when a longitudinal force is exerted upon the anchoring structure. An annularly circumferential penile skin covering material is affixed to the anchoring structure and sized to fit over at least a portion of the penis. A seal is affixed to at least a portion of a covering material, a covering material orifice, or an anchoring structure. A conduit is affixed to at least one of a covering material, a covering material orifice, a seal and an anchoring structure created to permit the flow of urinary fluid away.

15 Claims, 55 Drawing Sheets

Related U.S. Application Data continuation of application No. 13/343,626, filed on Jan. 4, 2012, now abandoned.

(60) Provisional application No. 61/475,469, filed on Apr. 14, 2011, provisional application No. 61/475,489, filed on Apr. 14, 2011, provisional application No. 61/475,530, filed on Apr. 14, 2011, provisional application No. 61/429,687, filed on Jan. 4, 2011, provisional application No. 61/429,693, filed on Jan. 4, 2011.

(51) Int. Cl.
| | |
|---|---|
| A61F 5/453 | (2006.01) |
| A61F 13/00 | (2006.01) |
| A61F 13/04 | (2006.01) |
| A61F 13/10 | (2006.01) |
| A61F 13/20 | (2006.01) |
| A61L 28/00 | (2006.01) |
| A61L 31/14 | (2006.01) |
| A61F 5/451 | (2006.01) |
| A61F 13/14 | (2006.01) |
| A61L 2/02 | (2006.01) |

(52) U.S. Cl.
CPC .. *A61F 13/00008* (2013.01); *A61F 13/00034* (2013.01); *A61F 13/00063* (2013.01); *A61F 13/041* (2013.01); *A61F 13/10* (2013.01); *A61F 13/2005* (2013.01); *A61F 13/2017* (2013.01); *A61L 28/0049* (2013.01); *A61L 31/145* (2013.01); *A61F 13/00068* (2013.01); *A61F 13/141* (2013.01); *A61F 2013/00174* (2013.01); *A61F 2013/00246* (2013.01); *A61F 2013/00268* (2013.01); *A61F 2013/00536* (2013.01); *A61F 2013/00646* (2013.01); *A61F 2013/00655* (2013.01); *A61F 2013/00902* (2013.01); *A61L 2/02* (2013.01); *Y10T 428/24008* (2015.01); *Y10T 428/24802* (2015.01); *Y10T 428/31826* (2015.04); *Y10T 428/31938* (2015.04)

(56) References Cited

U.S. PATENT DOCUMENTS

| | | | |
|---|---|---|---|
| 3,779,241 A | 12/1973 | Vennard et al. | |
| 3,822,702 A | 7/1974 | Bolduc et al. | |
| 3,918,443 A | 11/1975 | Vennard et al. | |
| 3,933,153 A | 1/1976 | Csatary et al. | |
| 4,509,504 A | 4/1985 | Brundin | |
| 4,537,186 A | 8/1985 | Verschoof et al. | |
| 4,759,753 A * | 7/1988 | Schneider | A61F 5/453 604/352 |
| 4,769,215 A | 9/1988 | Ehrenkranz | |
| 4,858,613 A | 8/1989 | Fry et al. | |
| 4,922,917 A | 5/1990 | Dory | |
| 4,957,487 A * | 9/1990 | Gerow | A61F 5/4405 604/133 |
| 5,007,897 A * | 4/1991 | Kalb | A61M 25/0043 604/43 |
| 5,150,711 A | 9/1992 | Dory | |
| 5,336,211 A * | 8/1994 | Metz | A61F 5/453 604/352 |
| 5,354,258 A | 10/1994 | Dory | |
| 5,377,678 A | 1/1995 | Dumoulin et al. | |
| 5,409,473 A | 4/1995 | Rosenshein | |
| 5,513,652 A | 5/1996 | Schwartz | |
| 5,622,186 A | 4/1997 | Schwartz | |
| 5,626,149 A | 5/1997 | Schwartz | |
| 5,827,247 A * | 10/1998 | Kay | C08L 5/04 604/327 |
| 5,897,552 A | 4/1999 | Edwards et al. | |
| 5,935,137 A | 8/1999 | Saadat et al. | |
| 5,966,745 A | 10/1999 | Schwartz et al. | |
| 5,995,875 A | 11/1999 | Blewett et al. | |
| 6,016,452 A | 1/2000 | Kasevich | |
| 6,098,205 A | 8/2000 | Schwartz et al. | |
| 6,152,137 A * | 11/2000 | Schwartz | A61F 9/026 2/430 |
| 6,217,530 B1 | 4/2001 | Martin et al. | |
| 6,231,496 B1 | 5/2001 | Wilk | |
| 6,263,232 B1 | 7/2001 | Norman | |
| 6,285,902 B1 | 9/2001 | Kienzle et al. | |
| 6,425,867 B1 | 7/2002 | Vaezy et al. | |
| 6,494,886 B1 | 12/2002 | Wilk et al. | |
| 6,508,774 B1 | 1/2003 | Acker et al. | |
| 6,656,136 B1 | 12/2003 | Weng et al. | |
| 6,666,835 B2 | 12/2003 | Martin et al. | |
| 6,685,639 B1 | 2/2004 | Wang et al. | |
| 6,726,627 B1 | 4/2004 | Lizzi et al. | |
| 6,738,656 B1 | 5/2004 | Ferre et al. | |
| 6,960,204 B2 | 11/2005 | Ggerse et al. | |
| 6,989,129 B2 | 1/2006 | Mak et al. | |
| 7,015,859 B2 | 3/2006 | Anderson | |
| 7,166,092 B2 * | 1/2007 | Elson | A61F 5/453 604/352 |
| 7,699,056 B2 | 4/2010 | Tran et al. | |
| 7,739,907 B2 | 6/2010 | Boiarski | |
| 7,909,836 B2 | 3/2011 | McLean et al. | |
| 8,042,548 B2 | 10/2011 | Neuwirth et al. | |
| 8,366,719 B2 | 2/2013 | Markey | |
| 8,408,212 B2 | 4/2013 | O'Brien et al. | |
| 8,434,489 B2 | 5/2013 | Gopal et al. | |
| 8,880,149 B2 | 11/2014 | Barbot et al. | |
| 9,107,737 B2 | 8/2015 | Schwartz | |
| 9,636,188 B2 | 5/2017 | Gattani | |
| 2001/0037098 A1 | 11/2001 | Snyder | |
| 2003/0018251 A1 | 1/2003 | Solomon | |
| 2003/0029457 A1 | 2/2003 | Callister et al. | |
| 2003/0032995 A1 | 2/2003 | Handy | |
| 2003/0060702 A1 | 3/2003 | Kuth et al. | |
| 2003/0163177 A1 | 8/2003 | Eggers | |
| 2003/0208195 A1 | 11/2003 | Thompson et al. | |
| 2004/0097806 A1 | 5/2004 | Hunter et al. | |
| 2004/0171924 A1 | 9/2004 | Mire et al. | |
| 2005/0240170 A1 | 10/2005 | Zhang et al. | |
| 2006/0052820 A1 | 3/2006 | Haig | |
| 2006/0184003 A1 | 8/2006 | Lewin et al. | |
| 2007/0299464 A1 | 6/2007 | Cruise et al. | |
| 2007/0163601 A1 | 7/2007 | Pollock | |
| 2007/0225550 A1 | 9/2007 | Gattani | |
| 2007/0250139 A1 | 10/2007 | Kanzius | |
| 2007/0293458 A1 | 12/2007 | Shamsuddin | |
| 2008/0017201 A1 | 1/2008 | Sawhney | |
| 2008/0051776 A1 | 2/2008 | Bliweis et al. | |
| 2008/0097468 A1 | 4/2008 | Adams et al. | |
| 2008/0097469 A1 | 4/2008 | Gruber et al. | |
| 2008/0178890 A1 | 7/2008 | Townsend | |
| 2008/0215042 A1 | 9/2008 | Swanson | |
| 2008/0300571 A1 | 12/2008 | LePivert | |
| 2009/0131959 A1 | 5/2009 | Rolland | |
| 2009/0171241 A1 | 7/2009 | Garcia | |
| 2009/0277455 A1 | 11/2009 | Lee-Sepsick et al. | |
| 2010/0006105 A1 | 1/2010 | Carter et al. | |
| 2010/0043802 A1 | 2/2010 | O'Brien et al. | |
| 2010/0152687 A1 | 6/2010 | Carlozzi | |
| 2010/0186750 A1 | 7/2010 | Tran et al. | |
| 2010/0192959 A1 | 8/2010 | Shandas et al. | |
| 2010/0241129 A1 | 9/2010 | Markey | |
| 2010/0256620 A1 | 10/2010 | Maytal | |
| 2011/0094519 A1 | 4/2011 | Gopal et al. | |
| 2011/0106021 A1 | 5/2011 | Ruegg et al. | |
| 2011/0220120 A1 | 9/2011 | Frigstad et al. | |
| 2013/0060116 A1 | 3/2013 | Messerly | |
| 2014/0163300 A1 | 6/2014 | Rigney et al. | |

(56) References Cited

U.S. PATENT DOCUMENTS

2014/0303719 A1* 10/2014 Cox ............... A61F 2/2445
623/2.37
2015/0032233 A1 1/2015 Cheng et al.

FOREIGN PATENT DOCUMENTS

| RU | 2342172 | 12/2008 |
|----|---------|---------|
| RU | 2381525 | 2/2010 |
| RU | 2410136 | 1/2011 |
| RU | 2434600 | 11/2011 |
| WO | 200218967 | 3/2002 |
| WO | 2011141829 | 11/2011 |

OTHER PUBLICATIONS

Khati et al., AJR "Multimodality Imaging Of The Essure Permanent Birth Control Device: Emphasis On Commonly Overlooked Abnormalities," vol. 196, pp. 648-658 (2011).

Goel et al. "Endometrial Thickness," URL <http://radiopaedia.org/articles/endometrial-thickness>.

Peckham et al. The Histology Guide: Female: Oviduct <http://www.histology.leeds.ac.uk/female/oviduct.php>, University of Leeds.

Formerly Chapel Hill Tubal Reversal Center <https://www.tubal-reversal.net/blog/migrating-essure-coils-is-it-possible-can-essure-coils-move/> (2005).

Woolridge et al., "In Vitro Effects Of Oxytocin, acepromazine, detomidine, xylazine, butorphanol, terbulatine, soproterenol, and dantrolene on smooth smooth muscles of the equine esophagus," Am. Journal Vet. Res., vol. 63 (12), pp. 1732-1737 (Dec. 2002).

Encyclopedia Britannica, <http://www.britannica.com/EBchecked/topic/200908/fellopian-tube.com> (2009).

Clemente et al., Wiliams & Wilkins, "Anatomy, A Regional Atlas Of The Human Body," Plate 263, (1997).

Ades et al., Lippincott Williams & Wilkins "Stedman's Medical Dictionary", 28th Edition, pp. 641, 1274, 1459, 1670, 1401, 2078, (2006).

* cited by examiner

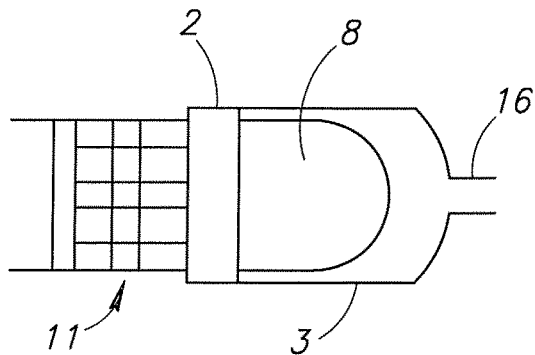
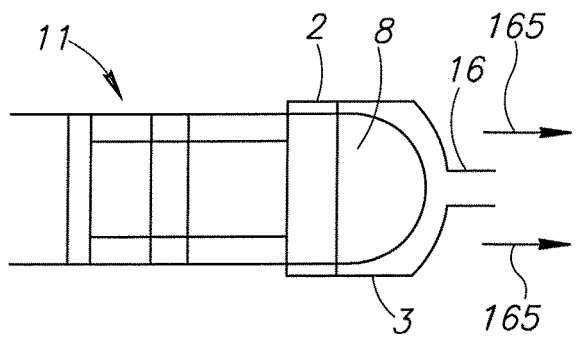
FIG.66A                FIG.66B
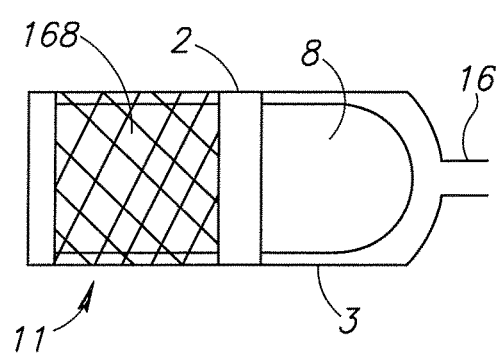
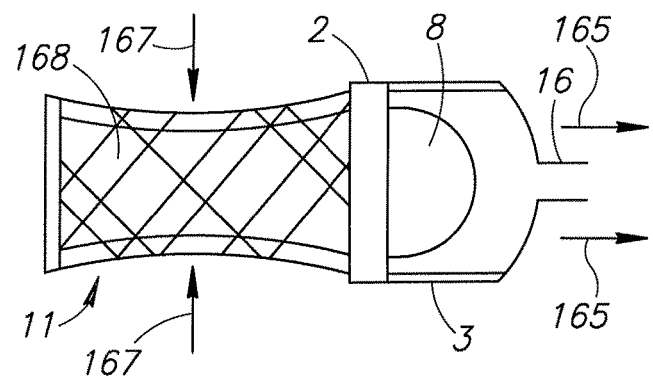
FIG.66C                FIG.66D

PENILE CONDOM CATHETER FOR FACILITATING URINE COLLECTION AND EGRESS OF URINARY FLUIDS AWAY FROM THE BODY TORSO

CROSS-REFERENCE TO RELATED APPLICATION

This non-provisional patent application is a continuation of U.S. patent application Ser. No. 14/663,348, filed Mar. 19, 2015, Abandoned, which is a continuation of Ser. No. 13/343,626, filed Jan. 4, 2012, abandoned, which claims priority under 35 U.S.C. § 119(e) to U.S. Provisional Patent Application No. 61/429,687, filed Jan. 4, 2011, U.S. Provisional Patent Application No. 61/429,693, filed Jan. 4, 2011, U.S. Provisional Patent Application No. 61/475,469, filed Apr. 14, 2011, U.S. Provisional Patent Application No. 61/475,489, filed Apr. 14, 2011, and U.S. Provisional Patent Application No. 61/475,530, filed Apr. 14, 2011, the disclosures of which are incorporated herein by reference in their entireties.

FIELD

The field of the invention is pliable and resilient gelatinous elastomer seals for isolation of a user's skin from external or internal environments.

BACKGROUND

Sealing and cushion pads made of a compliant and resiliently deformable gelatinous elastomer suitable to conform under pressure to form a substantially airtight or watertight seal with a least a portion of a user's skin adjacent to the sealing pad are disclosed in U.S. Pat. No. 6,152,137, issued Nov. 28, 2000, which is a continuation-in-part of application Ser. No. 08/794,154, now U.S. Pat. No. 6,098,205, issued Aug. 8, 2000, which is a continuation of application Ser. No. 08/377,257, Jan. 23, 1995, abandoned. The disclosure of these patents is hereby incorporated herein by reference in their entireties.

Many medical devices are equipped to attach to or append from the human body. However, most devices are uncomfortable to wear for extended periods or in sensitive areas of the body. Also, many devices are unable to properly seal to the human body without applying excessive pressure to the skin which can be uncomfortable and in the worst cases can irritate or deteriorate the skin. There is a need for a device that can be fixed to various portions of the human body with a proper seal and without causing discomfort.

SUMMARY

One embodiment provides a human female contraceptive device. The contraceptive device includes a lumen surface-conforming occlusive agent that is shaped to occlude a fallopian tube of a human female and a skeleton affixed to the occlusive agent. The skeleton includes a cavity-conforming material that is shaped to fit at a junction of a uterus and the fallopian tube of the human female, and anchors affixable onto the skeleton and into the myometrium of the uterus of the human female.

A further embodiment provides a method for placing a human female contraceptive device. An occlusive agent sized to occlude at least a portion of the channel of a fallopian tube of a human female is fitted. A skeleton is placed as an anchor for the collusive agent, including, fitting a material engaged with the occlusive agent at a junction of a uterus and the fallopian tube of the human female, retaining the occlusive agent is in place in the fallopian tube by fixedly attaching the material with anchors into the myometrium of the uterus.

A further embodiment provides a penile condom catheter for facilitating urine collection and egress of urinary fluids away from the body torso of a living organism. A circumferential anchoring structure includes a web of flexible strands sized and is arranged to at least partially contact a portion of the penis, wherein the penis consists of a shaft of the penis originating near the body torso and a head of the penis comprising the distal part of the penis away from the body torso, wherein the head of the penis is the part of the penis containing an urethra orifice, and wherein the transition point between the shaft of the penis and the head of the penis is the corona of the penis. The anchoring structure provides a flexible yet secure hold against the penis when the penis is in a flaccid state. The anchoring structure provides an increase in the flexible yet secure hold against the penile skin of the flaccid shaft of the penis, when a longitudinal force, a vector force predominantly directed parallel to the length of the penis, is exerted upon the anchoring structure. The longitudinal force exerted on the anchoring structure is directed at least one of an along the length of the shaft of the penis and an away from the body torso. The longitudinal force exerted upon the anchoring structure stretches the flexible web strands. The stretching of the flexible web strands of the anchoring structure results in at least a component of the flexible web strands, constricting circumferentially, wherein the circumferentially constricting component of the anchoring structure exerts a force upon at least one of the penis. The force exerted is at least one of an increasing coefficient of friction and an increasing suction between the anchoring structure and at least one of the penis and the penile skin. An annularly circumferential penile skin covering material is affixed to the anchoring structure and is sized to fit over at least a portion of the penis. The annular circumferential covering material distally contains at least one orifice created to permit flow of urinary fluid away from at least one of the urethra orifice, the penile skin and the penis. At least one seal is affixed to at least a portion of at least one of a covering material, a covering material orifice, and an anchoring structure. At least a portion of the seal conformably maintains at least one of a covering material and an anchoring structure against at least one of the penis and the penile skin in a substantially watertight manner. At least one conduit is affixed to at least one of a covering material, a covering material orifice, a seal and an anchoring structure created to permit the flow of urinary fluid away from at least one of a urethra orifice, a penis, a penile skin, and a covering material orifice.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIGS. 66A-D are fixation methods and devices that can include but are not restricted to include a lattice or web or integral or interconnected strands with overlapping that are used with a condom catheter.

DETAILED DESCRIPTION

Figure 1:
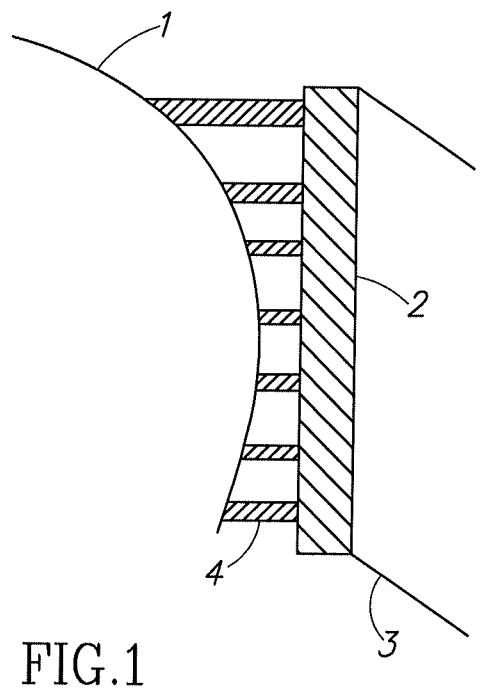
FIG. 1 is a sagittal view of the user's skin 1 and a sealing pad 2 with a skin covering material 3, which is interposed between the user's skin 1 and the sealing pad 2 and which uses one or more flanges 4.

Included herein at embodiments described for various unique applications of pliable and resilient gelatinous elastomer seals for isolation of a user's skin from external or internal environments. As used herein, the gelatinous elastomer seals are referred to as seals or pads or cushions. The pads may be used to form airtight or watertight seals or to provide cushions or covering, or both. The pads of the present invention conform to the numerous variations in topography of the user's skin, and when used as sealing pads distribute the compressive force throughout the pad to form an airtight or watertight seal with less pressure or compressive force that is required for solid or semisolid materials. As a result, the otherwise prominent surface characteristics of the user to which the pad is applied do not become pressure points since the pressure necessarily to form the airtight or watertight seal is more evenly distributed. This in turn has the potential to pad. The seals can be made of a gel or a non-gel material. In another embodiment the sealing pad can be non-resiliently deformable.

The described applications of the gelatinous elastomer seals may be used in a wide variety of situations to isolate the skin itself or to isolate an orifice such as the user's ears, eyes, nose, mouth, rectum or vagina. Skin refers to all membranes, mucosa and body cavity linings to include fascia, the peritoneal cavity lining, respiratory and oral and digestive cavity linings to include the stomach, bowel, intestines, uterus. ureters, bladder, rectum, anus, mouth, and nose. Other body cavities and linings can include the uterus, fallopian tubes, bladder, trachea, bronchi, meninges of the brain and spinal, the orbit and the ear and its related structures. Such isolation may need to be airtight or watertight, and such terms are used interchangeably herein.

The described applications of the gelatinous elastomer seals may be used in a wide variety of situations to isolate the skin itself or to isolate an orifice such as the user's ears, eyes, nose, mouth, rectum or vagina. Skin refers to all membranes, mucosa and body cavity linings to include fascia, the peritoneal cavity lining, respiratory and oral and digestive cavity linings to include the stomach, bowel, intestines, uterus. ureters, bladder, rectum, anus, mouth, and nose. Other body cavities and linings can include the uterus, fallopian tubes, bladder, trachea, bronchi, meninges of the brain and spinal, the orbit and the ear and its related structures. Such isolation may need to be airtight or watertight, and such terms are used interchangeably herein.

The description of various aspects of the invention included herein are given to explain certain features of the various devices and methods of the present invention. The examples given herein are for purposes of explanation and not limitation. Various devices are described herein, and it is to be appreciated that some of these devices have an accompanying method of use or manufacture, and that these associated methods are part of the disclosure. Similarly, where a method is described, the invention may include the corresponding device where applicable.

The gelatinous elastomer pad may be used as a cushion or seal or pad and covering material that is used for breathing mask. The breathing mask can be used for a continuous airway pressure (CPAP) mask and non-continuous positive airway pressure or alternating degrees of positive airway pressure or negative airway pressure or basic gas exchange. The breathing mask can be used for an environment protection mask, isolation mask, surgical mask, anesthesia and gas delivery mask, scuba and liquid submergence mask, a scent and smell delivery mask, a gas exchange mask, a fluid exchange mask that can be used for liquid delivery that facilitates ventilation, a pressure exchange mask, a pressure equalization mask, a cardio-pulmonary resuscitation (CPR) mask and a respiratory ventilation assistance mask to include active and/or passive assisted pulmonary ventilation. The sealing pad and the related devices and augmentations can be used with the sealing pad can be used for intubations. The seal of the mask in the preferred embodiment is composed of gel, which can create an airtight and watertight seal. The gelatinous elastomer pad may be used alone or in conjunction with non-gel materials and the pad can be a non-gel material or a combination of gel and non-gel material. The sealing pad can be perforated and connect to an external CPAP or respiratory or breathing machine or to exchange air or liquids or solids. The seals can include gels, Thermo Plastic Elastomers that can include CYBERSKIN™ and related thermal plastic elastomer, Silicon, Polystyrenes, Polystyrene and oil mixtures, and latex rubbers to include jelly rubber. The sealing pads disclosed herein can include microfiber materials or any other suitable materials having desirable characteristics, such as high or low friction, elasticity, etc.

A sealing pad can form a substantially airtight seal between a skin covering material and at least a portion of the user's skin. The sealing pad can be a compliant and resiliently deformable annular gelatinous elastomer suitable to conform under pressure to form a substantially airtight seal between the skin covering material and at least a portion of the user's skin. A gel can include a gelatinous elastomer suitable to conform under pressure to form a substantially airtight or watertight seal and at least a portion of the user's skin. A gel sealing pad can include a gelatinous elastomer suitable to conform under pressure to form a substantially airtight or watertight seal with at least a portion of the user's skin. A gel sealing pad and skin covering can include a gelatinous elastomer suitable to confirm under pressure to form a substantially airtight or watertight seal between the skin covering material and at least a portion of the user's skin. In another embodiment the sealing pad can be non-resiliently deformable.

In the preferred embodiment the mask would utilize flexible materials for the frame and attachment and covering materials and membranes. Other embodiments could include hardened material for the frame but these would be positioned to minimize discomfort to the user.

The sealing pad may be affixed to an outer or inner covering membrane or material. In one embodiment the fixation can be through integration of the gel into the material or through an adhesive material. The sealing pad may be separate or detachable from the outer or inner membrane or frame so that it can be replaceable. The skin covering material can be flexible or semi-flexible or not flexible.

The sealing pad may be composed of projections that can vary in shape and serve as flanges or valves that form an airtight or watertight seal with the skin. The sealing pad may be composed of projections that can vary in shape and serve as flanges that serve to separate the skin from the pad or covering material. The projections can be geometric or non-geometric. The projections can form an airtight seal in some sections and be non-airtight in others allowing for breathability of the skin. The projections can be constructed to follow or adjust to the contours of a body part. The body part can be superficial or can be internal. It can be in a cavity or organ. It can be on the skin, within the skin layers or deep to the skin within the organism.

The seal can be annular or the seal can be non-annular. The seal can be composed of a series of circumferential valves/flanges/slats that can be composed of a material that can include a gel but can be made of a material that is not a gel or a combination of a gel and a non-gel.

In the preferred embodiment the gel seal can be composed of a series of circumferential flanges or slats that can be composed of a material that is a gel. The flanges can be all oriented in the same direction or in opposing directions. The flanges can be one row or multiple rows. The flanges can be oriented to create a variable pattern that can create a watertight seal and can better conform to the user's skin contours. The flanges can be created such that the flange composed of gel or non-gel has an endoskeleton. The seal can be one or more continuous pieces or non-continuous pieces of material that can be circumferential or non-circumferential, which can include being spiral or overlapping. The seal flanges can be one or more non-continuous pieces of material that can be circumferential, with the ends of each piece overlapping, or with the ends of each piece having a transition piece that serves as an attaching or fastening element. In the preferred embodiment the gel mask and flanges can be used to form a breathing mask, that can conform to the variable contours of the skin of the face. In one embodiment the sealing pad can have a tackifying agent. The seal can be a gel or non-gel that is tacky to create a tacky seal with the skin.

In one embodiment the pressure can be used to improve the seal. The pressure can be created by an external circumferential or non-circumferential material. The seal can have the seal improved by one or more expandable chamber that contains a gas, liquid or solid. The expandable chamber can lie external to the circumference of the seal. The expandable chamber can lie within the seal. The expandable chamber can lie between the skin and the seal or can be a combination of chamber locations.

In another embodiment the gel seal can be a material that when expanded is resiliently deformable and returns to its original size. In another embodiment the seal can return to a size larger than its original size or to a size smaller than its original size. In another embodiment the seal can be non-resiliently reformable.

In another embodiment sealing pad can contain vents for the ingress and egress of air. The seal can be coated or impregnated with a substance or medication. The use of the substance or medication can include agents that are antibiotic, antibacterial, antifungal, antiviral; anti-fogging; scented; detoxifying age or filter, heating or cooling, gas delivery, liquid or solid delivery. The flanges can be composed of gel or non-gel or a combination of gel and non-gel materials. The flanges, which can be composed of gel or non-gel or a combination of gel and non-gel materials, can be used with a sealing pad that can be gel or non-gel materials. The flanges, which can be composed of gel or non-gel or a combination of gel and non-gel materials, can be used with a sealing pad that can be gel or non-gel materials and a skin covering material.

A web-like fixation device can be constructed in a geographic or non-geographic pattern that can be random or non-random that has spaces between the seal to include a lace-like, web-like shape with alternating regions of sealing pad and absence of sealing pad such that the sealing pad can include and resemble a web, a series of crisscrossed regions of seal and no-seal; integral, web, or lattice, overlapping strands, non-overlapping strands, a weave or woven strands. a Chinese-finger puzzle configuration; curvilinear or circular patterns; and triangular patterns. The pattern of alternating regions of sealing pad and the absence of sealing pad can be referred to as a web or web-like pattern. The web-like fixation device can be composed of a material that is a gel, a non-gel or a combination of gel and non-gel.

Fixation methods can include but are not restricted to two methods that include overlapping strands and a weave. The first method and structure can include but is not restricted to stands that can be overlapping or non-overlapping and which in the preferred embodiment can include but are not restricted to a gel material that can include but is not restricted to a tackifying material or an adhesive or which can be naturally tacky or: a fabric-like material that can include a microfiber with a high coefficient of friction and increased drag on the skin when the material when a force to include but not restricted to pulling is exerted. When said force to include but not restricted to pulling is exerted on the fixation device, the portions of the fixation in contact with the skin exert an increased coefficient of friction or drag that can increase or accumulate the more the fixation device is pulled upon. This embodiment is based at least in part on an increase in the surface area of the high coefficient material that is in contact with the skin. This represents both a method and a device. A second method and structure and embodiment of the fixation can include but is not restricted to a fixation device that is in the shape to include but not restricted to a weave that can include but is not restricted to resemble the weave of a Chinese Finger Puzzle. The weave when exposed to a force to include but not restricted to a pulling force will tighten in some areas and not in other areas. The weave when exposed to a force such as pulling will tighten and narrow the diameter of the fixation device and constrict around the body part to which it is in contact. The fixation device can be associated with but not restricted to a sealing pad and a skin covering material and an anchoring device and method.

The fixation device can be formed from a high coefficient of friction material that at least a portion of the fixation device can include a gel that can include but is not restricted to a tackifying material or an adhesive or which can be naturally tacky; or a fabric-like material that can include a microfiber with a high coefficient of friction and increased drag on the skin. Properties of a tacky gel or a high coefficient of friction material are uniquely suited to be used in a fixation device, in particular because of the tackifying adherent nature of a gel to the skin and the capillary action of a microfiber to the skin or a structure that can resemble the structure of a Gecko's footpad, to the skin and because the gel stretches and at least portions of the gel when pulled remains adherent to the skin. In turn, when the gel stretches the gel distributes an increased pressure to portions of the skin. In addition, portions of the gel in one embodiment constrict when dynamically pulled upon. The combination of the high coefficient of friction in concert with the increased pressure of the gel relative to the skin which can be contributed by the constriction on the gel fixation device on the skin create a situation where the gel becomes even more resistant to being pulled off or away from the skin and is an example of a higher coefficient of friction or high drag or resistance to being removed when the gel is in the dynamic state than in the static state. This can represent a greater dynamic to static coefficient of friction for a gel material when a force to include but not restricted to a pulling force is exerted on the gel. Put simply the tackiness of the gel on the skin does not pull away when a limited dynamic force is exerted. The gel can however be pulled off if a strong enough or an accelerated pulling force is applied to the gel fixation device when it is in contact with the skin. The force required for maintaining a fixed position on a body part is highly dependent on the shape and form and size of the body part. In one embodiment an experiment was performed. In another embodiment a simple weave or a more complex weave that is similar to a Chinese finger puzzle that is made of a gel or a high confident of friction can create be constructed to form a fixation device and may provide additional fixation. A fixation device was constructed that was a web-like design which was six centimeters long and which was composed of tacky gel strands with a total of four strands each approximately a half of a centimeter wide. The fixation device was place on a finger one and a half centimeters by two centimeters thick or in maximum diameter. The resting diameter of the fixation device was slightly smaller in width than the finger by approximately a quarter of a centimeter in width at the maximum diameter of the finger. The fixation device was placed over a six centimeter length of the finger. A string was tied with on end on a half a pound weight and the other half tied between the strands of the fixation device. The weight was suspended from the fixation device. The strands elongated. Some regions of the strands appeared to attenuate and other regions appeared to thicken. In some regions of the fixation device the diameter of the fixation device appeared to decrease and exert a compressive force on the skin of the finger. The fixation device remained suspended for over one minute without signs of falling off. The user walked around and the fixation device remained attached as the weight gently bobbed up and down which was done to simulate the real life use of the compression device. The compression device could be force off of the finger if the weight was violently yanked up and down. This is also an important element of the fixation device which should be able to detach itself from the skin if the force is great enough that it might damage the skin but to remain fixed to the skin if the force is a routine daily actions and life physical force. This experiment was performed to simulate the forces that might be exerted on a penis with a condom catheter with a fixation device.

The web-like pattern can have multiple functions to include making the sealing pad more breathable so that the underlying skin is aerated and so that the sealing pad can be worn for extended periods of time; making the sealing pad more biocompatible so that the web-like sealing pad can move more freely with the user's skin, body part or appendage; making the sealing pad more capable of staying in place or fixed or affixed to a body part by creating more than one region of attachment or friction or fixation; by making increasing the functional surface area of the skin to sealing pad. The sealing pad can be annular or non-annular or a combination of annular and non-annular. The sealing pad can be circumferential or non-circumferential or a combination of circumferential or non-circumferential.

The web-like device fixation device can be used with a sealing pad that can be at least partially covered by a membrane. The web-like device fixation device can be used with a sealing pad that can use a skin covering material.

In the preferred embodiment the web-like sealing pad can be annular and circumferential around the shaft of the penis nearest to the torso and the web-like sealing pad is composed of gel and conforms to the movements of the penis. Distal to the torso the web-like sealing pad transitions into a solid sealing pad with a bulbous out-pouching that is annular and circumferential around the corona or transition point between shaft and head of the penis. The bulbous out-pouching fits snugly into the corona in circumcised male and in uncircumcised males can fit over the foreskin if un-retracted or on or near the corona if the foreskin is retracted. An alteration in the design can be adapted for uncircumcised males. The bulbous circumferential annular transition of the seal can continue as a gel sealing pad or can transition into the skin covering material that can have the form of a condom catheter of bag like shape that is watertight and can have one or more conduits or tubes that can allow for the egress of urine away from the penis. In addition, one of the tubes can deliver solids, liquids or gasses to the penis that can assist in the comfort or biologic function of the penis that can include delivering a drying agent to include dry air, silicon dioxide, powder, cornstarch, or an alcohol based solution or gel; a medication that can include an antibacterial, antifungal, or antiviral agent; a medication that can treat a disease or condition to include cancer, HIV or other viruses, skin conditions, and pleasure delivery stimulating or anaesthetizing agents.

In another embodiment the web-like sealing pad and skin covering material can be used with a wound cover to include a bruise, laceration, burn, surgical site or site of trauma either natural or animal or man-made; a cast cover a breast cover or pump, a mask, goggles, eyewear, nose pieces or nostril plugs or devices, earpieces or earplugs or ear-buds, hand covers or gloves, garments, clothing, shoes, socks, a condom catheter or urinary processing device to include a urine bag, a semen processing device to include a male condom, a female condom or a male or female contraceptive device, a diaper or fecal processing device to include an ostomy bag. environmental suit or environmental protective gear, and a medication delivery system that requires areas of the body or skin that are preferentially treated with areas of medication delivery that have spaces or gaps between the sites of medication delivery.

These alternating patterns of sealing pad can be uniform in frequency of the pattern or can be more frequent at one end of the web of the pattern than at the other end. The seal can be used to anchor or fix the pad or the skin covering material or the device to parts of an organism's body to include the appendages, penis, vagina, internal organs, torso, neck, head, ear, nose, mouth. In the preferred embodiment the spider-like configuration can be used externally or on the skin to include fix and attach a condom-catheter onto the penis or fix a cast or bandage or wound cover onto a body part to include an arm or finger. Other embodiments can include internal body use and can include fix and attach a covering material onto a body organ to include a kidney. ovary, uterus, or bowel.

The web-like design can be used on non-living objects or substances to include two objects that need to be held in close approximation but require some separation and movement to include earphones and earbuds, or two objects that need to be closely bound to include two electronic communication devices such as an IPOD™ and a cellular phone or earbuds to an electronic device.

The web-like design can be used as an interface between a living organism and a non-living object to include a finger and sensing device to include a medical device to include a pulse-oximeter, glucose-meter or a blood saturation meter; or non-medical uses to include a children's toy, a music device that attaches to the body to include an IPOD™ or cellular phone attached to an arm.

In the preferred embodiment the web-like fixation device can be gel and can be placed around the upper arm and can have a pocket that can being water-proof. The pocket can hold a musical device that can include an IPOD™-like device that can be without a jacket or can have a waterproof jacket waterproof jacket. This combination can be used for use in the water to include swimming or surfing or the sand, which can include beach volleyball or sun tanning.

In one embodiment the gel seal and fixation device and skin cover in combination with the fixation gel web-like anchoring device or in any combination with these elements can include a cast cover, a wound cover, a bandage, a male condom catheter, a female condom catheter, a male or female contraception device, a breathing mask that can include a surgical mask, a ventilation mask, a positive airway pressure mask that can include a CPAP or BIPAP mask, an intubation device, nose plugs, earplugs to include music ear-buds, earplugs with a conduit or channel for the transmittal of a solid, liquid or gas, eye protection or goggles to include use for industry, medicine, water usage to include scuba, and swimming, a diaper, a device to preserve the integrity or sterility of a surgical field to include inside and outside of the body or body organ or cavity, a garment cover that can include a shoe cover a glove cover and a pants of sleeve or collar or hat cover; an environmental protection gear or device.

In one embodiment the web-like material can be a gel or a non-gel or a combination of gel and non-gel. In one embodiment at least a portion of the web-like material can have one or more tackifying agents. In another embodiment at least a portion of the web-like material has no tackifying agent. In another embodiment the web-like material can have a combination of tackifying agent and no tackifying agent.

In another embodiment the web-like fixation device can serve as a cushioning or air-tight seal if the channels are properly organized. Uses can include CPAP and positive pressure masks and a surgical mask.

The gel seal can be folded upon itself so that the external layer compresses the internal layer to form a self-sealing external compressive force. The skin covering can be wedged between the outer and inner layer of the gel seal. The gel seal can be folded upon itself so that the external layer compresses the internal seal layer to form a self-sealing external compressive force. The skin covering can be wedged between the skin and the inner and outer layer of the gel seal. The gel seal can be folded upon itself so that the external layer compresses the internal layer to form a self-sealing external compressive force. The skin covering can be external to the outer and inner layer of the gel seal.

In the preferred embodiment the skin covering material will be attached to the seal to form a substantially airtight and watertight seal to at least a portion of the seal.

The gel sealing pad can be composed of gel or can be composed with a combination of gel and non-gel materials. The gel seal can be composed of one or more folds to form a self-sealing external compressive force. The seal can be composed of one of more projections or folds that can be configured similar to the shape of the letter 'E' or 'W' or 'N' or 'M' or 'C or 'S' or any combination of these shapes such that insinuation of the seal and the skin covering material form an airtight and watertight seal between the skin and the seal and the skin covering material. The sealing pad can be folded or molded or can include a combination of both to form these configurations. The sealing pad can be manufactured or created with a flat cross-sectional shape which can be folded into a desired shape in combination with a skin covering, another sealing pad, or any other suitable device, or it can be manufactured or produced to have an independent structure such as a U-shape or a C-shape or any other suitable shape to include but not restricted to those shapes disclosed herein.

The skin covering can be composed of one or more skin covering materials or layers of which one or more of these skin covering materials can be attached or wedged onto the seal or between the folds of the seal.

The skin covering material can be composed of one or more redundant elements or folds that can be configured similar to the shape of the letter 'E' or 'W' or 'N' or 'M' or 'C or 'S' or 'O' or '8' or any combination of these shapes or variations on these shapes such that insinuation of the seal and the skin covering material form an airtight and watertight seal between at least a portion of the skin and the seal and the skin covering material In another embodiment the seal with projections or folds, and the skin covering can include a cast cover, a wound cover, a bandage, a male condom catheter, a female condom catheter, a male or female contraception device, a breathing mask that can include a surgical mask, a ventilation mask, a positive airway pressure mask that can include a CPAP or BIPAP mask, an intubation device, nose plugs, earplugs to include music ear-buds, earplugs with a conduit or channel for the transmittal of a solid, liquid or gas, eye protection or goggles to include use for industry, medicine, water usage to include scuba, and swimming, a diaper, a device to preserve the integrity or sterility of a surgical field to include inside and outside of the body or body organ or cavity, a garment cover that can include a shoe cover a glove cover and a pants of sleeve or collar or hat cover; an environmental protection gear or device.

In one embodiment, the sealing pad can be used as a seal that prevents the egress of humidified warm exhaled air from reaching the eye-glasses or a protective eye device or mask of the user and thus prevents the fogging of the eye-glasses or a protective eye device or mask. In the preferred embodiment the sealing pad forms either a single projection or flange or a C shape to embrace the surgical mask. In another embodiment the sealing pad can have a projection or flange or the C-shape attached to a flat cushion that can form a broader part of the based component that interfaces with the skin to give a more substantial anchoring base while the remainder of the projection or flange or the C shape acts as an additional barrier to the exhaled gas and also serves as an investing or coupling or holding or fixation or invaginating device for and to include a mask which can include a surgical mask. The fold can be composed of gel or non-gel or a combination of gel and non-gel materials.

The gel seal material can have a geometric shape that is a female or receptive configuration. The shape can be a groove or indentations, invagination or endophytic shape. The gel seal material can have a geometric shape that is a male or protuberant configuration. The shape can be a protuberance or projection or exophytic shape. The skin covering material can have a geometric shape that is a female or receptive configuration. The shape can be a groove or invagination, indentations, or endophytic shape. The skin covering material can have a geometric shape that is a male or protuberant configuration. The shape can be an extuberance or projections or exophytic shape.

The skin covering material can have one of more geometric shapes that can be male, one of more geometric shapes that can be female or one of more geometric shapes that can be a combination of male and female configurations.

The seal can have one of more geometric shapes that can be male, one of more geometric shapes that can be female or one of more geometric shapes that can be a combination of male and female configurations. The seal can have one of more geometric or non-geometric shapes that can be mirror images of each other. The skin covering material can have one or more geometric or non-geometric shapes that can be mirror images of each other.

In the preferred embodiment the skin covering material will have one or more male protuberances that insinuate themselves into one or more of the female indentations of the gel seal which has a mirror image female configuration of the male protuberances of the skin covering material. The seal can have a geometric or non-geometric shape that insinuates itself into the skin covering material. The skin covering material can have a geometric or non-geometric shape that insinuates itself into the gel seal.

The gel seal, the male projections, the female invaginations or in any combination of these elements can be at least partially composed of non-gel material and can be a combination of gelatinous and non-gelatinous materials. The gel seal, the male projections, the female invaginations or any combination of these components of the seal can be singular or redundant. The gel seal, the male projections, the female invaginations of the gel seal or any combination of these elements can be circumferential or partially circumferential or a combination of both circumferential and partially circumferential.

The gel seal, the male projections, the female invaginations or any combination of these elements, can be of variable hardness and softness to include softer away from the skin than at the skin covering material, softer away from the skin covering material than at the skin, or a combination or a variation on combinations of hardness and softness between the skin and the skin covering material. The protuberances and invaginations can be composed of gel, non-gel or a combination of gel and non-gel materials.

In one embodiment the gel seal and skin cover in combination with either the folded gel, the male projections, female invaginations or any combination with these elements can be used to form or augment a product to include a cast cover, a wound cover, a bandage, a male condom catheter, a female condom catheter, a breathing mask that can include a surgical mask, a ventilation mask, a positive airway pressure mask that can include a CPAP or BIPAP mask, an intubation device, nose plugs, earplugs to include music ear-buds, earplugs with a conduit or channel for the transmittal of a solid, liquid or gas, eye protection or goggles to include use for industry, medicine, water usage to include scuba, and swimming, a diaper, a device to preserve the integrity or sterility of a surgical field to include inside and outside of the body or body organ or cavity, a garment cover that can include a shoe cover a glove or glove cover and a pants cover, a sleeve cover, a collar cover or a hat or hat cover; a garment or garment cover or an environmental protection gear or device, In another embodiment the web fixation device, the sealing pad or the sealing pad with or without redundant elements or folds, the male projections, the female indentations and the skin covering or any combination of these elements can be used to form a product to include a cast cover, a wound cover, a bandage, a male condom catheter, a female condom catheter, a breathing mask that can include a surgical mask, a ventilation mask, a positive airway pressure mask that can include a CPAP or BIPAP mask, an intubation device, nose plugs, earplugs to include music ear-buds, earplugs with a conduit or channel for the transmittal of a solid, liquid or gas, eye protection or goggles to include use for industry, medicine, water usage to include scuba, and swimming, a diaper, a device to preserve the integrity or sterility of a surgical field to include inside and outside of the body or body organ or cavity, a garment cover that can include a shoe cover a glove or glove cover and a pants cover, a sleeve cover, a collar cover or a hat or hat cover; a garment or garment cover or an environmental protection gear or device, In another embodiment a sealing pad or a sealing pad with a skin covering material or a combination of a sealing pad or a sealing pad with a skin covering material can be fixed or anchored with a method to include a gel or a non-gel that can that uses a method to include placing a material that can include an anchoring object that can be an protuberant shape to include a natural shape such as the penis or a geometric shape such as a cylinder, an invaginated shape to include an annular or non-annular shape to include a natural shape such as a nostril, ear canal, mouth, vagina, anus or rectum or a geometric shape to include a funnel shape a hollow cylinder or a hollow rectangle or pyramid which can be formed from gel, CYBERSKIN™ and related thermal plastic elastomer, rubber latex, or silicon such that the anchor is formed by placing said material into an orifice. The orifice can include the nostrils, mouth, ears, anus, urethra, vagina, digestive track to include the esophagus, the respiratory track to include trachea and larynx.

The anchoring device can be used in combination with a gel seal to create an airtight or watertight seal with at least a component of the user's skin. The seal and the anchor can be used with a skin covering material or a fixation device that does not enter an orifice to include the web-fixation device, adhesives and tapes, or a living or non-living device that can include a catheter or tube, a urinary regulator, a sphincter regulator, a respiratory regulator, a heat or cold device, a pain regulator, an electrical or non-electrical physiologic device that can include a physiologic indicator and measuring device, monitoring device, feedback device, delivery device, permissive or inhibitory device, a tissue replication device or any combination of said devices; biological tissue that can be used to monitor, feedback or deliver or permit or inhibit a biological function or assist or create biological growth or hormone or substance delivery for biological and physiological development, growth, homeostasis or regulation; or any combination of these elements.

In the preferred embodiment is an anchoring device can be placed into the vagina, and can consist of a gel or CYBERSKIN™ and related thermal plastic elastomer tampon-like device that can simulate the shape of the vagina for comfort. The vaginal anchor can be attached to a seal that can be a gel that forms an airtight or watertight seal with the female urethra. The seal can have a skin covering material that can capture the urine released by the urethra and can be in a form to include a bag or condom or tube. The sealing pad and skin covering material can serve as a watertight conduit for removal of urine away from the body without leakage of urine. This application can be used use in females with an incompetent urethral sphincter, pelvic floor muscular dysfunction, muscle and nerve wasting conditions or medical diseases or entity to include multiple sclerosis, senility and amyotrophic lateral sclerosis and in situations where a female cannot use a toilet to include fighter pilots, racecar drivers, surgeons, and astronauts. The fixation device and method can also be used to for sexual stimulation and pleasure and to enhance or improve sexual function or gratification in conjunction with a physiologic device to include a feedback, inhibitory, permissive, delivery, and augmentation methods or devices. Another embodiment can be used as a male or female contraceptive device.

In another embodiment the anchoring orifice can be the anus and a urinary catheter can be used in a female and the orifice anchor can be used alone or in conjunction with the vaginal anchor. In another embodiment the anchoring orifice can be the anus and a male condom catheter can be attached to the anchoring device.

In another embodiment the anchoring orifice can be the ear and a skin covering can include a mask, a pair of swimming goggle, or a CPAP mask, and said anchoring device can be attached to the anchoring device.

In another embodiment the anchoring device can be used with a web fixation device, the sealing pad or the sealing pad with or without redundant elements or folds, the male projections, the female indentations and the skin covering or any combination of these elements can be used to form a product to include a cast cover, a wound cover, a bandage, a male condom catheter, a female condom catheter, a breathing mask that can include a surgical mask, a ventilation mask, a positive airway pressure mask that can include a CPAP or BIPAP mask, an intubation device, nose plugs, earplugs to include music ear-buds, earplugs with a conduit or channel for the transmittal of a solid, liquid or gas, eye protection or goggles to include use for industry, medicine, water usage to include scuba, and swimming, a diaper, a device to preserve the integrity or sterility of a surgical field to include inside and outside of the body or body organ or cavity, a garment cover that can include a shoe cover a glove or glove cover and a pants cover, a sleeve cover, a collar cover or a hat or hat cover; a garment or garment cover or an environmental protection gear or device, In another embodiment the gel seal or the fixation device or a combination of these elements, which can be made of a gel, can be used with a skin covering material that can include shoes. Sleeves and socks.

The orifice-anchoring device can be used alone or in conjunction with the web fixation or anchoring-device. In one embodiment the anal and a penile web fixation device can be used in conjunction with a skin covering material that can include a condom catheter. This application can be used use in males and females with an incompetent urethral sphincter, pelvic floor muscular dysfunction, muscle and nerve wasting conditions or medical diseases or entity to include multiple sclerosis, senility and amyotrophic lateral sclerosis and in situations where a female cannot use a toilet to include fighter pilots, racecar drivers, surgeons, and astronauts. This can also be used to for sexual stimulation and pleasure and to alter, enhance or improve sexual function or gratification. Another embodiment can be used as a male or female contraceptive device.

In another embodiment, the anchor can include the nostril or nose into the mouth or around the mouth or lips can include Tacky or a sticky or a non-tacky attachment that can include the inner nose or outer nose, pressure on the inner wall of the nostril, fixation band around all or a portion of the users head; connection to the mouthpiece; inside or around the ears; the eyes or a goggle or flexible or inflexible eye piece; a head cap or hat; the hair or moustache; a piecing through the skin or mucosa of the mouth or nose; to the teeth; to one or more teeth; which can be the upper palatine teeth or lower mandibular/buccal teeth or both which can include braces or denture-like or mouth guard or a molded fixation piece that conforms to the inner teeth, the outer teeth the biting surface, a combination of the above, the gums or a combination of the gums and teeth.

In another embodiment the anchor can be placed within a skin tunnel or crease in the body. A crease in the body can include the crease of the buttocks or adipose folds of the belly in an obese individual or a surgically constructed crease or tunnel can be created. A tunnel in the body can include a surgically constricted crease, an internal cavity, a natural tunnel such as a muscle and bone interface or an internally or externally constructed skin tunnel which can be constricted near and ostomy site. In one embodiment the seal and the skin covering material can be used as an ostomy seal and bag and a skin tunnel to house the anchoring device which can be composed of a material to include a biological compatible silicon, gel, metal or other solid of gel. In one embodiment the anchoring device between the seal and the skin can be magnetic and the anchoring device can anchor the gel seal with the use of a method to include electromagnetic forces or energy.

In another embodiment the sealing pad or the sealing pad and the skin covering can be joined together using a method to include ZIP-LOCK™, VELCRO™ and related fabric hook and loop fasteners, thread, ties, hooks, zippers, adhesives, buttons, elastic materials or any electromagnetic attachment to include electromagnetic forces and energy to include magnets or mechanical or electromechanically devices such as retractable grappling, hooks or interlocking devices. A combination of closure methods can be used in combination.

In another embodiment the sealing pad or the sealing pad and the skin covering can be directly in apposition without overlap and can use a closure mechanism to include ZIP-LOCK™, VELCRO™ and related fabric hook and loop fasteners, thread, ties, hooks, zippers, adhesives, tackifying agents, buttons, elastic materials or any electromagnetic attachment to include electromagnetic forces and energy to include magnets or mechanical or electromechanically devices such as retractable grappling, hooks or interlocking devices. A combination of closure devices can be used in combination.

In another embodiment the sealing pad or the sealing pad and the skin covering can be directly in apposition without overlap and can use a closure mechanism to include ZIP-LOCK™, VELCRO™ and related fabric hook and loop fasteners, thread, ties, hooks, zippers, adhesives, tackifying agents, buttons, elastic materials or any electromagnetic attachment to include electromagnetic forces and energy to include magnets or mechanical or electromechanically devices such as retractable grappling, hooks or interlocking devices. A combination of closure devices can be used in combination. This can be used as a wound covering or cast covering.

In another embodiment the sealing pad or the sealing pad and the skin covering can be directly in apposition with overlapping elements of either the sealing pad or the sealing pad and the skin covering or a combination of these elements and can use a closure mechanism to include ZIP-LOCK™, VELCRO™ and related fabric hook and loop fasteners, thread, ties, hooks, zippers, adhesives, tackifying agents, buttons, elastic materials or any electromagnetic attachment to include electromagnetic forces and energy to include magnets or mechanical or electromechanically devices such as retractable grappling, hooks or interlocking devices. A combination of closure devices can be used in combination.

In another embodiment the seal can be removable and replaceable. The sealing pad and skin cover and fixation device and the anchor or a combination of these elements can be removable or replaceable.

One embodiment can include attached to include the sealing pad and skin cover and fixation device and the anchor or a combination of these elements, can use an attachment device that can include ZIP-LOCK™, VELCRO™ and related fabric hook and loop fasteners, thread, ties, hooks, zippers, adhesives, buttons, elastic materials or any electromagnetic attachment to include electromagnetic forces and energy to include magnets or mechanical or electromechanically devices such as retractable grappling, hooks or interlocking devices. A combination of attachment devices can be used with a combination of anchoring devices.

The preferred embodiment can use a gel seal with a skin covering material that forms and ostomy bag in which the ostomy has a tunnel that contains a silicone ring that is magnetized. The gel seal can also be magnetized or can be ferromagnetic and create a tight bond between the anchor and the gel seal. The gel seal creates an airtight and watertight seal with the skin and the skin covering material, which is an ostomy bag allows for the capture and the flow of fecal material away from the body, This method avoids adhesives, which serve to break down the skin over time and lead to ulcers and infections of the skin. In another embodiment the orifice or a structure in an orifice can be used to include a tooth or teeth for an anchor.

In another embodiment the orifice or a structure in an orifice can be used to include a tooth or teeth for an anchor. which can be used with a garment or a material to include clothing or a garment or a belt that can be composed of a material to include cloth, fabric, natural or synthetic-man-made materials to include nylon, rayon, and polyester-like materials, plastics, plant based materials, metals and metal mesh material.

In the preferred embodiment a female urethral urine collector can include a vaginal anchor which can be used to fix a gel sealing pad in position that surround the urethra and forms a watertight seal. To support the fixation of the sealing pad a thong-like garment can be worn that is composed of a comfortable and mildly stretchable fabric that can fit around the buttocks or in the buttock crease of a combination of both. The fabric is attached to either the sealing pad that is softer near the skin than the away from the skin such that the fabric and sealing pad anchor is secure or the fabric material can be attached to the skin covering material which can include the catheter bag, condom catheter, or a frame either flexible or non-flexible or to the vaginal anchor.

In another embodiment the sealing pad and skin covering material, which is a male condom catheter. To support the fixation of the sealing pad a thong-like garment can be worn that is composed of a comfortable and mildly stretchable fabric that can fit around the buttocks or in the buttock crease of a combination of both. The fabric is attached to either the sealing pad that is softer near the skin than the away from the skin such that the fabric and sealing pad anchor is secure or the fabric material can be attached to the skin covering material which can include the catheter bag, condom catheter, or a frame either flexible or non-flexible.

In another embodiment the sealing pad and the skin covering device and the orifice anchor can include uses as a wound cover to include a bruise, laceration, burn, surgical site or site of trauma either natural or animal or man-made; a cast cover a breast cover or pump, a mask, a breathing mask that can include a CPAP or BIPAP or positive pressure ventilation mask, an intubation device, goggles, eyewear, nose pieces or nostril plugs or devices, earpieces or earplugs or ear-buds, hand covers or gloves, garments, clothing, shoes, socks, a condom catheter or urinary processing device to include a urine bag, a semen processing device to include a male condom, a female condom or a male or female contraceptive device, a diaper or fecal processing device to include an ostomy bag. environmental suit or environmental protective gear, and a medication delivery system that requires areas of the body or skin that are preferentially treated with areas of medication delivery that have spaces or gaps between the sites of medication delivery.

In another embodiment the seal can be removable and replaceable and can be attached to an anchor using an intermediary or transitional material that can include a fabric or elastic or gel or a solid to include a metal such that the seal and the anchor are not contiguous but are connected and attached using an intermediary attachment device that can include ZIP-LOCK™ VELCRO™ and related fabric hook and loop fasteners, thread, ties, hooks, zippers, adhesives, buttons, elastic materials or any electromagnetic attachment to include electromagnetic forces and energy to include magnets or mechanical or electromechanically devices such as retractable grappling, hooks or interlocking devices. A combination of attachment devices can be used with a combination of anchoring devices and transitional materials. In the preferred embodiment the anchoring device is a bite plate in the mouth that has a transitional material composed of a rubbery consistency that attaches to a skin covering material with a gel seal that can be used for use as a CPAP mask.

In another embodiment the anchoring device is a metal band, which can be the metal band-like structures used in braces that surrounds one or multiple teeth. The metal band can have an attachment projection that can be an annular or non-annular projection that is capable of attaching a wire or rubber band-like structure to the anchored-metal band on the tooth or teeth simulating braces. The anchored-metal band on the tooth or teeth can have a rubber-band like intermediary connector that can connect to connect the skin covering material which can include a frame that can be flexible or non-flexible or it can connect directly to the seal which in the preferred embodiment is a gel seal that can form an airtight or watertight seal that can regulate the inhaled and exhaled gases pressure within the respiratory track and this forms a mask that can be used for use as a CPAP or BIPAP or positive or negative pressure mask that can be used for sleep apnea, assisted ventilation.

In another one embodiment a ventilation mask can be a low profile mask. The low profile mask can be used for a CPAP device that is composed of smaller and less bulky tubes to minimize discomfort to the user and improve comfort and secondarily improve sleep or the mask can produce resistance to exhalation. The mask can be made of lightweight materials to improve comfort.

In the preferred embodiment the skin covering material is airtight and the gel seal forms an airtight seal with at least a portion of the skin. In another embodiment the skin covering can be breathable and permeable to air. In another embodiment the skin covering material can be a combination of breathable and non-breathable and can have variable air-tightness and air permeability. The amount pressure and the volume of air passage or non-air passage can be alternated or varied.

In one embodiment the mask can be composed of a single valve or a series of valves that can alter the pressure and resistance of inhaled and exhaled gas or liquids or solids of a combination of gas, liquids and solids. Another embodiment can include a covering material that can experience variations in the permeability of inhaled and exhaled gas or can be composed of a series of covering materials that can have variable permeability and resistance to inhaled and exhaled gases.

Another embodiment can use a combination of channels and reservoirs that can be controlled to alter the variability in permeability and resistance of inhaled and exhaled gases. The control of the air permeability and resistance can utilize devices that include mechanical, chemical, electromagnetic, vibrational, heating and cooling or a combination of these methods.

In another embodiment the airway pressure within the mouth can be altered by changing the shape or the volume of the shape or volume or a combination of the shape and volume of the skin covering material to create a device in which the pressure of the exhaled and inhaled gas can be increased or decreased or set at a steady state depending on the resistance within the skin covering material.

A low profile mask that is composed of smaller and less bulky tubes to minimize discomfort to the user and improve comfort and secondarily improves sleep. In the preferred embodiment it can be used for CPAP. The mask can combine a seal to include a gel, silicone, CYBERSKIN™ and related thermal plastic elastomer or ThermoPlastic Elastomers, with a lightweight material that can include fabric, paper, plastic, metal or other gels. solids liquids or gases to form a more flexible and comfortable breathing unit. In the preferred embodiment, the low profile breathing mask can fit closer to the skin and can be composed of materials, which in one embodiment are breathable and permeable to air and would be composed of a material to include Gortex, paper-wood products The seal of the mask in the preferred embodiment is composed of gel, which can create an airtight and watertight seal. The mask can be comprised of conduits and receptacles and orifices, which can perforate and connect to an external CPAP or respiratory or breathing machine or to exchange air or liquids or solids. In the preferred embodiment the mask would utilize flexible materials for the frame and attachment and covering materials and membranes. Other embodiments could include hardened material for the frame but these would be positioned to minimize discomfort to the user. The mask can combine a lightweight material and a gel to form a more flexible and comfortable breathing unit to include a CPAP mask.

The breathing mask or ventilation or intubation device can use a gel sealing pad or a sealing pad with a skin covering material in conjunction with a liquid solution or a solid material or a gas or a mixture of these substances as an exchange material that can facilitate the organism gas exchange of substances such as oxygen or carbon dioxide. The mask can facilitate the osmotic exchange of other blood containing substances such as urea, glucose, and electrolytes and minerals and can form as a form of dialysis. The introduction of substances such as medications can be facilitated by the breathing mask to include antibiotics, anti-fungal and anti-viral drugs, surfactant materials and other lung performance facilitating medications. Some of the substances that can be used to exchange vital gases for organisms can include chemical compounds which can carry and release oxygen perfluorocarbons (PFCs of which a specific PFC used is perfluorodecalin; haemoglobin derived from humans, animals, or artificially via recombinant technology, Haemoglobin-based oxygen carriers, to include lecithin surfactants, Oxygent, Oxycyte PHER-O2, and Perftoran.

In the preferred embodiment a gel sealing pad with a skin covering material that serves as a ventilation tube can be used to intubate an organism. The ventilation tube forms an airtight seal with the digestive track to include the esophagus and GE junction and stomach to prevent liquids from entering the stomach this seal should be airtight and watertight. Coincidentally a second seal is formed with the respiratory track to include the larynx, trachea or bronchi or their branches. Once a seal is formed with at least one of the two passages, the digestive passage or the respiratory passage or with both passages, the liquid ventilation can commence.

In the preferred embodiment the intubation device can be branched with on branch extending into the esophagus and digestive track and the other appendage extending into the trachea or bronchi.

In another embodiment the sealing pad can be used to isolate a portion of a body cavity to include the oral pharyngeal space for diagnostic or therapeutic care that can include radiation, radiation augmentation or protection, and the delivery of medication or the restriction of medication delivery. The sealing pad can be used to prevent the flow of a substance or to isolate two regions to include preventing reflux of digestive juices from the stomach and the esophagus from entering the oral airway.

In another embodiment the isolation of a portion of the esophagus can be created using gel seal plugs to include the treatment of a portion of the esophagus for cancer or pre-cancerous lesions such as Barret's esophagus by placing sealing pads caudad and cranial (above and below) the area of the esophagus to be treated. The seals will serve as plugs and can have one or multiple conduits that can provide for the instillation and removal or medication or therapeutic substances into the treatment region.

In another embodiment the isolation of a portion of the bladder can be created using an annular ring and a sealing cover that can be a gel or a non-gel material to isolate a portion of the requiring treatment. The seal or the sealing cover can have one or multiple conduits that can provide for the instillation and removal or medication or therapeutic substances into the treatment region while protecting the remainder of the bladder from the effects or side-effects of the medication or therapeutic substances In another embodiment a sealing pad or a seal pad and skin covering can contain a reservoir containing a solid or liquid or gel or gas that can include a therapeutic, pleasurable, moisturizing, humidifying or drying, heating or cooling substance or medication. The use of the substance or medication can include agents that are antibiotic, antibacterial, antifungal, antiviral; anti-fogging; scented; detoxifying agent or filter, heating or cooling, gas delivery, liquid or solid delivery.

In the preferred embodiment an airtight and watertight wound cover can deliver medication to a wound in a dose and a periodicity that can be regulated to include mechanical or digital or nanotechnology or electromagnetically or kinetically or by vibration. In another embodiment a CPAP mask cast with a gel seal and skin covering material can deliver humidified air to the skin mucosa of the mouth to preserve internal humidification.

In another embodiment the reservoir can be used with a breast pump and a scent simulating an infant's scent can be released. In another embodiment aerosolized Oxytocin can be released. In another embodiment the reservoir can be controlled by an indicator and measuring device or a feedback device. In another embodiment the reservoir can be controlled by an indicator and measuring device or a feedback device that can measure and respond to physiologic and non-physiologic measurements to include the need to control upstream arterial flow in a laceration with bleeding. In this circumstance the seal acts both as a seal and a tourniquet.

In another embodiment the seals can have an equal pressure or force compressing or holding them in place against the skin or at least one of the seals can have having a greater pressure or force compressing or holding the seal in place against the skin than other seals.

In another embodiment the reservoir can be a compressive device that can adjust the airtight seal in situations that require greater force this can include a situation where a laceration includes an uncontrolled bleed that fills the sealing pad and skin covering internal chamber with blood. In that situation the goal is to attain a pressure in the internal chamber that is equal to, or greater than or less than the arterial inflow pressure which in one embodiment can be the upstream sealing pad, which is acting as a tourniquet. In this situation the object is to allow some arterial inflow to keep the tissue alive but restrict the bleeding. In the preferred embodiment this can be measured with a monitor to include an oxygen monitors at the distal downstream seal to access tissue viability while the upstream arterial flow with a monitor to include an a blood pressure monitor or an ultrasound Doppler device to access the arterial waveform.

In one embodiment the gel seal can include a reservoir that can be used with a skin covering material which can be used as a cooling or anti-itch or anti-irritation device for the skin beneath a cast in a cast or wound cover.

In one embodiment the gel seal can include a reservoir in combination with channels or conduits or tubes or wires or optics can as change the sensation or biology or physiology of the skin to include a cooling or anti-itch or anti-irritation device for the skin beneath a cast or wound in a cast or wound cover.

In one embodiment the gel seal can include a reservoir that can be used with a skin covering material and can be used as uses as a wound cover to include a bruise, laceration, burn, surgical site or site of trauma either natural or animal or man-made; a cast cover a breast cover or pump, a mask, a breathing mask that can include a CPAP or BIPAP or positive pressure ventilation mask, an intubation device, goggles, eyewear, nose pieces or nostril plugs or devices, earpieces or earplugs or ear-buds, hand covers or gloves, garments, clothing, shoes, socks, a condom catheter or urinary processing device to include a urine bag, a semen processing device to include a male condom, a female condom or a male or female contraceptive device, a diaper or fecal processing device to include an ostomy bag. environmental suit or environmental protective gear, and a medication delivery system that is benefited by the delivery of a substance from said reservoir.

The sealing pad, the skin covering or a combination of the sealing pad and skin covering can contain a feedback or indicator or measuring device which shall be referred to as an indicator, or an indicator and measuring device, or sensor device. The indicator and measuring device can assess and can include physiology of the body that can include pulse, blood pressure, temperature, glucose levels, biomechanical measurements, carbon dioxide and oxygen and gas levels, oxy and deoxyhemoglobin levels and other basic metabolic functions and measurements to include wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, muscular function, substance levels to include drugs and medications and non-physiologic measurements to wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, substance levels to include drugs and medications a combination of physiologic and non-physiologic measurements.

In one embodiment the sealing pad and skin covering can have a physiologic feedback measurements such as pulse and blood pressure detector in which measurement information can be transmitted using a method to include a visual signal that is projected using a method to include an image on a screen, to an object that can be transparent, translucent or opaque; onto the retina, onto a region in the visual field of a pair of swimming goggles that monitors a swimmers work-out.

In another embodiment the sealing pad and skin covering can have an indicator of wetness or dryness which can be displayed using a method to include a color indicator to include encapsulated cobalt chloride, which is blue when dry and pink when wet or fizzy tablets to include Alka-Seltzer-like tablets which fizz when wet, which can be used with a wound or cast cover.

In another embodiment the sealing pad and skin covering can have an indicator to include pH, which can be displayed using a method to include a color indicator to include a pH indicator dye to include the detection of urine using a method to include standard pH detection strips or materials for detecting the alkaline part of urine which s ammonia, NH3, which can permeate low-density poly-ethylene (LDPE) and changing their color; which can be used with a urinary condom.

In another embodiment the sealing pad and skin covering can have an indicator to include pH protein, sperm, or fructose or other sugars, which can be displayed using a method to include a color indicator to include a pH indicator dye to include the detection of semen or vaginal fluid. For the male the pH of semen is 7.2 to 7.8 and for the female the pH of vaginal fluid is 3.8 to 4.5 also semen contains specialize proteins which can include a method to include anti-semen antibodies or using biuret solution to indicate the presence of protein which can be measure using a microchip or a color indicator which can give a signal to include an analog or digital signal, which can be used with a female or male contraceptive device to indicate mingling or leakage or loss of integrity between the penile and the vaginal side of the seal and skin covering material. In one embodiment to include if a male condom is used then an indicator can be place on the outside of the condom. If sperm and seminal fluid leaks to the outside then the pH of the vaginal fluid will change because of the difference between the vaginal and seminal pH and this change can be measured with a color indicator, or an indicator containing anti-sperm antibodies which when in the presence of sperm reacts and creates a reaction that can be detected by an analog or digital method or a sugar indicator which when fructose is present (fructose is found in seminal fluid) will be detected and will provide an analog or digital signal.

In another embodiment the sealing pad and skin covering can have an indicator to include a gas or pressure indicator with a breathing mask which can include a CPAP, BIPAP, variable, ventilation, intubation device, that can detect Oxygen and Carbon Dioxide level or can detect pressure levels or can detect a combination of gas and pressure levels. This detection device can then provide feedback to either an internal or external device that provides for variations and delivery or gas or pressure.

In another embodiment a sealing pad and skin covering can become a contained and localized isolation chamber or environment to include managing a body part or the entire body to include managing the pH, gas content, the aerobic or anaerobic nature of the isolated environment, elemental content, substance or medication content, electromagnetic content to include radiation or visible or non-visible light spectra to include UV and infrared light, to wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, substance levels to include drugs and medications.

In the preferred embodiment the sealing pad and the skin covering material can serve as an isolation chamber which can serve as a mini therapeutic or hyperbaric oxygen chamber in which the management of the pressure or gas levels can utilize a reservoir in the sealing pad or skin covering or channels or conduits for the ingress and egress of gas to include oxygen and other gases and to manage the pressure in the chamber to include a pressure that is less than, equal to or greater than atmospheric pressure. Uses of this isolation chamber can include the treatment of wounds, infections to include aerobic infections which can be denied oxygen, anaerobic infections which can be killed with oxygen or in an oxygen only environment, antibiotic resistant infections to include MRSA infections in which the antibiotic level, or a toxin or a gas mixture or a combination of these elements can be used to treat the infection at a localized site with specific therapeutic methods while isolation other regions of the body from these same therapeutic levels.

In another embodiment the sealing pad and the skin covering material can serve as an isolation chamber which can serve as a therapeutic chamber to deliver radiation sensitizing materials that can include 5-chlorodeoxycytidine (5-CldC) or 5-halo-2'-halo-2'-deoxy-cytidine or -uridine derivatives, Tetrahydrouridane (H.sub.4 U) and 2'-deoxytetrahydrouridine (dH.sub.4 U) co-administered with the deoxycytidine derivative to inhibit deamination of the deoxycytidine derivatives, agents to reduce the amount of competing metabolites to favor CldC, such as 5-fluorodeoxyuridine, 1-(2-chloroethyl)-3-cyclohexyl-1-nitrosourea (CCNU), chlorozotocin, 1,3-biscyclohexyl-1-nitrosourea (BCyNU), and 1,3-bis(2-chloroethyl)-1-nitrosourea (BCNU). CCNU, BCyNU, and BCNU; such that when radiation is administered the area being isolated can achieve an added effect from the radiation.

In another embodiment the sealing pad and the skin covering material can serve as an isolation chamber which can serve as a therapeutic chamber to deliver radiation resistant materials to include antioxidant compounds such that when radiation is administered the area being isolated can achieve a diminished effect from the radiation.

In another embodiment the sealing pad and the skin covering material can serve as an isolation chamber, which can serve as a therapeutic chamber which can be used to treat a laceration with uncontrolled bleeding. The sealing pad can contain a reservoir or bladder of have a device that constricts or contracts the gel seal between the seal and the skin, within the seal or external to the seal, In the preferred embodiment the constricting seal is placed at the location of the wound where there is arterial inflow. The compressive seal can serve as a tourniquet that can allow blood flow into the wound to increase, decrease, remain the same, vary the flow or any combination of these flow speeds or elements. The wound can be isolated to achieve keeping the wound clean, tamponating the wound, stopping the bleeding and treating the wound that can include medicines to include antibiotics, coagulants and anticoagulants, QUIKCLOT™ and related gauze and Chitosan, an extract from shrimp shells and blood products to include platelets. The pressure within the isolation chamber can also be regulated to increase, decrease, remain the same, equilibrate or vary or be a combination of these elements relative to the seals, tourniquet, tamponating agents, atmospheric pressures, arterial or venous or body pressure or a combination of these elements can be used to regulate the optimal equilibrium between adequate blood flow and oxygenation to the tissue and at and distal to the laceration. The oxygen and gas content in the isolation chamber can be controlled and regulated to also include assist in physiologic homeostasis and cell survival and clotting and other primary biological functions for survival of the organism and the components of the organism. In the preferred embodiment can include the combination of the inflow gel seal controlling and regulating arterial inflow in the lacerated artery through regulated pressure on the artery, in combination with regulated oxygenation within the isolation chamber, in combination with varied pressure within the chamber, in combination with medications to induce clotting, in combination with wound isolation and medications to reduce infections, may provide for greater cell and tissue and limb and organism survival. In another embodiment one or more chambers can be utilized which can include treating the tissue distal to the laceration with a second isolation chamber with characteristics dissimilar from the first chamber. Additional treatments can include electromagnetic energy to include UV energy, Infrared energy, radiation, visual energy fields, kinetic, and vibrational energy. The isolation chamber can be surrounded by or integrated into an air-cast to supplement isolation and external pressure.

In another embodiment the sealing pad and the skin covering material can serve as an isolation chamber which can serve as a therapeutic chamber to have a pressure less than the ambient atmospheric pressure to include induce blood flow to a tissue to include a muscle group that is a risk for compartment syndrome.

In another embodiment the sealing pad and the skin covering material can serve as an isolation chamber which can serve as a therapeutic chamber to treat a varieties of conditions to include burns, to remove tattoos, to heal wounds, ulcers and lacerations in patients to include diabetes, immune-compromised individuals, patients with oxygen deprivation to tissue to include diabetics, patients with atherosclerosis, frostbite, stroke, emboli from solids, gels, liquids or gases to include nitrogen in scuba divers; to induce sensory stimuli that can include pleasure or perceived pleasure to include organs such and the skin, penis or vagina or breasts, to induce or reduce pain to include uses for diagnostic or therapeutic purposes; to treat a body part to include the skin, mucosa, fascia, a muscle, a body organ, to treat a whole body or a body part that requires a change in metabolic and physiologic characteristics to include decreasing the metabolism using a method to include cooling and delivering a medication locally; increasing the metabolism to include warming, and medication delivery to include amphetamine, to increase or decrease pain and pleasure and all other animal sensations which can be used for the treatment for cancer, pain relief, oxygen and vascular function and cell function and dysfunction to include stoke, cell death, aging and rejuvenation.

In another embodiment the sealing pad and the skin covering material can include an indicator device that can be utilized to provide feedback to the regulate the seal, the skin covering material, the internal environment between the seal and the skin covering material complex and the skin, the external environment outside of the seal and the skin covering material complex, or a combination of these regions and elements. The indicator can be used to regulate and adjust and measure parameters to include the pH, gas content, the aerobic or anaerobic nature of the isolated environment, elemental content, substance or medication content, electromagnetic content to include radiation or visible or non-visible light spectra to include UV and infrared light, to wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, substance levels to include drugs and medications, and the biologic and physiologic parameters of the tissue or body part being isolated. The material or energy being delivered or removed from the isolation chamber can be located between the sealing pad and skin covering material and the skin, or can be a part of the sealing pad and skin covering, or can be external to the sealing pad and skin covering or can be a combination of these elements.

The delivery or removal system for material or energy being delivered to or removed from the isolation chamber and the skin, body part or organism, can be located between the sealing pad and skin covering material and the skin, or can be a part of the sealing pad and skin covering, or can be external to the sealing pad and skin covering or can be a combination of these elements. The matter or energy being delivered or removed can be delivered or removed by methods to include channels, tubes, wires, osmosis, kinetic energy or electromagnetic energy.

The indicator and the adjustment can provide feedback can include physiology of the body that can include pulse, blood pressure, temperature, glucose levels, biomechanical measurements, carbon dioxide and oxygen and gas levels, oxy and deoxyhemoglobin levels and other basic metabolic functions and measurements to include wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, muscular function, substance levels to include drugs and medications and non-physiologic measurements to wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, substance levels to include drugs and medications a combination of physiologic and non-physiologic measurements.

The sealing pad and the skin covering and the indicator can be connected to at least one device that can adjust, regulate, manage, and assess the physiology or biology of the isolated tissue or body part or organism and adjust the device to optimize, alter or coordinate the needs or biologic function or physiology of the isolated tissue or body part or organism.

In the preferred embodiment the combination of a sealing pad and the skin covering and at least one indicator can be connected to an isolation chamber which can serve as a mini therapeutic or hyperbaric oxygen chamber in which the management of the pressure or gas levels is controlled by at least one indicator which provides feedback to adjust, regulate or manage the pressure and gas levels and mixture in the chamber. Uses of this isolation chamber and skin covering and indicator can include the management and regulation and assessment and treatment of wounds, infections to include a wound, a laceration, aerobic infections which can be denied oxygen, anaerobic infections which can be killed with oxygen or in an oxygen only environment, an antibiotic or antifungal or antiviral resistant infections to include MRSA infections in which the antibiotic level, or a toxin or a gas mixture or a combination of these elements can be used to treat the infection at a localized site with specific therapeutic methods while isolation other regions of the body from these same therapeutic levels.

In another embodiment the sealing pad and the skin covering material and at least one indicator can serve as an isolation chamber which can serve as a therapeutic chamber in which at least one indicator can be used for the adjustment, management and regulation and assessment and treatment which can be used to treat an ailment to include cancer and in which the feedback mechanism can be used to locally deliver radiation sensitizing materials that can include 5-chlorodeoxycytidine (5-CldC) or 5-halo-2'-halo-2'-deoxycytidine or -uridine derivatives, Tetrahydrouridane (H.sub.4 U) and 2'-deoxytetrahydrouridine (dH.sub.4 U) co-administered with the deoxycytidine derivative to inhibit deamination of the deoxycytidine derivatives, agents to reduce the amount of competing metabolites to favor CldC, such as 5-fluorodeoxyuridine, 1-(2-chloroethyl)-3-cyclohexyl-1-nitrosourea (CCNU), chlorozotocin, 1,3-biscyclohexyl-1-nitrosourea (BCyNU), and 1,3-bis(2-chloroethyl)-1-nitrosourea (BCNU). CCNU, BCyNU, and BCNU; such that when radiation is administered the area being isolated can achieve an added effect from the radiation.

In another embodiment the complex of the sealing pad and the skin covering material and at least one indicator can measure and be used to include manage, adjust, regulate and assess the oxygen and carbon dioxide and pressure in a breathing apparatus that can include a ventilator, CPAP device, or anesthesia device that can measure the physiology of the organism, with parameters to include oxygen and carbon dioxide levels, anesthetic levels and the breakdown products of the anesthesia, the pressure of the gas being inhaled and exhaled and delivered and removed, the sound of the snoring of the organism and the biological and physiological parameters of the organism including arterial oxygen saturation levels.

In another embodiment the complex of the sealing pad and the skin covering material and at least one indicator can measure and be used to include manage, adjust, regulate or assess the sound of the snoring which can be used manage, adjust, regulate and assess the physiologic or biologic parameters of the organism who is snoring and adjust the gas levels and the pressure to minimize snoring while maintaining proper homeostasis and health of the organism.

In the preferred embodiment the organism with the complex of the sealing pad and the skin covering material and at least one indicator to assess and give feedback on physiology and biology, which can include gas exchange, sleep apnea, arterial saturation, and CO2 levels are coordinated with the organisms physiology which can include causes of snoring or restless-leg-syndrome, that are affecting at least one organism, which can include the second organisms restful sleep.

In the preferred embodiment there can be a combination of a sealing pad, a skin covering, an anchoring device, a Web-like Fixation and a feedback device or any combination of these elements can be used as a condom catheter and can train or affect or improve function to include the neuro-musculature units for micturition, urination, control of urination, penile, prostate, bladder, vaginal muscular contraction and relaxation, neuro-musculature control, anal and rectal, the pelvic floor muscle and fascial control. In the preferred embodiment an indicator can be present to provide neuro-muscular strength and tone and signal that can be connected or can be used separate from a neuro-musculature stimulating unit that can help train the neuro-muscular system for urination or can automatically trigger a neuro-muscular stimulus that can provide neuro-muscular control to the dysfunctional body function to include the neuro-musculature units in an effort to improve and control urinary function. The indicator and sensor and the feedback and stimulating unit can be in the sealing pad, a skin covering, an anchoring device, and a feedback device or any combination of these elements and located in the vagina, rectum and anus, the tissue around the penis or vagina or anus, prostate, pelvic floor. In one embodiment there can be wires implanted in the musculature that assist urination that have an input and an output component that can connect the tissue of interest that is internal within the body to the skin or external to the skin or another internal tissue which can be interfaced to the condom catheter or training unit through electrodes. Other applications of this form of stimulation can include treating or facilitating and enhancing erectile function, orgasm, pleasure, arousal and prolongation of these and related biological functions.

In another embodiment the feedback mechanism can contain at least one input and one output signal or any combination of inputs or outputs that can include electromagnetic, kinetic, and motion and other sensory signals.

In the preferred embodiment the complex of the sealing pad and the skin covering material and at least one indicator can assess and give feedback on physiology and biology, or mechanical or environmental stimulus or information, and said information can be transmitted to a device that can alter the physiology or biology or mechanical or environmental stimulus or other information In another embodiment the indicator can be used to improve an organism's physiology and biology, which can include gas exchange, sleep apnea, arterial saturation, CO2 levels, muscle twitching to include restless-leg syndrome in order to improve the biology of at least one organism.

In the preferred embodiment the complex of the sealing pad and the skin covering material and at least one indicator can assess and give feedback on physiology and biology, or mechanical or environmental stimulus or information, and said information can be transmitted to a device that can alter the physiology or biology or mechanical or environmental stimulus or other information to include snoring or the sound of the ventilator or tubes near the snoring individual, which can be measured and the information transmitted to a device to include an acoustic altering device that can include noise cancellation computers, electrical devices, earbuds or earphones which from a distance or be located on or near or at one organism can cancel mute, transmute or alter the sound of the snoring, for at least on organism.

In another embodiment at least one indicator can be used to assess and give feedback on physiology and biology or mechanical or environmental stimulus or information, and said information can be transmitted to a device that can alter the physiology or biology or mechanical or environmental stimulus or other information to include snoring, which can be measured and the information transmitted to a device to include an acoustic altering device that can include noise cancellation computers, electrical devices, earbuds or earphones which from a distance or be located on or near at one organism can cancel mute, transmute or alter the sound of the snoring, for at least one organism In another embodiment the indicator device can have its function to include noise from a ventilator be measured and the information transmitted to a device to include an acoustic device that can include a computer or noise cancellation device or earbuds or earphones which can affect from a distance with speakers or be located on or near or at least one organism or one machine to cancel the sound of the machine which can include a ventilator or monitoring device, treatment device, pleasure device to include background sounds, environmental device to include an air conditioner or humidifier or dehumidifier.

In another embodiment at least one indicator can measure and be used to include manage, adjust, regulate or assess the sound of the snoring which can be used manage, adjust, regulate or assess the physiologic or biologic parameters of the organism who is snoring and the audio signal can be transmitters using a method of wires or optics or other transmitter methods or wirelessly or a combination of these methods, to the snoring organism or at least on other organism such that the snoring sound can be cancelled out using a device to include acoustic canceling or sound canceling techniques that is the preferred embodiment can be include earphones, earbuds, or a room speaker to cancel or minimize or mute or transmute the sound to provide a more beneficial or pleasant or acceptable sound to one or more of the snoring and the non-snoring individuals.

In another embodiment a sensing device can be used to create a signal that can include a digital or analog signal that can be stored and processed and transmitted by or into a device that can include a computer-like device, an electrical or mechanical device that can store and process information digitally or analog. That information can be utilized to control a second device that can include a sealing pad, a sealing pad with a skin covering, a sealing pad with a skin covering and indicator device, a feedback device, or a machine that can include a machine used for biologic and physiologic functions that can include breast feeding, pumping the breast for the extraction of breast milk, pleasurable stimuli or sensations or pain and pleasure to include or alteration of physiology or biologic functions of bodily organs to include the breasts, lips, ears, skin, mouth, rectum and anus, penis and related structures such as the scrotum, clitoris and vagina and related local structures such as the labia, toes and fingers. Sensations and stimuli and material applications can include wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, substance levels to include drugs and medications and non-physiologic measurements to wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, substance levels to include drugs and medications a combination of physiologic and non-physiologic measurements.

Other embodiments include auditory signals to include the human hearing range and above and below the human hearing range; electromagnetic signals to include infrared and ultraviolet; sensory stimulus to include heat and cold, wet and dry, pain and non-painful and pleasurable stimulation; olfactory and smell sensations to include pleasant and unpleasant odors; taste to include salt, sweet, acrid, bitter, sour, umami, pleasant and un pleasant tastes; vibration and kinetic stimulus to include pinching, piercing, hard touch, light touch, vibration, and proprioceptive stimulus. The stimuli can be used singular or multiple and can be used as one or multiple stimuli or categories.

In the preferred embodiment a nipple shape device to simulate the natural shape of a mother's breast can have sensing devices that can include touch and pressure wetness and motion and suction pressure sensors. A baby can suck onto this device and the touch and pressure wetness and motion and suction pressure can be recorded and stored in a device with can include a computer-like storage device. This signal can then be transmitted to a breast pump that can then simulate one or more of these sensory inputs and outputs that best simulates the natural sucking sensation of the infant breastfeeding. The purpose of this is to simulate natural breastfeeding and improve the let-down reflex and the natural sensation of the infant and mother breastfeeding bond. Other sensory inputs that can be acquired and stored and transmitted and simulating during breast pumping can include the olfactory to include the scent of the infant, wetness, visual including images to include the infant breastfeeding and not breastfeeding, auditory including sounds to include the infant breastfeeding and not breastfeeding, taste including taste to include the infant breastfeeding and not breastfeeding, kinesthetic and touch including touch to include the infant breastfeeding and not breastfeeding, and other sensory input that might stimulate breast milk let-down and quantity. The sealing pad or the sealing pad and the skin covering material or the sealing pad and skin covering material can contain a device to include a vibrational, compressive, suction, undulating device that is contained within or on the sealing pad or the sealing pad and the skin covering material or the sealing pad and skin covering material and can be used to simulate and mimic the input to include the suckling or breast feeding of the organism to include an infant that is human or non-human.

In another embodiment, the infant can be taught how to breastfeed or suck from a man-made nipple using a similar device to teach the infant how to bottle feed. In another embodiment, a massage can be simulated to recreate the massage or touch of a massaging individual an a body part that can include relief of pain, muscle spasm, pleasure, or for the sense of human contact.

In another embodiment, sexual pleasure can be simulated and attained using a similar device with a shape that can include a mouth, tongue, lips, or combination of these body parts that can be used for pleasure to simulate licking, and sex to include oral sex for and on either gender and on or by any body part. In one embodiment the device can be a sex toy which is programmed to simulate another human beings sensory input and output to include touch, caress, probing, sucking, kissing, licking thrusting, ejaculating, or having an orgasm, and can be shaped like a hand, mouth, tongue, lips, penis, vagina or anus.

Other embodiments auditory signals to include the human hearing range or above or below the human hearing range; electromagnetic signals to include infrared and ultraviolet; sensory stimulus to include heat and cold, wet and dry, pain and non-painful and pleasurable stimulation; olfactory and smell sensations to include pleasant and unpleasant odors; taste to include salt, sweet, acrid, bitter, sour, umami, pleasant and un pleasant tastes; vibration and kinetic stimulus to include pinching, piercing, hard touch, light touch, vibration, and proprioceptive stimulus. The stimuli can be used singular or multiple and can be used as one or multiple stimuli or categories.

In one embodiment an animal to include an organism to include a human, a pet, a cat, a horse or a dog that can utilize a device that can be in the form or simulate the form or function of a hand, which is programmed to simulate the touch of the pets owner. This can be used in a kennel crate, a car, or used in a time when an owner is not available to the pet such as when the owner is at work, driving the car, or busy with other activities, In another embodiment a camera or viewing or listening or sensory device be present to assess at least one viewed organism at a distance. Viewing can occur on a television, computer like device to include a computer, iPad-like device, cell phone, IPOD™-like device, a screen, an audio speaker-like device or other sensory devices that be multiple sensory inputs which can be combined. At least one organism can be programmed into a computer-like device to input and output sensory information that can include touch and voice or scents and non-sensory information to include deliver food or water. Both the viewed and the viewing organism can deliver the sensory and non-sensory information to the viewed or viewing organism.

In the preferred embodiment the owners of a dog could have their voices and touch programmed into a computer and when the dog is lonely it can call the owner by a signal and the owner can provide a sensory or non-sensory stimulus to the dog to include an auditory signal to include soothing words which can be either programmed words or live words, or touch which can be either programmed petting or live petting. In another embodiment a cats purr can be simulated or recorded or transmitted with an auditory device can be simulated with an auditory device for the cat's owner as recipient or the brushing up or rubbing of a cats fur against a hand can be simulated or transmitted with a tactile device to simulate the cat's fur for the cat's owner as recipient.

The sealing pad, sealing pad and the skin covering can contain a device. The device can be an auditory unit for amplifying sound. The device can be an auditory analog to digital converter with wireless capabilities. The device can be an auditory unit that is hard wire connected to another device that promotes auditory communication such as an electronic device that has input and output capabilities to communicate with one or multiple individuals. Some uses can include airplane travel, operating room communication, hospitals, old age homes, subways, buses, trains, manufacturing and non-mechanical and include HEPPA filters, specific agent detoxifying or anti-germ filters, a substance or medication can include agents that are antibiotic, antibacterial, antifungal, antiviral; anti-fogging; scented; detoxifying agent or filter; heating or cooling device, alter the pressure relative to the ambient air, humidifying.

The device can be mechanical to include a small fan, a mechanical filter, a small heater or cooler, a defogging device, alter pressure, HEPPA filters, specific agent detoxifying or anti-germ filters, a substance or medication can include agents that are antibiotic, antibacterial, antifungal, antiviral; anti-fogging; scented; detoxifying agent or filter; heating or cooling device, alter the pressure relative to the ambient air. The device can be a nanotechnology device to include a device that serves as an air filter, anti-germ agent and detoxifying agent, defogging agent, heating and cooling, alter the pressure. The device can have a mechanism device to facilitate healing utilizing electrical stimulation, ultrasonic waves, electromagnetic wave, pressure, vibration, alter the gas mixture.

The low profile breathing mask can have a feedback device that can assess the users' physiologic measurements and non-physiologic measurements. The low profile breathing mask can have an audio or visual device that can assess the user. The mask can have fenestrations to allow flow of materials between the outer environment and the environment between the mask and the user. The fenestrations can be expandable material, a humidity filter, and a gas exchange material. Uses of the fenestrated mask can include a surgical mask, a ski mask, an athletic mask, and an industrial mask. The CPAP can be combined with a noise cancellation unit to fit into the ear orifice or surround the ear orifice. The CPAP Mask can fit over or surround a portion or all of the head.

In one embodiment a cast cover can incorporate a device that can include a fan that can be used to cool the skin or reduce itching or irritation from the cast.

In one embodiment a wound cover can incorporate a device that can include the ability to deliver a substance which can be a solid, a gel, a liquid or a gas that can be used to cool the skin or reduce itching or irritation from the wound. The delivery device can receive its substance from a reservoir that is incorporated in the cast cover or from an external source that can be delivered through wires, optics, channels, conduits or tubes.

In another embodiment, the device can include an olfactory device that can be worn as a nasal mask and can deliver the scent of a mother or a father to a premature infant in an incubator or in isolation such that the infant received sensory stimulation to bond with one or more organisms.

In another embodiment, the device can include a sensory device worn at the movies that can deliver a sensory input that can include the use of a mask that can deliver an olfactory input, or a sucking device that can deliver a gustatory or taste sensation.

In another embodiment the sealing pad or the sealing pad and skin covering material can be an auditory device with the ability to transmit and receive an auditory signal and transmit it through an auditory modulating device to a second organism with a sealing pad or the sealing pad and skin covering material can be an auditory device with the ability to transmit and receive an auditory signal.

In the preferred embodiment the sealing pad or the sealing pad and skin covering material can include an earbud and a microphone receiving auditory device, the input microphone can also be separate from the output listening device be separate. These devices can be used on a vehicle or on a noisy environment to include a train or boat or car or airplane where the ambient noise is very high and can be damaging to the ears and speaking to an individual often involves turning the head to the individual which at the end of the travel can result in a stiff neck and a hoarse voice At least one organism can speak into the microphone and the audio signal is processed by an audio processing and modulating device which can amplify the voice or noise cancel the non-voice audio signal using standard devices for amplification of voice and noise cancellation. The device then transmits the signal to at least one organism who can then listen and speak to at least one organism using a similar mechanism and device such that the receiving and sending audio signal can be shared by at least one organism. In one embodiment this device can be an accessory for or be built into a computer, IPOD™-like device, iPad-like device, cell phone-like device or walkie-talkie like device.

The device can be incorporated in the sealing pad and or the sealing pad and skin covering material or the device can be external to the sealing pad and or the sealing pad and skin covering material and obtain input from an external source that can be delivered through wires, optics, channels, conduits or tubes.

Current CPAP devices create positive end expiratory airway pressure. This allows the airways and the bronchi to remain open and/or distended. These devices require an external machine that creates positive airway pressure. These machines are bulky and uncomfortable. Patient compliance is limited by these machines. These machines leak and fall off and can be over variable effectiveness. This invention reduces or simplifies or eliminates the need for external positive airway pressure generating mechanical machines.

The goal of this variation on a CPAP mask and device is to miniaturize the CPAP product and make it more users friendly. The miniaturized breathing mask which can be used as a CPAP device can be composed of a reservoir system wherein the air intake is equal or nearly equal to the normal inflow of air and has ambient pressure-inflow equal to or approximately equal to unimpeded inflow and equal or approximately equal to the users environment. The device will create a resistance to outflow this creating a continuous positive airway pressure or device can be internal to the user's mouth or nose. The device can be a combination of internal and external to the user's mouth or nose. The device can be used on the user's nose/nostril, mouth, or a combination of nose/nostril and mouth. The device can be composed of a gelatinous elastomer that fits into or around the nasal orifice/nostrils.

The device can be composed of a gel, a non-gel or a combination of a non-gelatinous material and gelatinous elastomer that fits into or around the nasal orifice/nostrils. The device can be composed of a gelatinous, a non-gelatinous material that fits into or around the mouth or oral orifice a combination of a non-gelatinous material and gelatinous elastomer that fits into or around the mouth or oral orifice. The device component is composed of at least one valve that provides for unimpeded inflow of air and with impeded outflow of air that increases the air way or air resistance to the outflow of air. The valve or valves can be arranged to increase outflow air resistance in a steady consistent manner near the user relative to the external environment; in a manner in which the pressure is greater near the user relative to the external environment; in a manner in which the pressure is less near the user relative to the external environment.

The device can be composed of at least one reservoir that provides for nearly or unimpeded inflow of air and with impeded outflow of air that increases the airway or air resistance to the outflow of air. The reservoir or reservoirs can be arranged to increase outflow air resistance in a steady consistent; in a manner in which the pressure is greater near the user relative to the external environment. The device can be composed of at least one reservoir and at least one valve that provide for nearly or unimpeded inflow of air and with impeded outflow of air that increases the airway or air resistance to the outflow of air. The reservoir or reservoir s and valve or valves can be arranged to increase outflow air resistance in a steady consistent manner near the user relative to the external environment; in a manner in which the pressure is greater near the user relative to the external environment or; in a manner in which the pressure is less near the user relative to the external environment.

The nasal piece can be composed of one or more materials. The nasal piece can be composed of one or more materials that allow the minimal or unimpeded inflow or air but create an increase in outflow pressure while allowing the egress of exhalent such as carbon dioxide. The mouthpiece can be composed of one or more materials. The mouthpiece can be composed of one or more materials that allow the minimal or unimpeded inflow or air but create an increase in outflow pressure while allowing the egress of exhalent such as carbon dioxide. Any combination of the nasal and mouthpiece can be composed of one or more materials or membranes.

Any combination of the nasal and mouthpiece can be composed of can be composed of one or more materials that allow the minimal or unimpeded inflow or air but create an increase in outflow pressure while allowing the egress of exhalent such as carbon dioxide or membranes. The nasal piece can consist of a nasal plug. The nasal piece can nasal covering; the nasal piece can fit into the nostril; can fit around the nostril or can be a combination of; fit into and around the nostril.

In another embodiment, the nasal piece can create and airtight and watertight seal with the nostril or nose. The nasal piece can create and airtight and watertight seal with the skin of the nostril or nose but allow water or air to pass through the nasal piece. The nasal piece can be annular or non-annular or a combination of annular and non-annular. The nasal piece can be annular or non-annular or a combination of annular and non-annular and contain at least on conduit.

The mouthpiece can be annular or non-annular or a combination of annular and non-annular. The mouthpiece can contain at least on conduit. The anchor or fixing of the nasal piece into the nostril or nose into the mouth or around the mouth or lips can include Tacky or a sticky or a non-tacky attachment that can include the inner nose or outer nose, pressure on the inner wall of the nostril, fixation band around all or a portion of the users head; connection to the mouthpiece; inside or around the ears; the eyes or a goggle or flexible or inflexible eye piece; a head cap or hat; the hair or moustache; a piecing through the skin or mucosa of the mouth or nose; to the teeth; to one or more teeth; which can be the upper palatine teeth or lower mandibular/buccal teeth or both which can include braces or denture-like or mouth guard or a molded fixation piece that conforms to the inner teeth, the outer teeth the biting surface, a combination of the above, the gums or a combination of the gums and teeth.

In another embodiment regulating the humidity of the user's internal and external body environment. Can be used with for respiratory needs to include CPAP for assisted ventilation needs, assisted ventilation that requires a full or partial seal of a respiratory orifice, measurement of gases or water/humidity. Athletic training or events, improve or assist or measure respiratory function. The device can utilize an air detector that can measure gases to include carbon dioxide, oxygen, and nitrogen. The device can utilize a vapor or water detector that can measure water vapor and humidity. The device can use a gas delivery system that can deliver gases to include oxygen. The device can use a gas delivery system that can remove gases to include carbon dioxide. The device can use a gas exchange or removal system that can exchange gases to include the delivery of oxygen and the removal of carbon dioxide. The device can use an internal device integrated into the breathing mask or external machine that produces negative, positive or neutral or a combination of negative, positive or neutral airway pressure device.

The mouthpiece can be a gel or an airtight membrane that surrounds the teeth and/or gums. The mouthpiece can be anchored to the teeth by a mouth-guard that is molded to the gums and, a mouthpiece molded a component of the teeth. The mouthpiece can be a combination of the above. The mouthpiece can be a breathable membrane. The breathable membrane can be made to have variable pores or fenestrations or can be made of a machine can utilize an oscillating or variable airflow or pressure; a non-oscillating or non-variable airflow or pressure or a combination of variable and non-variable airflow or pressure.

The CPAP machine can vary its air delivery based on gas sensors such as oxygen and carbon dioxide. The CPAP machine can deliver oxygen to the user. The CPAP machine can extract carbon dioxide. In one embodiment uses for the CPAP mask can include treating premature infants with respiratory challenges that can include IRDS, TTNB, wet lungs or infection; adults with ARDS, pneumonia, wet lungs, volume overload, emphysema, or non-human living beings that require assisted ventilation.

One preferred embodiment can use a gel seal that surrounds the eyes and has a skin covering material a portion that is overlying the eyes and is transparent and a component that is made of a designer fabric that acts as a Zorro-like mask the mask fits around the back of the head or around the ears or a combination of the back of the head or the ears.

In another embodiment, the eye goggles or mask can be one continuous flexible material, which can include a gel that can include a gel that varies in hardness and softness and transparency.

In another embodiment, the eye goggles or mask can be one continuous flexible material with a separate lens. The goggle can include a gel that can include a gel that varies in hardness and softness and transparency.

In another embodiment, the eye goggles or mask can be one continuous flexible material with a separate lens and a separate sealing pad. The goggle can include a fabric a plastic or polymer or gel that can include a gel that varies in hardness and softness and transparency.

In another embodiment, the eye goggles or mask can be one continuous flexible material with a separate sealing pad. The goggle can include a fabric a plastic or polymer or gel that can include and can include a gel that varies in hardness and softness and transparency.

In another embodiment, an eye goggle can incorporate a viewer that can include viewing objects more clearly or seeing laterally or behind is useful. The viewer can be an electrical device that can include a camera and viewing device that can include a screen, a direct retinal projection or a projection onto the lens of the eye goggle or mask; or at least on lens or mirror that is incorporated onto the goggle that can serve like a periscope-like apparatus, a wide or narrow angle lens that can include at least a portion of the goggle or lens. Uses for this eye goggle or mask can include scuba diving, where seeing the fish laterally or close up or behind can be useful, competitive racing where seeing the competitors laterally or behind in the adjacent lanes can be useful.

Another embodiment can include an eye goggle or mask that is a viewing screen that is used with a device to include a medical process that will allow the device user to be able to continuously view the patient and not have to turn their head to view a screen on the machine.

In the preferred embodiment, the medical machine would include but would include an Ultrasound machine. The Sonographer can wear a pair of viewing eye goggles or a mask or glasses that can project the ultrasound image onto the glasses while the Sonographer is scanning the patient. Currently the Sonographers have to continuously turn their heads to the ultrasound machine and back to the patient. Sonographers are prone to develop herniated discs and degenerative diseases in their necks and spasms and muscular difficulties in their shoulders. The method of the transmission of the ultrasound signal from the machine to the eye viewing devise can include wires, wireless, optics or other means of transmission electromagnetic signals.

Other uses for medical eye viewing devices can include robotic surgery, angiography and catheterization procedures, endoscopy and medical and surgical procedures that require ancillary screen viewing.

In another embodiment, eye goggle or mask viewing devices can be combined with a sealing pad and a skin covering material to be used in a surgical field or in an emergency field or battlefield or in a situation where toxic or infectious or dangerous biologic or non-biologic agents are present and there is a need to view a screen and keep attention focused on a task in a viewing plane different than a viewing screen and where a part of the body to include the eyes, nose or mouth or an opening or cavity in the superficial skin needs to be protected.

In another embodiment, the sealing pad or a sealing pad with a skin covering material can contain a material within the gel sealing pad to include a solid or liquid or gas or another gel. This embodiment can be used for an ear plug, nose plug, intubation device, anal or vaginal device for a seal in which to create greater buoyancy, for delivering substances to include medication, gas, detoxifying agents, or to serve as acoustic reflectors or absorbers, or to alter the cushioning or the hardness or softness of the gel.

In the preferred embodiment, a sealing pad or a sealing pad with a skin covering material can be used as an earplug in which the sealing pad or the sealing pad with a skin covering material contains an acoustic absorbing or reflecting material that can include a solid, liquid or a gas or another gel or a combination of these elements, which be used to reduce noise in an environment in which noise reduction is desired. The earplug can contain at least on conduit or channel or tube that can transmit or contain a solid, liquid or gas.

In one embodiment a sealing pad or a sealing pad with a skin covering material can be used as an earplug in which the sealing pad or the sealing pad with a skin covering material contains an acoustic absorbing or reflecting material that can include a solid, liquid or a gas or another gel or a combination of these elements, which be used to reduce noise in an environment in which noise reduction is desired can be an acoustic delivering device to include a speaker. In another embodiment it can be a delivery device to deliver a gas or medication.

In another embodiment, a sealing pad or a sealing pad with a skin covering material can be used as a detoxifying agent in a sealing pad that is used for an isolation suit in which the sealing pad or the sealing pad with a skin covering material contains a detoxifying agent for absorbing or reflecting toxic materials and the detoxifying agent can include a solid, liquid or a gas or another gel or a combination of these elements, which can include activated charcoal or chelating agents to include dimercaptosuccinic acid (DMSA). 2,3-dimercapto-1-propanesulfonic acid (DMPS) and alpha lipoic acid (ALA), which be used to reduce toxins to the body in an environment in which toxin reduction is desired.

All of the designs of sealing pads and skin coverings and fixation devices and anchors and flanges and indicators and reservoirs and delivery methods and eye viewing devices and all other methods described herein can be used alone or in combination to include and uses as a wound cover to include a bruise, laceration, burn, surgical site or site of trauma either natural or animal or man-made; a cast cover a breast cover or pump, a mask, a breathing mask that can include a CPAP or BIPAP or positive pressure ventilation mask, an untubation device, goggles, eyewear, nose pieces or nostril plugs or devices, earpieces or earplugs or ear-buds, hand covers or gloves, garments, clothing, shoes, socks, a condom catheter or urinary processing device to include a urine bag, a semen processing device to include a male condom, a female condom or a male or female contraceptive device, a diaper or fecal processing device to include an ostomy bag. environmental suit or environmental protective gear, and a medication delivery system that requires areas of the body or skin that are preferentially treated with areas of medication delivery that have spaces or gaps between the sites of medication delivery and can include all other applications and related applications described herein, as well as applications that are derivatives of the applications described herein.

In one embodiment the sealing pad, fixation device, anchoring device and skin covering material or any combination of these elements can be composed a material to include a gel or solid that has the ability to alter its physical properties to include but not restricted to its hardness and softness, its thickness or length or width, its coefficient of friction, or its repair capabilities, or any combination of these properties. In one embodiment the sealing pad, fixation device, anchoring device and skin covering material or any combination of these elements can be composed a material to include a gel or solid that has the ability to alter its hardness or softness or thickness or any combination of these properties using a method or device to include a heating or cooling unit, or a reservoir, or can have impregnated materials that can be a solid or liquid or gel or gas and can be formed from a material to include an elastomer to include a thermoplastic elastomer, gel, rubber, latex, and metals polymer and alloy materials to include temperature-responsive polymers which are materials which undergo changes upon temperature changes, smart metals to include Nitenol and shape memory alloys and non-metal shape memory polymers in which large deformation can be induced and recovered through temperature changes or stress changes and martensitic phase changes, piezoelectric materials that produce a voltage when forces or stress are applied resulting in structure altering shape to include bend, expand or contract when said voltage is applied, shape memory alloys and shape memory polymers which can have large deformations which can be induced and recovered through temperature changes or stress changes (pseudoelasticity), magnetostrictive materials which can change in shape under the influence of a magnetic field and can exhibit a change in their magnetization under the influence of mechanical stress, magnetic shape memory alloys which are materials that change their shape in response to a significant change in a magnetic field, pH-sensitive polymers which are materials that change in volume and shape when the pH of the surrounding environment changes, halochromic materials which can change their color as a result of changing acidity which can also be used as indicators to include condoms which can include a sensor to detect a breach in the condom integrity or intubation devices to include a sensor to detect whether gastric reflux or aspiration has occurred or wound covers that can include detect infectious agents that change the pH of the wound to include bacteria, fungi, viruses and other infectious pathogens, chromogenic systems which can change color in response to electrical, optical or thermal changes which can include electrochromic materials, which change their color or opacity on the application of a voltage to include liquid crystal displays, thermochromic materials change in color depending on their temperature, and photochromic materials, which change color in response to light, ferrofluids, photomechanical materials change shape under exposure to light, self-healing materials have the intrinsic ability to repair damage due to normal usage, thus expanding the material's lifetime, dielectric elastomers (DEs) are smart material systems which produce large strains under the influence of an external electric field, magnetocaloric materials are compounds that undergo a reversible change in temperature upon exposure to a changing magnetic field, Thermoelectric materials are used to build devices that convert temperature differences into electricity and the reverse.

Some embodiments include a head cooling device that can be worn over the head whose use is to treat body to include brain or biologic or physiologic conditions that can include overheating during warm weather, heat stroke, febrile seizures, muscle cramping, hair loss, heart disease and respiratory disease and renal diseases; and psychiatric disorders to include anger or rage or anxiety, suicide, depression, schizophrenia, memory and mania and other biological and psyschiatric conditions thought to be caused or felt to be caused or exacerbated by excess body or brain heating, conditions that would benefit from body or brain cooling or slow body or brain metabolism to include ischemic stroke, seizures, brain tumor growth. In one embodiment the cooling device can be composed of a sealing pad, skin covering material, fixation device, anchoring device and indicators or feedback device or any combination of these elements.

Incorporated into this device is a cooling device that can include a solid of liquid or gas or gel material that can be used to interface with the sealing pad which can be airtight and water tight but does not have to be airtight or watertight. Methods of cooling can include conduction which can include direct transfer of heat through cooling devices to include cooling tubes conduits or channels that can contain water, Freon, thermoelectric cooling, or vapor compression cooling; or convection which can include fans, blowers impellers, and evaporation which can include refrigeration and fan and air-conditioning like devices. In one embodiment the cooling head cap is composed of a sealing pad that can include a gel or a non-gel that can form an airtight or watertight seal with at least a portion of the user's head or neck to form an isolation chamber. In the preferred embodiment the seal is a gel seal.

In some embodiments, the isolation chamber is created such that there can be a liquid or gel or a gas or solid or combination of these elements that passes between the user's skin which can include the scalp, face or neck and torso and serves as a means of removing heat or transferring heat away from the user's brain. In one embodiments some orifices or some given body parts can be kept separate from the isolation chamber and these body parts can include a body that can include the user's mouth and nose and ears or torso such that these body parts can be sequestered from the remainder of the isolation chamber by additional sealing pads or isolation chambers. There can be zero or one or more than one isolation chamber used for the head cooling device. There can be one or more than one isolating chambers that affect and effect cooling. In another embodiment sealing pads or isolation chambers can be used to isolate body parts that contains sensors or feedback devices or surgical areas of intervention and in which the material that can include solids, liquids and gels and gases between the user's skin and the cooling device is isolated and sequestered from the actual cooling portion of the head cooling device.

In other embodiments, the gel sealing pad can contain methods or transferring heat away from the body that can include conduction, convection or evaporation. These embodiments can be used alone or in combination. Sensors and feedback units can be used to monitor and feedback control of physiologic and biologic functions to regulate core body and brain temperature. There are some brain functions to include febrile seizure and ischemic stroke that can benefit by reducing oxygen and metabolic requirements of the brain more than other body parts.

Other embodiments include a head warming device that can be worn over the head whose use is to treat the body or body parts to include brain or biologic or physiologic conditions that can include overheating during warm weather, hypothermia, hair loss, and psychiatric disorders to include depression, memory and other biological and psychiatric conditions thought to be caused or felt to be caused or exacerbated by excessive body or brain cooling, conditions that would benefit from body or brain heating or more rapid body or brain metabolism to include warming from hypothermia, brain tumor growth to include during chemotherapy. In one embodiment the heating device can be composed of a sealing pad, skin covering material, fixation device, anchoring device and indicators or feedback device or any combination of these elements. Incorporated into this device can be a heating device that can include a solid of liquid or gas or gel material that can be used to interface with the sealing pad which can be airtight and water tight but does not have to be airtight or watertight. Methods of cooling can include conduction which can include direct transfer of heat through heating devices to include heating tubes conduits or channels that can contain water, thermoelectric heating, or radiator-like warming devices; radiant heating or convection which can include heated substances through fans, blowers. In one embodiment the heating head cap is composed of a sealing pad that can include a gel or a non-gel that can form an airtight or watertight seal with at least a portion of the user's head or neck to form an isolation chamber.

In the preferred embodiment the seal is a gel seal. In some embodiments the isolation chamber is created such that there can be a liquid or gel or a gas or solid or combination of these elements that passes between the user's skin which can include the scalp, face or neck and torso and serves as a means of adding heat or transferring heat toward the user's brain. In one embodiments some orifices or some given body parts can be kept separate from the isolation chamber and these body parts can include a body that can include the user's mouth and nose and ears or torso such that these body parts can be sequestered from the remainder of the isolation chamber by additional sealing pads or isolation chambers. There can be zero or one or more than one isolation chamber used for the head warming device. There can be one or more than one isolating chambers that affect and effect cooling. In another embodiment sealing pads or isolation chambers can be used to isolate body parts that contains sensors or feedback devices or surgical areas of intervention and in which the material that can include solids, liquids and gels and gases between the user's skin and the cooling device is isolated and sequestered from the actual cooling portion of the head cooling device.

In other embodiments the gel sealing pad can contain methods or transferring heat toward the body that can include conduction, convection or radiation, radiant heat. These embodiments can be used alone or in combination. Sensors and feedback units can be used to monitor and feedback control of physiologic and biologic functions to regulate core body and brain temperature. There are some brain functions to include febrile seizure and ischemic stroke that can benefit by reducing oxygen and metabolic requirements of the brain more than other body parts. Some brain functions to include hypothermia, depression and tumor sensitivity during chemotherapy can benefit by increasing oxygen and metabolic requirements of the brain more than other body parts. Heating and cooling of the brain may have changing benefits depending on tissue and brain sensitivity during treatments to include tumor treatment and psychiatric conditions.

The heating and cooling body part devices can be utilized on just the head or on the head and neck region for greatest effect on the brain and body but these devices are not isolated to the head and neck and can be used on other body parts to include the torso, appendages and internal organs using the sealing pad, skin covering material, fixation device, anchoring device and indicators or feedback device or any combination of these elements described herein.

These heating and cooling devices can be used to include treatment for treating peripheral vascular disease, Raynaud's disease, diabetes, and neuropathies and can be used to treat and provide symptom relief for sensory discomfort. These devices can be used for providing pleasure and can be used on appendages to include the penile and vaginal and anal regions for sexual pleasure and to improve sexual function to include erectile function, orgasm, and sexual pleasure and stimulation. These devices can be used for relieving pain and discomfort and can be used on appendages to include the arms and legs and anal regions and can be combined with other devices to include vibrational and ultrasonic devices and substances that can invoke sensory responses.

Another embodiment of a gel sealing pad is a gel sealing pad that can incorporate gel within a portion of a foam material that can include standard and memory foam which can include the gel incorporated into at least a portion of foam and can include surrounding the foam or insinuating gel within the inside of the foam or into the interstices of the foam.

Some embodiments include a sealing pad for interfacing with a body surface. The sealing pad can include a pad, a first perimeter flange projecting from the pad and sealably contacting the skin and having a contour, and a second perimeter flange projecting from the pad spaced apart from the first perimeter flange and sealably contacting the skin and having a contour. The sealing pad can further include end portions extending from the pad and sealably contacting the skin, wherein the end portions, the first perimeter flange, and the second perimeter flange, the pad, and a portion of the skin define a space. The sealing pad can also include an internal flange projecting from the pad between the first and second perimeter flanges and sealably contacting the skin and having a contour, wherein the first perimeter flange, the internal flange, and the second perimeter flange together define a redundant seal between the pad and the skin.

Further embodiments include a fixation device comprising a web of strands configured to encircle a portion of a human body. The strands cover a portion of the human body beneath the strands and can define spaces between the strands through which a portion of the human body is exposed. At least some of the strands are made of a gel material.

Still further embodiments include a method for positioning a fixation device relative to a human body. The method can include positioning a fixation device comprising a web of strands over a portion of a human body, wherein the strands cover a portion of the human body beneath the strands, and wherein the strands define spaces between the strands through which a portion of the human body is exposed. At least some of the strands are made of a gel material. The method can also include positioning a seal member over a portion of the human body, wherein the seal member is connected to the fixation device, and wherein the seal member has an envelope extending from the sealing member and defining a space in fluid communication with the human body sealed by the sealing member, and administering a substance to or removing a substance from the human body within the envelope.

Other embodiments of the present invention include an annular seal for a skin covering, the seal comprising a first portion having a first radius, a proximal portion and a distal portion, and a second portion having a second radius greater than the first radius. The second portion having a proximal portion and a distal portion, wherein at least one of the first, second, and end portions are generally elastic, and wherein at least one of the first, second, and end portions are made of a gel material. The annular seal can include an end portion extending between the first portion and the second portion at the proximal portions of the first and second portions, wherein the first portion, the end portion, and the second portion define a generally U-shaped cross section. The annular seal is configured to receive a portion of a human body with the first portion being inward of the second portion, and the distal portion of the first portion is thicker than the proximal portion of the first portion to define a first projection. The distal portion of the second portion is thicker than the proximal portion of the second portion to define a second projection. The end portion, the first projection, and the second projection are configured to receive a skin covering between the first projection, the second projection, and the end portion to resist withdrawal of the skin covering from the annular seal. The embodiments described herein can be used with an organism that can be human and non-human.

The preferred embodiment for a female urinary catheter can include a gel sealing pad surrounding the urethra. Attached to the sealing pad is a skin covering which has a bag shape that is designed to collect about 200 cc of urine with a conduit or tube at its end, which will divert the urine away from the body and the proximal urinary bag. There would be an one-way valve at the opening of the tube, which would allow fluid to flow away from the body and not toward the body. The gel sealing pad will create a watertight seal around the urethra. Attached to the gel pad is an anchoring device that would be made of a semi-solid gel that conforms and fits into the vagina in a manner reminiscent of a tampon. Also attached to the sealing pad and the anchor is a web-like gel fixation device that conforms and surrounds the vaginal region. The fixation device in the preferred embodiment is attached to a garment that is in the form of a bikini or undergarment or thong or a straps that surrounds both waist and the outer buttocks.

In the preferred embodiment a breast pump is configured to simulate the suction and motion of the mother's infant breastfeeding. To accomplish this the sucking motion of the infant is codified and determined by having the infant suck on a simulated-nipple that can simulate a mother's breast. Sensors are placed in and on the simulated-nipple and the suction and motions of the infant are recorded for an extended period of time and the information is transferred to a computer that can capture and store this information. When the mother is ready to pump her breasts, the computer information can be transmitted to the breast pump and the mother's breast pump sealing pad and the suctioning device of the breast pump. The computer signal will then reproduce from the stored information a simulation of the infant's suction and sucking motions. In some embodiments the scent of the infant or pheromones can be released to stimulate the mother's let down reflex that starts the flow of milk. The computer can analyze maternal breast milk parameters to include but not restricted to the interval prior to milk let down, the quantity of milk and breast characteristic such as temperature in order to determine the best simulated infant sucking program. This process can be used for but not restricted to newly nursing and breastfeeding mothers or infants or mothers or infants who are benefited by the program. The same or a variation on the same or similar device can be used to teach newly nursing infants to nurse better and can be used when an infant is transitioning from breast to bottle-feeding nipples.

Fixation methods can include but are not restricted to two methods that include overlapping strands and a weave. The first method and structure can include but is not restricted to stands that can be overlapping or non-overlapping and which in the preferred embodiment can include but are not restricted to a gel material that can include but is not restricted to a tackifying material or an adhesive or which can be naturally tacky or: a fabric-like material that can include a microfiber with a high coefficient of friction and increased drag on the skin when the material when a force to include but not restricted to pulling is exerted. When said force to include but not restricted to pulling is exerted on the fixation device, the portions of the fixation in contact with the skin exert an increased coefficient of friction or drag that can increase or accumulate the more the fixation device is pulled upon. This embodiment is based at least in part on an increase in the surface area of the high coefficient material that is in contact with the skin. This represents both a method and a device. A second method and structure and embodiment of the fixation can include but is not restricted to a fixation device that is in the shape to include but not restricted to a weave that can include but is not restricted to resemble the weave of a Chinese Finger Puzzle. The weave when exposed to a force to include but not restricted to a pulling force will tighten in some areas and not in other areas. The weave when exposed to a force such as pulling will tighten and narrow the diameter of the fixation device and constrict around the body part to which it is in contact. The fixation device can be associated with but not restricted to a sealing pad and a skin covering material and an anchoring device and method.

The fixation device can be formed from a high coefficient of friction material that at least a portion of the fixation device can include a gel that can include but is not restricted to a tackifying material or an adhesive or which can be naturally tacky; or a fabric-like material that can include a microfiber with a high coefficient of friction and increased drag on the skin.

In the preferred embodiment of the cast cover is composed of a waterproof skin covering material and an annular gel sealing pad which is tacky and elastic can be formed so that when it is in its resting or relaxed state it is approximately the same circumference or very slightly less circumference than the user's appendage. The gel sealing pad will have the ability to stretch to many times it's resting and will be resiliently deformable such that the sealing pad will return to its resting circumference. This will allow the sealing pad to easily fit over the appendage or a structure or device associated with the appendage to include but not restricted to a cast, a wound cover, a central intravenous or arterial catheter in a manner that the skin of the appendage or the structure or device associated with the appendage is not damaged. The sealing pad can be placed over the distal aspect of the appendage, which for example may be the fingers of the hand and arm. One place comfortably over the distal aspect of the appendage the sealing pad can be positioned over the appendage and the structure or device, which can include but is not restricted to a cast, until the sealing pad are proximal to the cast and rest comfortably on the proximal skin with the sealing pad lying flat against the skin. Once the sealing pad is in place a waterproof skin covering material can be placed into position. If the sealing pad is to be used for a distal arm cast then there will be an open end of the waterproof skin covering material and a closed end. The open end will be place over the fingers first and positioned in a similar manner such that it rests in the middle aspect of flat sealing such that the distal half portion of the sealing pad is covered by the waterproof skin covering material while the proximal half portion of the sealing pad is not covered by the waterproof skin covering. Next the distal half portion of the sealing pad is folded cover the proximal half portion. This creates a sealing pad with a C shape such that the distal half of the sealing pad forms a watertight seal with the skin; the waterproof skin covering material is wedged between the proximal and distal halves of the sealing pad in a manner that the sealing pad forms a waterproof seal with the skin covering material on side of the skin covering material that is both interior and exterior or closest and farthest to the skin. The proximal half portion of the sealing pad is now external to the distal half portion and rests on the distal half of the sealing pad and creates a gentle compression on the distal half of the sealing pad that is creating and airtight and watertight seal and this gentle compression further assists with creating the airtight and watertight seal. In the preferred embodiment the open end of the skin covering material will be wider than the remainder of the skin covering material and will serve as a bulbous end portion that can serve as a male end or protuberance or bulbous insinuator. The sealing pad can have a groove or female invagination. When the sealing pad is folded over the skin covering's male bulbous end portion will insinuate itself into the female invagination or groove of the sealing pad and create a lock and key like mechanism for the sealing pad and the skin covering material. The sealing pad can include but is not restricted to being folded more than or less than in half. The locking mechanism can include but is not restricted to multiple shapes to include geometric shapes that are more or are less resistant to tugging or disengaging. The skin covering can have more than one opening especially when the skin covering is place such that it is important for the middle portion of the body part or appendage to be covered but a proximal and distal portion of the body part is to remain uncovered. One example of this can include a PIC line that is placed in the antecubital region near the elbow and the shoulders are uncovered and it is desirable to have the hands uncovered so that the hands can be without a covering to be used freely. Waterproof can mean airtight and watertight. Although the sealing pad in the preferred embodiment is singular and flat and is folded over only one, less than or more than one folding or molded forms of the sealing pad can be used and more than one sealing pad can be used. The skin covering can have bulbous ends or can be flat or have invaginations. The sealing pad can have bulbous ends or can be flat or have invaginations. The sealing pad can have a different radius that varies from distal to proximal.

The fixation device can be annular or circumferential or non-circumferential. The fixation device can be used with another material to include but not restricted to fabrics. The fixation device can be used to engage a substantial portion of the user's skin. The definition of substantial can vary widely because each application or use varies to include but is not restricted to use as a female condom catheter or a male condom catheter or an ostomy bag or a device holder; and because each body part to be engaged varies to include but is not restricted to use on the and body parts to include the penis, the vagina, the arm and the torso; and because each organism varies and can be of a different size and shape and form and hairiness and because the fixation device can be used on human and non-human organisms and the weight that the condom catheter must tolerate. Optimally for the penis when used with a condom catheter with a sealing pad and skin covering then an annular fixation device that engages the penis can engage to include but is not restricted to a minimum of one-third of the flaccid penile length that may constitute the minimal desirable definition of substantial but this is not a fixed amount and can vary to include more of or less than that amount of substantial engagement and can change based on the tackiness and friction of coefficient of the gel and based on how tightly the fixation annular is engaged, and whether the penis is dry or wet, or whether the gel is used with microfibers that resist wetness and whether the urine bag attached is empty or full In another embodiment if the fixation device is used as a contraceptive or disease preventing condom substantial can include but is not restricted to be as small as ten-percent of the erect length of the penis and the percent of engagement can vary upward or downward depending on factors that include but are not restricted to the tumescent nature of the penis, the tightness of the fixation device on the penis and whether the device is place onto the penis in a dry or a whet state. In another other embodiment the fixation device can be used with a female condom catheter which can be non-annular and lie flat against the skin and substantial can be defined as covering a portion of the vaginal ring and can engage an amount to include but not restricted to as small as a semi-circle about the more caudad portion of the vagina allowing and this can vary on the users desire and comfort with having the opening of the vagina to remain free of a fixation device to reduce irritation\to the labia or can be dependent upon whether an anchoring device similar to a tampon in the vagina is used with the fixation device. Another variation on substantial can include whether the placement of the fixation device on the arm to hold an electronic device such as an IPOD™. In this embodiment the fixation device can be used with a stretchable fabric and in this case as little as to twenty percent of the annular fixation device may need to be the gel fixation component and will vary on parameters to include but not restricted to the tightness on the arm, the vigorousness of the exercise or body function and the amount that an individual sweats.

The application of the term substantial can be applied to other devices herein this application to include but not restricted to the sealing pad and the anchoring device.

The fixation device can be used in both a dynamic and a non-dynamic or static state and the portion and part of the user's body that are in contact with the gel or high coefficient of friction material and the user's skin. In each of these states and circumstances there are a range of forces acting upon the gel and the skin. One embodiment can include a flaccid penis and a static state with a dry environment where the forces are primarily the constrictive forces in a perpendicular plane relative to the penis and tackiness or coefficient of friction and the surface area of the skin to fixation device ratio. In another embodiment the fixation device can be used with a condom catheter that is being pulled with a force that is in alignment with the penis and parallel to the fixation device. In this embodiment the forces on the gel and the skin of the penis become more complex. The pulling force on the gel creates a vector force that has components that are both parallel and perpendicular to the penis. The surface area varies and in regions increases when the gel strands are more condensed and in other areas my decrease when the gel strands are more attenuated. Additionally the gel can constrict on the penile skin and create a vector that is predominantly perpendicular to the penis and exerts compression on the penis and the gel or high coefficient of friction material. The application of the forces can be applied to other devices herein this application to include but not restricted to the sealing pad and the anchoring device.

All of the designs of sealing pads and skin coverings and fixation devices and anchors and flanges and indicators and reservoirs and delivery methods and eye viewing devices and all other methods describer in this patent can be used alone or in combination to include but are not restricted to uses as a wound cover to include but not restricted to a bruise, laceration, burn, surgical site or site of trauma either natural or animal or man-made; a cast cover a breast cover or pump, a mask, a breathing mask that can include but is not restricted to a CPAP or BIPAP or positive pressure ventilation mask, an untubation device, goggles, eyewear, nose pieces or nostril plugs or devices, earpieces or earplugs or ear-buds, hand covers or gloves, garments, clothing, shoes, socks, a condom catheter or urinary processing device to include but not restricted to a urine bag, a semen processing device to include but not restricted to a male condom, a female condom or a male or female contraceptive device, a diaper or fecal processing device to include but not restricted to an ostomy bag. environmental suit or environmental protective gear, and a medication delivery system that requires areas of the body or skin that are preferentially treated with areas of medication delivery that have spaces or gaps between the sites of medication delivery and can include but are not restricted to all other applications and related applications described in this patent, as well as applications that are derivatives of the applications described in this patent.

FIG. 1 is a sagittal view of the user's skin 1 and a sealing pad 2 with a skin covering material 3, which is interposed between the user's skin 1 and the sealing pad 2 and which uses the one or more flanges 4, which is used to include contour and form an airtight and watertight seal with the user's skin 1.

Figure 2:
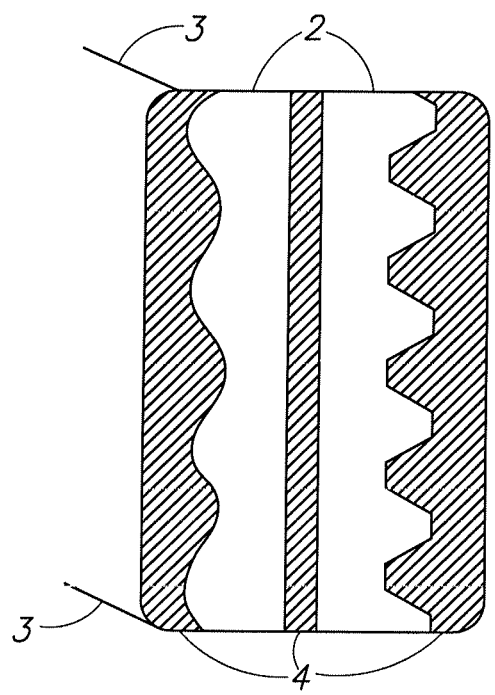
FIG. 2 is a frontal view of a sealing pad 2 with a skin covering material 3, in which the one or more flanges 4 can include varying shapes and sizes and thicknesses or elasticity.

FIG. 2 is a frontal view of a sealing pad 2 with a skin covering material 3, in which the one or more flanges 4 can include varying shapes and sizes and thicknesses and elasticity.

Figure 3:
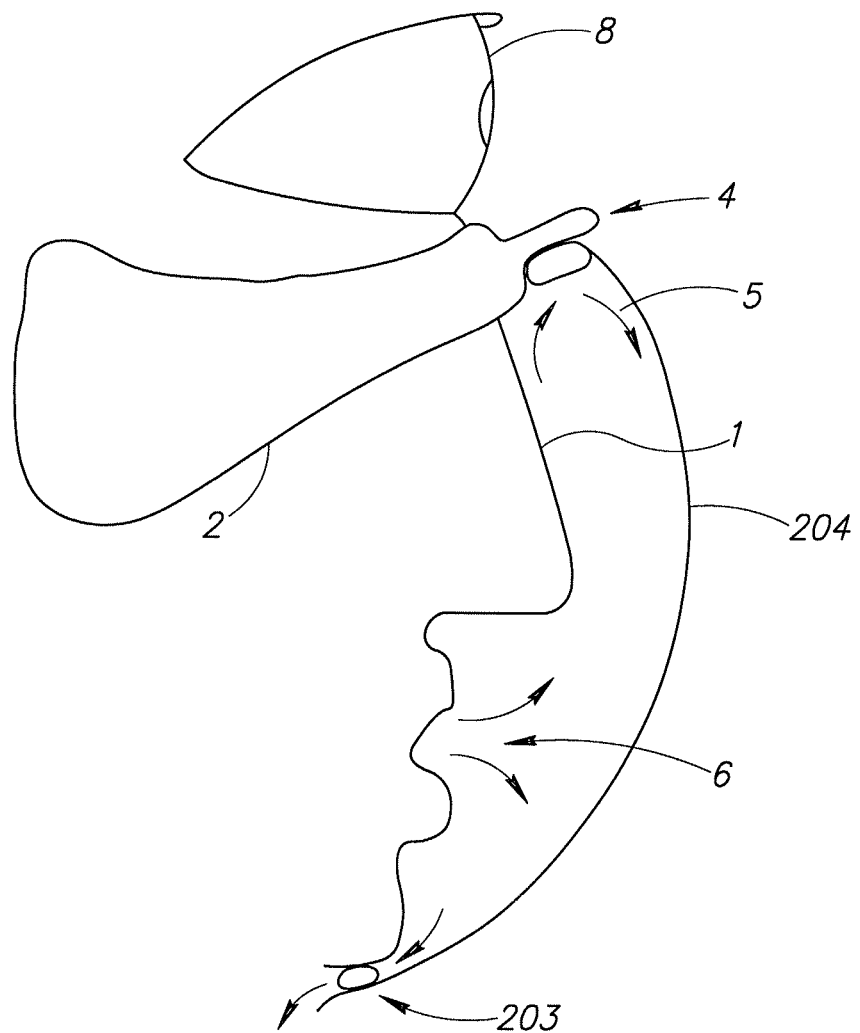
FIG. 3 is a sagittal view of the sealing pad 2 and surgical mask 204, which can include the one or more flanges 4 that can be on the surface away from the user's skin 1 to serve as a wall or barrier and can deflect 5 solids or liquids or gases to include inhaled or exhales gas 6.

FIG. 3 is a sagittal view of a sealing pad 2 and skin covering material 3, which can include the one or more flanges 4 that can be on the surface away from the user's skin 1 to serve as a wall or barrier and can deflect 5 solids or liquids or gases to include inhaled or exhaled gas 6. The one or more flanges 4 serve as a barrier which can include form an airtight and watertight seal with at least a portion of the user's skin 1. This embodiment includes a surgical mask 204 that can include a flat gel sealing pad 2 that lies against the user's skin 1, and the one or more flanges 4 that serves as a wall or barrier that lies on the surface of the sealing pad 2 that is spaced apart from the user's skin 1 and deflects inhaled and exhaled gases 6 and humidity 203 away from a body part 8, such as the eyes. The surgical mask 204 can contain vents or valves or humidity or air absorbing substances to vent air out of or into the environment between the sealing pad 2 and the skin covering material 3 and the user's skin 1 and a portion of a user's body part 8 such as the eyes. The sealing pad 2 may be a gelatinous elastomer pad and used as a cushion or seal or pad and covering material that is used for a breathing mask. The breathing mask can be used for a continuous airway pressure (CPAP) mask and non-continuous positive airway pressure or alternating degrees of positive airway pressure or negative airway pressure or basic gas exchange.

The present breathing mask can be used for an environment protection mask, isolation mask, surgical mask, anesthesia and gas delivery mask, scuba and liquid submergence mask, a scent and smell delivery mask, a gas exchange mask, a fluid exchange mask that can be used for liquid delivery that facilitates ventilation, a pressure exchange mask, a pressure equalization mask, a cardio-pulmonary resuscitation (CPR) mask and a respiratory ventilation assistance mask to include active and/or passive assisted pulmonary ventilation. The sealing pad and the related devices and augmentations can be used with the sealing pad can be used for intubations. The dimensions and materials of the mask can be varied depending on the intended application of the mask. For example, for more potentially dangerous applications such with a hazmat suit, the mask can include the one or more flanges 4 having more varied contours.

The seal of the mask in the preferred embodiment is composed of gel, which can create an airtight and watertight seal with the user's skin 1. The gelatinous elastomer sealing pad 2 may be used alone or in conjunction with non-gel materials and the sealing pad 2 can be a non-gel material or a combination of gel and non-gel material. The seals can include gels, Thermo Plastic Elastomers that can include CYBERSKIN™ and related thermal plastic elastomer, Silicon, Polystyrenes, Polystyrene and oil mixtures, and latex rubbers to include jelly rubber. The mask can include a frame to support some portion of the mask, and can utilize flexible materials for the frame and attachment and the skin covering material 3 and the one or more flanges 4. Other embodiments could include hardened material for the frame but these would be positioned to minimize discomfort to the user.

The sealing pad 2 may be affixed to the skin covering material 3. In one embodiment the fixation can be through integration of the gel into the material of the sealing pad and/or the skin covering, or through an adhesive material. The sealing pad 2 may be separate, detachable, from the skin covering material 3 so that it can be replaceable. The skin covering material can be flexible or semi-flexible or rigid.

The one or more flanges 4 of the sealing pad 2 may be composed of projections that can vary in shape and serve as flanges, walls, or valves that form an airtight or watertight seal with the user's skin 1. The one or more flanges 4 can have geometric shapes or non-geometric shapes. The one or more flanges 4 can form an airtight seal in some sections and be non-airtight in others allowing for breathability of the user's skin 1. The one or more flanges 4 can be constructed to follow or adjust to the contours of a body part. The body part can be superficial or can be internal. For example, the body part can be in a cavity or organ, on the skin, within the skin layers or deep to the skin within the organism. The seal between the sealing pad 2 and the user's skin 1 can be annular (forming a complete and closed envelope) or the seal can be partial or non-annular.

The one or more flanges 4 can be all oriented in the same direction or in opposing directions. The one or more flanges 4 can be one row or multiple rows. The one or more 4 flanges can be oriented to create a variable pattern that can create a watertight seal and can better conform to the user's skin contours. The one or more flanges 4 can be created such that the flange composed of gel or non-gel has an endoskeleton. The seal between the one or more flanges 4 and the user's skin 1 can be one or more continuous or discontinuous sections that can be circumferential or non-circumferential, which can also be spiral or overlapping. The one or more flanges 4 can be one or more non-continuous pieces of material that can be circumferential, with the ends of each piece overlapping, or with the ends of each piece having a transition piece that serves as an attaching or fastening element.

In one embodiment, the mask can include a source of positive or negative pressure within the mask to improve the seal between the one or more flanges 4 and the user's skin 1. The pressure can be created by an external circumferential or non-circumferential material. The seal can have the seal improved by one or more expandable chamber that contains a gas, liquid or solid. The expandable chamber can lie external to the circumference of the seal. The expandable chamber can lie within the seal. The expandable chamber can lie between the skin and the seal or can be a combination of chamber locations.

In another embodiment the gel seal can be a material that when expanded is resiliently deformable and returns to its original size. In another embodiment the seal can return to a size larger than its original size or to a size smaller than its original size.

Figure 4:
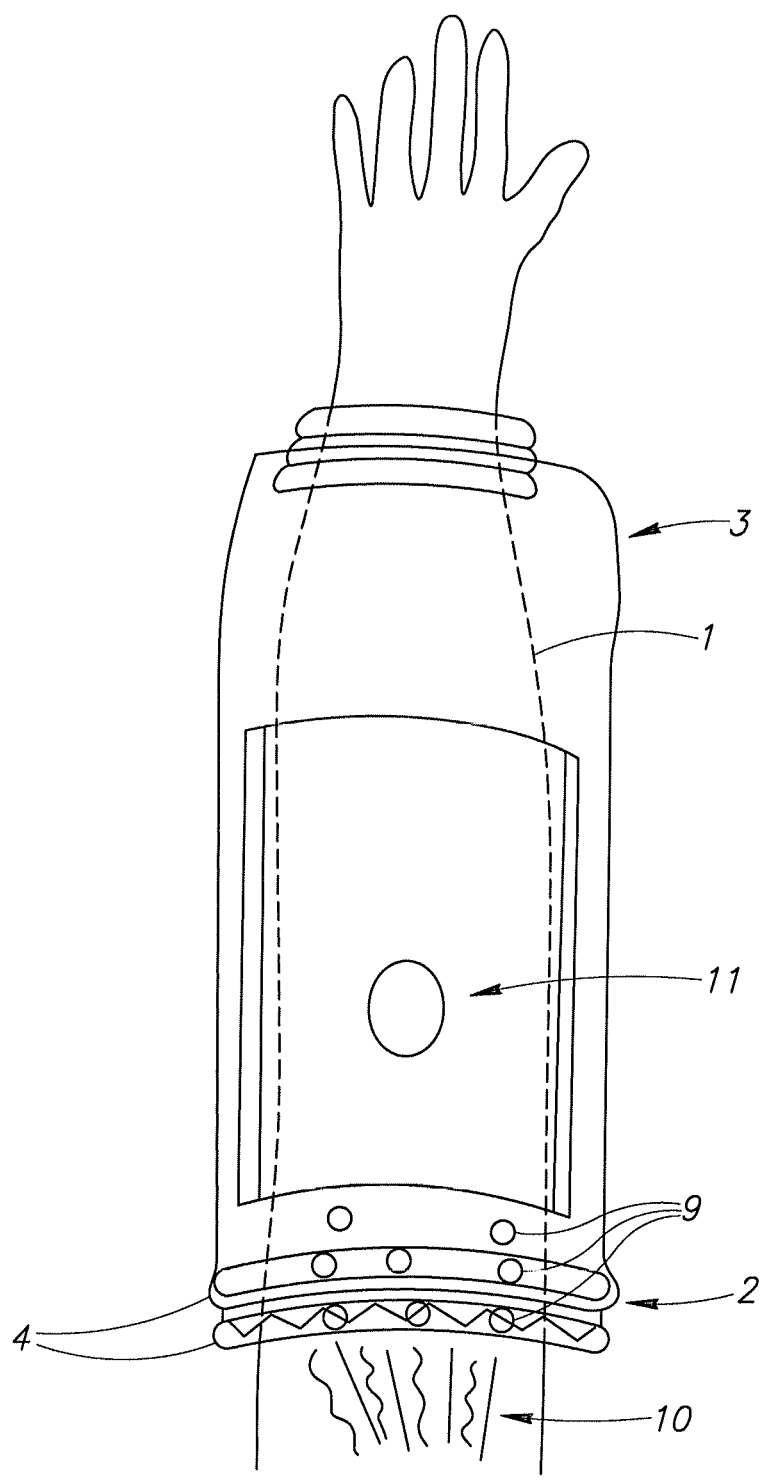
FIG. 4 is a front view of a sealing pad 2 with the one or more flanges 4 and a skin covering material 3 which can be coated or impregnated with a substance or medication.

FIG. 4 is a front view of the sealing pad 2 with the one or more flanges 4 and the skin covering material 3 which can be coated or impregnated with a substance or medication. The use of delivered substance or energy 9 which can include agents that are antibiotic, antibacterial, antifungal, antiviral; anti-fogging; scented; detoxifying age or filter, heating or cooling, gas delivery, liquid or solid delivery. The substance can be activated or delivered to the user's skin 1 or the user's body part when activated by an activating agent 10 that can include a toxin, a temperature, a pressure, an organism, electromagnetic or kinetic energy or a substance such as a gas or liquid or solid activates the agent.

Figure 5:
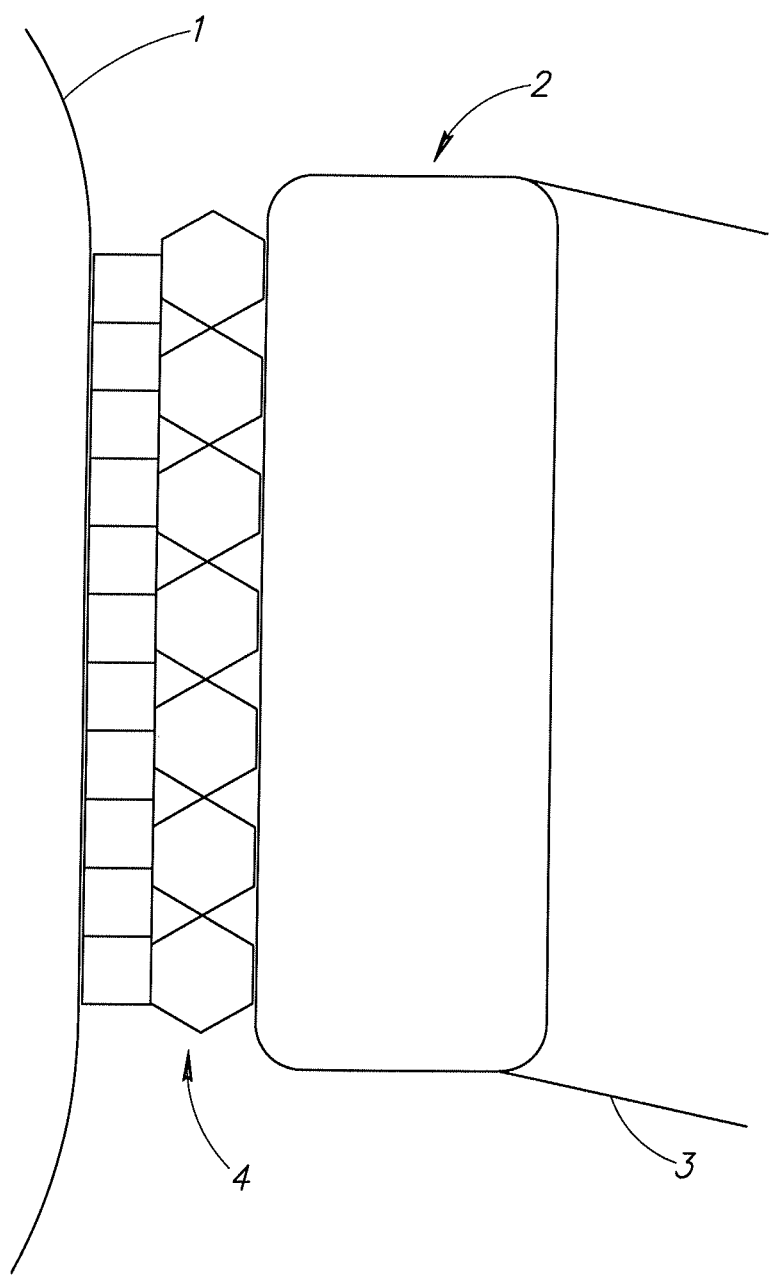
FIG. 5 is a sagittal view of a sealing pad 2 with the one or more flanges 4 and a skin covering material 3, in which the one or more flanges 4 can be stacked or constructed to form a geometric shape that can have volume and can create a network and can include a pyramid, a hexagon, a pentagon, a cylinder, or a box or a honey-comb-like configuration.

FIG. 5 is a sagittal view of a sealing pad 2 with the one or more flanges 4 and a skin covering material 3, in which the one or more flanges 4 can be stacked or constructed to form a geometric shape that can have volume and can create a network and can include a pyramid, a hexagon, a pentagon, a cylinder, or a box or a honey-comb-like configuration.

Figure 6:
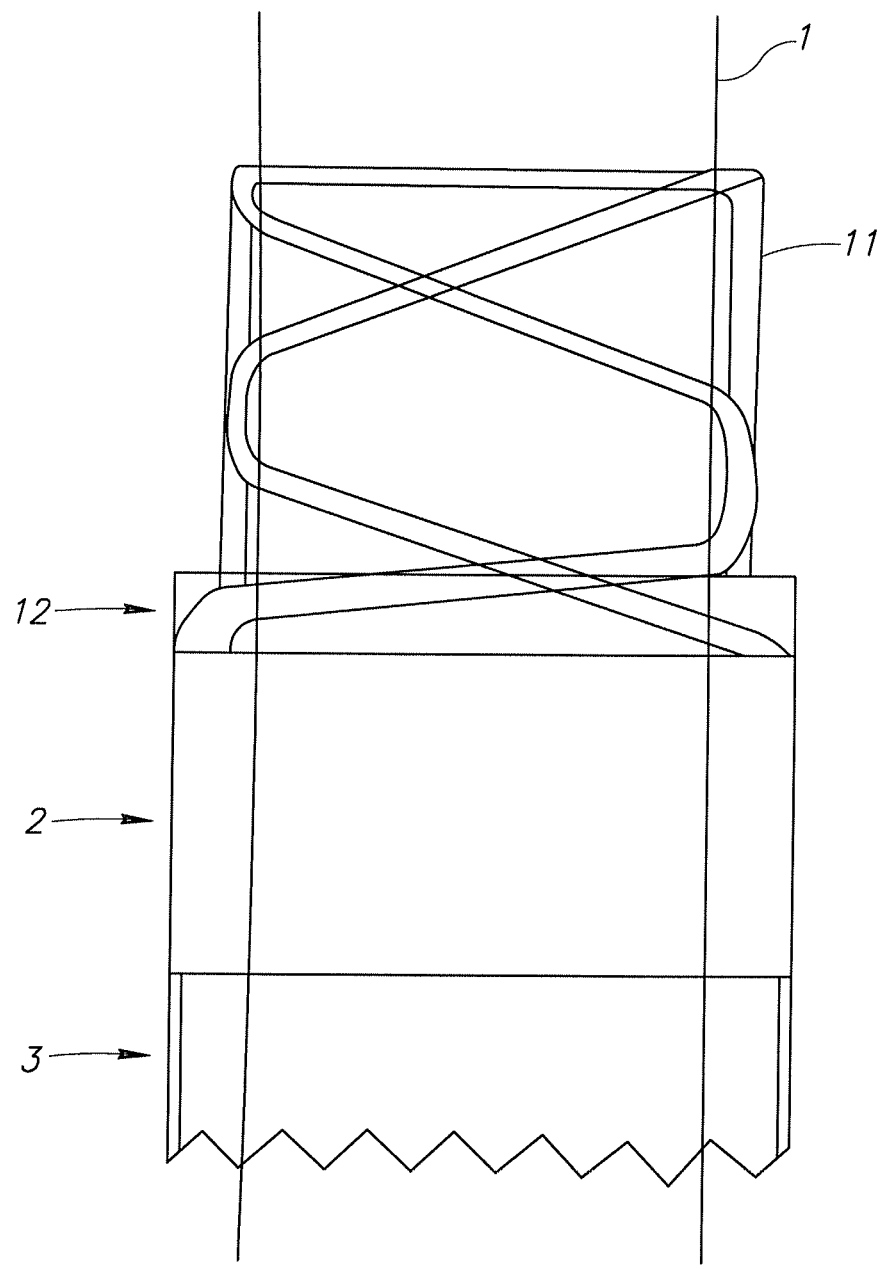
FIG. 6 is a front view of a sealing pad 2 with a skin covering material 3 with a fixation device.

FIG. 6 is a front view of a sealing pad 2 with a skin covering material 3 with a fixation device 11 that can be constructed in a geographic or non-geographic pattern that can be random or non-random that has spaces between the fixation device 11 and the seal or the sealing pad and skin covering material to include a lace-like, web-like shape with alternating regions of sealing pad and absence of sealing pad such that the sealing pad can include and resemble a web, a web-like structure, a series of crisscrossed regions of seal and no-seal; a weave, a Chinese-finger puzzle configuration; curvilinear or circular patterns; and triangular patterns. The fixation device 11 can have a junction point 12 with the sealing pad 2 or the skin covering material 3.

Figure 7:
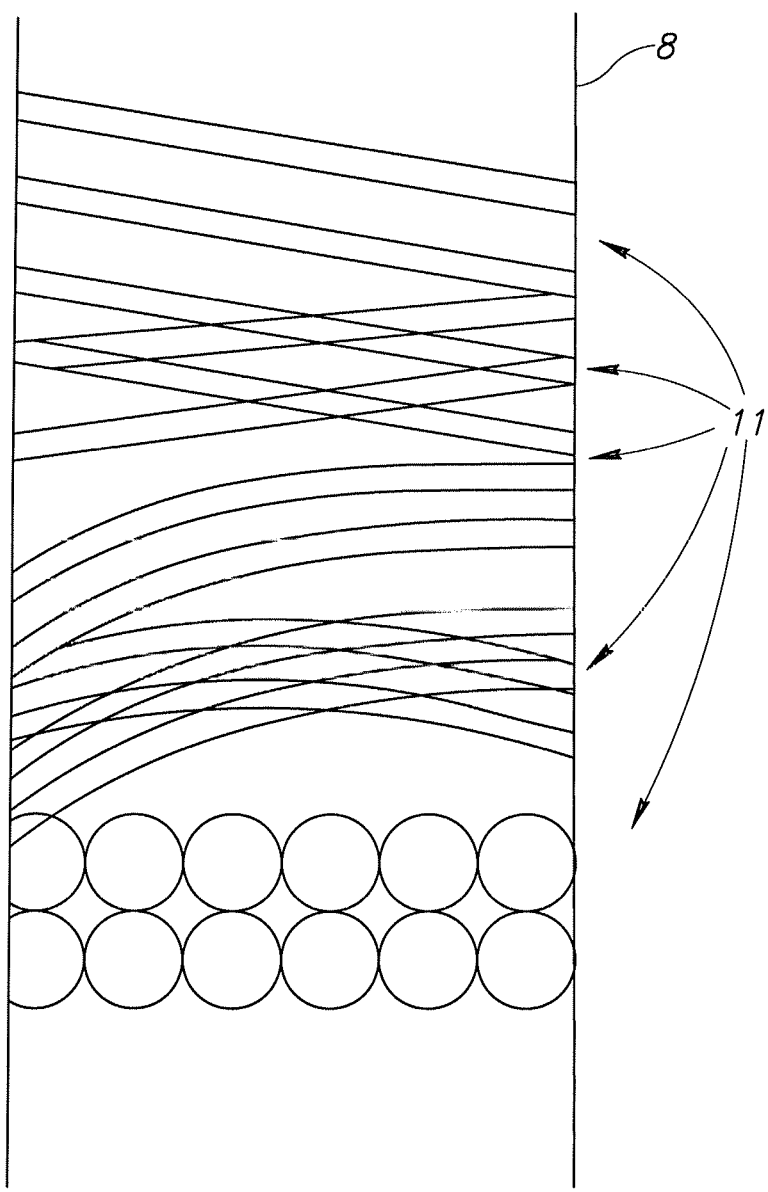
FIG. 7 is a front view of a fixation device 11 that can include a gel that can include a pattern to include linear, curvilinear, crossing, crisscrossing, intersecting, and non-intersecting and non-crisscrossing or a weave or any combination of these methods and the pattern can include alternating regions of sealing pad 2 and the absence of sealing pad 2 can be referred to as a web or web-like pattern.

FIG. 7 is a front view of a fixation device 11 that can include a gel that can include a pattern to include linear, curvilinear, crossing, crisscrossing, intersecting, and non-intersecting and non-criss-crossing or a weave or any combination of these methods and the pattern can include alternating regions of sealing pad 2 and the absence of sealing pad 2 can be referred to as a web or web-like pattern. The fixation device 11 can have multiple functions to include serving as a sealing pad 2 or making the sealing pad more breathable so that the user's skin 1 is aerated and so that the sealing pad 2 can be worn on the user's skin 1 for extended periods of time; making the sealing pad 2 more biocompatible so that the web-like sealing pad can move more freely with the user's skin 1, body part 8 or appendage; making the sealing pad 2 more capable of staying in place or fixed or affixed to a body part 8 by creating more than one region of attachment or friction or fixation; by making increasing the functional surface area of the user's skin 1 to sealing pad and allowing for greater dynamic movement in body part 8. The sealing pad 2 can be annular or non-annular or a combination of annular and non-annular. The fixation device 11 and the sealing pad 2 can be circumferential or non-circumferential or a combination of circumferential or non-circumferential and at least a portion of the fixation device 11 and the can be tacky or non-tacky.

Figure 8:
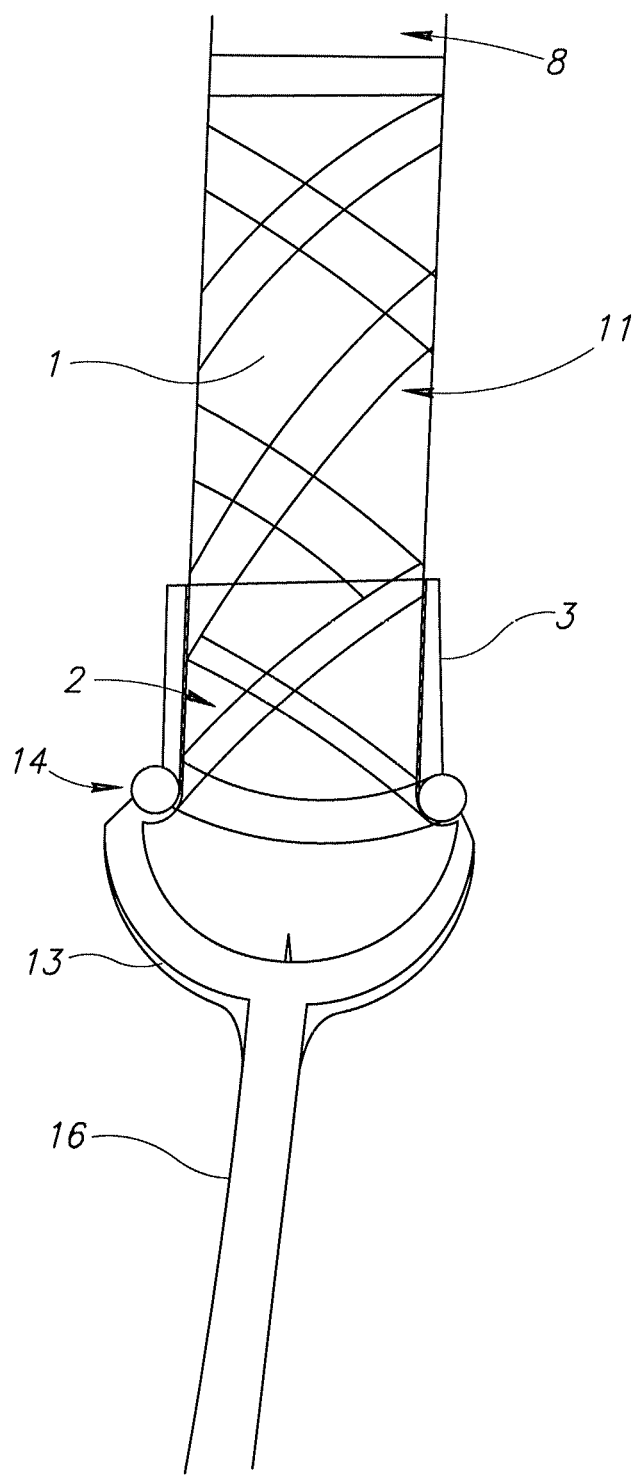
FIG. 8 is a front view of a fixation device 11 used with a condom catheter 13.

FIG. 8 is a front view of a fixation device 11 used with a condom catheter 13. The sealing pad 2 can be annular and circumferential around the shaft of a body part 8 to include the penis. Nearest the torso there is a fixation device 11 composed of gel and conforms to the movements of the penis. Distal to the torso the fixation device 11 transitions into a solid sealing pad 2 with a bulbous component 14 that is annular and circumferential around the corona or transition point between shaft and head of the penis. The bulbous component 14 fits snugly into the corona in circumcised male and in uncircumcised males can fit over the foreskin if un-retracted or on or near the corona if the foreskin is retracted. An alteration in the design can be adapted for uncircumcised males. The bulbous circumferential annular transition of the seal can continue as a gel sealing pad or can transition into the skin covering material 3 that can have the form of a condom catheter 13 of bag like shape that is watertight and can have one or more conduits 16 or tubes that can allow for the egress of urine away from the penis. In addition one of the conduit 16 can deliver solids, liquids or gasses to the penis that can assist in the comfort or biologic function of the penis that can include delivering a drying agent to include dry air, silicon dioxide, powder, cornstarch, or an alcohol based solution or gel; a medication that can include an antibacterial, antifungal, or antiviral agent; a medication that can treat a disease or condition to include cancer, HIV or other viruses, skin conditions, and pleasure delivery stimulating or anaesthetizing agents.

Figure 9:
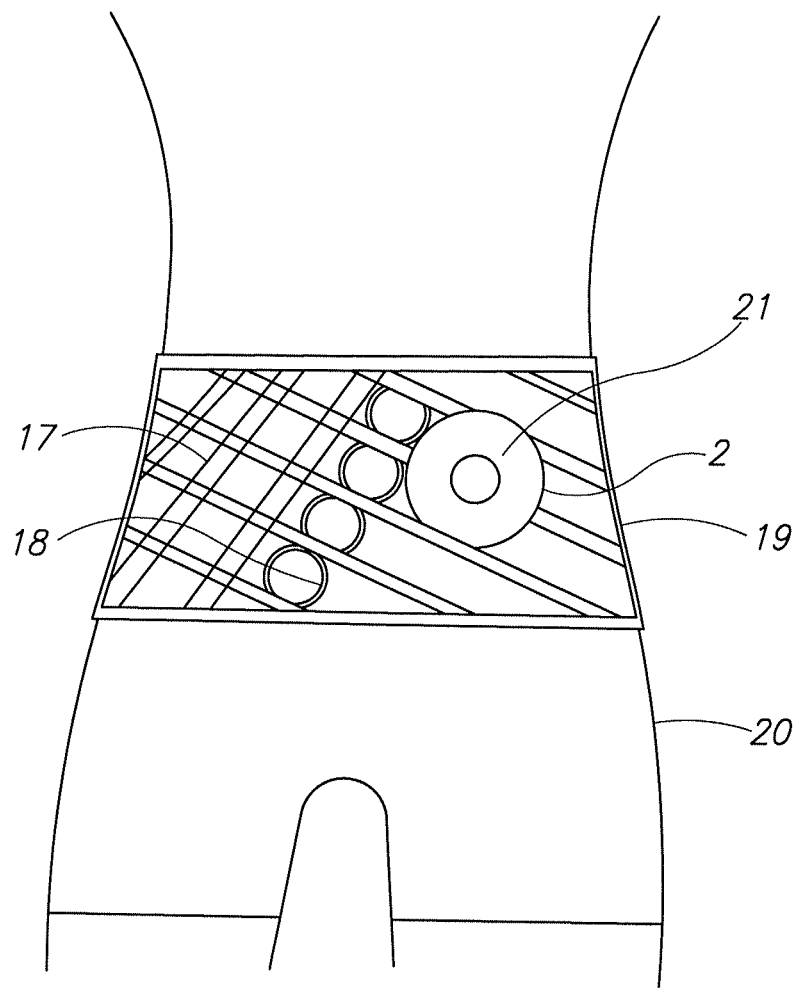
FIG. 9 is a frontal view in which the fixation device can be used with a garment and the fixation pattern.

FIG. 9 is a frontal view in which the fixation device 11 can include a pattern 17 that can be a crossing pattern, a web-like pattern, a weave pattern, or a spider-like configuration. The fixation device 11 can also have a curvilinear pattern 18 or a non-crossing pattern 19. The fixation device 11 can be used with a sealing pad 2 or a sealing pad and a skin covering material 3, which can be used with a wound cover 3 to dress a condition such as a bruise, laceration, burn, surgical site or site of trauma either natural or animal or man-made, a cast cover a breast cover or pump, a mask, goggles, eyewear, nose pieces or nostril plugs or devices, earpieces or earplugs or ear-buds, hand covers or gloves, attach or be integrated into a garment 20 to include shorts, under garments, pants, shirts, shoes, or socks. The device can be used with a condom catheter or urinary processing device to include a urine bag, a semen processing device to include a male condom, a female condom or a male or female contraceptive device, a diaper or fecal processing device to include a sealing pad 2 to seal an ostomy site 21. The sealing pad 2 can be used with an environmental suit or environmental protective gear and a medication delivery system that requires areas of the body or skin that are preferentially treated with areas of medication delivery that have spaces or gaps between the sites of medication delivery.

These alternating patterns of sealing pad 2 can be uniform in frequency of the pattern or can be more frequent at one end of the web of the pattern than at the other end. The seal can be used to anchor or fix the pad or the skin covering material or the device to parts of an organism's body to include the appendages, penis, vagina, internal organs, torso, neck, head, ear, nose, mouth. In the preferred embodiment, the sealing pad 2 having one or more of the patterns 17, 18, or 19 can be used externally or on the user's skin 1 to include fixing and attaching a condom-catheter onto the penis or fix a cast or bandage or wound cover onto a body part to include an arm or finger. Other embodiments can include internal body use and can include fix and attach a covering material onto a body organ to include a kidney. ovary, uterus, or bowel.

The web-like design can be used on non-living objects or substances to include two objects that need to be held in close approximation but require some separation and movement to include earphones and earbuds, or two objects that need to be closely bound to include two electronic communication devices such as an IPOD™ and a cellular phone or earbuds to an electronic device.

Figure 10:
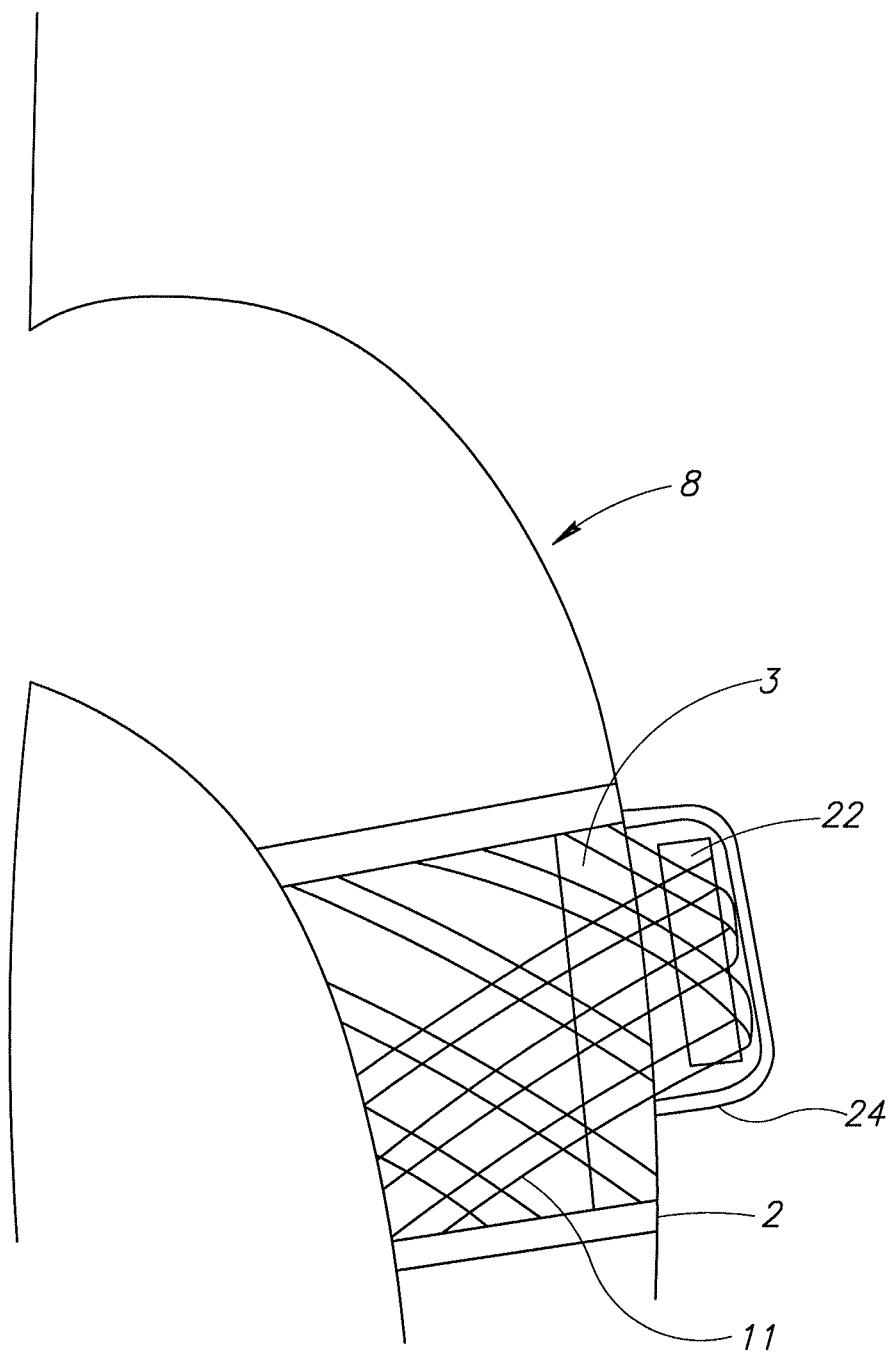
FIG. 10 is a frontal view in which the fixation device can include a fixation device that can be used with a sealing pad 2 or a sealing pad 2 and a skin covering material 3, which can be an interface between a living organism body part 8 and a non-living object.

FIG. 10 is a frontal view in which the fixation device 11 can include a fixation device that can be used with a sealing pad 2 or a sealing pad 2 and a skin covering material 3, which can be an interface between a living organism body part 8 and a non-living object 22 to include a device 225 to include a user's body part 8 to include a finger and sensing device to include a medical device to include a pulse-oximeter, glucose-meter or a blood saturation meter; or non-medical uses to include a children's toy, a music device that attaches to the body to include an IPOD™ or cellular phone attached to an arm. In the preferred embodiment the fixation device 11 can be gel and can be placed around the upper arm and can have a pocket-like holder 24 that can be water-proof. The pocket-like holder can hold a musical device that can include an IPOD™-like musical device that can be without a jacket or can have a waterproof jacket waterproof jacket or device covering material or pocket-like holder 24 that is incorporated into the fixation device 11 or the pocket-like holder 24. This combination can be used for use in recreation to include swimming or surfing or playing in the sand, which can include beach volleyball or sun tanning.

Figure 11:
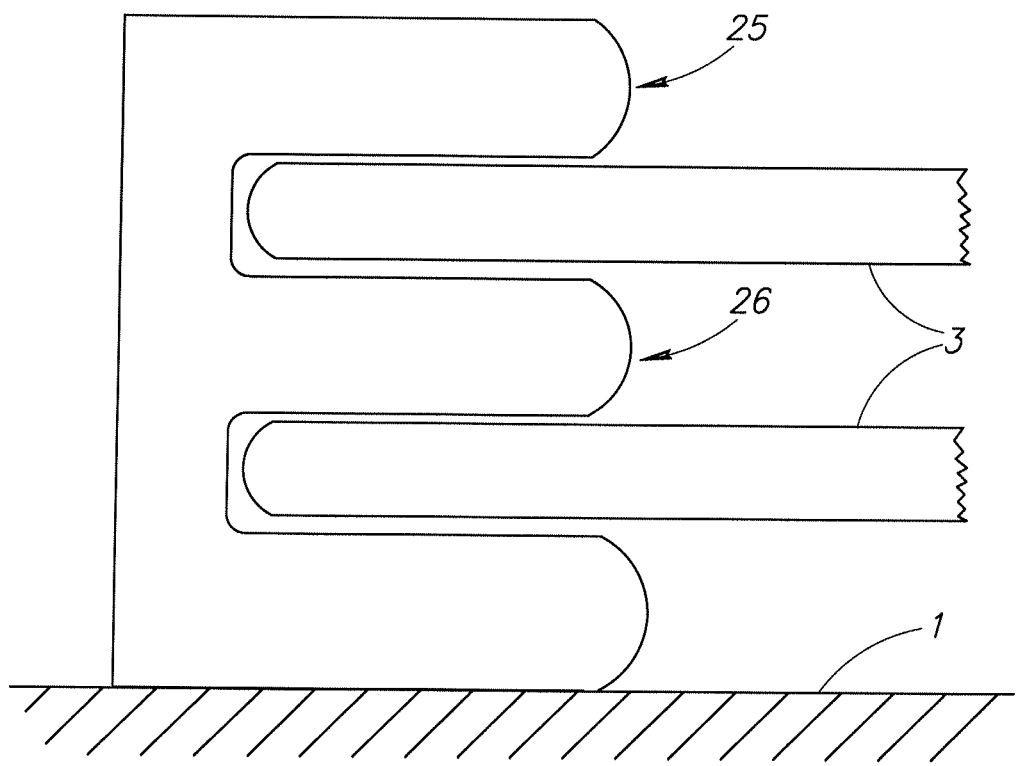
FIG. 11 is a sagittal view of a molded or geometric shape formed sealing pad 2, which can be gel or non-gel but in the preferred embodiment is a gel sealing pad 2. The gel sealing pad 2 can be folded upon itself so that the outer or external layer 25 of the sealing pad 2 compresses the internal layer 26 to form a self-sealing external compressive force.

FIG. 11 is a sagittal view of a molded or geometric shape formed sealing pad 2, which can be gel or non-gel but in the preferred embodiment is a gel sealing pad 2. The gel sealing pad 2 can be folded upon itself so that the outer or external layer 25 of the sealing pad 2 compresses the internal layer 26 to form a self-sealing external compressive force. The skin covering material 3 can be wedged between the outer or external 25 and the internal layer 26 of the gel sealing pad 2. The gel sealing pad 2 can also be folded upon itself so that the outer or external layer 25 compresses the internal layer 26 to form a self-sealing external compressive force that can be air-tight and water tight. The skin covering material 3 can be wedged between the skin and the inner and outer layer of the gel seal. The skin covering material 3 will be attached to the sealing pad 2 to form a substantially airtight and water-tight seal to at least a portion of the seal or it can be non-attached and the skin covering material 3 can be replaceable.

Figure 12A:
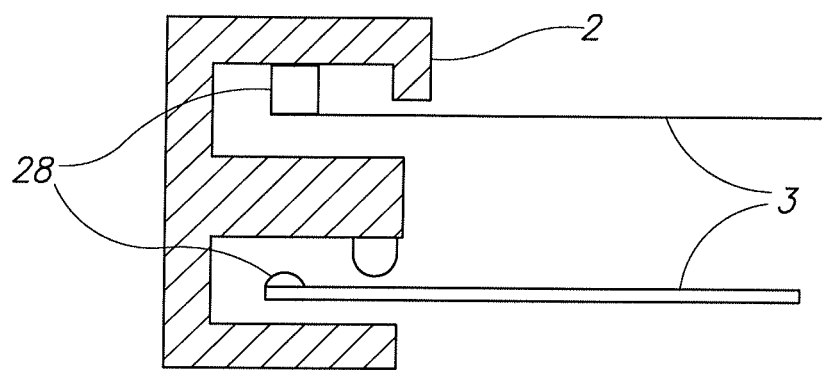
FIGS. 12A-C are a series of views of sealing pad 2, which can be composed of one of more projections or folds that can be configured similar to the shape of the letter 'E' or 'W' or 'N' or 'M' or 'C' or 'S' or any combination of these shapes such that insinuation of the sealing pad 2 and the skin covering material 3 to form an airtight and watertight seal between the user's skin 1 and the sealing pad 2 and the skin covering material 3.
Figure 12B:
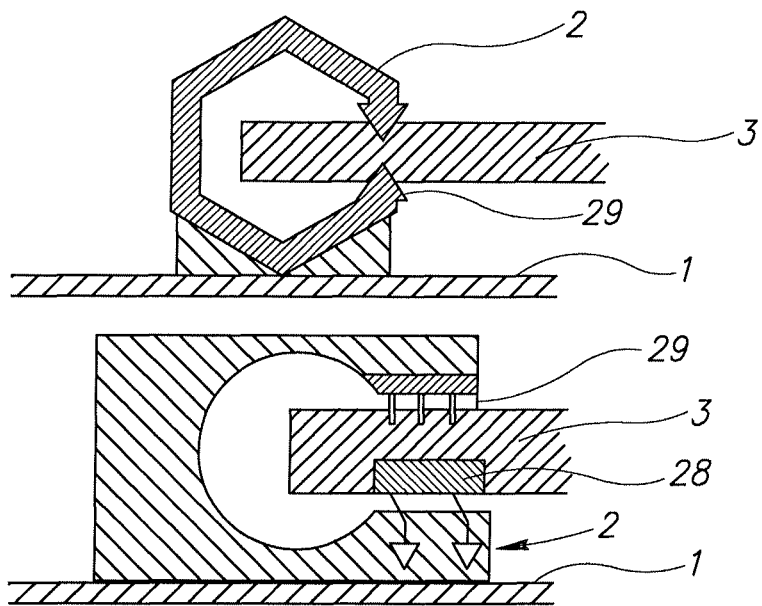
Figure 12C:
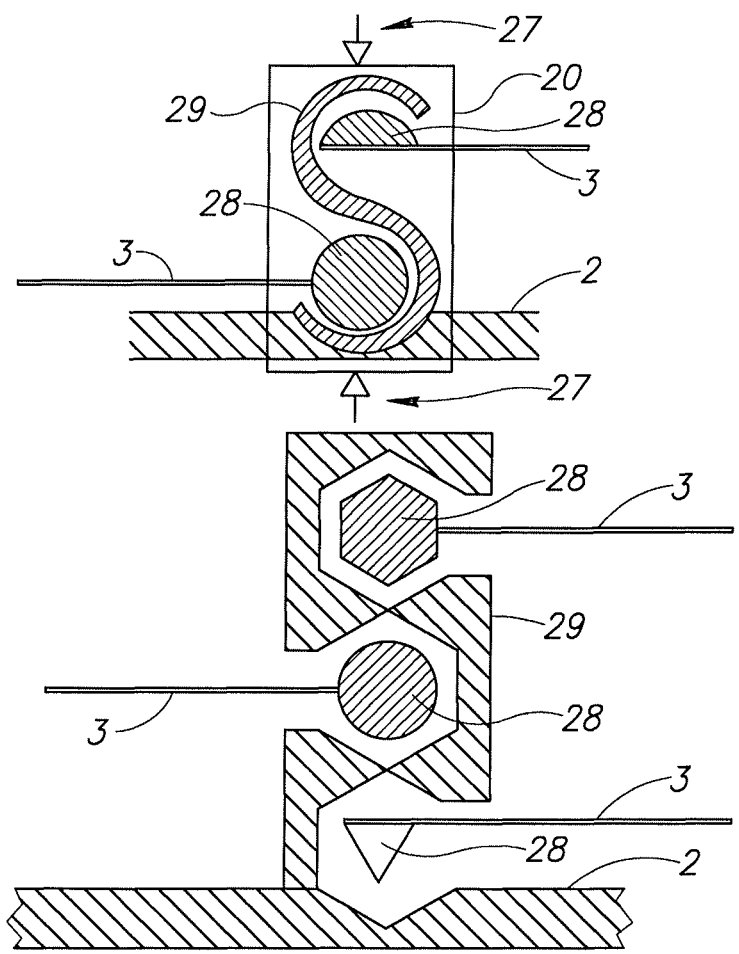

FIGS. 12A-C are a series of views of sealing pad 2, which can be composed of one of more projections or folds that can be configured similar to the shape of the letter 'E' or 'W' or 'N' or 'M' or 'C' or 'S' or any combination of these shapes such that insinuation of the sealing pad 2 and the skin covering material 3 to form an airtight and watertight seal between the user's skin 1 and the sealing pad 2 and the skin covering material 3. The compressive force 27 can be created by the inherent structure of the sealing pad 2 or by the folding of the sealing pad 2 or by an external device 23, which can include a garment 20 to include a circumferential belt, strap or item of clothing or the fixation device 11. The skin covering material 3 can contain a securing structure or device 28 that can include bulbous projection or an invagination or a geometric or a random shape or an anchoring device to include VELCRO™ and related fabric hook and loop fasteners, ZIP-LOCK™, zippers, buttons, and pin-like projections that secure the skin covering material 3 and the sealing pad 2 in place. The sealing pad 2 can contain a locking structure or device 29 that can include bulbous projection or an invagination or a geometric or a random shape or an anchoring device to include VELCRO™ and related fabric hook and loop fasteners, ZIP-LOCK™, zippers, buttons, and pin-like projections that secure the skin covering material 3 and the sealing pad 2 in place.

Figure 13A:
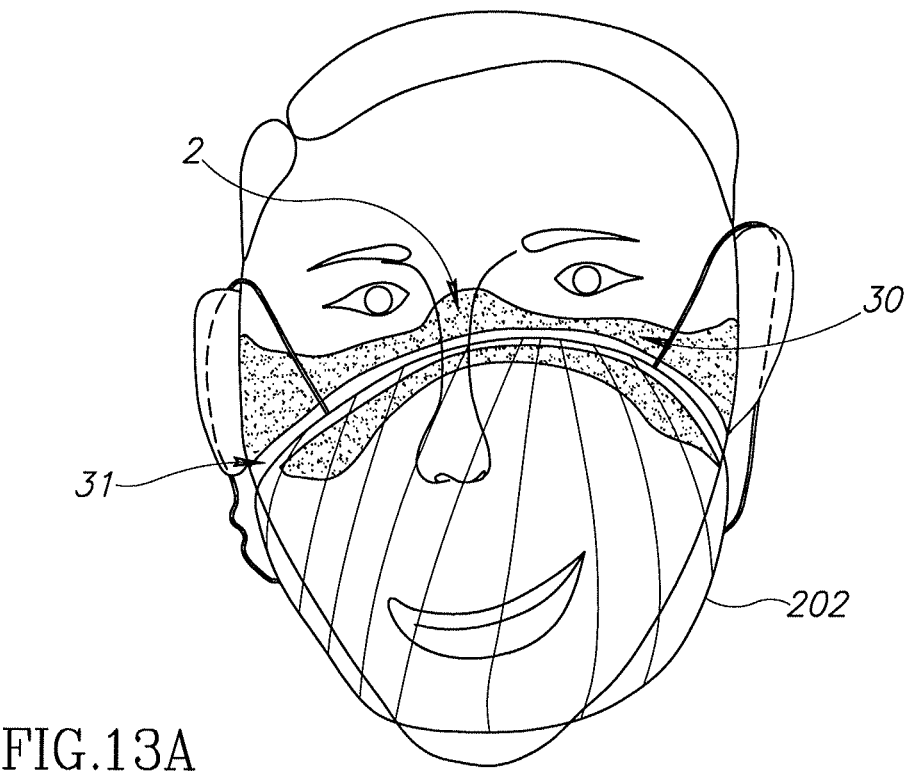
FIG. 13A is a frontal view and FIG. 13B is a sagittal view of a folded or molded attachment 30 gel sealing pad 2 used to hold a skin covering material 3 in place, and form a seal with at least a portion of the user's skin 1 and, forms a barrier to include inhaled or exhaled gas 6 and in one embodiment this can include a breathing mask 202.
Figure 13B:
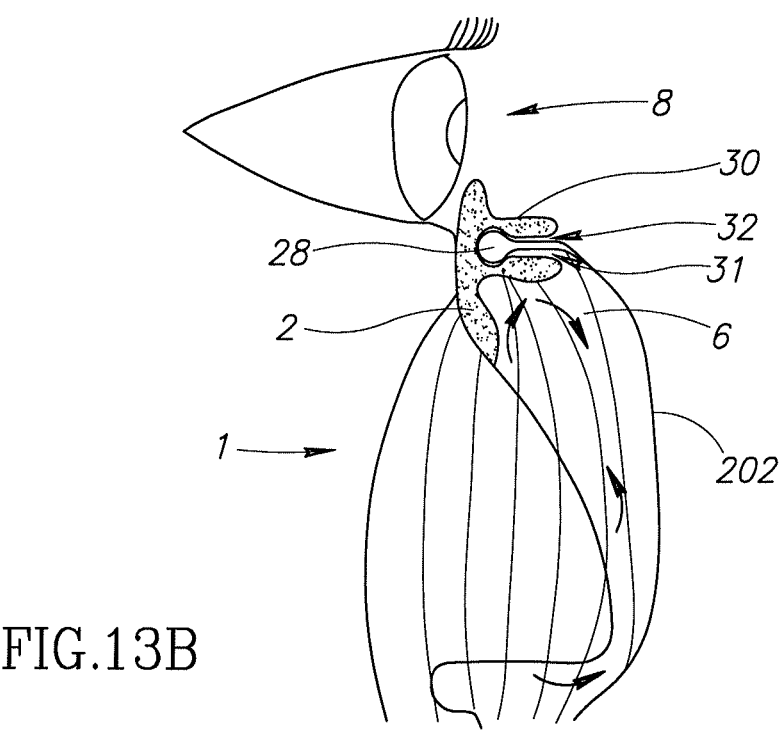

FIG. 13A is a frontal view and FIG. 13B is a sagittal view of a folded or molded attachment 30 gel sealing pad 2 used to hold a skin covering material 3 in place, and form a seal with at least a portion of the user's skin 1 and, forms a barrier to include inhaled or exhaled gas 6 and in one embodiment this can include a breathing mask. The sealing pad 2 can have a C-shape folded or molded attachment 30 that arises from the sealing pad 2 or from the skin covering material 3. In the preferred embodiment the folded or molded attachment 30 device also serves as a barrier or one or more flanges 4 that is attached to an elongated flat sealing pad 2 that conforms to the user's skin 1 of the user's face and forms a broad base that forms a substantial sealing pad 2 that interfaces with the user's skin 1 while the C shape barrier or one or more flanges 4 act as a barrier to the inhaled or exhaled gas 6 and also serves as an investing or coupling or holding or fixation or invaginating or attaching structure for and to include a breathing mask 202 which can include a surgical mask. The skin covering material 3 can include a securing structure or device 28 and the sealing pad 2 and the folded or molded attachment 30 can include a sealing pad 2 or a folded or molded attachment 30 locking structure or device 29. In the preferred embodiment the mask can be removed and the skin covering sealing pad 2 can be replaced or the skin covering sealing pad 2 can be permanently or semi-permanently attached to the sealing pad 2 and the folded or molded attachment 30 using methods to include adhesives, tackifying agents, pins, VELCRO™ and related fabric hook and loop fasteners, ZIP-LOCK™, buttons and zippers. The folded or molded attachment can have invagination 31 and protuberance 32 or a combination of invagination 31 and protuberance 32.

Figure 14A:
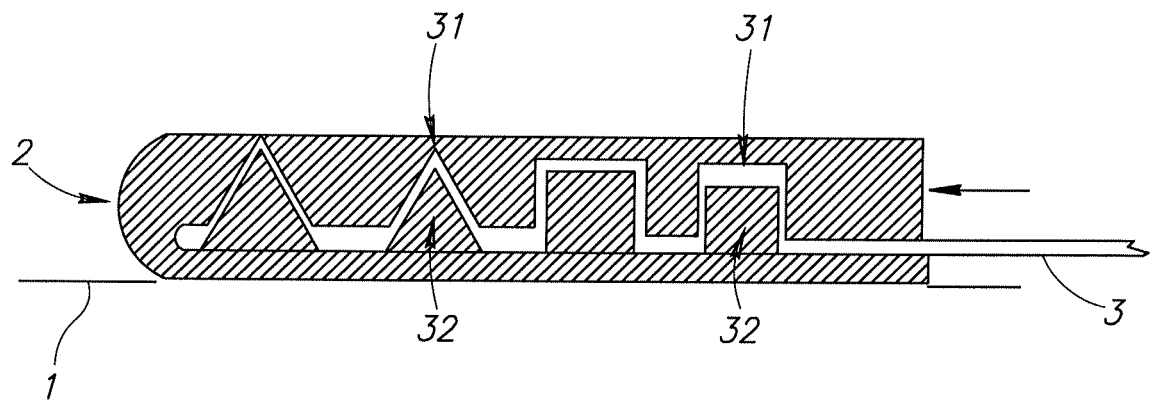
FIGS. 14A and 14B depicts a sagittal view of a device for securing a sealing pad 2 and securing a sealing pad 2 and a skin covering material 3.
Figure 14B:
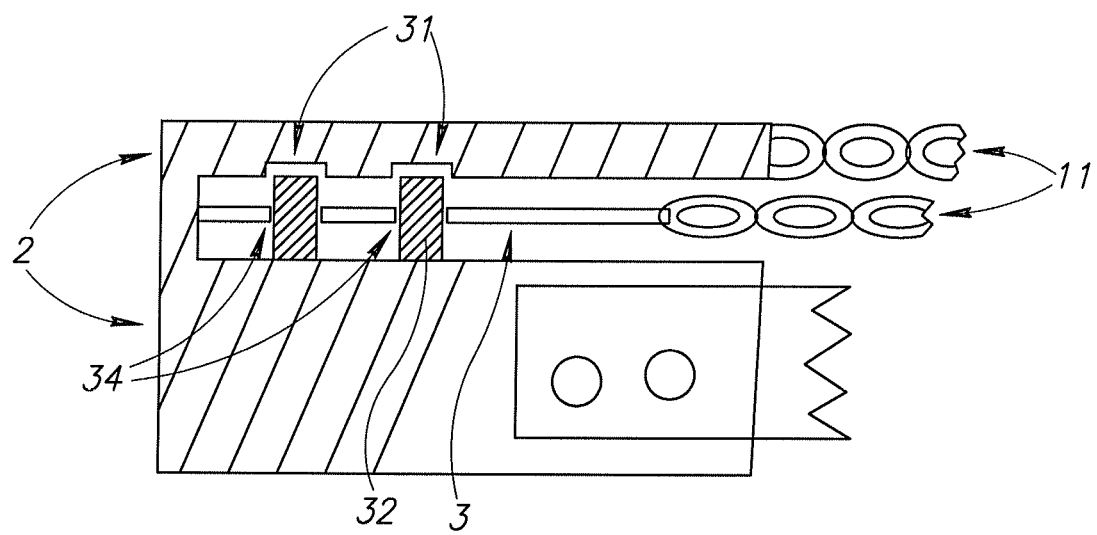

FIGS. 14A and 14B depict a sagittal view of a method for securing a sealing pad 2 and securing a sealing pad 2 and a skin covering material 3. The gel sealing pad can include a geometric shape that is an invagination 31 or female or receptive configuration. The shape can include a groove or indentations, invagination 31, or endophytic shape. The gel seal material can include a geometric shape that is a male or protuberance 32 or protrusion or projection configuration. The shape can include a male or protuberant or protrusion or projection configuration or exophytic shape. The skin covering material can include a geometric shape that is a female or receptive configuration. The shape can include a groove or invagination, indentations, or endophytic shape. The skin covering material 3 can include a geometric shape that is a male or protuberant configuration. The shape can include an extuberance or projections or exophytic shape. The skin covering material 3 can have one of more geometric shapes that can be protuberance 32, one of more geometric shapes that can be invagination 31 or one of more geometric shapes that can be a combination of protuberance 32 and invagination 31 configurations. The sealing pad 2 can include one of more geometric shapes that can be protuberance 32, one of more geometric shapes that can be invagination 31 or one of more geometric shapes that can be a combination of protuberance 32 and invagination 31 configurations. The sealing pad 2 can have one of more geometric or non-geometric shapes that can be mirror images of each other. The skin covering material 3 can have one or more geometric or non-geometric shapes that can be mirror images of each other. The skin covering material 3 and regions of the sealing pad 2 can have fenestration 34 which can include holes or areas where material is absent. The sealing pad 2 and the skin covering material can have fixation device 11 that can include attaching or integrating into the sealing pad 2, or the skin covering material 3 or the invagination 31 of the folded or molded attachment 30.

Figure 15:
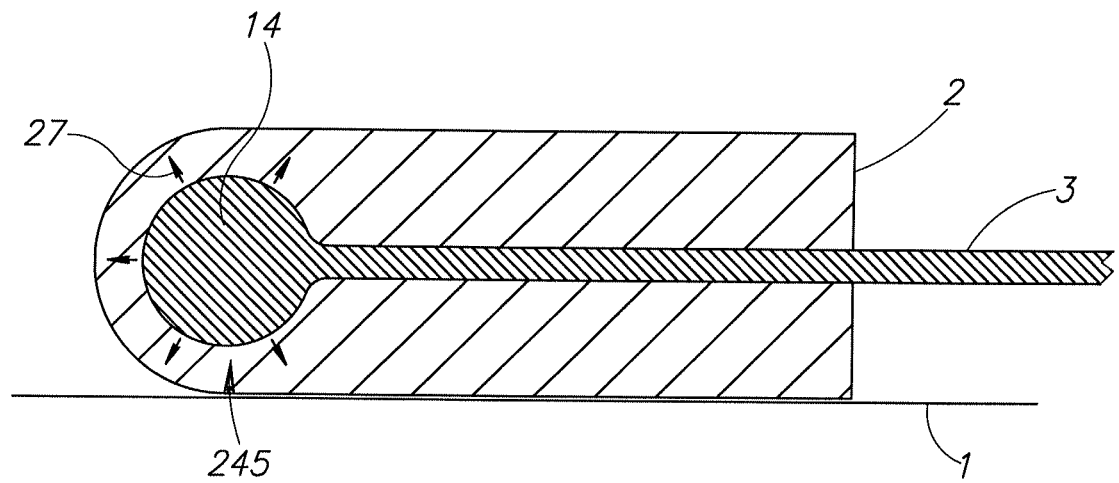
FIG. 15 is a sagittal view of the user's skin 1 and a sealing pad 2 that is configured as a folded or molded 245 configuration in which the there is a single skin covering material 3 that has a bulbous component 14 that can include the edge of the skin covering material 3 and the bulbous component 14 of the skin covering material 3 is compressed by compressive force 27 created from the surrounded sealing pad 2 which can include a folded or molded 245 gel sealing pad 2 such that the skin covering material 3 is secured and constitutes a secured skin covering attachment.

FIG. 15 is a sagittal view of the user's skin 1 and a sealing pad 2 that is configured as a folded or molded 245 configuration in which the there is a single skin covering material 3 that has a bulbous component 14 that can include the edge of the skin covering material 3 and the bulbous component 14 of the skin covering material 3 is compressed by compressive force 27 created from the surrounding sealing pad 2 which can include a folded or molded 245 gel sealing pad 2 such that the skin covering material 3 is secured and constitutes a secured skin covering attachment. Embodiments of the sealing pad 2 and skin covering material in combination with either the folded or molded 245 gel sealing pad 2, the protuberance 32, invagination 31 or any combination with these elements can be used to form or augment a product where the skin covering material 3 and the sealing pad 2 can include a cast cover, a wound cover, a bandage, a male condom catheter, a female condom catheter, a breathing mask that can include a surgical mask, a ventilation mask, a positive airway pressure mask that can include a CPAP or BIPAP mask, an intubation device, nose plugs, earplugs to include music ear-buds, earplugs with a conduit or channel for the transmittal of a solid, liquid or gas, eye protection or goggles to include use for industry, medicine, water usage to include scuba, and swimming, a diaper, a device to preserve the integrity or sterility of a surgical field to include inside and outside of the body or body organ or cavity, a garment cover that can include a shoe cover a glove or glove cover and a pants cover, a sleeve cover, a collar cover or a hat or hat cover; a garment or garment cover or an environmental protection gear or device.

In some embodiments, the protuberance 32 of two engaging sections can be similar. A first protuberance 32 can engage a similar, second protuberance 32 on a different section of the sealing pad 2. The seal can have a geometric or non-geometric shape that insinuates itself into the skin covering material. The skin covering material can have a geometric or non-geometric shape that insinuates itself into the gel seal. The gel seal, the male projections, the female invaginations or in any combination of these elements can be at least partially composed of non-gel material and can be a combination of gelatinous and non-gelatinous materials. The gel seal, the male projections, the female invaginations or any combination of these components of the seal can be singular or redundant.

The gel seal, the male projections, the female invaginations or any combination of these elements, can be of variable hardness and softness to include softer away from the skin than at the skin covering material, softer away from the skin covering material than at the skin, or a combination or a variation on combinations of hardness and softness between the skin and the skin covering material.

Figure 16:
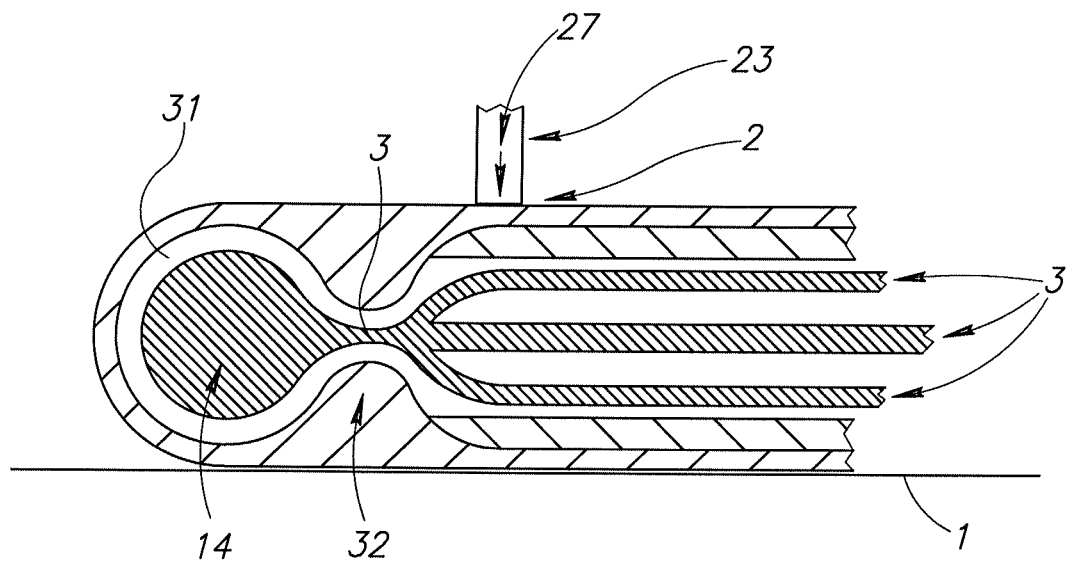
FIG. 16 is a sagittal view of the user's skin 1, a sealing pad 2 and skin covering material 3 which can include multiple layers and combinations of protuberance 32 and invagination 31, which can include one or more than one protuberance 32 and invagination 31 or can be a combination of one or more protuberances and invaginations or a series of protuberances 32 and invagination 31.

FIG. 16 is a sagittal view of the user's skin 1, a sealing pad 2 and skin covering material 3 which can include multiple layers and combinations of protuberance 32 and invagination 31, which can include one or more than one protuberance 32 and invagination 31 or can be a combination of one or more protuberances and invaginations or a series of protuberance 32 and invagination 31. In one example the multilayer skin covering material 3 can merge or may not merge into one solid skin covering material 3 and the sealing pad 2 can be assisted by compressive force 27 exerted by an external device 59 that can include adhesive tape, a fixation device 11, a garment 20 to include a belt, a strap or an elastic band; or the external device 59 to include to a vice-like structure, a rubber-band like structure or a compressive bandage.

Figure 17:
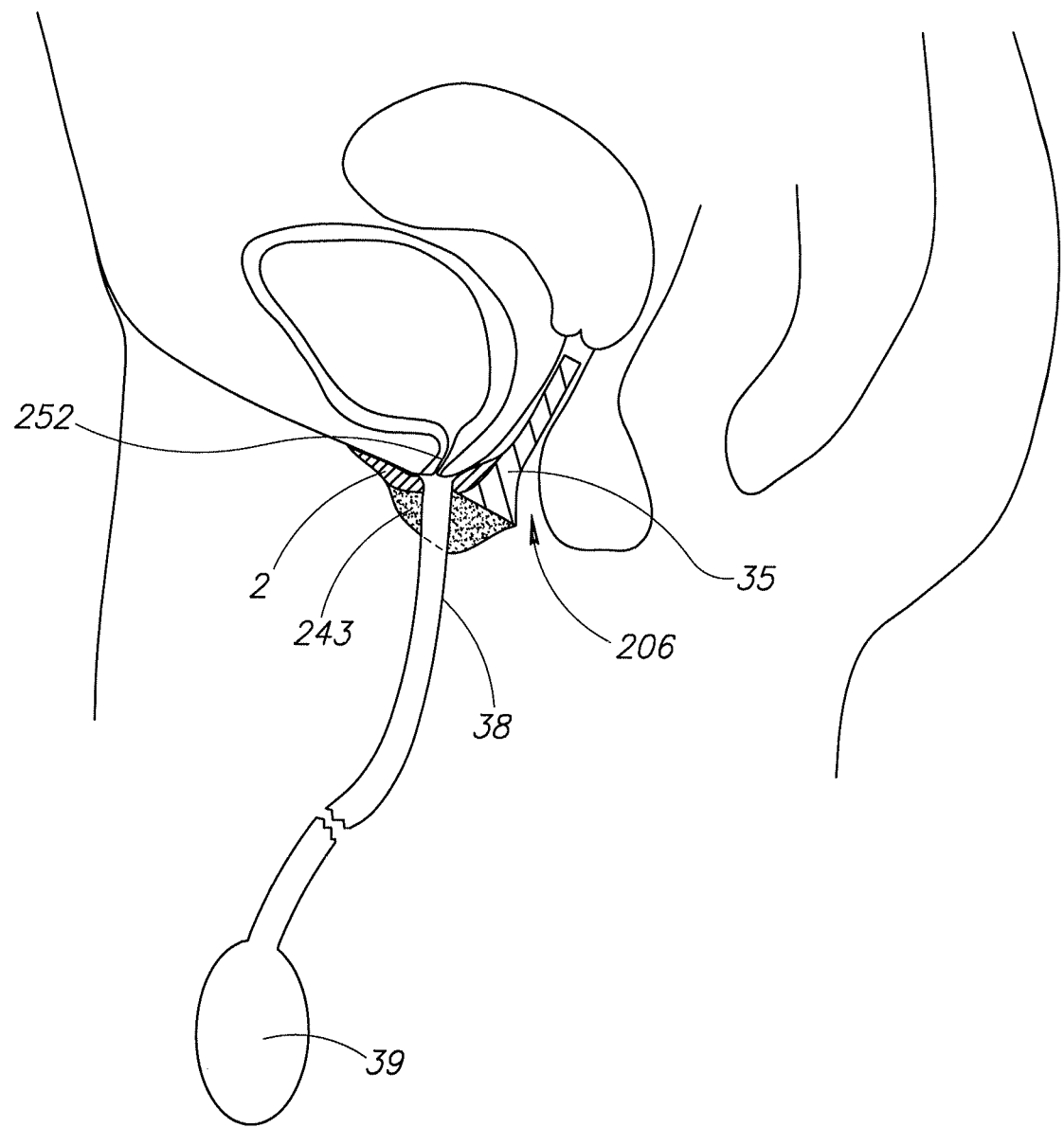
FIG. 17 is a sagittal view of an anchoring device that is used in conjunction with a sealing pad 2 and a skin covering material 3 to form a female urinary diversion system or condom catheter.

FIG. 17 is a sagittal view of an anchoring device that is used in conjunction with a sealing pad 2 and a skin covering material 3 to form a female urinary diversion system or condom catheter. In this embodiment a sealing pad 2 or a sealing pad 2 with a skin covering material 3 or a combination of a sealing pad 2 and a skin covering material can be anchored with an anchoring device 35 to include a gel or a non-gel that can that uses a method to include placing a material that can include an anchoring object that can be a protuberance 32 to include a natural shape such as the penis or a geometric shape such as a cylinder, an invagination 31 to include an annular or non-annular shape to include a natural shape such as a body part to include a nostril, ear canal, mouth, vagina, anus or rectum or a geometric shape to include a funnel shape a hollow cylinder or a hollow rectangle or pyramid which can be formed from a solid or liquid, or a liquid that morph into a gel or a solid; a gel to include CYBERSKIN™ and related thermal plastic elastomer, rubber latex, or silicon such that the anchor is formed by placing the anchoring material into orifice 206. The orifice 206 can include the nostrils, mouth, ears, anus, urethra, vagina, digestive track to include the esophagus, the respiratory track to include trachea and larynx; a surgical cavity or a natural body cavity to include an omphalocele or meningocele. The anchoring device 35 can be used in combination with a gel sealing pad 2 or a skin covering material 3 to create an airtight or watertight seal with at least a component of the user's skin 1. The sealing pad 2 and the anchoring device 35 can be used with a skin covering material 3 or a fixation device 11 that can enter the orifice 206 or not enter the orifice 206 or can be a combination of both enter and not enter the orifice 206 to include the fixation device 11, or standard attaching devices to include adhesives and tapes, and can be used with a living body part or a biological or living or non-living device that can include a catheter or tube 38, or a device to include a urinary regulator, a sphincter regulator, a respiratory regulator, a heat or cold device, a pain regulator, an electrical or non-electrical physiologic device that can include a physiologic indicator, monitoring device, feedback device, delivery device, permissive or inhibitory device, tissue replication device or any combination of said devices; biological tissue that can be used to treat or to monitor, feedback or deliver or permit or inhibit a biological function or assist or create biological growth or hormone or substance delivery for biological and physiological development, growth, homeostasis or regulation; or any combination of these elements and devices 23. In the preferred embodiment is an anchoring device 35 can be placed into the vagina, and can consist of a gel or CYBERSKIN™ and related thermal plastic elastomer tampon-like device that can simulate the shape of the vagina for comfort. The vaginal anchor can be attached to a sealing pad that can be a gel that forms an airtight or watertight seal with the female urethra 252. The seal can have a skin covering material 3 that can capture the urine released by the urethra 252 and can be in a form to include a receptacle 39 to include a bag or condom or conduit or tube 38. The sealing pad 2 and skin covering material 3 can serve as a watertight tube 38 for removal of urine away from the body without leakage of urine. This application can be used in females with an incompetent urethral sphincter, pelvic floor muscular dysfunction, muscle and nerve wasting conditions or medical diseases or entity to include multiple sclerosis, senility and amyotrophic lateral sclerosis and in situations where a female cannot use a toilet to include fighter pilots, racecar drivers, surgeons, and astronauts. The anchoring device 35 can also be used to for sexual stimulation and pleasure and to enhance or improve sexual function or gratification in conjunction with a physiologic device to include a feedback, inhibitory, permissive, delivery, and augmentation methods or devices. Another embodiment can be used as a male or female contraceptive device. The anchoring device 35 can be a protuberant shape that lies within an orifice and in some embodiments can conform to the orifice or a structure within the orifice. The anchoring device 35 can be composed of a gel material or a non-gel material.

An embodiment for a female urinary catheter can include a gel sealing pad surrounding the urethra. Attached to the sealing pad is a skin covering 243 which has a bag shape that is designed to collect about 200 cc of urine with a conduit or tube at its end, which will divert the urine away from the body and the proximal urinary bag. There would be an one-way valve with the opening of the tube which would allow fluid to flow away from the body and not toward the body. The gel sealing pad will create a watertight seal around the urethra. Attached to the gel pad is an anchoring device that would be made of a semi-solid gel that conforms and fits into the vagina in a manner reminiscent of a tampon. Also attached to the sealing pad and the anchor is a web-like gel fixation device that conforms and surrounds the vaginal region. The fixation device in the preferred embodiment is attached to a garment that is in the form of a bikini or undergarment or thong or a straps that surrounds both waist and the outer buttocks.

Figure 18:
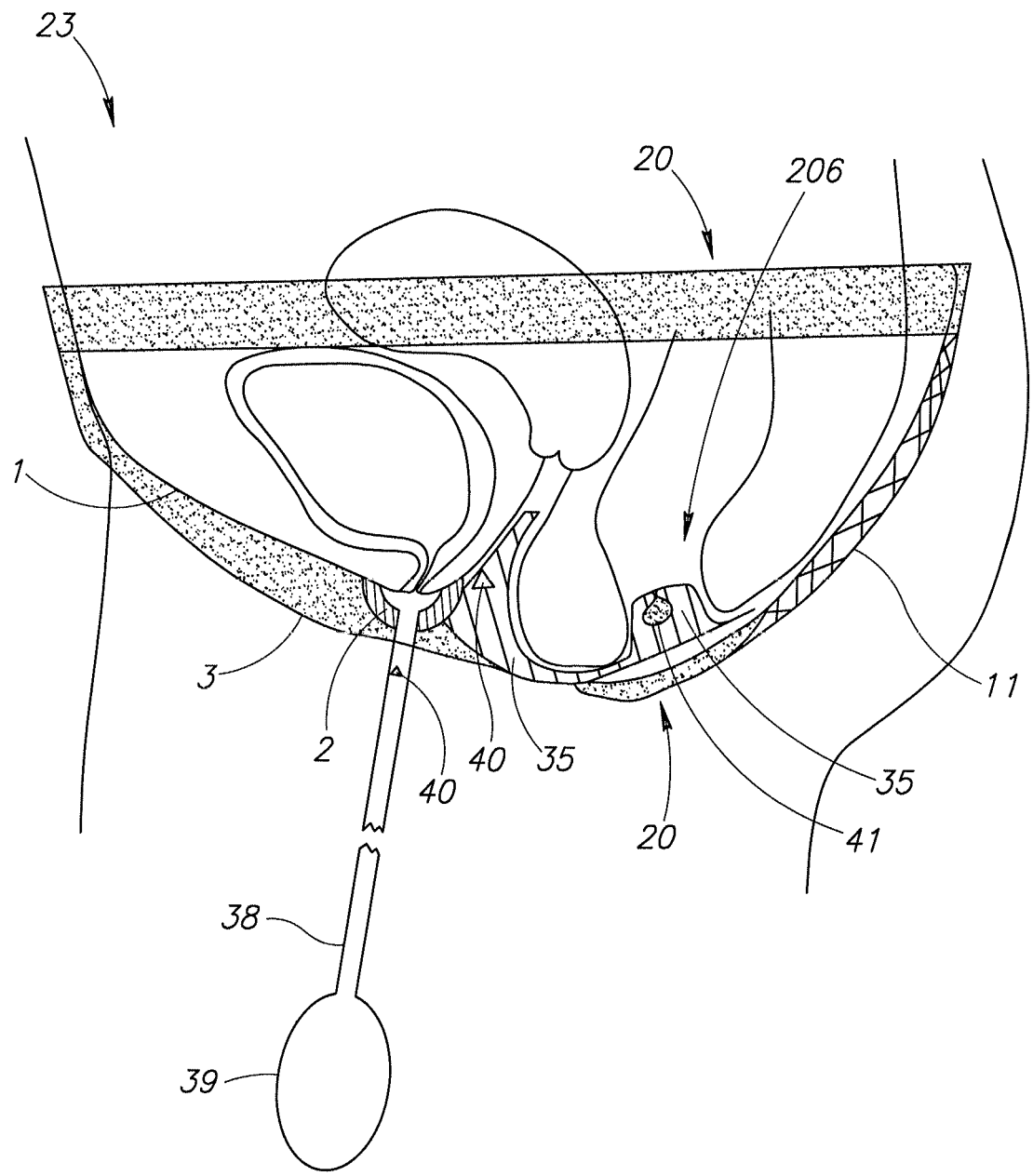
FIG. 18 is a sagittal view and depicts a urinary collection device 23 which can include are one or more than one orifice 206 anchoring device 35 and can be placed into and include the anus and the vagina.

FIG. 18 is a sagittal view and depicts a urinary collection device 23 which can include are one or more than one orifice 206 anchoring device 35 and can be placed into and include the anus and the vagina. The orifice anchoring device 35 can include one or more than one anchoring device 35 per orifice 206 and can be used in a male or a female. In this embodiment the urinary collection device is used with a female. The orifice anchoring device 35 can be used alone or in combination with one or a combination of elements to include a fixation device 11 or a garment 20 or a sealing pad 2, or a skin covering material 3, or a medication delivery system or urinary collection device 23 or can be impregnated 40 with a substance or can reside within a reservoir 41 delivery system that can include a solid or liquid or gel or gas that can alter or augment or diminish a biological function that can include a biological acting material to include a medicine to include an antibiotic, a lubricant, a sexual stimulant or inhibitor, an anaesthetizing agent or stimulating agent, a pain altering agent, a neutralizing agent, an agent that changes the pH of a non-biological structure or body part, or an agent that cleanses or disinfects an non-biological structure or body part.

Figure 19:
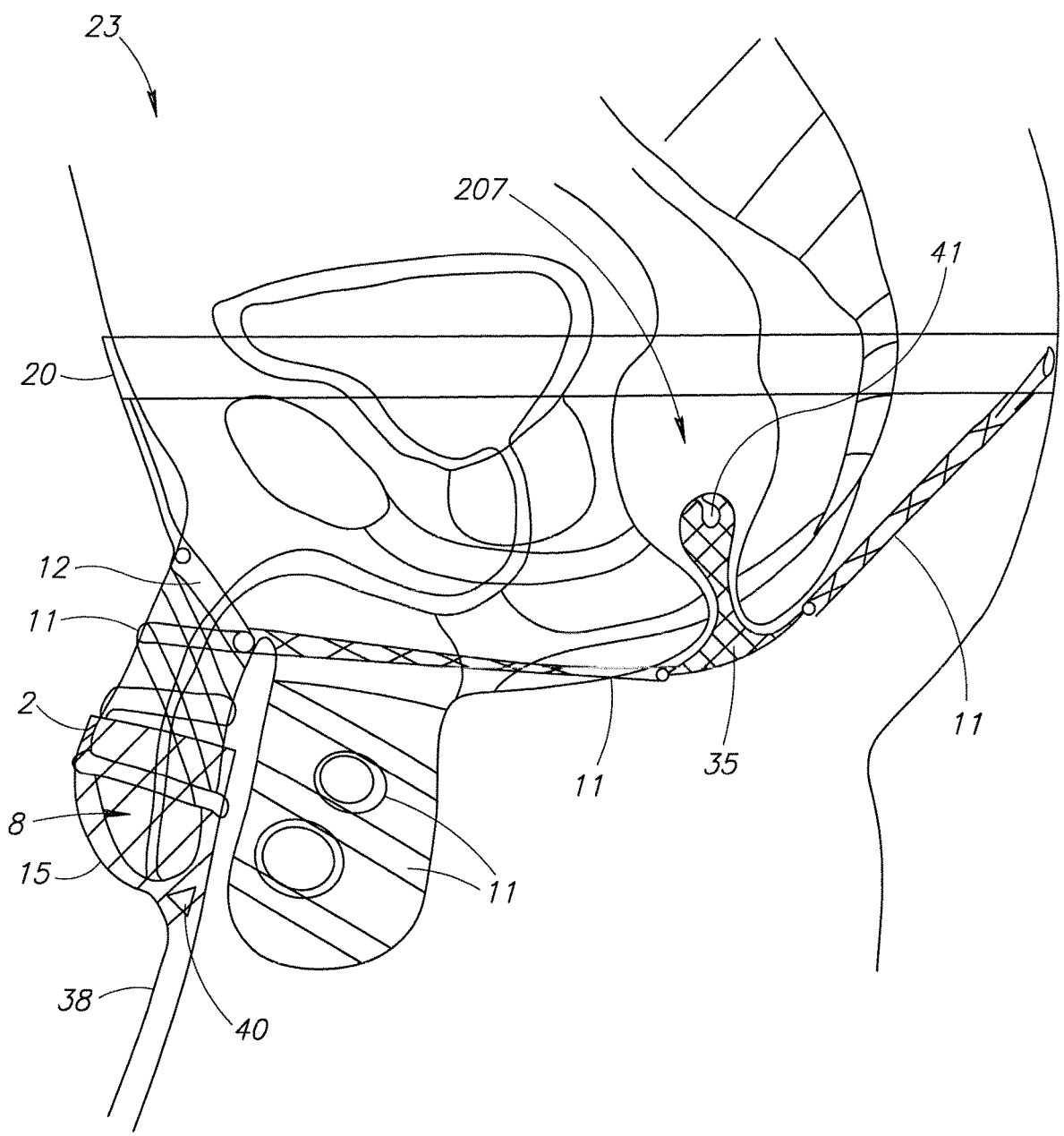
FIG. 19 is a sagittal view of a urinary collection device 23 or condom catheter 15 in which the anchoring orifice can be the anus and the condom catheter 15 can be attached to the anchoring device 35.

FIG. 19 is a sagittal view of a male urinary collection device 23 or male condom catheter 15, in which the anchoring device 35 can be the anus and a male condom catheter 15 can be attached to the anchoring device 35. The male urinary collection device 23 has one orifice anchoring device 35 in the anus 207. The orifice anchoring device 35 can be used alone or in combination with one or a combination of elements to include a fixation device 11 or a garment 20 or a sealing pad 2, or a skin covering material 3, or a medication delivery system or urinary collection device 23 or can be impregnated 40 with a substance or can reside within a reservoir 41 delivery system that can include a solid or liquid or gel or gas that can alter or augment or diminish a biological function that can include a biological acting material to include a medicine to include an antibiotic, a lubricant, a sexual stimulant or inhibitor, an anaesthetizing agent or stimulating agent, a pain altering agent, a neutralizing agent, an agent that changes the pH of a non-biological structure or body part 8, or an agent that cleanses or disinfects an non-biological structure or body part 8.

Figure 20:
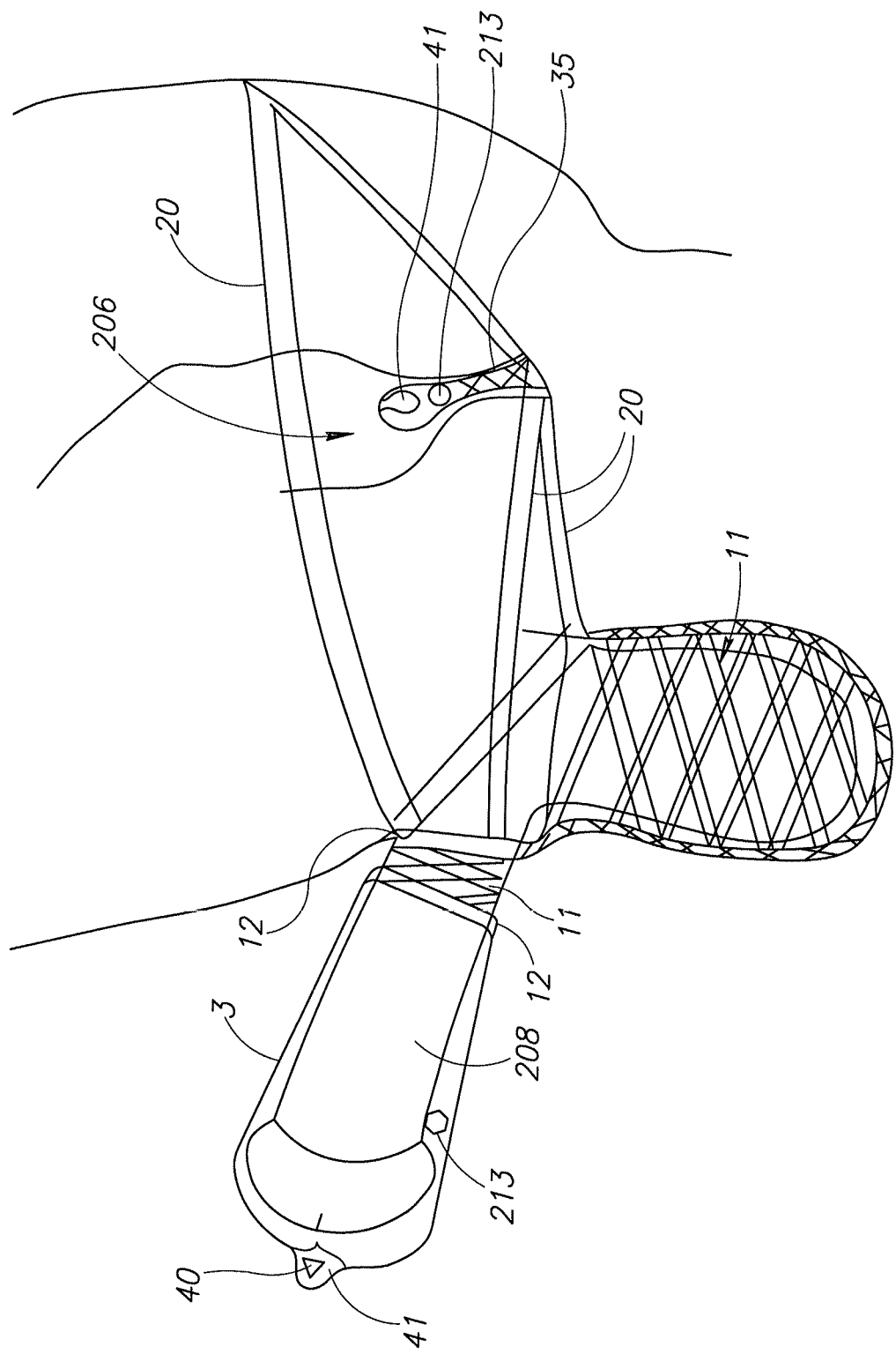
FIG. 20 is a sagittal view of a contraceptive device 209 which can include one or more than one orifice 206 anchoring device 35 and can include orifice 206 to include the anus and the vagina.

FIG. 20 is a sagittal view of a contraceptive device 209 which can include one or more than one orifice anchoring device 35 and can include orifice 206 to include the anus and the vagina. The contraceptive device can include an orifice anchoring device 35 which can be used alone or in combination with one or more elements to include a fixation device 11 or a garment 20 or a sealing pad 2, or a skin covering material 3, or a medication delivery system or device 213 or can be impregnated 40 with a substance or can reside within a reservoir 41 or medication delivery system or device 213 and the substance can include a solid or liquid or gel or gas or energy source that can alter or augment or diminish a biological function that can include a biological acting material to include a medicine to include an antibiotic, a lubricant, an erection or a sexual stimulant or inhibitor, an anaesthetizing agent or stimulating agent, a pain altering agent, a neutralizing agent, an agent that changes the pH of a non-biological structure or body part, or an agent that cleanses or disinfects an non-biological structure or body part. This embodiment depicts an erect male penis 208 with a skin covering material 3 which is a condom which can contain a substance, a receptacle 39, an impregnated 40 substance, or a reservoir 41 or a medication delivery system or device 213 that can contain a substance that can include a medication, a lubricant, a contraceptive material, a substance that alters sensation, a pleasuring substance or a biological substance that can include antibodies to a biological substance to include sperm or to an infectious agent such as Herpes virus and HIV virus and papaloma virus; or a sexual pleasuring medication delivery system or device 213 to include a vibrator or electrical stimulator or feedback device 42. The condom 3 can be intimately associated with or include a fixation device 11, and a sealing pad 2, and a garment 20. The contraceptive device can be anchored using an orifice anchoring device 35 which can include an anal anchor. The anal anchor can be used alone or in combination with one or more elements to include a fixation device 11 or a garment 20 or a sealing pad 2, or a skin covering material 3, or a medication delivery system or device 213 or can be impregnated 40 with a coating substance or can reside within a reservoir 41 delivery system that can include a solid or liquid or gel or gas that can alter or augment or diminish a biological function that can include a biological acting material to include a medicine to include an antibiotic, a lubricant, a sexual stimulant or inhibitor, an anaesthetizing agent or stimulating agent, a pain altering agent, a neutralizing agent, an agent that changes the pH of a non-biological structure or body part, or an agent that cleanses or disinfects an non-biological structure or body part. The anchor can contain a coated substance, a receptacle 39, an impregnated 40 substance, or a reservoir 41 or a medication delivery system or device 213 that can contain a substance that can include a medication, a lubricant, a contraceptive material, a substance that alters sensation, a pleasuring substance or a biological substance that can include antibodies to a biological substance to include sperm or to an infectious agent such as Herpes virus and HIV virus and papaloma virus; or a sexual pleasuring medication delivery system or device 213 to include a vibrator or electrical stimulator or a feedback device 42. In the female the vagina or the anus or the local skin and skin covering material 3 between the vagina and anus can contain a medication delivery system or device 213 or can be impregnated 40 with a coating substance or can reside within a reservoir 41 delivery system that can include a solid or liquid or gel or gas that can alter or augment or diminish a biological function that can include a biological acting material to include a medicine to include an antibiotic, a lubricant, a sexual stimulant or inhibitor, an anaesthetizing agent or stimulating agent, a pain altering agent, a neutralizing agent, an agent that changes the pH of a non-biological structure or body part, or an agent that cleanses or disinfects an non-biological structure or body part. The anal anchoring device 35 can contain a coated substance, a receptacle 39, an impregnated 40 substance, or a reservoir 41 or a medication delivery system or device 213 that can contain a substance that can include a medication, a lubricant, a contraceptive material, a substance that alters sensation, a pleasuring substance or a biological substance that can include antibodies to a biological substance to include sperm or to an infectious agent such as Herpes virus and HIV virus and papaloma virus; or a sexual pleasuring medication delivery system or device 213 to include a vibrator or electrical stimulator or a feedback device 42.

Figure 21:
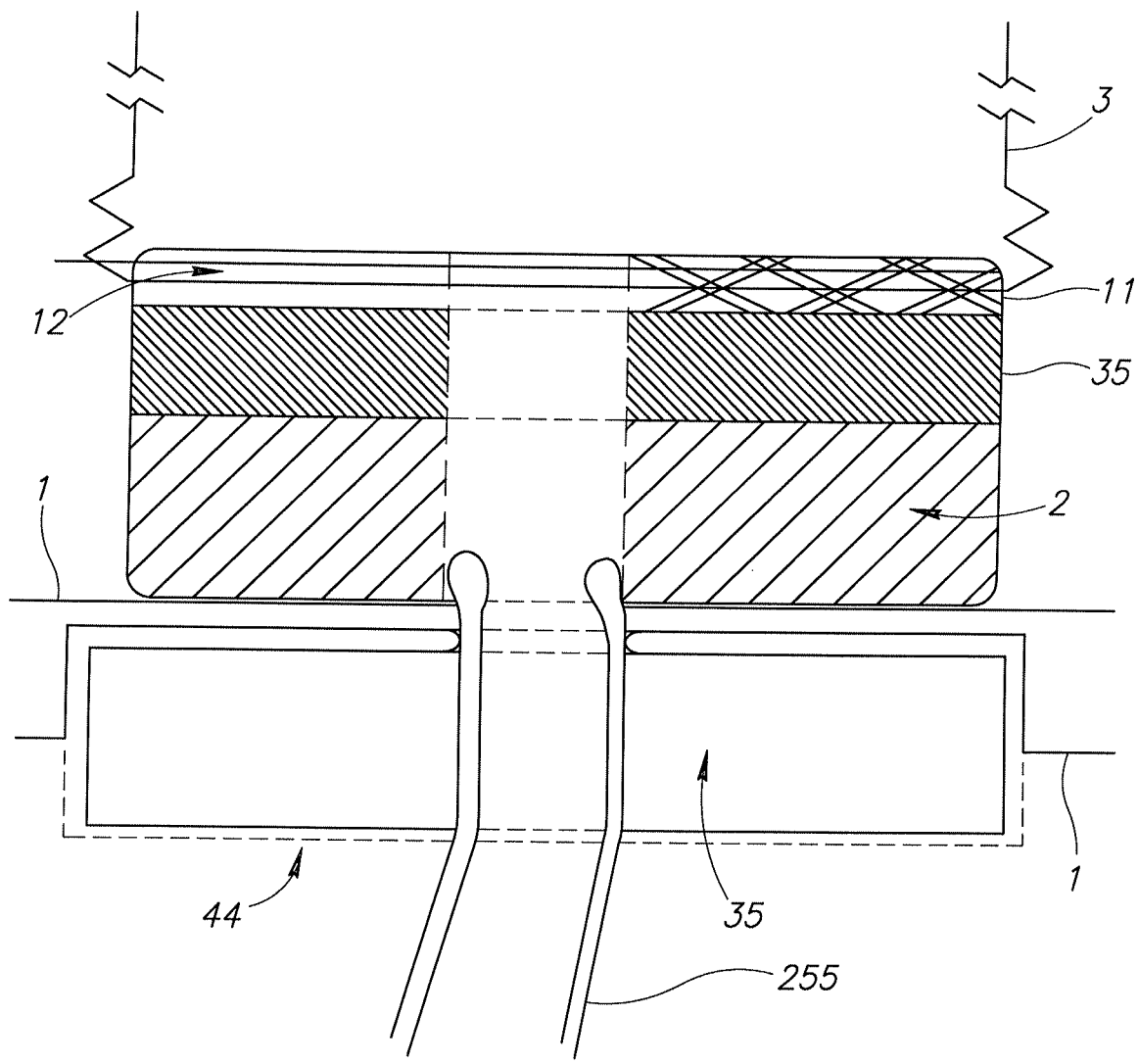
FIG. 21 is a sagittal view of an ostomy 255 sealing pad 2 and skin covering material 3.

FIG. 21 is a sagittal view of an ostomy 255 sealing pad 2 and skin covering material 3. In this embodiment the anchoring device 35 can be placed within a user's skin 1 tunnel or crease 44 in the body. A crease 44 in the body can include the crease of the buttocks or adipose folds of the belly in an obese individual or a surgically constructed crease or tunnel can be created. A tunnel in the body can include a surgically constricted crease, an internal cavity, a natural body part tunnel such as a muscle and bone interface or an internally or externally constructed user's skin 1 tunnel which can be constricted near and ostomy site. One embodiment can include the use of the sealing pad 2 and the skin covering material 3, as an ostomy seal and bag, respectively, with a user's skin 1 surgically tunnel to house the anchoring device which can be composed of a material to include a biological compatible silicon, gel, metal or other solid of gel. In one embodiment at least one component of the anchoring device 35 can reside between the layers of the user's skin 1 or within the user's skin 1 or deep to the user's skin 1 or in a body part to include a muscle. A second component of the anchoring device 35 can reside between the layers of the user's skin 1 or within the user's skin 1 or deep to the user's skin 1 or in a body part to include a muscle or external to the user's skin 1 or body part. In one embodiment the one embodiment the seal can be a gel seal, and that sealing pad 2 can include a sealing pad 2 that resides between the two anchoring components or one or more of the anchoring components can reside within the sealing pad 2, the skin covering material 3 or a fixation device 11 or a garment 20. One or more than one of the anchoring components in the preferred embodiment can be magnetic and can be ferromagnetic or a combination ferromagnetic magnetic. The anchoring device can anchor the gel seal with the use of a method to include electromagnetic forces or energy. Other methods can be used in alone or in combination with electromagnetic energy for attaching the tunnel or crease 44 anchoring device 35 and can include the fixation device 11 as well as standard methods of attaching and anchoring to include adhesives, tackifying agents, hooks, VELCRO™ and related fabric hook and loop fasteners, ZIP-LOCK™, straps, belts and elastics. In the preferred embodiment the either the gel sealing pad 2 or the skin covering material 3 or both can form an ostomy bag in which the ostomy 255 has a tunnel that contains a silicone ring that is magnetized. The gel sealing pad 2 can also be magnetized or can be ferromagnetic and create a tight bond between the anchor and the gel seal. The gel sealing pad 2 creates an airtight and watertight seal with the skin and the skin covering material 3, which is an ostomy bag allows for the capture and the flow of fecal material away from the body, This method avoids adhesives, which serve to break down the skin over time and lead to ulcers and infections of the skin. Either the sealing pad 2 or the skin covering material 3 or both can be removable and replaceable. A sealing pad 2 and skin covering material 3 and fixation device 11 and the anchor or a combination of these elements can all be removable and replaceable. Another embodiment not depicted is an appliance that is subcutaneous that can include an appliance that has projections that project from the appliance that can include in the preferred embodiment projections that exit from the skin and contain a method for attachment to an external appliance or ring that can include a ZIP-LOCK™-like device or VELCRO™ and related fabric hook and loop fasteners like device or magnet or any male and female connection that can include a screw or pin or hook or locking mechanism or any combination of these attachments. Between the skin appliance and the external appliance there is a sealing pad 2 or gasket that can include allow an ostomy to remain airtight and watertight. In the preferred embodiment the external appliance can have a skin covering material that can capture the body's discarded contents. Other embodiments can include use with a condom, or a urinary or condom catheter, the anus and fecal material, enzyme and organ secretions or excretions or discards that can include biliary and pancreatic bowel and intestinal and gastric contents.

FIG. 21 also depicts a closure method and device that can include projections and invaginations that in the preferred embodiment can include magnetic pins, hooks, VELCRO™ and related fabric hook and loop fasteners, ZIP-LOCK™, buttons, and other fastening devices that secure the skin tunnel appliance to the external appliance or sealing pad 2 and skin covering material 3 using a method that provides adequate resistance to separation such that the sealing pad 2 and skin covering material 3 are securely attached to the skin tunnel appliance but can also be removed for disposal contents and also will not tear the skin or tear out the skin tunnel appliance if there is a sudden force or tug placed on the sealing pad 2 and skin covering material 3.

Figure 22:
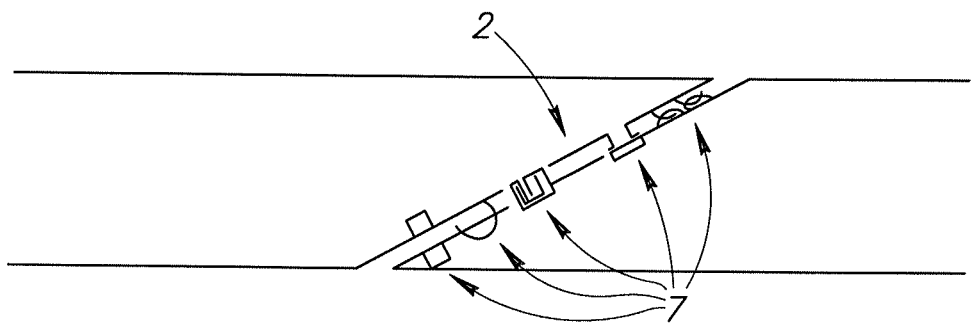
FIG. 22 is a sagittal view of a sealing pad 2 with overlapping ends and depicts how the sealing pad 2 or skin covering material 3 or the fixation device 11 or the combination of the sealing pad 2 and the skin covering material 3 and the fixation device 11 can be joined together using closure devices 7 to include ZIP-LOCK™, VELCRO™ and related fabric hook and loop fasteners, pins or pegs, thread, ties, hooks, zippers, adhesives, buttons, elastic materials or any electromagnetic attachment to include electromagnetic forces and energy to include magnets or mechanical or electromechanically devices such as retractable grappling, hooks or interlocking devices.

FIG. 22 is a sagittal view of a sealing pad 2 with overlapping ends and depicts how the sealing pad 2 or skin covering material or the fixation device or the combination of the sealing pad 2 and the skin covering material and the fixation device can be joined together using closure devices 7 to include ZIP-LOCK™, VELCRO™ and related fabric hook and loop fasteners, pins or pegs, thread, ties, hooks, zippers, adhesives, buttons, elastic materials or any electromagnetic attachment to include electromagnetic forces and energy to include magnets or mechanical or electromechanically devices such as retractable grappling, hooks or interlocking devices. Closure devices 7 can be used alone or in combination. The sealing pad 2 or the skin covering or the fixation device can be closed overlapping or not overlapping and placing the ends adjacent or in opposition to each other. If a gel is used for the sealing pad 2 then the gel can be variable in its softness and hardness and can include being firmer and harder near the closure devices 7 than away from the closure devices 7.

Figure 23:
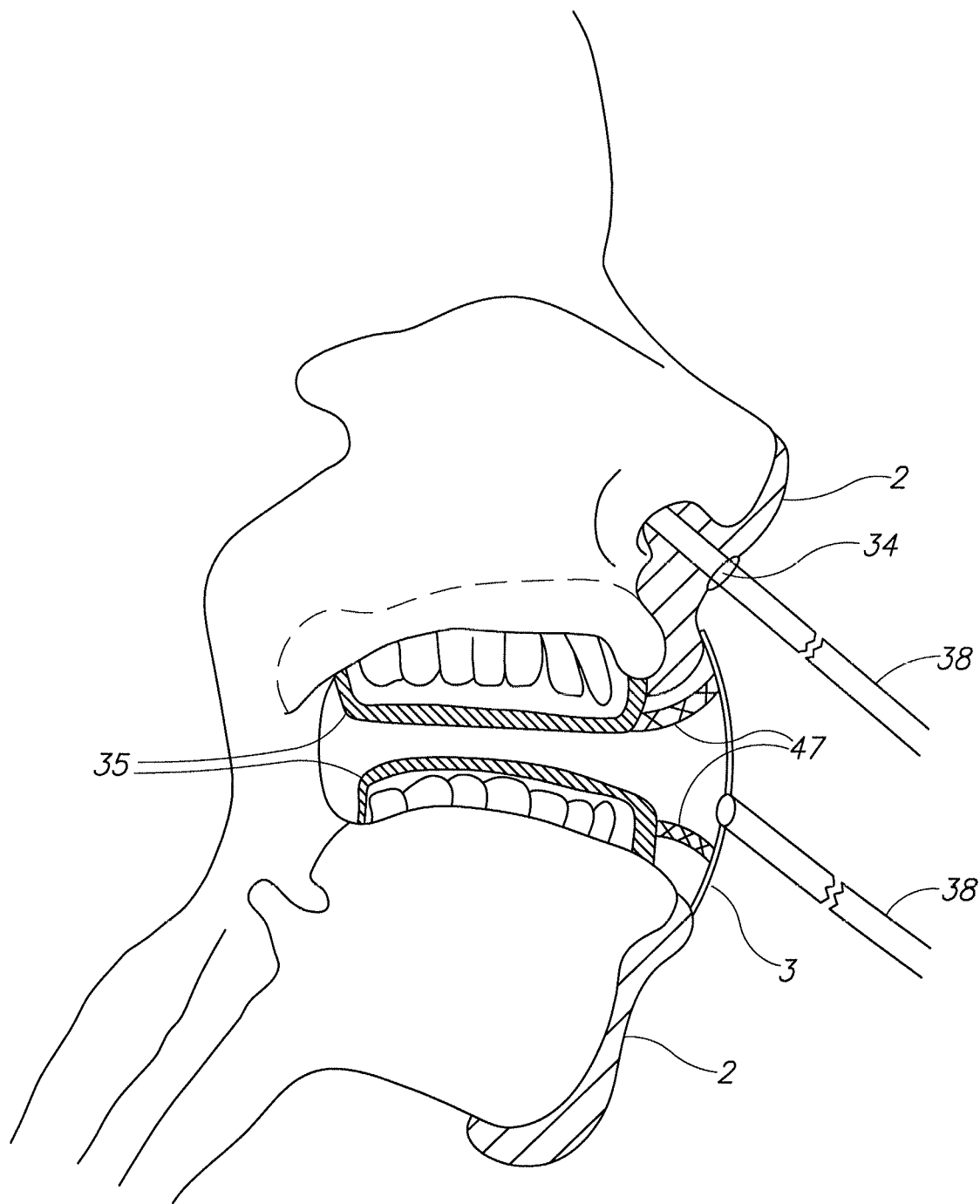
FIG. 23 is a sagittal view of a device, which uses an anchoring device 35 that is formed by anchoring the anchoring device 35 to a body part which can include a tooth or the teeth.

FIG. 23 is a sagittal view of a device, which uses an anchoring device 35 that is formed by anchoring the anchoring device 35 to a body part which can include a tooth or the teeth. In the preferred embodiment the anchoring device 35 can include using one or more mouth-guards that can include at least a portion of the gums or mucosa, a tooth, the teeth or a groups of teeth or the upper or lower rows of teeth or any combination of these teeth. The anchoring device can be used with a sealing pad 2 or skin covering material 3 or the fixation device or the combination of a sealing pad 2 and skin covering material 3 and fixation device to create a device to include a breathing mask to include a ventilation unit, a CPAP or BIPAP or positive ventilation mask, or anesthesia mask or other means to ventilate the user which can include human and non-human creatures. The skin covering material 3 can be attached directly to the anchoring device 35 or can have a bridging structure 47 between the anchoring device 35 and the skin covering material 3. The skin covering material 3 can include fenestration 34 tube 38 for the transfer of solids or liquids or gases or gels for uses to include ventilation or irrigation or aspiration. The sealing pad 2 and the skin covering material 3 can include covering body part and orifices to include the mouth, ear, nose and nostrils, ear canals, a surgical or natural body cavity, the vaginal, urethra, anus and rectum and ostomy which can include an intestinal or bowel diversion or ureteral or urethral diversion or tracheostomy or diversion of another body part.

Figure 24:
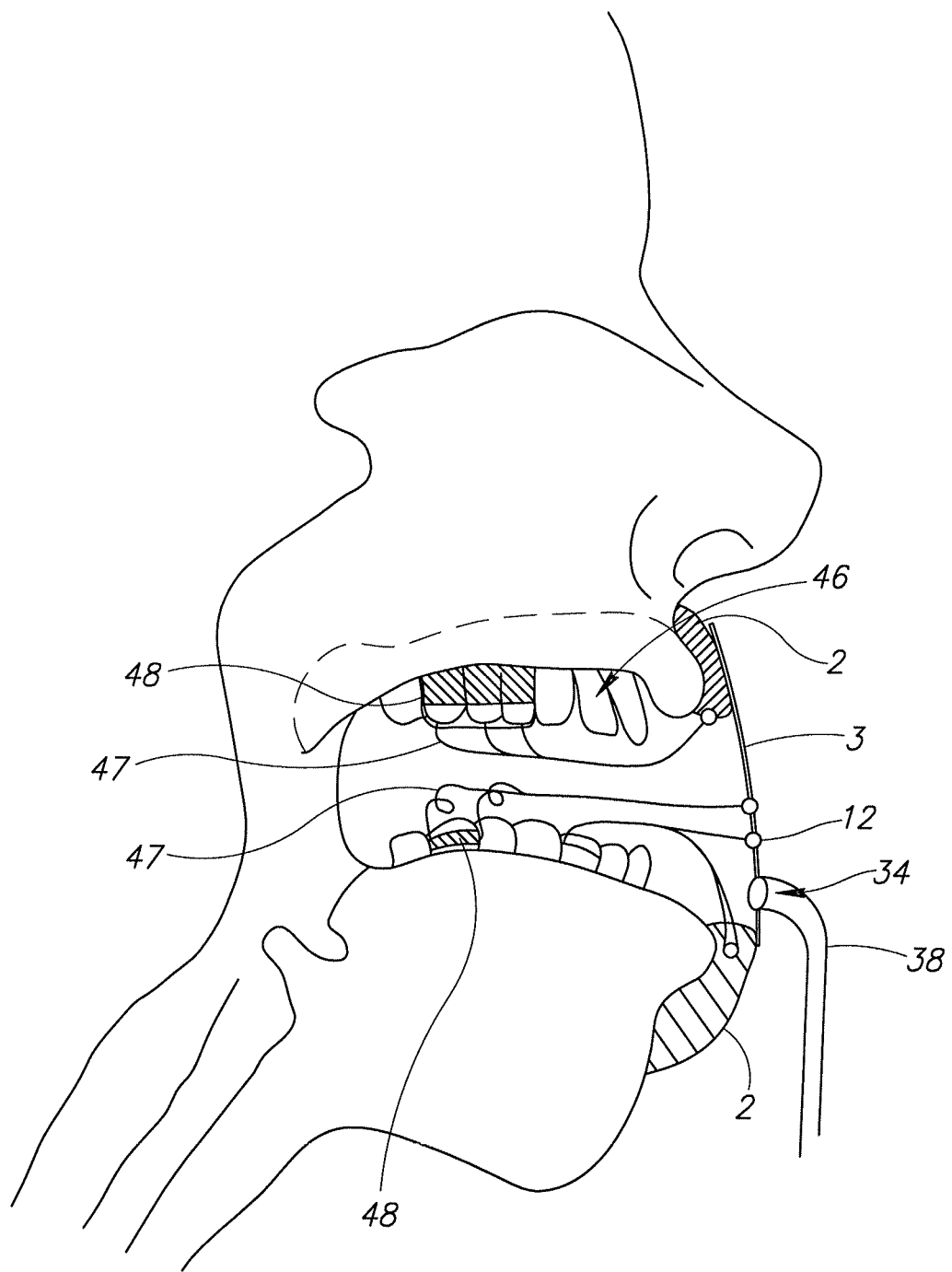
FIG. 24 is a sagittal view of a device, which uses an anchoring device that is formed by anchoring the anchoring device by a means to include anchoring the anchoring device using at least one brace or tooth appliance.

FIG. 24 is a sagittal view of a device, which uses an anchoring device that is formed by anchoring the anchoring device by a means to include anchoring the anchoring device using at least one brace or tooth appliance 48 that can include anchoring device that anchors a tooth or teeth 46 by surrounding at least a portion of the tooth or teeth 46 with a solid or gel material that can include metal braces, plastic braces, latex, non-latex materials, a rubberdam and rubberdam-like device, rubber and rubber-like materials that can include at least a portion of a body part to include a tooth, the teeth or a groups of teeth or the upper or lower rows of teeth or any combination of tooth or teeth 46 or gums. The anchoring device can be used with a sealing pad 2 or skin covering material 3 or the fixation device or the combination of a sealing pad 2 and skin covering material 3 and fixation device to create a device to include a breathing mask to include a ventilation unit, a CPAP or BIPAP or positive ventilation mask, or anesthesia mask or other means to ventilate the user which can include human and non-human creatures. The skin covering material 3 can be attached directly to the anchoring device or can have a bridging structure 47 between the anchoring device and the skin covering material 3. The skin covering material 3 can include fenestration 34 tube 38 for the transfer of solids or liquids or gases or gels for uses to include ventilation or irrigation or aspiration. The sealing pad 2 and the skin covering material 3 can include covering body parts and orifices to include the mouth, ear, nose and nostrils, ear canals, a surgical or natural body cavity, the vaginal, urethra, anus and rectum and ostomy.

Figure 25:
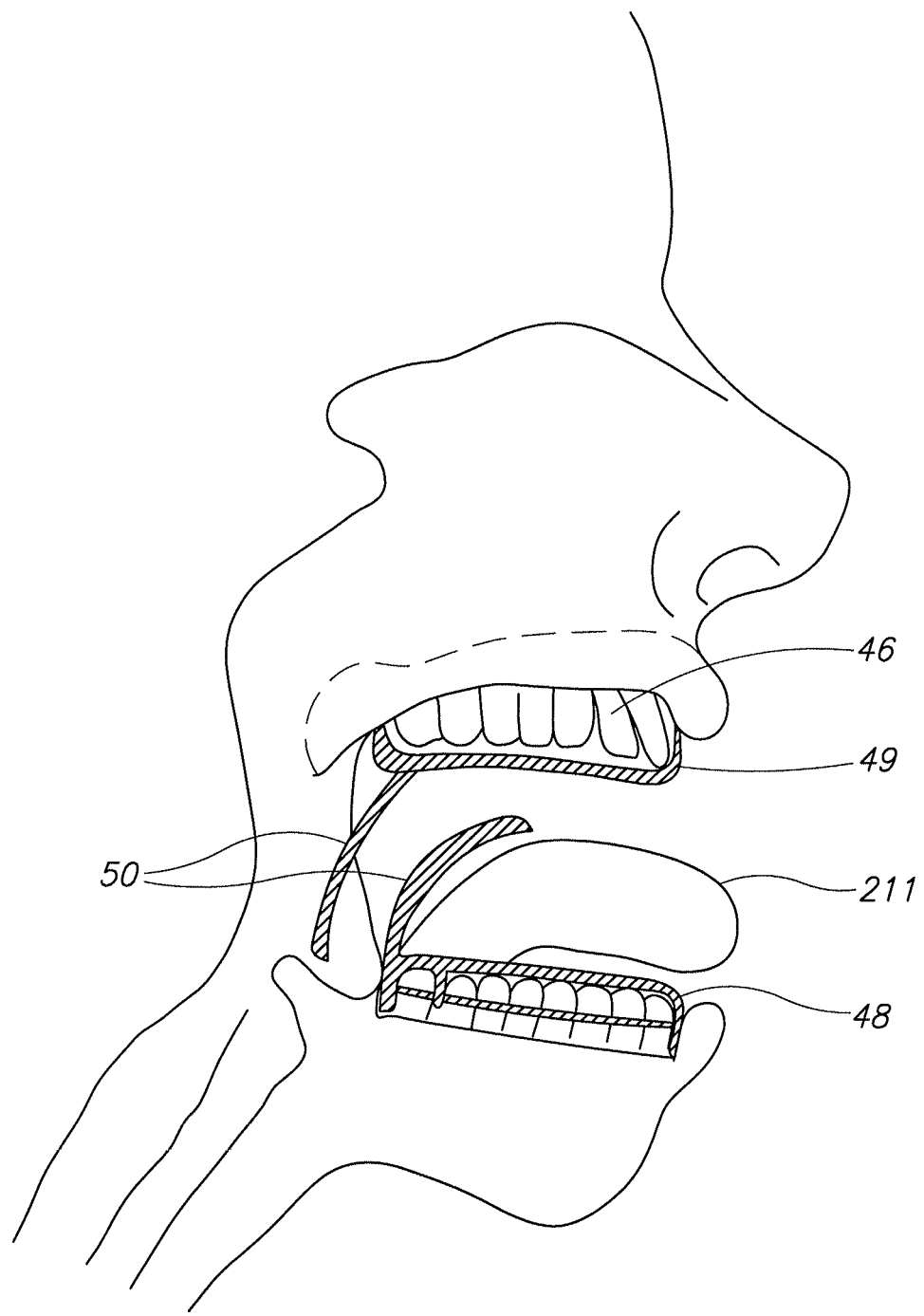
FIG. 25 is a sagittal view of a device, which uses an anchoring device that can restrict movements of structures to include tongue movement posteriorly for preventing sleep apnea.

FIG. 25 is a sagittal view of a device, which uses an anchoring device that is formed by anchoring the anchoring device by a means to include anchoring the anchoring device using at least one brace or tooth appliance 48 that can include anchoring device that anchors a tooth or teeth 46 by surrounding at least a portion of the tooth or teeth 46 with a solid or gel material that can include metal braces, plastic braces, latex, non-latex materials, a rubberdam and rubberdam-like device, rubber and rubber-like materials that can include at least a portion of a body part to include a tooth, the teeth or a groups of teeth or the upper or lower rows of teeth or any combination of these tooth or teeth 46 or gums and the anchoring device can include using one or more mouth-guards that can include at least a portion of the gums or mucosa, a tooth, the teeth or a groups of teeth or the upper or lower rows of teeth or any combination of these teeth.

The anchoring device can be used with a sealing pad 2 or skin covering material 3 or the fixation device 11 or the combination of a sealing pad 2 and skin covering material 3 and fixation device 11. In the preferred embodiment the anchoring device can include using at least one mouth-guards 49, or bite-block or brace or tooth appliance 48, that can include a device that anchors the tooth or teeth 46 by surrounding at least a portion of the tooth with a solid or gel material that can include metal braces, plastic braces, latex, non-latex materials, a rubberdam and rubberdam-like device, rubber and rubber-like materials that can include at least a portion of a tooth, the teeth or a groups of teeth or the upper or lower rows of teeth or any combination of these teeth that can be used with a tongue 211 appliance that can restrict or alter the tongue's movements to include preventing the tongue 211 from sliding backwards and obstructing the respiratory airway; or an tongue appliance 50 that can restrict or alter the epiglottis movements to include preventing the epiglottis from sliding down or backwards and obstructing the respiratory airway; or a soft palate or mucosal appliance that can restrict or alter the epiglottis movements to include preventing the epiglottis from sliding down or backwards and obstructing the respiratory airway or a combination of the above appliances. This can be used for sleep apnea or other conditions that are dependent on the position of the tongue, lips, teeth, or other components of the human mouth.

Figure 26:
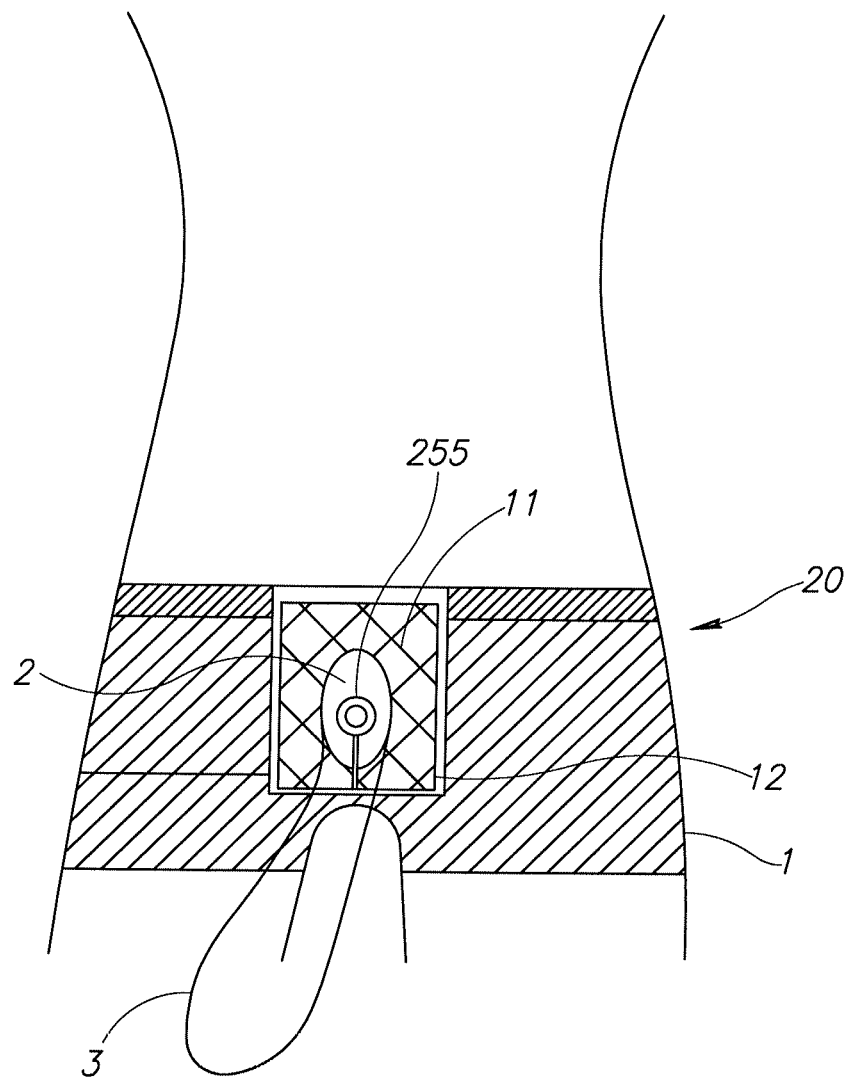
FIG. 26 is a frontal view of an ostomy fixation device 11 that can be used with a garment 20 or a material.

FIG. 26 is a frontal view of an ostomy 255 fixation device 11 that can be used with a garment 20 or a material to include clothing or a garment 20 or a belt that can be composed of a material to include cloth, fabric, natural or synthetic-man-made materials to include nylon, rayon, and polyester-like materials, plastics, plant based materials, metals and metal mesh material. In the preferred embodiment a fixation device 11 can include gel and is intimately associated with a garment 20 and the fixation device 11 can be separate or integrated into the garment 20. The fixation device 11 and the garment 20 can be associated with or be integrated into a sealing pad 2, a skin covering material 3, and anchoring device 35 and in the preferred embodiment the garment 20 and fixation device 11 and utilize to assist in fixing an ostomy sealing pad 2 and skin covering material 3 in the form of an ostomy bag in proper location and other uses can include use with a urinary diversion catheter, a contraceptive device, a breathing mask, a device to alter sensations to include pain and pleasure and temperature and touch and pressure.

Figure 27:
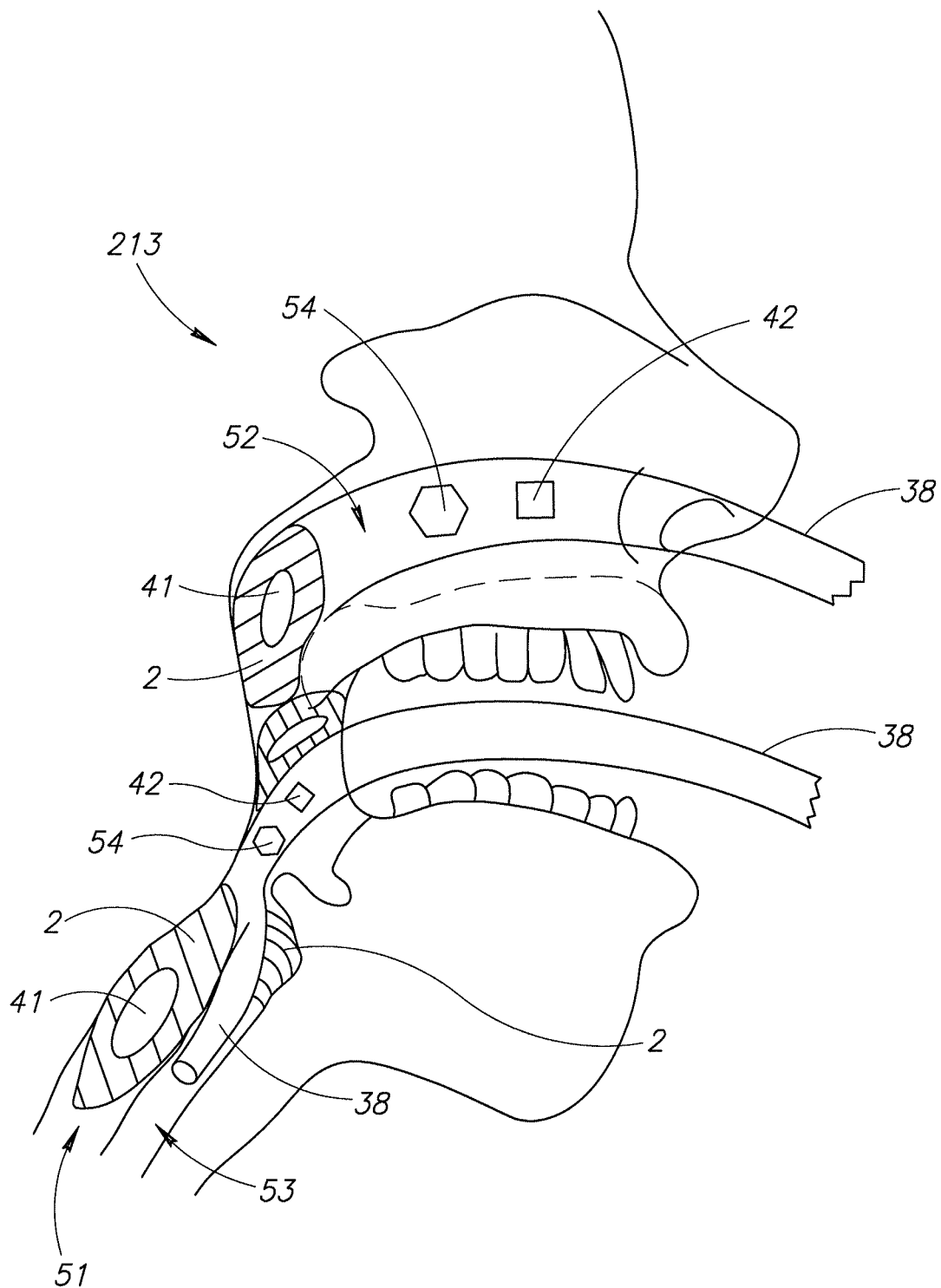
FIG. 27 is a breathing mask or ventilation or intubation device which can use a sealing pad 2 with a skin covering material 3 in conjunction with a liquid solution or a solid material or a gas or a mixture of these substances as an exchange material that can facilitate the organism gas exchange of substances such as oxygen or carbon dioxide.

FIG. 27 is a breathing mask or ventilation or intubation device which can use a sealing pad 2 with a skin covering material 3 in conjunction with a liquid solution or a solid material or a gas or a mixture of these substances as an exchange material that can facilitate the organism gas exchange of substances such as oxygen or carbon dioxide. The skin covering material 3 can facilitate the osmotic exchange of other blood containing substances such as urea, glucose, and electrolytes and minerals and can form as a form of dialysis. The introduction of substances such as medications can be facilitated by the breathing mask to include antibiotics, anti-fungal and anti-viral drugs, surfactant materials and other lung performance facilitating medications. Some of the substances that can be used to exchange vital gases for organisms can include chemical compounds which can carry and release oxygen perfluorocarbons (PFCs of which a specific PFC used is perfluorodecalin; hemoglobin derived from humans, animals, or artificially via recombinant technology, Hemoglobin-based oxygen carriers, to include lecithin surfactants, Oxygen, Oxycyte PHER-O2, and Perftoran.

In the preferred embodiment a gel sealing pad 2 with a skin covering material 3 that serves as a ventilation tube can be used to intubate an organism. The sealing pad 2 forms an airtight seal with the digestive track to include the esophagus and GE junction and stomach to prevent liquids from entering the stomach this seal should be airtight and watertight. Coincidentally a second seal is formed with the respiratory track to include the larynx, trachea or bronchi or their branches. Once a seal is formed with at least one of the two passages, the digestive passage or the respiratory passage or with both passages, the liquid ventilation can commence. In the preferred embodiment the ventilation or intubation device can be branched with one or more branches with one branch extending into the esophagus and digestive tract 51 and the other branch appendage extending into the nasal pharynx 52 and another branch extending into the portion of the respiratory track that includes the trachea and bronchi 53. A gel sealing pad 2 can contain a reservoir 41 that is filled with a solid or liquid or a gas and can expand to create an airtight or watertight seal to include one or more than one body parts and orifices to include the digestive tract 51, the nasal pharynx 52, the respiratory track trachea and bronchi 53. Indicators and measuring device 54 and feedback devices 42 can be used to control the degree of expansion of the gel sealing pad 2 and the reservoir 41 to include regulation of reflux, water tightness and airtightness, substance exchange to include solids and liquids and gels and gases. In another embodiment the intubation device can contain indicator and measuring device 54 on the surface or internal to the sealing pad 2 that can feedback to the individual who is ventilating or intubating the individual who is intubated with measurements to include the pressure of the gel on the mucosa or skin or cavity and feedback can include altering the reservoir inflation or deflation. In another embodiment additional sensors can include temperature probes and softness and hardness probes which can be used with one or more indicator and measuring device 54 and in one embodiment a method for softening or hardening the gel can include a reservoir 41 that can be expanded or a heating or a cooling feedback device 42 that can be placed into the gel sealing pad or near the gel sealing pad 2 or into the skin covering material 3 or near the skin covering material 3 to alter the physical characteristics of the gel sealing pad 2 to make the gel sealing pad 2 and its seal more effective or to reduce the stress of the intubation device on the mucosa or cavity skin and lining depending on the indicator and measuring device 54.

Figure 28:
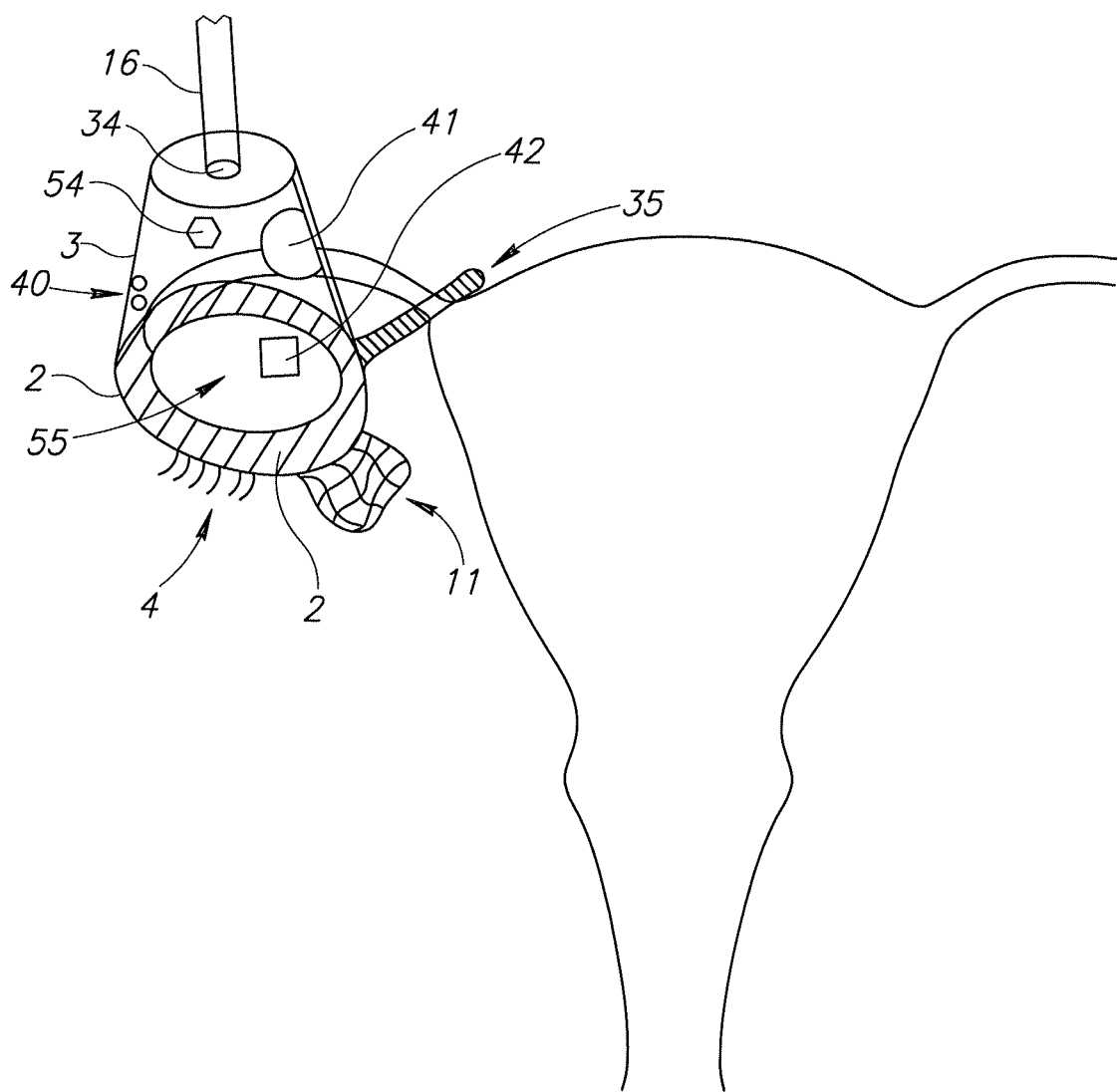
FIG. 28 is a frontal view that depicts the isolation of a body part on the external portion of the body or the internal portion of the body to include a cavity or within a cavity or within the body part or within a hollow viscous organ.

FIG. 28 is a frontal view that depicts the isolation of a body part on the external portion of the body or the internal portion of the body to include a cavity or within a cavity or within the body part or within a hollow viscous organ can include the isolation of a body part to include an ovary can be created by using an annular sealing pad that can be a gel or a non-gel material and a skin covering material to include the isolation of a body part that can include the isolation of a cancerous ovary from the remainder of the pelvic cavity to include the prevention of the spillage of ovarian cancer cells into the pelvic cavity or to isolate the ovary 55 for the application of energy or a substance to include medication, chemotherapy or other gases or liquids or gels or solids or radiation or ultraviolet or infrared or visible light or other electromagnetic energy or kinetic energy that are to be delivered to the body part to include the ovary and restricted from other body parts to include the pelvic cavity. The sealing pad 2 or the skin covering material 3 can have one or multiple conduit 16 that can provide for the instillation and removal or medication or therapeutic substances into the treatment region while protecting the remainder of the body from the effects or side-effects of the energy, medication or therapeutic substances including the combination of energy and substances to activate or equilibrate or deactivate their effectiveness. The sealing pad and the skin covering material can include one or more or a combination of tube or conduit 16, reservoir 41, fenestration 34, impregnated materials indicator and measuring device 54, feedback device 42, anchoring device 35, receptacle 39, devices that create compression devices, fixation device 11, or the one or more flanges 4 or treatment devices.

Figure 29:
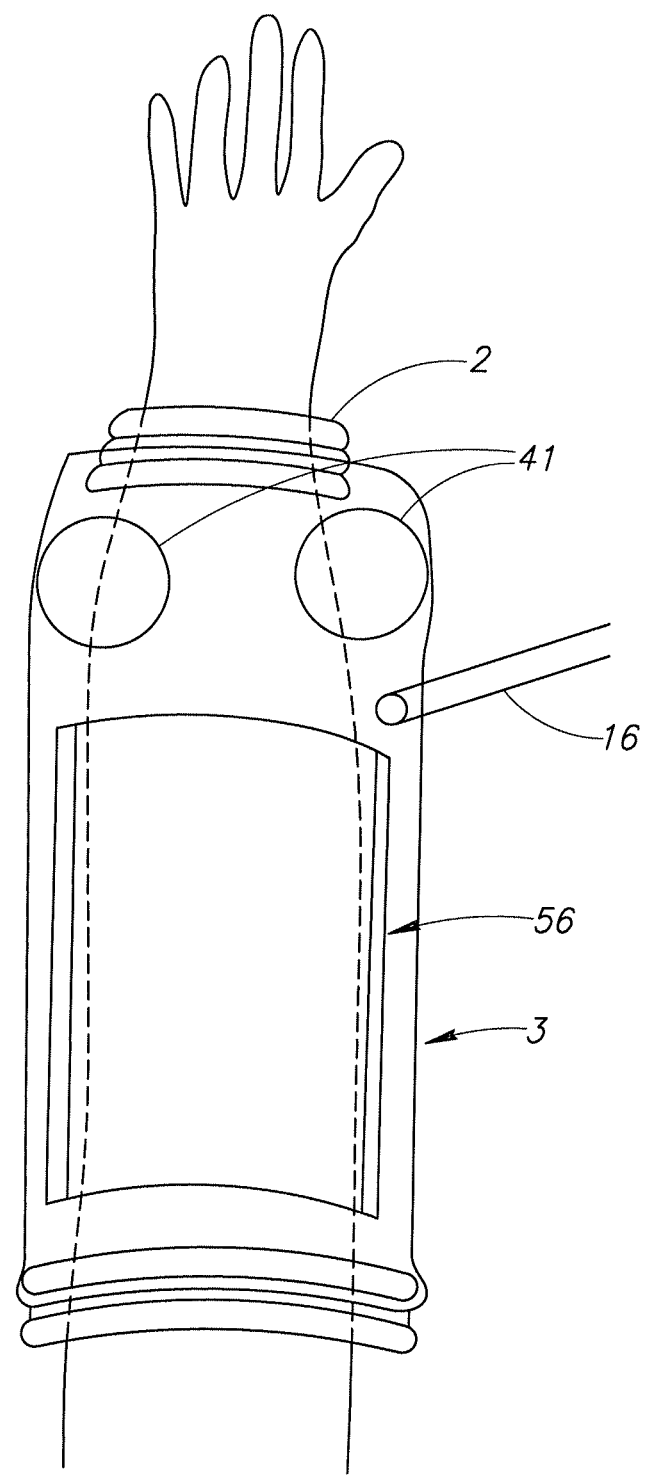
FIG. 29 is a frontal view that can consist sealing pad 2 and skin covering material 3 that can be utilized to include a cast or bandage or wound 56 cover 3 that can contain a reservoir 41 or one or more conduit 16 for delivery or removal of substances containing a solid or liquid or gel or gas that can include a therapeutic, pleasurable, moisturizing, humidifying or drying, heating or cooling, anti-itching substance or medication.

FIG. 29 is a frontal view that can consist the sealing pad 2 and skin covering material 3 that can be utilized to include a cast or bandage or wound 56 cover that can contain a reservoir 41 or one or more conduit 16 for delivery or removal of substances containing a solid or liquid or gel or gas that can include a therapeutic, pleasurable, moisturizing, humidifying or drying, heating or cooling, anti-itching substance or medication. The use of the substance or medication can include agents that are antibiotic, antibacterial, antifungal, antiviral; anti-fogging; scented; detoxifying agent or filter, altering sensation to include relieving pain; dehumidifying or humidifying, heating or cooling, or the delivery of a gas or gel or liquid, or solid for therapeutic purposes or to alter a biological function.

Figure 30:
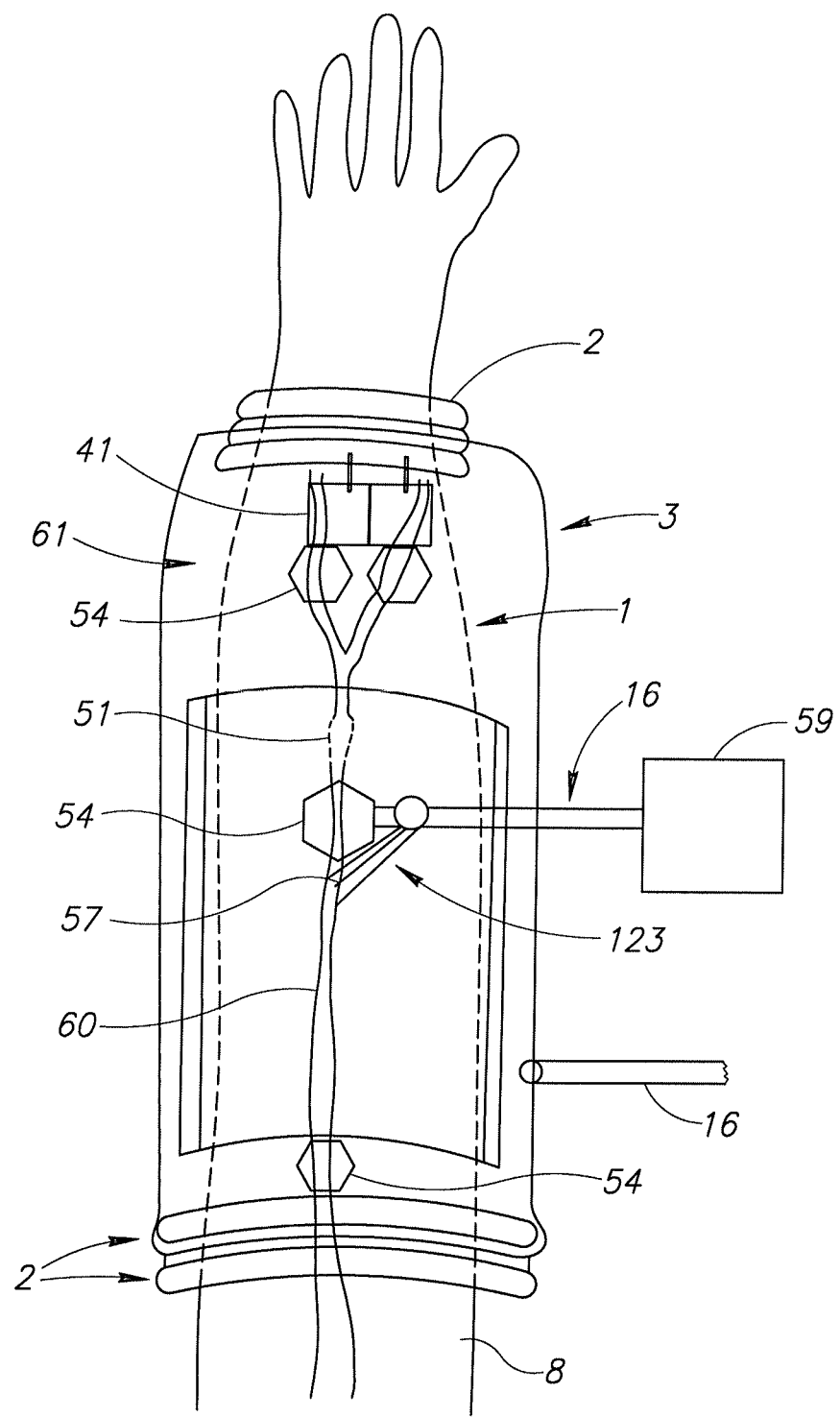
FIG. 30 is a frontal view that depicts a reservoir 41 that can be a compressive device and can contain a solid, liquid or gel or gas or a combination of these elements that can adjust the airtight sealing pad 2 in situations that require greater forces.

FIG. 30 is a frontal view that depicts a reservoir 41 that can be a compressive device and can contain a solid, liquid or gel or gas or a combination of these elements that can adjust the airtight sealing pad 2 in situations that require greater forces this can include a situation where there is a laceration 57 of a blood vessel 60 that includes uncontrolled bleed that fills the sealing pad 2 and skin covering material 3 and internal isolation chamber 61 with blood. In that situation the goal is to attain a pressure in the internal isolation chamber 61 that is equal to, or greater than or less than the arterial inflow pressure which in one embodiment can be the upstream sealing pad 2, which is acting as a tourniquet. In this situation the object is to allow some arterial inflow to keep the tissue alive but restrict the bleeding. In the preferred embodiment this can be measured with an indicator and measuring device 54 to include a measuring device or monitor to include an oxygen monitors to access tissue viability and blood vessel 60 flow with a monitor to include a blood pressure monitor or an ultrasound Doppler monitor to access the vascular waveform which can be connected to the external environment though conduit 16 that maintain the airtight and watertight seal and can communicate with an external device 59 either through wireless or non-wireless methods.

In another embodiment the sealing pad 2 and the skin covering material 3 can serve as an internal isolation chamber 61, which can serve as a therapeutic chamber which can be used to treat a laceration 57 with uncontrolled bleeding. The sealing pad can contain a reservoir 41 or have a device that constricts or contracts the gel sealing pad 2 between the sealing pad 2 and the user's skin 1, within the sealing pad 2 or external to the sealing pad 2. In the preferred embodiment the constricting sealing pad is placed at the location of the wound where there is arterial inflow. The compressive sealing pad 2 can serve as a tourniquet that can allow blood flow through blood vessel 60 into the wound to increase, decrease, remain the same, vary the flow or any combination of these flow speeds or elements. The wound can be isolated to achieve keeping the wound clean, tamponating the wound, stopping the bleeding and treating the wound that can include medicines to include antibiotics, coagulants and anticoagulants, QUIKCLOT™ and related gauze and Chitosan, an extract from shrimp shells and blood products to include platelets. The pressure within the internal isolation chamber 61 can also be regulated to increase, decrease, remain the same, equilibrate or vary or be a combination of these elements relative to the seals, tourniquet, tamponating agents, atmospheric pressures, arterial or venous or body pressure or a combination of these elements can be used to regulate the optimal equilibrium between adequate blood flow and oxygenation to the tissue and at and distal to the laceration. The oxygen and gas content in the internal isolation chamber 61 can be controlled and regulated to also include assist in physiologic homeostasis and cell survival and clotting and other primary biological functions for survival of the organism and the components of the organism.

In the preferred embodiment this can include the combination of regulating the inflow gel sealing pad 2 controlling and regulating arterial inflow in the lacerated artery through regulated pressure on the artery, in combination with regulated oxygenation within the isolation chamber, in combination with varied pressure within the chamber, in combination with medications to induce clotting, in combination with wound isolation and medications to reduce infections, may provide for greater cell and tissue and limb and organism survival. In another embodiment one or more chambers can be utilized which can include treating the tissue distal to the laceration with a second isolation chamber with characteristics dissimilar from the first chamber. Additional treatments can include electromagnetic energy to include UV energy, Infrared energy, radiation, visual energy fields, chemical energy, kinetic, and vibration energy and these treatments can be used alone or in combination to activate, deactivate or equilibrate the treatment. Additional devices that can be used in conjunction with these embodiments can include indicator or measuring device 54, feedback device 42, fixation device 11 or anchoring device 35.

One or more than one additional skin covering materials or chambers can reside lie within the chamber or be integrated into the skin covering material 3 or seal pad 2 or can lie external to the primary skin covering material 3 or a combination of these elements, which can include a rigid frame, a flexible chamber that can include an air-cast to supplement, an external pressure or compression chamber that can facilitate the function of the primary sealing pad 2 and skin covering material 3. One method of treatment can include a method where the blood vessel 60 arterial blood vessels bleeding can be controlled when the internal isolation chamber 61 is equivalent to or greater than systolic pressure. The systolic pressure in the lacerated artery can be regulated and decreased to a manageable level that provides some arterial inflow and oxygenation to the tissue adjacent to or distal to the lacerated vessel. If lower arterial inflow pressure simulating diastolic inflow to the distal tissue can be achieved and an element of venous return can be maintained, then it is more probable than not that a delicate equilibrium can be achieved and maintain to allow survival of the body part, specifically a limb, and its function. The sealing pad 2 serves as an inflow tourniquet. The arterial waveform can be measured by vascular measuring techniques device 54 to include Doppler ultrasound. The pressure of the inflow-sealing pad will be adjusted in response to multiple feedbacks including the inflow distal to the inflow-sealing pad, which can include a reduction peak systolic pressure and reduction in overall inflow volume. Other inflow feedbacks will include down-flow measurement to include Doppler ultrasound of the arteries and veins, tissue pressure, oxygenation which can be measured by indicator and measuring device to include pulse oximeters, and oxygen and carbon dioxide and lactic acid and sugar monitors to include glucose. Once inflow is regulated then the blood that is leaking from the vascular lacerations will fill the internal environment of the isolation chamber. The rigidity and the seal of the skin covering internal isolation chamber 61 can be assisted by one or more than one additional chamber or external skin covering material 3 to include a rigid skin covering material, an inflatable compression chamber that can simulate an inflatable air cast that is used for transport or a pressure body suit that is used for stabilization of transported individuals and the second skin covering material can in the preferred embodiment reside external and adjacent to the internal skin covering material 3 and the internal isolation chamber 61. Blood will fill the internal isolation chamber 61. This blood will be used to form a rigid clot that surround the laceration and can seal the laceration by utilizing clotting materials that can harden and clot exsanguinating blood. Methods of clotting can include solids, liquids, gels or gases to include substances and energy forms to include medications, medications that can be activated and deactivated and equilibrated using another substance to include solids, liquids, gels or gases and energy forms to include substances and energy forms to include medications, medications that can be activated and deactivated and equilibrated and energy forms to include electromagnetic energy, chemical reaction, kinetic energy to include Brownian-energy, heating and cooling and vibration energy forms. These can be delivered through conduit 16 or reservoirs 41 or devices that can deliver substances and energy from the internal isolation chamber 61 or from the external environment 62 or through the body part 8.

One of the objects of this therapy will include form a natural clot graft for the damaged blood vessel 60 during the critical period of transportation to a facility and to care that can more permanently repair the injured body part 8. In addition to forming the blood graft or clot, the oxygenation of the internal isolation chamber 61 chamber can be regulated to create a mini-hyperbaric chamber or mini-hyper-oxygenation chamber to hyper-oxygenate the tissue that is subject to the diminished perfusion. In addition, toxic by-products of ischemia can be removed through osmotic means to include a second adjacent isolation chamber (not depicted) that can have an internal environment that can address the needs of the distal aspect of an ischemic body part. In the preferred embodiment this can include treating a laceration of the femoral artery in the leg and placing the first and primary internal isolation chamber 61 around the leg and having a second internal isolation chamber 61 around the foot and ankle region and treating second isolation chamber that contains this ischemic portion of the limb or that same leg in a manner that differs from the first isolation chamber, One example can include focusing treatment of the first isolation chamber to control bleeding and preserving oxygenation of the local tissue and the attempting to supply some distal blood flow oxygenation while the second isolation chamber may focus on super-oxygenation the distal limb which in this case include the ankle and foot and this can be done by means to include a form of osmotic limb dialysis that bathes the distal extremity in materials to include solids and liquids and gels and gases that can include remove toxic biological materials to include lactic acid and carbon dioxide and deliver advantageous biological materials that can include oxygen, proper ph, and glucose. This process would be monitored by measuring and indicator and indicator and measuring device 54 and feedback devices 42.

Figure 31:
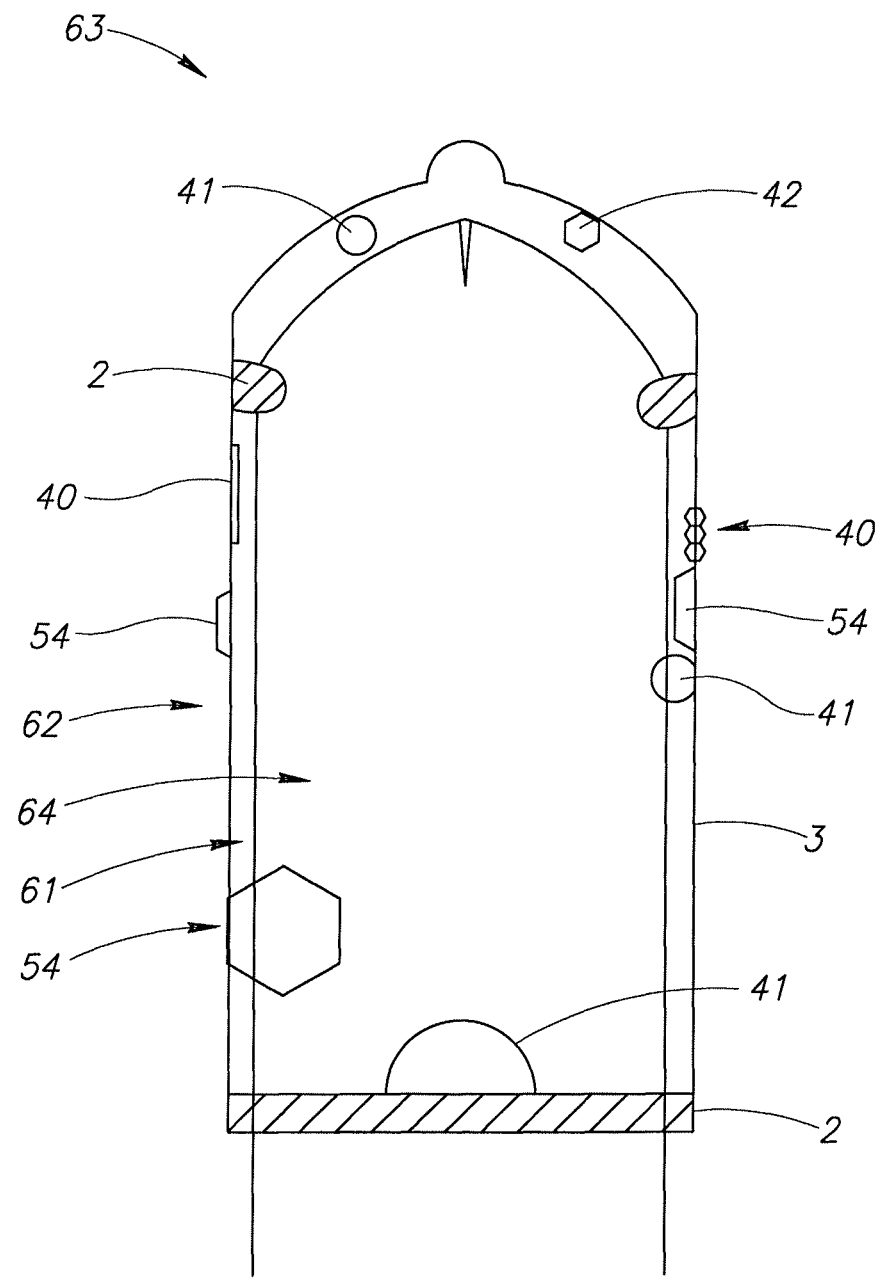
FIG. 31 is a frontal view of a condom which is a skin covering material 3. A condom 63 can include a skin covering material 3 or a skin covering material 3 and a sealing pad 2 or a combination of these elements. The sealing pad 2 and skin covering material 3 can have an indicator and measuring device 54.

FIG. 31 is a frontal view of a condom which is a skin covering material 3. The condom 63 can include a skin covering material 3 or a skin covering material 3 and a sealing pad 2 or a combination of these elements. The sealing pad 2 and skin covering material 3 can have an indicator and measuring device 54 that can measure or assess elements to include a pH, protein, sperm, or fructose or other sugars, which can be displayed using a method to include analog or a digital displays or halochromic materials which can change their color as a result of changing acidity to include a color indicator to include a pH indicator dye to include the detection of semen or vaginal fluid. For the male the pH of semen is 7.2 to 7.8 and for the female the pH of vaginal fluid is 3.8 to 4.5 also semen contains specialize proteins which can include a method to include anti-semen antibodies or using biuret solution to indicate the presence of protein which can be measure using a microchip or a color indicator which can give a signal to include an analog or digital signal, which can be used with a female or male contraceptive device to indicate mingling or leakage or loss of integrity between the penile 64 or and the vaginal side of the seal and skin covering material. In one embodiment to include if a male condom is used then an indicator can be place on the outside of the condom. If sperm and seminal or penile 64 fluid leaks to the outside then the pH of the vaginal fluid will change because of the difference between the vaginal and seminal pH and this change can be measured with a color indicator, or an indicator containing anti-sperm antibodies which when in the presence of sperm reacts and creates a reaction that can be detected by an analog or digital method or a sugar indicator which when fructose is present (fructose is found in seminal fluid) will be detected and will provide an analog or digital signal. In either the male or female condom the indicator and measuring device 54 can be placed on the internal isolation chamber 61 side or the external environment 62 side. If the indicator and measuring device 54 reveals a breach in the skin covering material 3 or sealing pad 2 then a feedback device 42 can release a substance which can include the condom 63 including a reservoir 41 that can mechanically release a substance to include a solid or liquid or gel or gas to neutralize or treat the effects of the breach which as related to this embodiment of contraception include the release of a contraceptive medication to include an anti-spermacide, a gas that kills the sperm, a substance that creates an unfavorable environment for fertilization to include a substance that changes the pH of the vaginal fluid. In another embodiment not depicted a female contraceptive device or condom 63 can be created using similar elements. In either the male or female contraceptive condom 63 the indicator and measuring device 54 or neutralizing substances can reside on the internal isolation chamber 61 or internal environment or external environment 62 relative to the isolated body part. In another embodiment the indicator can be integral to or impregnated 40 into the skin covering material 3 or sealing pad 2.

Figure 32:
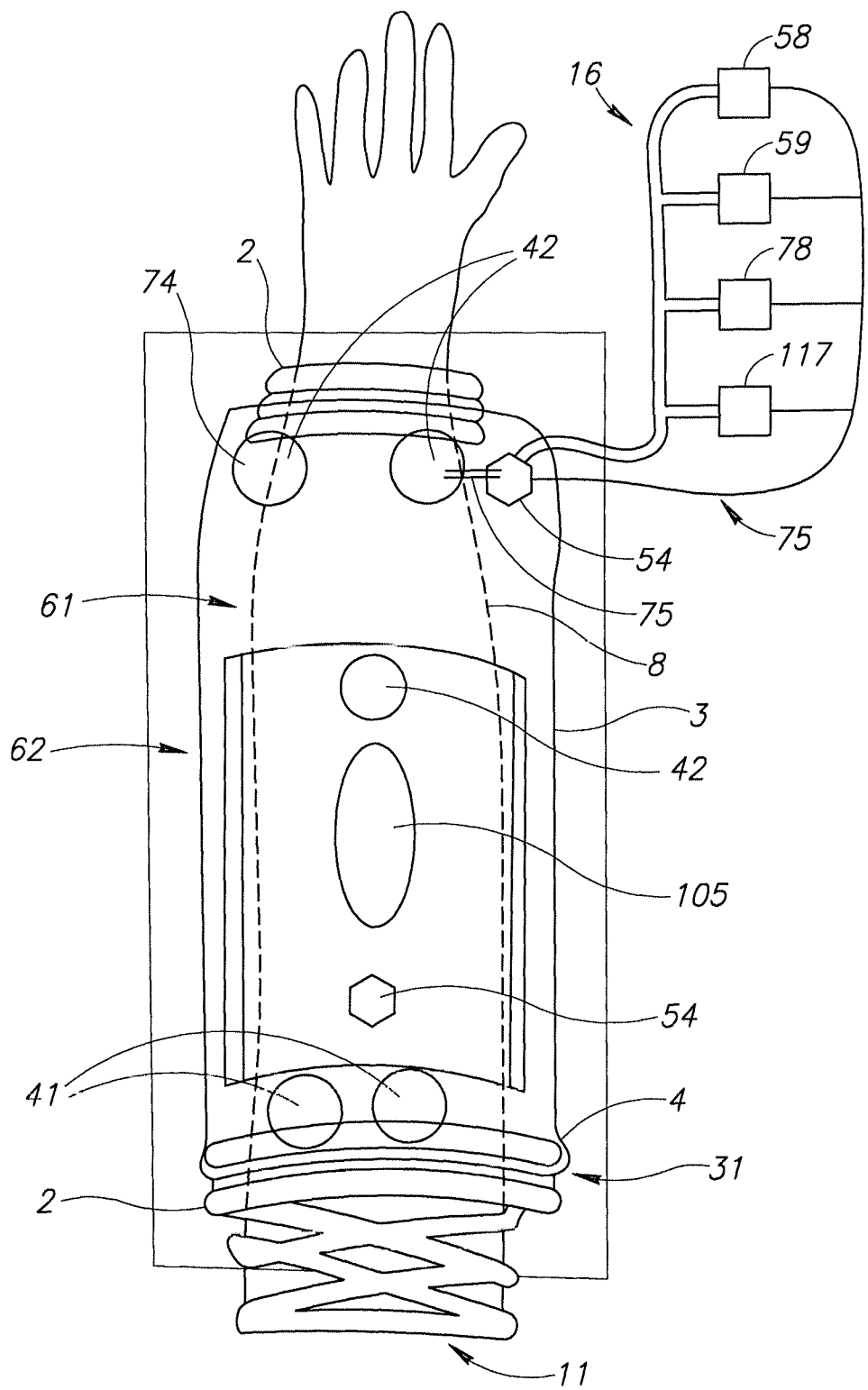
FIG. 32 is a frontal view of an isolation chamber, which include a sealing pad 2 and skin covering material 3 or fixation device 11 or an anchoring device and the one or more flanges 4 or one or more additional chamber or device.

FIG. 32 is a frontal view of an isolation chamber which include a sealing pad 2 and skin covering material 3 or fixation device 11 or an anchoring device 35 and the one or more flanges 4 or one or more additional chamber or device can be utilized within the internal isolation chamber 61 or environment or external environment 62 that can facilitate the effects of the isolation chamber can be added or any combination of these elements, which can become a contained and localized internal isolation chamber 61 or internal environment management chamber to include managing a body part 8 or the entire body to include using indicator and measuring device 54 and feedback mechanisms for managing to include the pH, gas content, the aerobic or anaerobic nature of the isolated environment, elemental content, substance or medication content, electromagnetic content to include radiation or visible or non-visible light spectra to include UV and infrared light, to wetness or dryness, oxygen and other gaseous levels and movement, toxin levels, infectious elements, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, substance levels to include drugs and medications. In the preferred embodiment the sealing pad 2 and the skin covering material 3 can serve as an isolation chamber which can serve as a mini therapeutic or hyperbaric or hyper-oxygen chamber in which the management of the pressure or gas levels can utilize a reservoir 41 in the sealing pad 2 or skin covering material 3 or conduit 16 or the internal isolation chamber 61 for the ingress and egress of gas to include oxygen and other gases and to manage the pressure in the chamber to include a pressure that is less than, equal to or greater than atmospheric pressure. Uses of this isolation chamber can include the treatment of wounds, infections to include aerobic infections which can be denied oxygen, anaerobic infections which can be killed with oxygen or in an oxygen only environment, antibiotic resistant infections to include MRSA infections in which the antibiotic level, or a toxin or a gas mixture or a combination of these elements can be used to treat the infection at a localized site with specific therapeutic methods while isolation other regions of the body from these same therapeutic levels. In another embodiment the sealing pad 2 and the skin covering material 3 can serve as an internal isolation chamber 61 which can serve as a therapeutic chamber to deliver radiation sensitizing materials that can include 5-chlorodeoxycytidine (5-CldC) or 5-halo-2'-halo-2'-deoxy-cytidine or -uridine derivatives, Tetrahydrouridane (H.sub.4 U) and 2'-deoxytetrahydrouridine (dH.sub.4 U) co-administered with the deoxycytidine derivative to inhibit deamination of the deoxycytidine derivatives, agents to reduce the amount of competing metabolites to favor CldC, such as 5-fluoro-deoxyuridine, 1-(2-chloroethyl)-3-cyclohexyl-1-nitrosourea (CCNU), chlorozotocin, 1,3-biscyclohexyl-1-nitrosourea (BCyNU), and 1,3-bis(2-chloroethyl)-1-nitrosourea (BCNU). CCNU, BCyNU, and BCNU; such that when radiation is administered the area being isolated can achieve an added effect from the radiation. In another embodiment the sealing pad 2 and the skin covering material 3 can serve as an internal isolation chamber 61 which can serve as a therapeutic chamber to deliver radiation resistant materials to include antioxidant compounds such that when radiation is administered the area being isolated can achieve a diminished effect from the radiation. In another embodiment the sealing pad 2 and the skin covering material 3 and at least one indicator and measuring device 54 and feedback device 42 can serve as an internal isolation chamber 61 which can serve as a therapeutic chamber in which at least one indicator can be used for the adjustment, management and regulation and assessment and treatment which can be used to treat an ailment to include cancer, auto-immune diseases, degenerative diseases, aging, and other biological condition and in which the feedback mechanism can be used to locally deliver a substance to include a solid, a liquid, a gel or a gas to include a substance that can include a medication that can include chemo0therapeautic agents to include steroids to include prednisone and dexamedrol; and carbo and cis-platinum adriamycin, avastin, methotrexate and taxol and medications to alter biological functions to include sensation to include the use of lidocaine or marcaine. Other devices can be used with these elements to include fixation device 11 and anchoring device 35.

Figure 33:
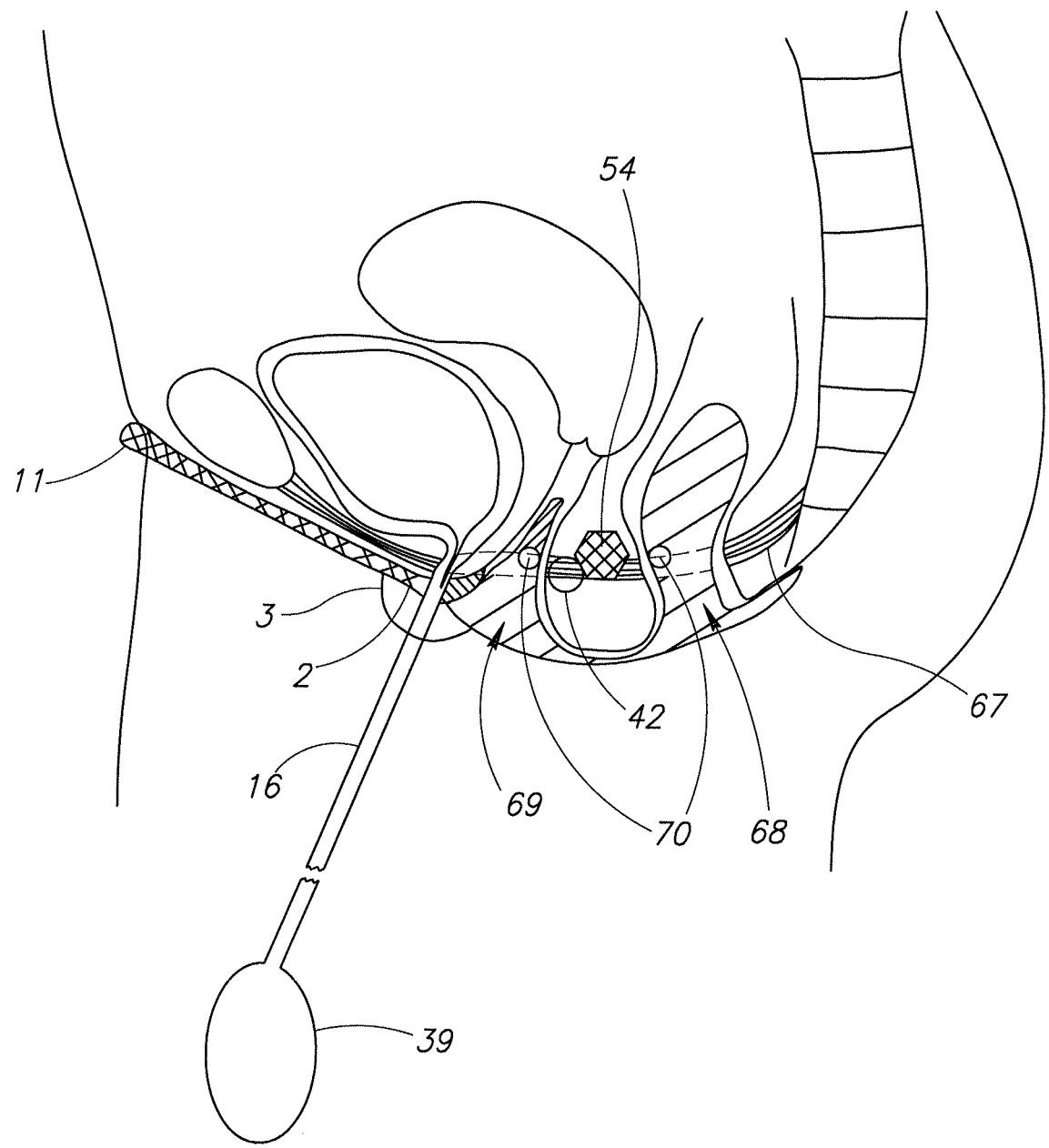
FIG. 33 is a sagittal view of a female urinary retention and diversion device that in the preferred embodiment there can be a combination of a sealing pad 2, a skin covering material 3, an anchoring device that can include an anal anchor 68 or a vaginal anchor 69, a fixation device 11, an indicator and measuring device 54 or a feedback device 42 or a stimulating device 70 or any combination of these elements can be used with a condom catheter or micturition device and can be used to include train or affect or improve urinary urethral and pelvic floor muscle 67 function to include indicators which are sensing and feedback device 42 and stimulating device 70 and can include neuro-musculature stimulating electrodes and sensing units for micturition and urination control.

FIG. 33 is a sagittal view of a female urinary retention and diversion device that in the preferred embodiment there can be a combination of a sealing pad 2, a skin covering material 3, an anchoring device 35 that can include an anal anchor 68 or a vaginal anchor 69, a fixation device 11, an indicator and measuring device 54 or a feedback device 42 or a stimulating device 70 or any combination of these elements can be used with a condom catheter or micurition device and can be used to include train or affect or improve urinary urethral and pelvic floor muscle 67 function to include indicators which are sensing and feedback and stimulating and can include neuro-musculature stimulating electrodes and sensing units for micturition and urination control and can also include biological and body part functions to include sexual, erectile, ejaculation and micturition and orgasm function, penile, prostate, bladder, vaginal muscular contraction and relaxation, neuro-musculature control, fecal and anal and rectal, the pelvic floor muscle and pelvic floor fascial control. In the preferred embodiment an indicator can be present to provide neuro-muscular strength and tone and signal that can be connected or can be used separate from a neuro-musculature stimulating unit that can help train the neuro-muscular system for urination or can automatically trigger a neuro-muscular stimulus that can provide neuro-muscular control to the dysfunctional body function to include the neuro-musculature units in an effort to improve and control urinary function. The feedback device 42 and the indicator and measuring device 54 and stimulating device 70 can be in the sealing pad 2, a skin covering 3, an anchoring device 35, a fixation device 11, an indicator and measuring device 54 or a feedback device 42 or any combination of these elements and located in the vagina, rectum and anus, the tissue around the penis or vagina or anus, prostate, pelvic floor. In one embodiment there can be wires implanted in the musculature that assist urination which can measure leakage of urine and can be interfaced with the condom catheter or training unit through stimulating device 70 or a medication delivery device or a warming or cooling device. Other applications of this form of stimulation can include treating or facilitating and enhancing sexual, ejaculation, erectile function, orgasm, pleasure, arousal and prolongation of these and related biological functions. In another embodiment the feedback mechanism can contain at least one input and one output signal or any combination of inputs or outputs that can include electromagnetic, kinetic, and motion and other sensory signals and feedback signals.

Figure 34:
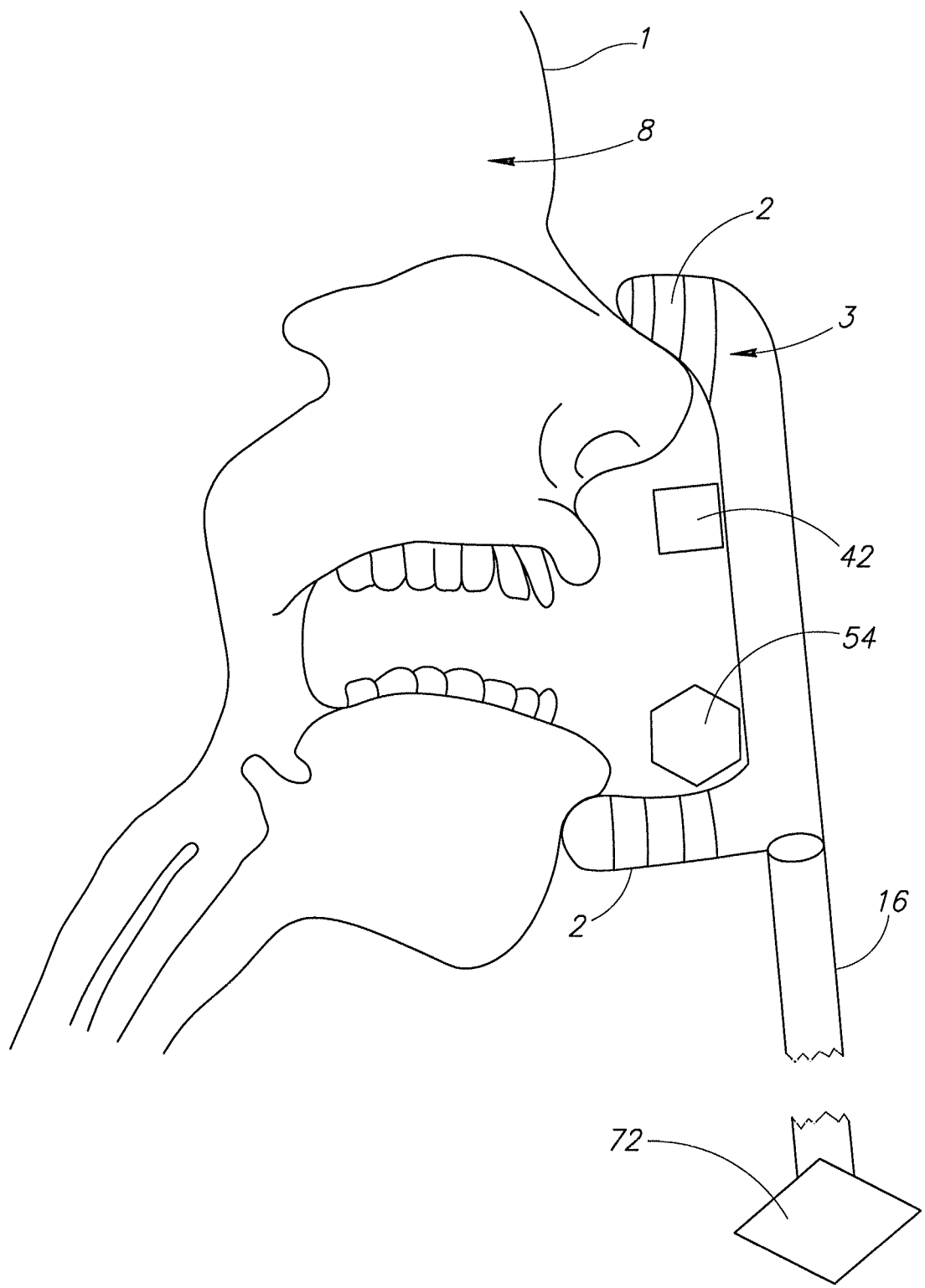
FIG. 34 is a sagittal view of a sealing pad 2 and a skin covering material 3 that contains indicator and measuring device 54 and feedback devices 42 that can used being used as a breathing mask.

FIG. 34 is a sagittal view of a sealing pad 2 and a skin covering material 3 that contains indicator and measuring device 54 and feedback device 42 that can used being used as a breathing mask to include a CPAP mask, a BIPAP mask, an anesthesia mask a scuba or snorkeling device. In one embodiment that can include a sealing pad 2 and a skin wound and cancer covering material 3 the sealing pad 2 and the skin covering material 3 can include an indicator and measuring device 54 that can be utilized to provide feedback to a feedback device 42 to the regulate the sealing pad 2, the skin covering material 3, the internal environment between the sealing pad 2 and the skin covering material complex 3 and the skin, the external environment 62 outside of the sealing pad 2 and the skin covering material complex 3, or a combination of these regions and elements. One or more than one indicator and measuring device 54 can be used to regulate and adjust and measure parameters and can include zero, one or more than one feedback device 42 to provide feedback through a feedback device to include the pH, gas content, the aerobic or anaerobic nature of the isolated environment, elemental content, substance or medication content, electromagnetic content to include radiation or visible or non-visible light spectra to include UV and infrared light, to wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, substance levels to include drugs and medications, and the biologic and physiologic parameters of the tissue or body part being isolated. The material or energy being delivered or removed from the isolation chamber can be located between the sealing pad 2 and skin covering material 3 and the skin 3 or body part 8, or can be a part of the sealing pad 2 and skin covering material 3, or can be external to the sealing pad 2 and skin covering material 3 or can be a combination of these elements. The delivery or removal system for material or energy being delivered to or being removed from the internal isolation chamber 61 and the user's skin 1, body part or organism, can be located between the sealing pad 2 and skin covering material 3 and the user's skin 1, or can be a part of the sealing pad 2 and skin covering material 3, or can be external to the sealing pad 2 and skin covering material 3 or can be a combination of these elements. The matter or energy being delivered or removed can be delivered or removed by methods to include channels and tubes, wires, osmosis, chemical reaction, kinetic energy or electromagnetic energy. The indicator and measuring device 54 and the adjustment can provide feedback can include physiology of the body that can include pulse, blood pressure, temperature, glucose levels, biomechanical measurements, carbon dioxide and oxygen and gas levels, oxy and deoxyhemoglobin levels and other basic metabolic functions and measurements to include wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, muscular function, substance levels to include drugs and medications and non-physiologic measurements to wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, substance levels to include drugs and medications a combination of physiologic and non-physiologic measurements.

The sealing pad 2 and the skin covering material 3 and the indicator and measuring device 54 can be connected to at least one device that can adjust, regulate, manage, and assess the physiology or biology of the isolated tissue or body part 8 or organism and adjust the device to optimize, alter or coordinate the needs or biologic function or physiology of the isolated tissue or body part or organism and contain zero, one or more than one feedback device 42. In one embodiment the complex of the sealing pad 2 and the skin covering material 3 and at least one indicator and measuring device 54 or feedback device 42 or any combination of indicator and measuring device 54 feedback device 42 can measure and be used to include manage, adjust, regulate and assess the oxygen and carbon dioxide and pressure in a breathing apparatus that can include a ventilator, CPAP device, or anesthesia device that can measure the physiology of the organism, with parameters to include oxygen and carbon dioxide levels, anesthetic levels and the breakdown products of the anesthesia, the pressure of the gas being inhaled and exhaled and delivered and removed, the sound of the snoring of the organism and the biological and physiological parameters of the organism including arterial oxygen saturation levels. In another embodiment the complex of the sealing pad 2 and the skin covering material 3 and indicator and measuring device 54 and feedback mechanism or any combination of these elements can measure and be used to include manage and feedback, adjust, regulate or assess the sound of the snoring which can be used to manage, adjust, regulate and assess the physiologic or biologic parameters of an external device 72 to include a ventilator to serve an organism who is snoring and adjust the gas levels and the pressure to minimize snoring while maintaining proper homeostasis and health of the organism.

Figure 35:
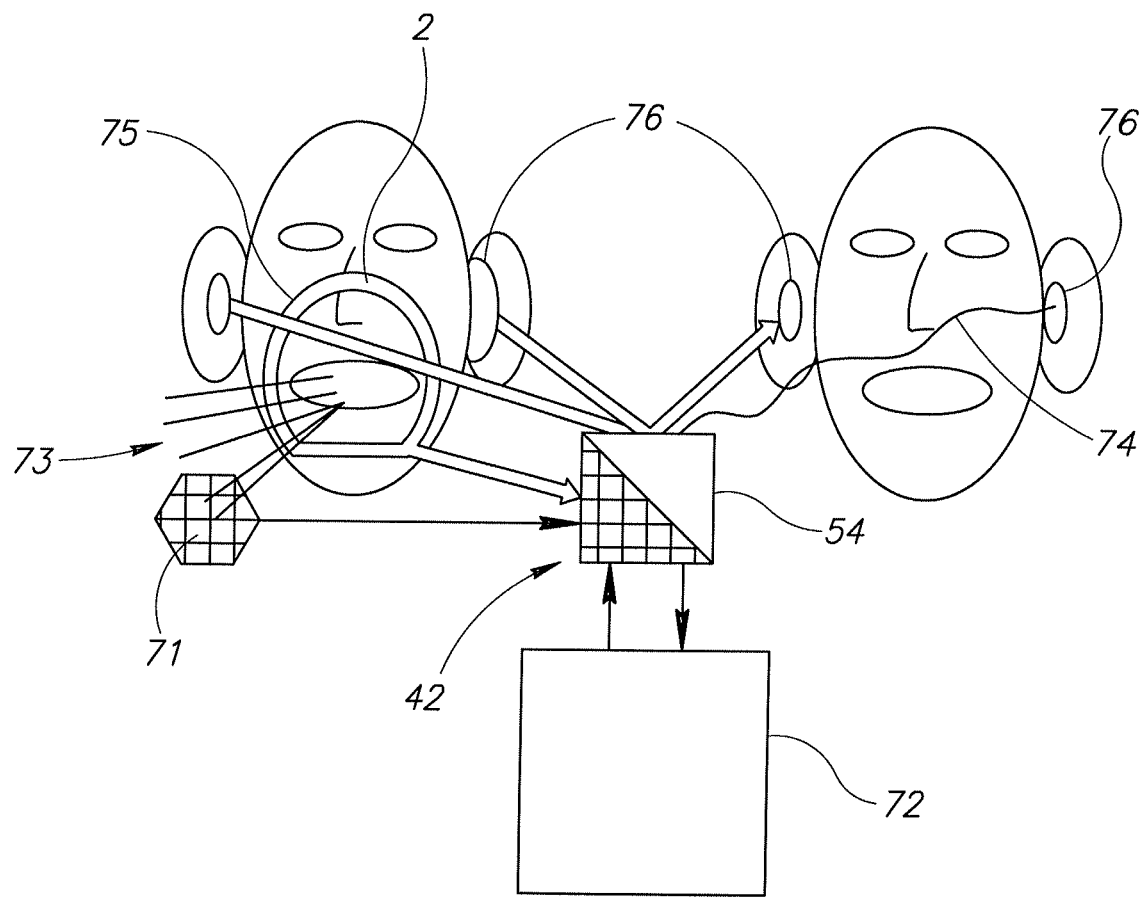
FIG. 35 is a frontal view of an indicator and measuring device 54 or measuring device 54 and a feedback device 42.

FIG. 35 is a frontal view of an indicator and measuring device 54 and a feedback device 42 that in the preferred embodiment include use with a sealing pad 2 and the skin covering material 3 and at least one indicator that can assess and give feedback and can use zero, one or more than one feedback device 42 to give information on physiology and biology, or mechanical or environmental stimuli and information 73, and said information can be transmitted to a feedback device 42 or an additional device that can include an external device 72 that can alter the physiology or biology or mechanical or environmental stimuli and information 73 to include snoring or the sound of the external device 72 or conduit 16 near the snoring individual, which can be measured and the information transmitted to an external device 72 to include an acoustic receiving or altering device that can include noise cancellation computers, equalizers, electrical devices, ear device 76 which from a distance or be located on or near or at one organism that can include cancel mute, transmute or alter the sound of the snoring, for at least on organism. In another embodiment the indicator and measuring device 54 and the feedback device can be used with or without the sealing pad 2 and with or without the sealing pad 2 or skin covering material 3 and can assess and give feedback on physiology and biology, or mechanical or environmental stimuli and information 73, and said stimuli and information can be transmitted to the acoustic receiving or altering device that can alter the physiology or biology or mechanical or environmental stimulus or other information to include snoring or the sound of the external device 72 or conduit 16 near the snoring individual, which can be measured and the information transmitted to an external device 72 to include the acoustic receiving or altering device that can include noise cancellation computers, electrical devices, ear device 76 which from a distance or be located on or near at one organism can cancel mute, transmute or alter the environmental stimuli and information 73 including snoring, for at least on organism. The transmission of information can include material transmission to include wires and fiber optics 75 or wireless 74. In another embodiment at least one indicator can be used to assess and give feedback on physiology and biology or mechanical or environmental stimulus or information, and said information can be transmitted to the acoustic receiving or altering device that can alter the physiology or biology or mechanical or environmental stimulus or other information to include snoring, which can be measured and the information transmitted to a device to include the acoustic receiving or altering device that can include noise cancellation computers, electrical devices, ear device 76 which from a distance or be located on or near at one organism can cancel mute, transmute or alter the sound of the snoring, for at least one organism. In another embodiment the indicator and measuring device 54 can have its function to include noise from an external device 72 be measured and the information transmitted to the acoustic receiving or altering device that can include a computer or noise cancellation device or ear device 6, which can affect from a distance with speakers or be located on or near or at least one organism or one machine to cancel the sound of the external device 72 which can include a ventilator or monitoring device, treatment device, pleasure device to include background sounds, environmental device to include an air conditioner or humidifier or dehumidifier, In another embodiment at least one indicator and measuring device 54 can measure and be used to include manage, adjust, regulate or assess the sound of the snoring which can be used manage, adjust, regulate or assess the physiologic or biologic parameters of the organism who is snoring and the audio signal can be transmitters using a method of wires and fiber optics 75 or wireless 74 other transmitter methods or wireless 74 or a combination of these methods, to the snoring organism or at least on other organism such that the snoring sound can be cancelled out using a method to include acoustic canceling or sound canceling techniques that is the preferred embodiment can be include ear device 76, or a room speaker or microphone to cancel or minimize or mute or transmute the sound to provide a more beneficial or pleasant or acceptable sound to one or more of the snoring and the non-snoring individuals. An input device for the acoustic sounds can include a microphone or acoustic receiving unit 71.

Figure 36:
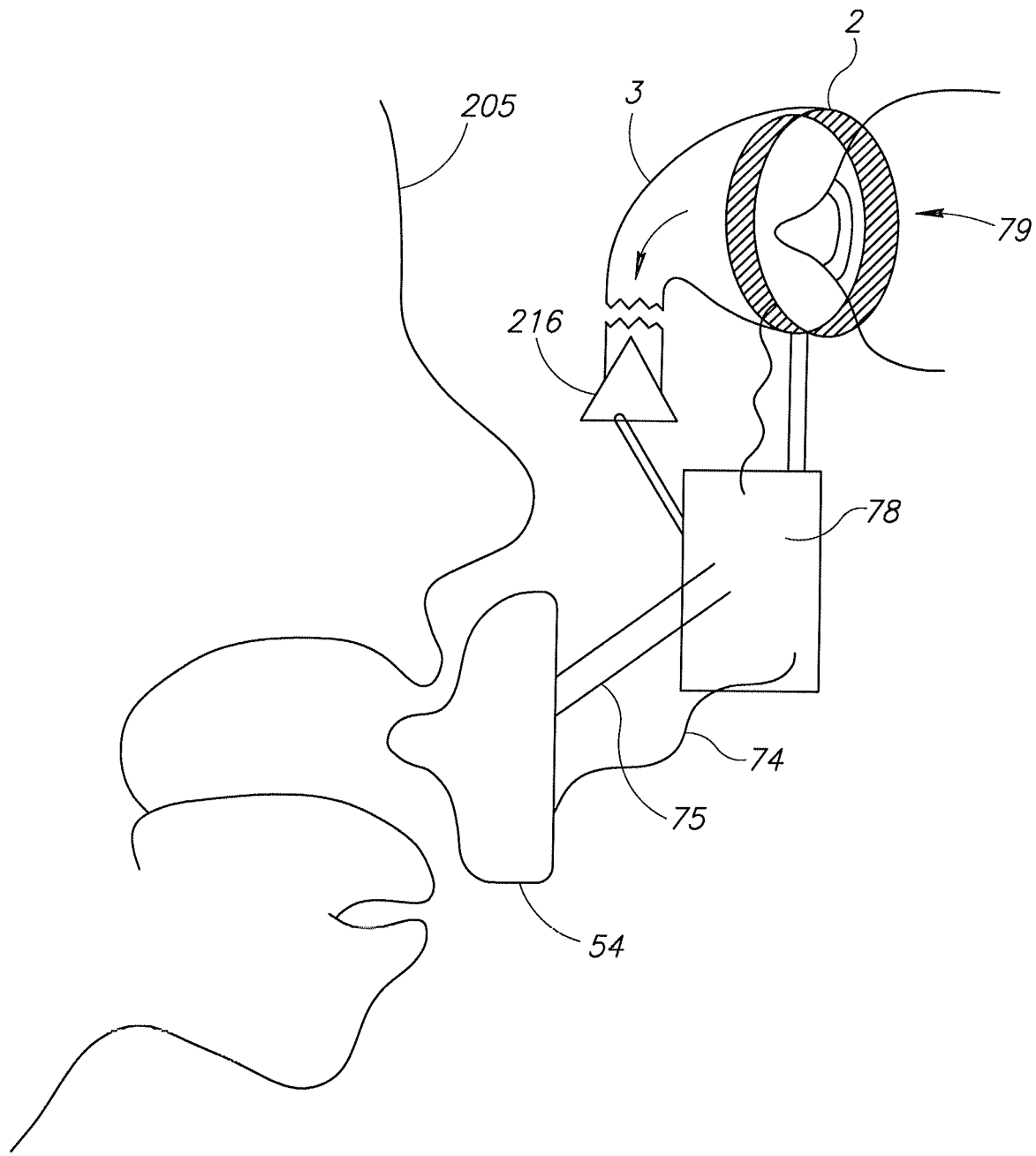
FIG. 36 is a sagittal depiction of a device to capture and then simulate breastfeeding and then simulate that sensation in a breast-pumping or breastfeeding device 23.

FIG. 36 is a sagittal depiction of a device to capture and then simulate breastfeeding and then simulate that sensation in a breast-pumping or breastfeeding device 23. In one embodiment an indicator and measuring device 54 containing sensory receptors that can include pressure and touch and compression and can be used to create a signal that can include a digital or analog signal that can be stored and processed and transmitted by or into a device that can include a computer or computer-like device 78, or an electrical or mechanical device that can store and process information digitally or analog. That information can be utilized to control a second device that can include a sealing pad 2, a sealing pad 2 with a skin covering material 3, a sealing pad 2 with a skin covering material 3 and indicator and measuring device 54, a feedback device 42, or a machine that can include a pump 216 used for biological and physiologic functions that can include breast feeding, pumping the breast for the extraction of breast milk, pleasurable stimuli or sensations or pain and pleasure to include or alteration of physiology or biologic functions of bodily organs to include the breasts, lips, ears, skin, mouth, rectum and anus, penis and related structures such as the scrotum, clitoris and vagina and related local structures such as the labia, toes and fingers.

In the preferred embodiment a breast pump is configured to simulate the suction and motion of the mother's infant breastfeeding. To accomplish this the sucking motion of the infant is codified and determined by having the infant suck on a simulated-nipple that can simulate a mother's breast. Sensors are placed in and on the simulated-nipple and the suction and motions of the infant are recorded for an extended period of time and the information is transferred to a computer that can capture and store this information. When the mother is ready to pump her breasts, the computer information can be transmitted to the breast pump and the mother's breast pump sealing pad and the suctioning device of the breast pump. The computer signal will then reproduce from the stored information a simulation of the infant's suction and sucking motions. In some embodiments the scent of the infant or pheromones can be released to stimulate the mother's let down reflex that starts the flow of milk. The computer can analyze maternal breast milk parameters such as the interval prior to milk let down, the quantity of milk and breast characteristic such as temperature in order to determine the best simulated infant sucking program. This process can be used for newly nursing and breastfeeding mothers or infants or mothers or infants who are benefited by the program. The same or a variation on the same or similar device can be used to teach newly nursing infants to nurse better and can be used when an infant is transitioning from breast to bottle-feeding nipples.

Sensations and stimuli and material applications can include wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, substance levels to include drugs and medications and non-physiologic measurements to wetness or dryness, oxygen and other gaseous levels and movement, toxin levels, electromagnetic signals, kinetic signals, light and darkness levels and vision, sound and silence, movement and stillness, pain and lack of pain, pleasure and lack of pleasure, taste sensations and lack of taste sensations; odor and olfactory sensations and lack of odor and olfactory sensations, touch both light and firm touch and lack of touch, proprioception and lack of proprioception, pressure and lack of pressure, substance levels to include drugs and medications a combination of physiologic and non-physiologic measurements.

Other embodiments include auditory signals to include the human hearing range and above and below the human hearing range; electromagnetic signals to include infrared and ultraviolet; sensory stimulus to include heat and cold, wet and dry, pain and non-painful and pleasurable stimulation; olfactory and smell sensations to include pleasant and unpleasant odors; taste to include salt, sweet, acrid, bitter, sour, umami, pleasant and un pleasant tastes; vibration and kinetic stimulus to include pinching, piercing, hard touch, light touch, vibration, and proprioceptive stimulus. The stimuli can be used singular or multiple and can be used as one or multiple stimuli or categories. Information can be transmitted by land lines to include wires and fiber optics 75 or wireless 74. In the preferred embodiment a nipple information gathering device 54 shape device to simulate the natural shape of a mother's breast 79 can have indicator and measuring device 54 that can include touch and pressure wetness and motion and suction pressure sensors. A baby can suck onto the indicator and measuring device 54 and the touch and pressure wetness and motion and suction pressure can be recorded and stored in a device with can include a computer-like storage device. This signal can then be transmitted through the processing computer or computer-like device 78 or to the pump 216 or to the sealing pad 2 that contains a device that assist with breast pumping in FIG. 37 that can then simulate one or more of these sensory inputs and outputs that best simulates the natural sucking sensation of the infant breastfeeding. The purpose of this is to simulate natural breastfeeding and improve the let-down reflex and the natural sensation of the infant and mother breastfeeding bond. Other sensory inputs that can be acquired and stored and transmitted and simulating during breast pumping can include the olfactory to include the scent of the infant, wetness, visual including images to include the infant breastfeeding and not breastfeeding, auditory including sounds to include the infant breastfeeding and not breastfeeding, taste including taste to include the infant breastfeeding and not breastfeeding, kinesthetic and touch including touch to include the infant breastfeeding and not breastfeeding, and other sensory input that might stimulate breast milk let-down and quantity.

Figure 37:
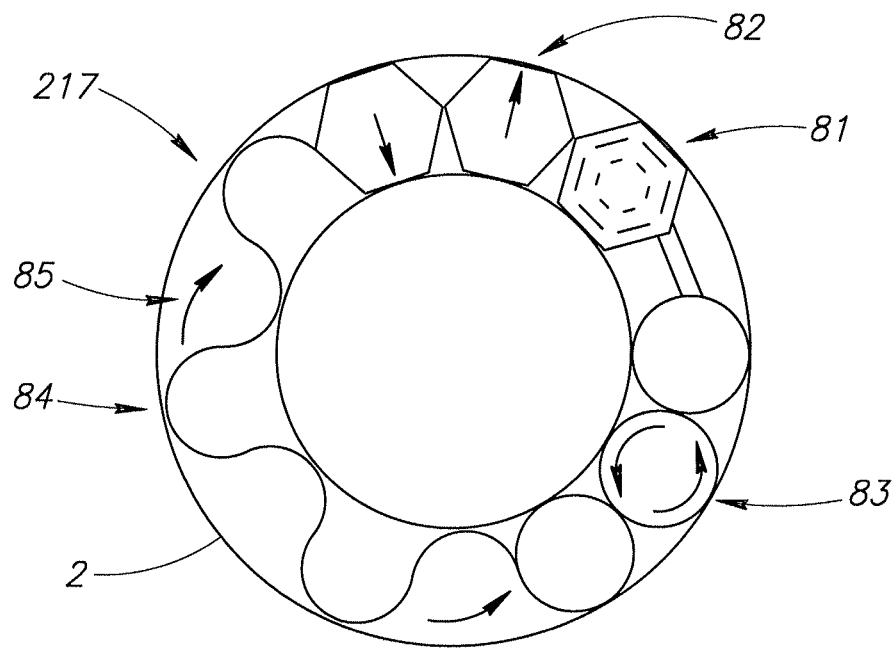
FIG. 37 is a close-up frontal view of the sealing pad 2 of the breast pump seal or stimulating device.

The sealing pad 2 or the sealing pad 2 and the skin covering material 3 or a combination of both can contain a breast pump seal or stimulating device 217 in FIG. 37 to include a vibration, compressive, suction, undulating device that is contained within or on the sealing pad 2 or the sealing pad 2 and the skin covering material 3 or the sealing pad and skin covering material combination can be used to simulate and mimic the input to include the suckling or breast feeding of the organism to include an infant that is human or non-human. In another embodiment, the infant can be taught how to breastfeed or suck from a man-made nipple using a similar device to teach the infant how to bottle-feed. In another embodiment, sexual pleasure can be simulated and attained using a similar device with a shape that can include a mouth, tongue, lips, or combination of these body parts that can be used for pleasure to simulate licking, and sex to include oral sex for and on either gender and on or by any body part. In one embodiment the device can be a sex toy which is programmed to simulate another human beings sensory input and output to include touch, caress, probing, sucking, kissing, licking thrusting, ejaculating, or having an orgasm, and can be shaped like a hand, mouth, tongue, lips, penis, vagina or anus.

FIG. 37 is a close-up frontal view of the sealing pad 2 of the breast pump seal or stimulating device 217. The sealing pad can include a gel or a non-gel material. In the preferred embodiment the seal is composed of a gel and can include a device to include a mechanical device to include vibration 81, a compression or pressure 82, a rotation 83, undulating 84 or a length changing 85, stroking, licking, fluid delivery, suction device, warming or cooling or other sensory simulating or creating devices.

Figure 38:
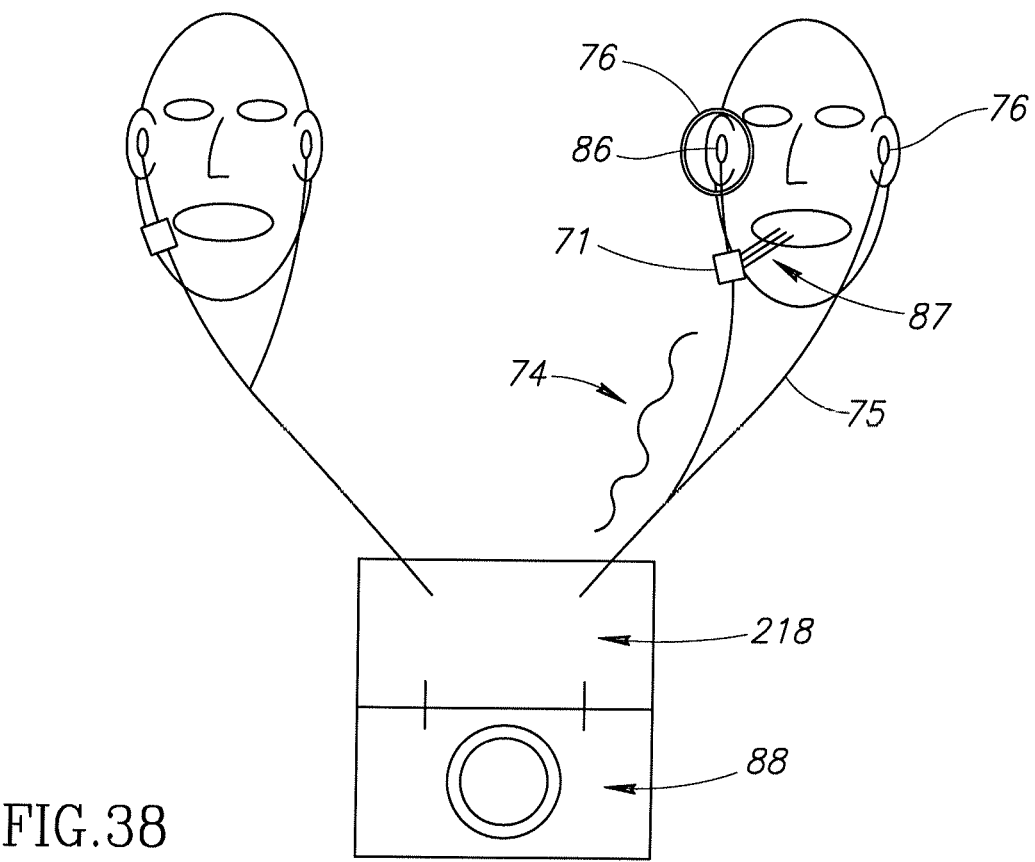
FIG. 38 is a frontal depiction of a communication device that can utilize or be used with or without a sealing pad or the sealing pad 2 and the skin covering material 3.

FIG. 38 is a frontal depiction of a communication device that can utilize or be used with or without a sealing pad or the sealing pad 2 and the skin covering material 3. The communication device can include an ear device 76 that can include earbuds or earphones, that can include containing an auditory device 218, which can include and an indicator and measuring device 54 or feedback device 42 to include a noise enhancement or noise cancellation device or an acoustic amplifier or equalizer device or a device for changing the pressure in the airway or a device for altering and measuring and feeding back information to alter gas exchange or pressure of a gas or gas or pressure a delivery system that can include allowing two individuals to communicate in a high stimulus noise environment to include a noise filled travel mode to include an airplane, car, boat, or train, or a noise filled work environment or in an environment with changing pressure to include in an airplane flight or other environments that have changing pressure or changing the external stimulus that can include but is not noise cancellation or sound or acoustic equalization or acoustic amplification. In another embodiment (not depicted) an earplug 102 or a headphone-like device that can contain a conduit 16, or reservoir 41, or an electrical device that contains a pressure altering bellows, diaphragm or membrane, one or more than one chambers or an auditory device 218 that contains a valve that slowly allows an adjustment to the pressure to equilibrate the pressure relative to the inner ear pressure, the outer ear pressure and the atmospheric pressure of the user. In another embodiment the auditory device 218 and pressure control device can be used together. In the preferred embodiment the sealing pad 2, or a combination of sealing pad 2 and the skin covering material 3 can include an earbud or earphone that can contain an auditory unit device 86 that can include a speaker or acoustic delivery system. The auditory device 218 can include an auditory device to include an auditory unit or computer or computer-like device 78 for amplifying sound, equalizing sound, subtracting sound, altering sound, increasing or suppressing sound, and modifying sound. The device can include an analog, an auditory analog to digital converter, a purely digital unit and can be land lines to include wires and fiber optics 75 and wireless 74.

The device can be an auditory unit that is hard wire 75 connected to another device that promotes auditory communication such as an electronic device that has input and output capabilities to communicate with one or multiple individuals. Some uses can include airplane travel, operating room communication, hospitals, old age homes, subways, buses, trains, manufacturing and non-mechanical. In the preferred embodiment the sealing pad or the sealing pad and skin covering material can include an ear device 76 and auditory unit device 86 and a microphone or acoustic receiving unit 71, the input microphone can together with or can be separate from the ear device 76. This communication method can be used on a vehicle or on a noisy environment to include a train or boat or car or airplane where the ambient noise is very high and can be damaging to the ears and speaking to an individual often involves turning the head to the individual which at the end of the travel can result in a stiff neck and a hoarse voice. At least one organism can speak into a microphone or acoustic receiving unit 71 and the audio signal is processed by an auditory device 218 which can amplify the voice or noise cancel the non-voice audio signal using standard methods for amplification of voice 87 and noise cancellation of the non-voice auditory signals. The auditory device 218 then transmits the signal to at least one organism who can then listen and speak to at least one organism using a similar mechanism and device such that the receiving and sending audio signal can be shared by at least one organism. In one embodiment this device can be an accessory for or be built into a computer or computer-like device 78, MP3 or digital music device 88 to include an IPOD™-like device, cell phone-like device or walkie-talkie-like device. In another embodiment the auditory device 218 can be incorporated in the sealing pad 2 and or the sealing pad 2 and skin covering material 3 or the device can be external to the sealing pad 2 and or the sealing pad 3 and skin covering material 3 and obtain input from an external source that can be delivered through land lines, conduit 16 or wireless 74 methods.

Figure 39:
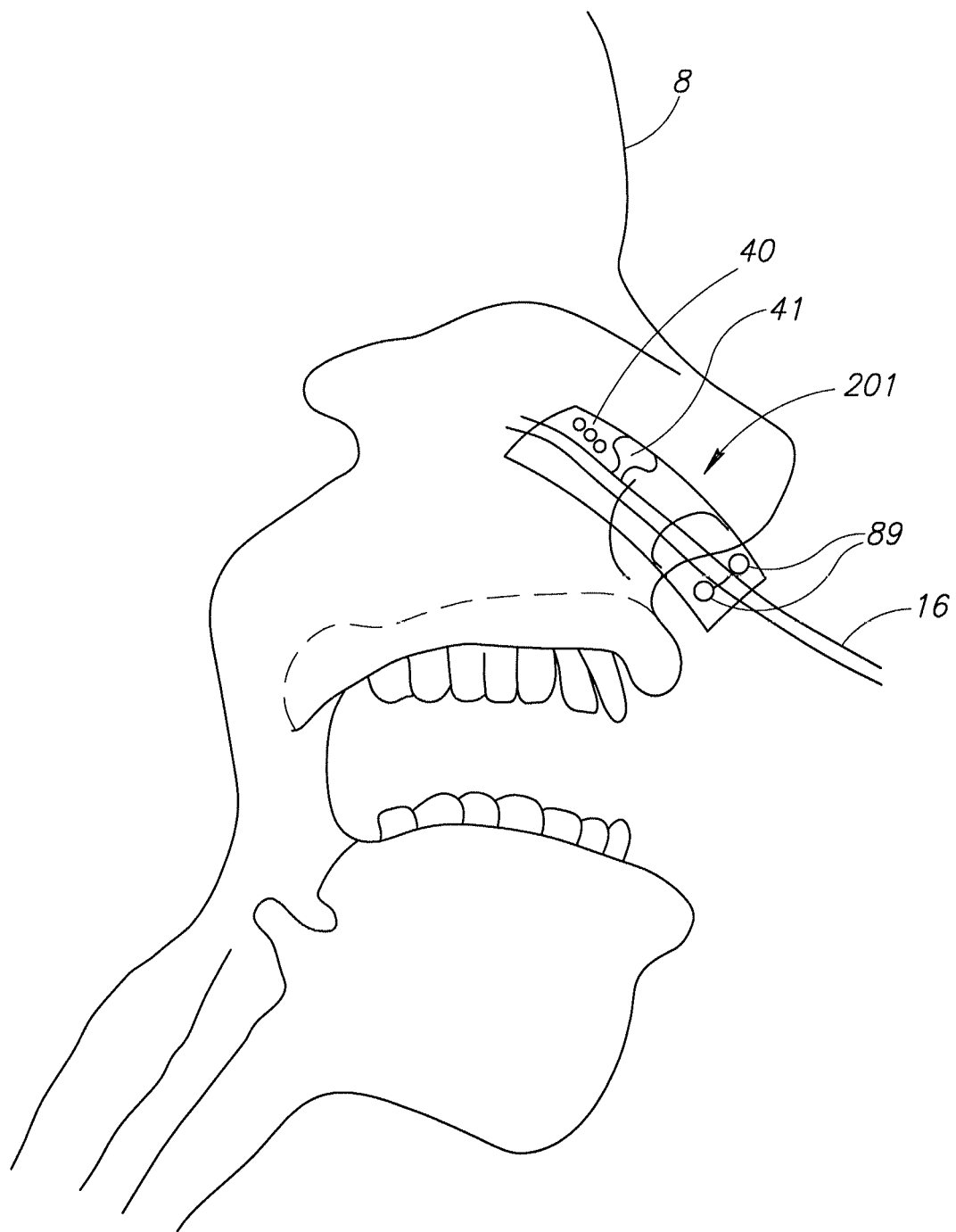
FIG. 39 is a sagittal depiction of a nose plug sealing pad.

FIG. 39 is a sagittal depiction of a nose plug sealing pad. The nose plug sealing pad can comprise a sealing pad 2 or skin covering without the sealing pad 2 that can include a nasal plug seal 201, which can include zero, one or more than one channel or conduit 16 and include delivery system for solids, liquids, gels or gases or a combination of these elements. The nasal plug seal 201 can include containing reservoir 41, conduit 16, electrodes or semiconductor sensation stimulating device 70 and devices that can include filters, fans and sensory stimulants and delivery systems, and impregnated 40 substances into the nasal plug seal 201. In one embodiment, the nasal plug seal 201 can include an olfactory device that can deliver the scent of an infant, and can be used to include use during breast pumping to deliver the scent of the infant to stimulate the mother's let-down reflex. In another embodiment, the nasal plug seal 201 can include an olfactory device that can deliver the scent of a mother or a father to a premature infant in an incubator or in isolation such that the infant received sensory stimulation to bond with one or more organisms. In another embodiment, the nasal plug seal 201 can include a sensory device worn at the movies that can deliver a sensory input that can include the use of a mask that can deliver an olfactory input. In another embodiment the nasal plug seal 201 can include at least one reservoir that provides for nearly or unimpeded inflow of air and with impeded outflow of air that increases the airway or air resistance to the outflow of air. The reservoirs which can expand or contract can be arranged to increase outflow air resistance in a steady or a variable manner and in a manner in which the pressure is greater or is lesser near the user relative to the external environment. The device can be composed of at least one valve that controls the inflow and outflow of a substance to include a solid, a liquid, a gel or a gas to deliver or to remove or maintain a substance to include a scent, air pressure, oxygen and other gases, or an olfactory stimulant or stimulating device 70 or smell, and air resistance. The reservoir and valve can be used to include being used separately or together or in any combination. The valve 89 or the reservoir 41 delivery can be mechanical or non-mechanical.

Figure 40A:
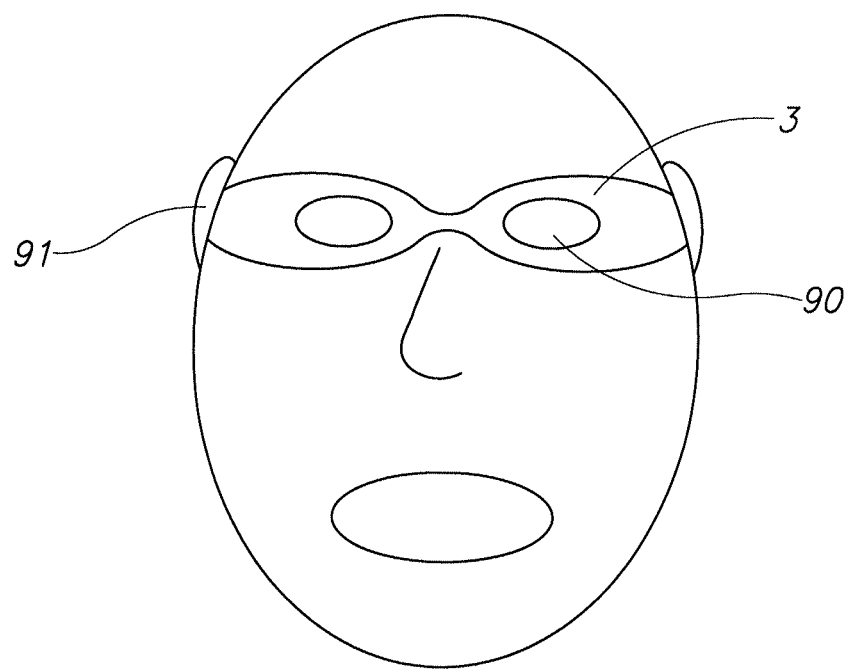
FIG. 40A is a frontal view and 40B is a sagittal view of a low profile flexible swimming goggle.

FIG. 40A is a frontal view and 40B is a sagittal view of a low profile flexible swimming goggle. In the preferred embodiment the swimming goggle can use a gel sealing pad 2 and a skin covering material 3 that surrounds the eyes 92 and has a skin covering material a portion that is overlying the eyes 92 is flush or nearly flush with the face and skin user's 1 and follows the contours of the face and user's skin 1. The skin covering material 3 can be being transparent and can include containing at least a component that is fabric that acts as a Zorro-like mask the mask fits around the back of the head or around the ears or a combination of the back of the head or the ears 91. The eyepiece 90 is flush or nearly flush with the face and user's skin 1 and the mask skin covering material 3 and follows the contours of the face and user's skin 1. The sealing pad can be gel or non-gel and in the preferred embodiment is gel. The sealing pad 2 lies between the skin covering material 3 and the skin and provides an airtight and watertight seal that contours and conformed to the face and user's skin 1.

Figure 40B:
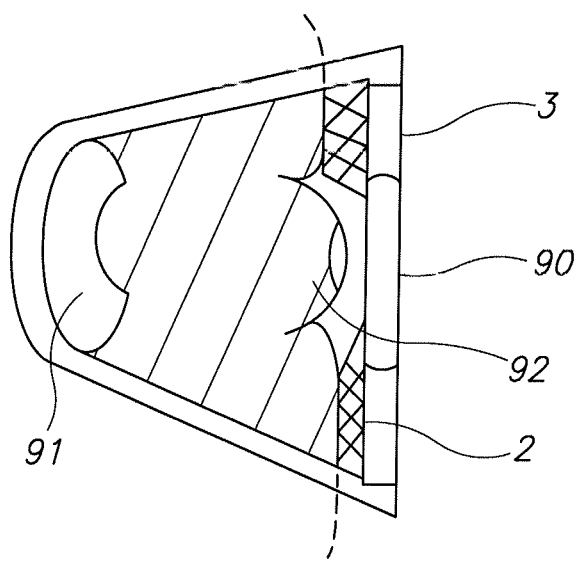
Figure 41:
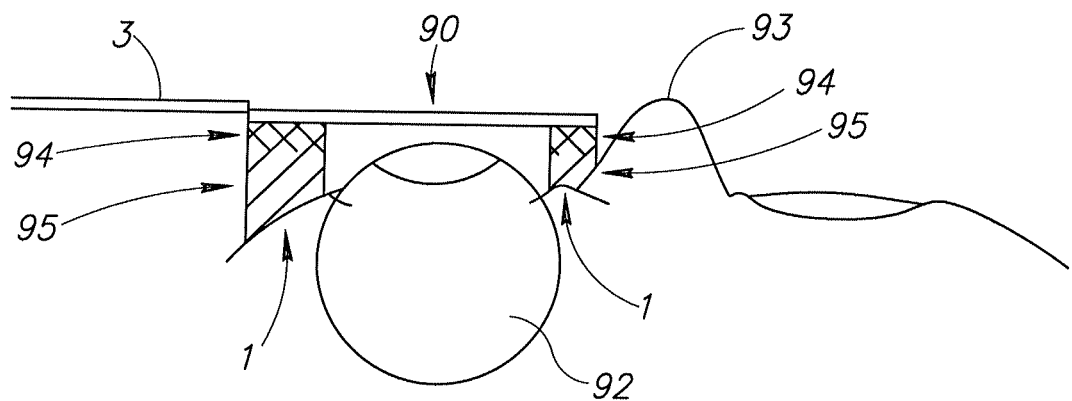
FIG. 41 is a close up top view of the sealing pad 2 and the skin covering material 3 that can include a goggle or eye 92 protection that can be airtight and watertight or non-airtight and watertight and can be gel or non-gel.

FIG. 41 is a close up top view of the sealing pad 2 and the skin covering material 3 that can include a goggle or eyes 92 protection that can be airtight and watertight or non-airtight and watertight and can be gel or non-gel. The sealing pad 2 conforms and contours to the facial contours and user's skin 1 and in the preferred embodiment causes the skin covering to be flush or nearly flush with the facial contour and user's skin 1. In the preferred embodiment the goggle is airtight and watertight and the preferred method by which the goggle is flush or nearly flush with the facial contour and user's skin 1 includes a sealing pad 2 that varies in thickness 95 and includes it being thicker in some regions than in other regions to include a sealing pad 2 that is thicker away from the eyes 92 than near the eyes 92. Since the facial shape of individuals varies greatly the thickness 95 is designed to vary to conform to the contours to include different ethnicities, races and phenotypic facial contours. In another embodiment the skin covering can include a sealing pad 2 or a skin covering material 3 or any combination of these elements that is thicker in some regions than in other regions to include a skin covering material 3 that is thicker away from the eyes 92 than near the eyes 92 or that is thicker near the eyes 92 than away from the eyes 92 or thicker near the cheek or user's skin 1 than the brow of the face and user's skin 1 or thicker away from the cheek or user's skin 1 than the brow of the face and skin or thicker near the user's skin 1 than away from the face and user's skin 1 or thicker away from the user's skin 1 than near the face and user's skin 1 or thicker near the nose than away from the nose 93 or thicker away from the nose 93 than near the nose 93. The sealing pad 2 and the skin covering material 3 with variable thickness can include the sealing pad 2 and the skin covering material 3 being used alone or in any combination. The eyepiece 90 can be constructed to include it being part of the skin covering material 3 or part of the sealing pad 2 or a combination of it being continuous or part of the skin covering material 3 or continuous or part of the sealing pad 2. The eyepiece 90 can also be separate from the sealing pad 2 or separate from the skin covering material 3 or a combination of separate and combined. The eyepiece 90 can be attached or integrated into the skin covering material 3 or sealing pad 2 to include adhesives, hooks, VELCRO™ and related fabric hook and loop fasteners, loops, ties, pins, protuberances and invaginations, sewing, molded or woven into the interstices of the skin covering material 3 or sealing pad 2 or into a gasket or frame-like structure that is intimately constructed with at least a portion of the eyepiece 90 but remains flush or relatively flush with the users face or skin 1. The advantage and goal of this design is to reduce water drag and resistance and to be comfortable and stylish. In another embodiment, the skin covering material 3 can be one continuous flexible material, which can include a gel that can include a gel that varies in hardness and softness 94. The sealing pad 2 or skin covering material 3 can include it being softer near the uses face or skin 1 than away from the users face or softer away from the user's nose 93 than near the users face or skin 1 or the sealing pad 2 can include it being softer near the user's nose 93 than away from the user's nose 93 or softer away from the user's nose 93 than near the user's nose 93 or the sealing pad 2 can include it being softer near the uses cheek or skin 1 than away from the users cheek or skin 1 or softer away from the users cheek or skin 1 than near the users cheek or any variation or combination of these elements. In another embodiment, the skin covering material 3 can be one continuous flexible material with a separate eyepiece 90. In another embodiment, the skin covering material 3 can be one continuous flexible material with a separate eyepiece 90 and a separate sealing pad 2. The goggle skin covering material 3 can include a fabric a plastic, fiberglass or polymer or gel that can include a gel that varies in hardness and softness 94 and transparency. In another embodiment, the skin covering material 3 can be one continuous flexible material with a separate or a continuous sealing pad 2. The embodiments of the sealing pad 2 and the skin covering described and discussed in FIGS. 40 and 41 and eye goggles and eye masks but can include application and masks that include nasal masks, oral or mouth masks, breathing masks, auditory or hearing or ear devices, urinary devices, penile, vaginal and anal or embryologic or surgical skin covering material 3 or sealing pad 2 or combination of these elements. The sealing pad 2 and the skin covering can be combined to provide a unique method of variability to include combinations of variable thickness 95 and variable hardness and softness 94.

Figure 42:
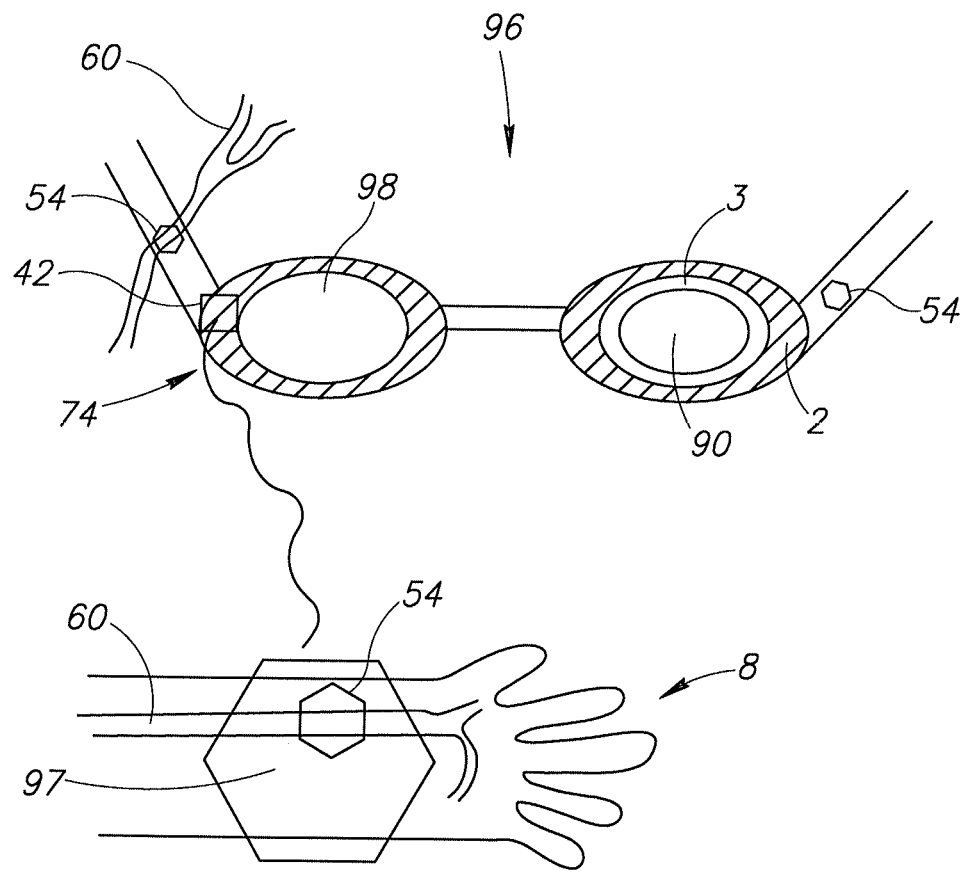
FIG. 42 is a frontal view of an eyepiece 90 that displays 98 or projects a sensory signal.

FIG. 42 is a frontal view of an eyepiece 90 that displays 98 or projects a sensory signal that can include blood flow through blood vessel 60 from an indicator and measuring device 54 to a feedback or display projection unit to include an electromagnetic signal in the visible range or outside of the visible range to be utilized with a user wearing an eye device which can include a sealing pad 2 and a skin covering material 3 to include swimming goggle 96, protective eyewear, workout glasses, sun-tanning eyewear or sporting eyewear for use with skiing, swimming, beach volleyball and ball and racket and biking and running sports. Signals can be sent by hard wiring to include wires, cables and optics or wirelessly 74. In the preferred embodiment the eyepiece 90 with a viewer or a projector that can be used with a sealing pad 2 or a skin covering material 3 or any combination of these elements. The eyepiece 90 can include a screen that can be transparent, translucent or opaque and transmit any combination of no light or maximal light and can incorporate a display or feedback device 42 to include a projector or camera or sensation creating device to include an analog or digital to include an LED, a light projector, a retinal display, a screen that becomes visible with electromagnetic energy projected onto a material that can respond to chemical, kinetic energy and electromagnetic energy to include visible light, ultraviolet light and infrared light. Information can be displayed on the screen that can provide feedback to include the form of the user swimming, physiologic information, or information from a non-user source that can include temporal information, sport related information to include lap number, physiologic information, instructional information, entertaining information, educational information. The transmission of the information can be wireless 74, or hard-wired to include optics or wires or tubes.

In one embodiment a physiologic indicator or measuring 54 can be attached to the swimming goggle 96 unit to monitor physiology to include blood pressure and pulse and carbon dioxide, or lactate or oxygen saturation levels that can be acquired from the vascular flow through blood vessel 60 to include the temporal artery. In another embodiment information the information can be transmitted from the eye device to include a watch or watch-like device 97 that can provide any combination to include blood vessel 60 information, physiological information, or sport related information. Information can be transmitted for a sensing or measuring or indicator and measuring device 54 and transmitted to a feedback device 42 that can display the information visually or can give a sensory feedback that can include a visual, auditory, olfactory, touch-like, or taste sensation. The material that is displayed can be physiologic and non-physiologic and can include feedback, instructional, entertainment, educational or any other forms of visual media and can be combined with auditory and other sensory inputs.

Figure 43:
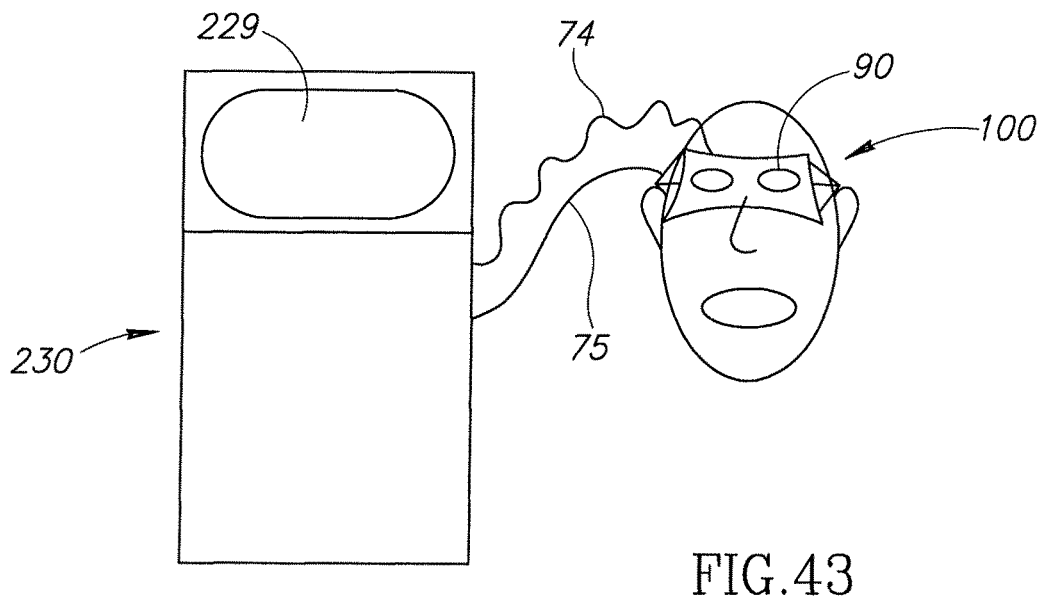
FIG. 43 is a frontal view of an eye-viewing device 100 that can be used with a medical device that traditionally has a screen such that the user has to turn their neck or body.

FIG. 43 is a frontal view of an eye-viewing device 100 that can be used with a medical device that traditionally has a screen such that the user has to turn their neck or body part. In the preferred embodiment, the medical device would include an Ultrasound machine 230. The Sonographer can wear a pair of viewing eye goggles or a mask or glasses or other eye-viewing device 100 that can project the ultrasound image onto an eyepiece 90 or directly onto the retina while the Sonographer is scanning the patient. Currently the Sonographers have to continuously turn their heads to the Ultrasound machine 230 and back to the patient. Sonographers are prone to develop herniated discs and degenerative diseases in their necks and spasms and muscular difficulties in their shoulders. The method of the transmission of the ultrasound signal from the Ultrasound machine to the eye-viewing device 100 can include wireless 74 or hardwired to include wires and fiber optics 75 or other means of transmission electromagnetic signals. In the preferred embodiment the transmission will be wireless 74. Other uses for medical eye-viewing device 100 can include robotic surgery, angiography and catheterization procedures, endoscopy and medical and surgical procedures that require ancillary screen viewing. In another embodiment, eye goggle or mask or other eye-viewing device 100 can be combined with a sealing pad 2 and a skin covering material 3 to be used in a surgical field or in an emergency field or battlefield or in a situation where toxic or infectious or dangerous biologic or non-biologic agents are present and there is a need to view a viewing screen 229 and keep attention focused on a task in a viewing plane different than a viewing screen 229 and where a part of the body to include a body part to include the eyes, nose or mouth or an opening or cavity in the superficial skin needs to be protected.

Figure 44:
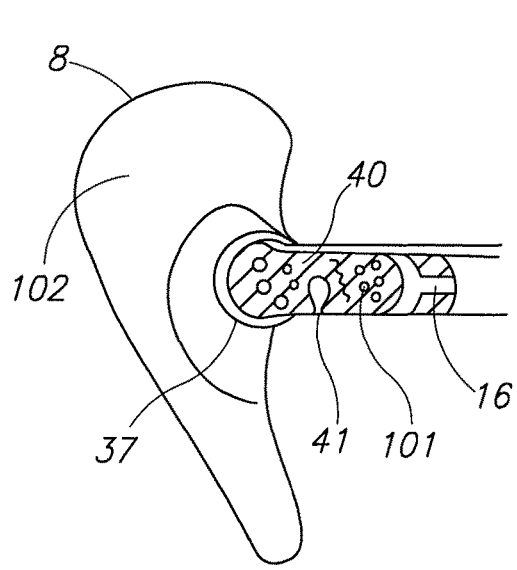
FIG. 44 is sagittal depiction of a sealing pad that contains inclusions 101 that can include an ear plug.

FIG. 44 is sagittal depiction of a sealing pad that contains inclusions 101. In the preferred embodiment, the sealing pad 2 or a sealing pad 2 with a skin covering material 3 can contain a material within the sealing pad 2 which can be composed of a gel or a non-gel material and the inclusions 101 and reservoir 41 channels or conduit 16 that pass through at least a portion of the sealing pad 2, and impregnated 40 materials can include a solid or liquid or gas or another gel. The inclusions 101 can include nanotechnology and nanoparticles that can include nanotubes and can include nanoparticles that are fine particle at 100-2500 nanometers (nm) or Ultrafine at 1-100 nm. The preferred embodiment can be used for an orifice anchoring device to include an earplug 102, nose plug, intubation device, anal or vaginal device for a seal in which to create greater buoyancy, can deliver substances to include medication, gas, detoxifying agents, or to serve as acoustic reflectors or absorbers, or to alter the cushioning or the hardness or softness of the gel sealing pad 2 or adapt to pressure changes to include pressure changes that occur while swimming, diving and flying in an airplane.

Figure 45:
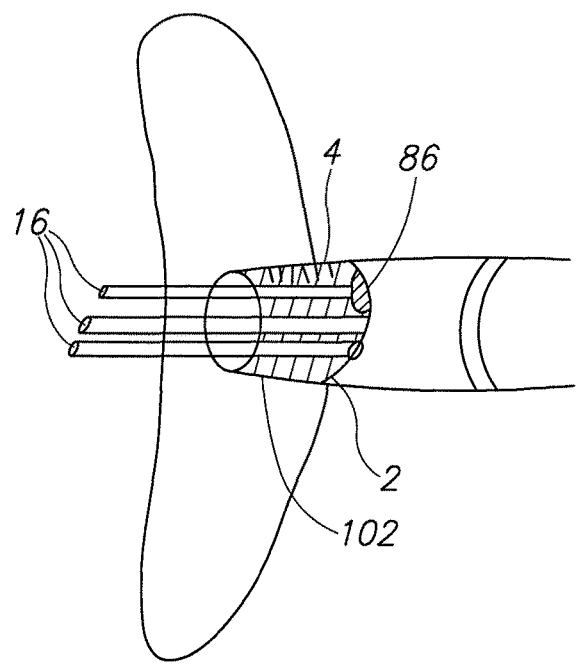
FIG. 45 is a sagittal depiction of a sealing pad 2 or a sealing pad 2 and a skin covering material 3 that can include an ear plug which can be composed of a gel or a non-gel material and which can contain conduit 16 through at least a portion of the sealing pad 2 which in the preferred embodiment is an earplug 102.

FIG. 45 is a sagittal depiction of a sealing pad 2 or a sealing pad 2 and a skin covering material 3 and which can be composed of a gel or a non-gel material and which can contain conduits or channels through at least a portion of the sealing pad which in the preferred embodiment is an earplug 102. The conduit 16 can include contain valves for equalizing the inflow and the outflow of pressure and can have graduated pressures at which the valve gives way and allows for the equalization between the atmospheric pressure within the space between the sealing pad 2 and the user, the inner chamber and the space external to the sealing pad 2 and external to the user. The conduit 16 can traverse at least a portion of the sealing pad 2 and can deliver a substance that can be a solid or a liquid or a gel or a gas. The channels or conduits can traverse at least a portion of the sealing pad 2 and can contain a device that can include an audio device that can include a skin covering material 3 material which can include auditory unit device 86, or electromagnetic energy delivery or reception devices. The sealing pad 2 which in the preferred embodiment is composed of gel or a non-gel can contain a sensing device that can reside within the gel or on the surface of the gel or within the channel and measure body and physiologic functions to include sound, temperature, and movement to include tympanography. The sealing pad 2 can include containing one or more flanges 4 on the outside within the sealing pad 2 or skin covering material 3.

Figure 46:
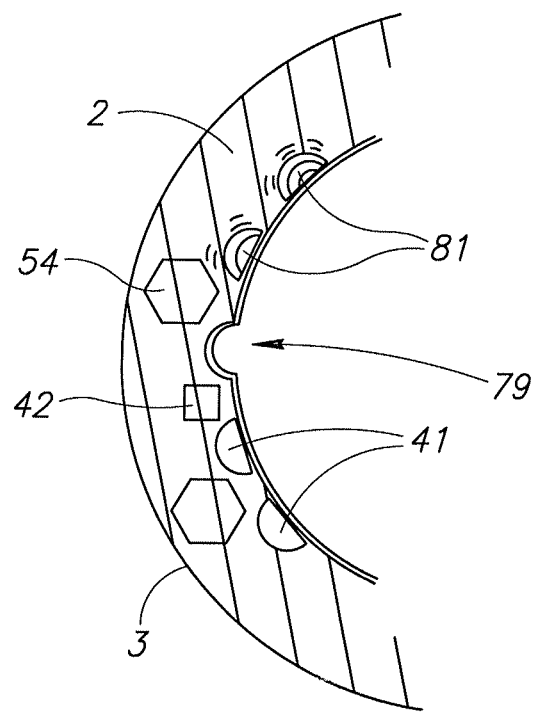
FIG. 46 is a sagittal depiction of a sealing pad 2 or a gel sealing pad 2 and a skin covering material 3 or a fixation device 11 or any combination of these elements that protects breast tissue that can be used for the purpose of tender breasts and nipples during maternal-infant breast feeding, after surgery, during or after chemotherapy or radiation therapy, during or after learning how to wear a bra, after trauma, or injury, alter sensation for comfort or pleasure.

FIG. 46 is a sagittal depiction of a sealing pad 2 or a gel sealing pad 2 and a skin covering material 3 or a fixation device 11 or any combination of these elements that protects breast tissue that can be used for the purpose of tender breasts and nipples during maternal-infant breast feeding, after surgery, during or after chemotherapy or radiation therapy, during or after learning how to wear a bra, after trauma, or injury, alter sensation for comfort or pleasure. The sealing pad 2 can include be used to protect or cover the nipple and breast tissue or a combination of these body parts. The sealing pad 2 can include at least one skin covering material 3. The sealing pad 2 can be but does not have to be airtight or watertight.

The sealing pad 2 can be a gel or a non-gel. The sealing pad 2 or skin covering material 3 can be annular or non-annular. The sealing pad 2 or skin covering material 3 can contain one or more than one fenestration. The sealing pad 2 or skin covering material 3 can include being coated or impregnated with a substance to include anti-viral or anti-bacterial or anti-fungal or anti-germ and disease materials, an anti-inflammatory, a cooling material, an anesthetic, a flavoring material, substance or medication for the offspring, substance or medication for the living creature with the breast such as substance or medications that reduce radiation treatment affects. The sealing pad 2 or skin covering material can include containing a reservoir 41 that can contain or be coated with or impregnated with a substance to include anti-viral or anti-bacterial or anti-fungal or anti-germ and disease materials, anti-inflammatory, a cooling material, an anesthetic, a flavoring material, substance or medication for the offspring, substance or medication for the living creature with the breast such as substance or medications that reduce radiation treatment affects. The breast shield can contain a device that can include a device that can change sensations to include heating and cooling, moistening or drying, or altering pain and pressure and touch sensations; amplifying sound or delivering electromagnetic energy to include ultrasound, infrared, ultraviolet, or magnetism, chemical energy, kinetic or Brownian energy to include vibration, heating and cooling, stimulation or sensory receptors and vascular flow.

The device can be an analog or digital and can be hard wired or wireless. The device can include containing a reservoir 41 or conduit 16 or can be impregnated with a solid or liquid or gel or gas or any combination these elements that can alter biology or physiology. The device can be mechanical or non-mechanical and include HEPPA filters, specific agent detoxifying or anti-germ filters, a substance or medication can include agents that are antibiotic, antibacterial, antifungal, antiviral; anti-fogging; scented; detoxifying agent or filter; heating or cooling device 122, alter the pressure relative to the ambient air, a small fan, a mechanical filter, a small heater or cooler, alter pressure, HEPPA filters, specific agent detoxifying or anti-germ filters, a substance or medication can include agents that are antibiotic, antibacterial, antifungal, antiviral; anti-fogging; scented; detoxifying agent or filter; heating or cooling device 122, alter the pressure relative to the ambient air. The device can be a nanotechnology device to include a device that serves as an air filter, anti-germ agent and detoxifying agent, defogging agent, heating and cooling, alter the pressure or compression. The breast shield can include containing indicator or measuring device 54 and feedback device 42 or devices for monitoring parameters to include sensory data to include temperature, color, and oxygen consumption and the ability to respond to these parameters by releasing substances mechanically or automatically to include medications, or vibration 81 or electric stimulation. In another embodiment this device can be used to treat other body part. In another embodiment the alteration of the biology or physiology can for create pleasure or sexual stimulation.

Figure 47:
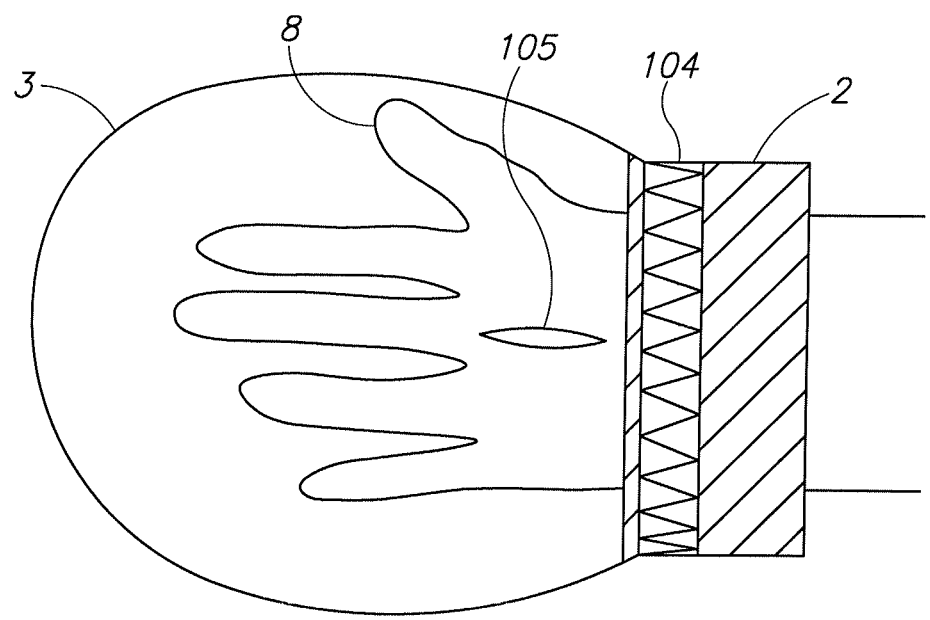
FIG. 47 is a sagittal depiction of a skin covering material 3 that can have a smaller circumference at one end than another end to be used with a sealing pad 2.

FIG. 47 is a sagittal depiction of a skin covering material 3 that can have a smaller circumference at one end than another end to be used with a sealing pad 2. In one embodiment the skin covering material 3 can have a smaller circumference at the sealing pad 2 than away from the sealing pad 2. In the preferred embodiment, the sealing pad 2 and skin covering material 3 can be used as a wound cover. In another embodiment the skin covering material 3 can have characteristics similar to a shower cap, and can include an elastic material that bunches 104 one end of the sealing pad 2 and has a smaller circumference to conform to the sealing pad 2 while the remainder of the sealing pad 2 has a larger circumference to conform to a larger body part 8 that can include a head, hand, foot, arm, leg, torso or appendage that can include the penis or finger. The skin covering material 3 can include containing an elastic material, a fabric, an elastomeric gel, latex, a rubber-like material, a polyurethane that can include stretching, bunching, expanding, contracting that can be resiliently deforming or non-resiliently deforming. In one embodiment the skin covering material 3 can have a larger circumference at the sealing pad 2 than away from the sealing pad 2. In one embodiment the skin covering material 3 can have an equal circumference at the sealing pad 2 than away from the sealing pad 2.

The combination of the sealing pad 2 and the skin covering material 3 of with these embodiments can include a shower cap, a cast cover, a wound cover, a breathing and intubation mask and device, a device covering that can include a device cover that is associated or intimate with the skin 1; a body part 8 cover that can include an appendage cover that can include a condom, a finger cover, an organ cover that can include an organ within a cavity or orifice or surgical site.

Figure 48:
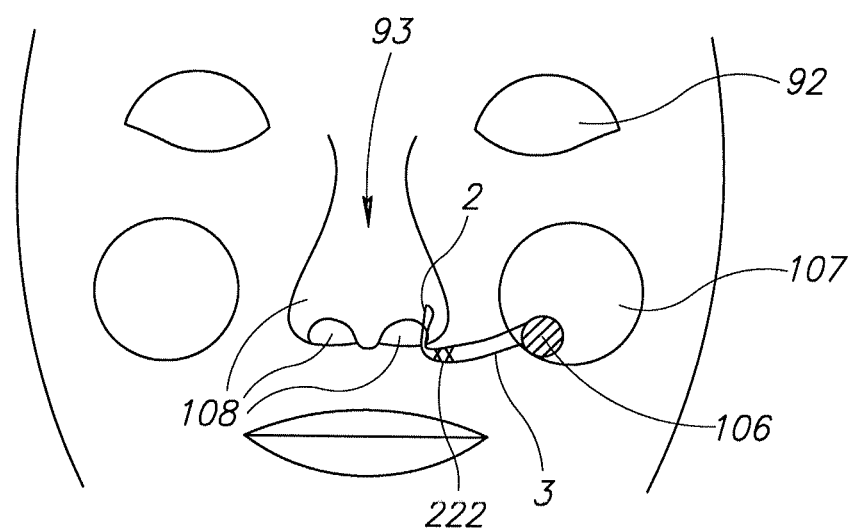
FIG. 48 is a frontal view of a nasal device that can be used to open the nares and nasal passages.

FIG. 48 is a frontal view of a nasal device 222 that can be used to open at least one or more nostrils and nares 108 or the nasal passages. One embodiment can include a device the fits into the nares and widens the diameter of the nares that can include containing no skin covering material 3 or containing a skin covering material 3 that can adhere to the skin through standard methods to include adhesives and tackifying agents. The skin covering material can be a connector between the adhesive and the nasal device 222. In another embodiment the nares can be widened by a nares device can be placed inside of the nares on the lateral inner portion of the nares and that nares device can be attached to a skin covering material that can stretch or maintain the nares and nasal passages in a more open position that can be attached to the skin that can include a region near the junction of the nose 93 and a cheek 107 and can be adhered to the skin through standard methods to include adhesive 106 and tackifying agents. The nasal device 222 can contain a gel sealing pad 2 that can be but does not have to be airtight and watertight.

Figure 49A:
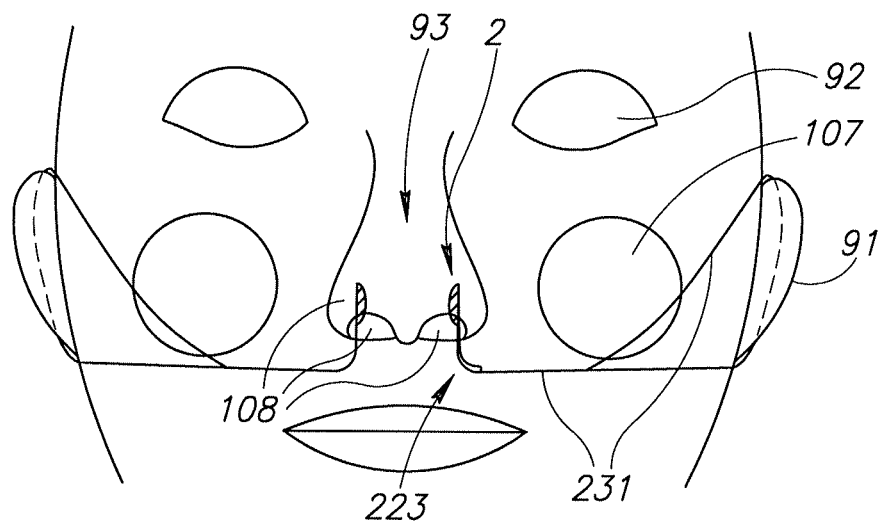
FIG. 49A is a frontal view of a nostril or nares-like 223 device that can be used to open the nares and nasal passages.

FIG. 49A is a frontal view of a nostril or nares-like 223 device that can be used to open the nares and nasal passages. In another embodiment a band or strap 231 can be placed around the head or ears 91 or a combination of these body parts and the ends of the band or strap 231 can be attached directly to the facial skin that can include attachment point near the skin of the cheek 107 or outer skin of the nose 93 or near the junction of the cheek 107 and nose 93 or any region or combination of these regions. There can be one or more than one attachment points and band or strap 231. In another embodiment the band or strap 231 can be combined with the device that resides inside of the nares and the methods of FIGS. 49A and 49B can be combined.

Figure 49B:
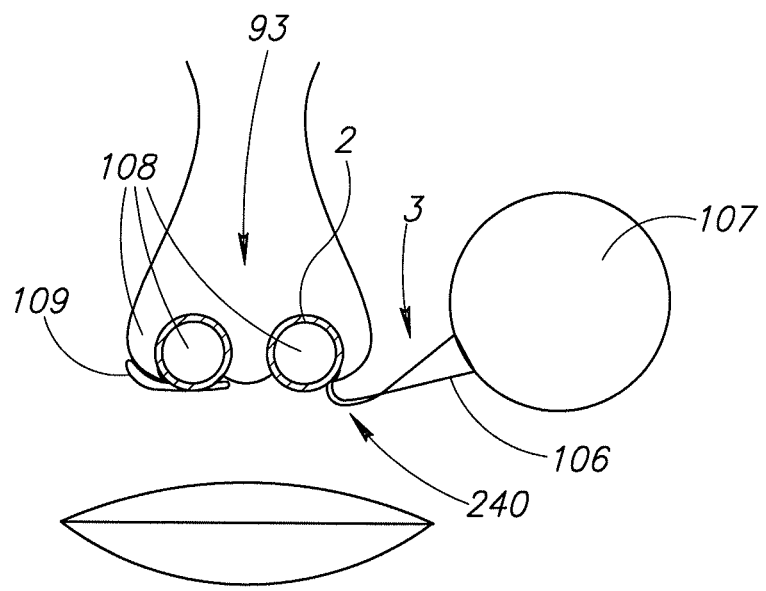
FIG. 49B is a frontal view of a nares separating device 240 that opens the nares to improve breathing.

FIG. 49B is a frontal view of a nares separating device 240 that opens the nares to improve breathing. This embodiment can include an annular or non-annular structure that resides within nostril and increases or keeps the inner diameter of the nostril open or expanded. In the preferred embodiment the structure is annular and can have an extension or shelf-like structure or lip-like structure or rim 109 that prevents the structure from extending too far into the nostril. In another embodiment the nostril device.

Figure 50A:
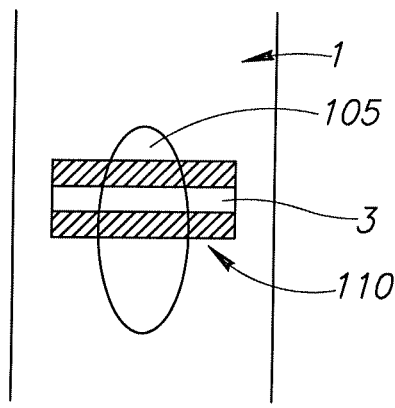
FIGS. 50A and 50B is a frontal view of a skin covering material 3 that forms a wound closure device and method. In the preferred embodiment the skin covering material wound strips.
Figure 50B:
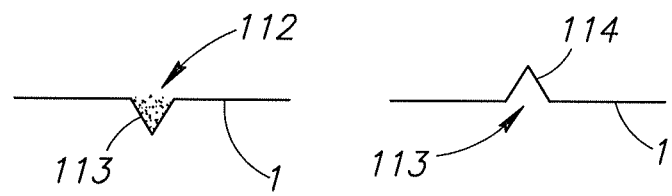

FIGS. 50A and 50B are a frontal views of a skin covering material 3 that forms a wound 105 closure device and method. In the preferred embodiment the skin covering material 3 forms wound 105 strips composed of strands that can include being composed of an elastomeric strip material 110 to include an elastomeric gel, rubber, latex, or fabric to include strips. The elastomeric skin covering material 3 can include one or more than one elastomeric strip material 110 of material and can be used in combination of non-elastomeric skin covering material 3 materials to include a fabric to include fibers, organic materials that can include wood and plant products, synthetic materials. The skin covering material 3 can adhere to the user's skin 1 through standard methods to include adhesives and tackifying agents.

This embodiment creates a tension that can hold the wound 105 closed and this differs from steri-strips that hold the wound 105 in place without tension. The usefulness of closing the wound 105 with tension is to place tension in specific locations of the wound. This new form of tension wound closure skin covering material 3 combined with the traditional steri-strip closures can assist assisting in the actual closure of the wound, healing, reduce infection because of earlier healing and intention and can more effective create closure of the wound 105 and can reduce scar 113. FIG. 50B depicts one theory on scar formation which is that a scar 113 are more likely to form when the wound 105 closes with a trough 112 with a shadow than a bump 114 with no shadow because of the manner that light reflects off of the wound.

Figure 51:
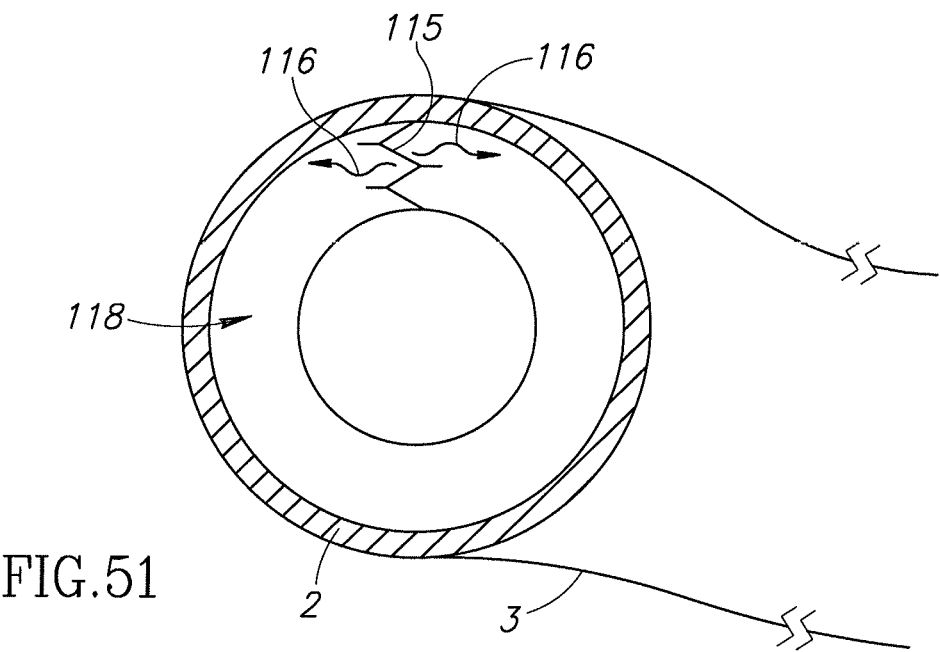
FIG. 51 is a frontal view of an applicator or expander that can be placed within a sealing pad 2 to assist in the application of the sealing pad 2 onto a body part.

FIG. 51 is a frontal view of an applicator 118 that can be placed within a sealing pad 2 to assist in the application of the sealing pad 2 onto a body part. There can be a challenge of placing a sealing pad 2, a skin covering material 3, a fixation device 11, an anchoring device 35 or any combination of these elements onto or in a body part that can include a user that has a broken hand or arm and has limited use of that limb, or to insure that that the sealing pad 2, a skin covering material 3, a fixation device 11 or any combination of these elements does not bunch up or tangle when being applied to the body part. The use of an applicator 118 can facilitate the placement of the sealing pad 2, a skin covering material 3, a fixation device 11 or any combination of these elements onto the body. The applicator 118 can be annular or non-annular. The applicator 118 can have a geometric or a random shape and can have zero, one or more than one protuberance or invagination. In the preferred embodiment the applicator 118 can be a circular structure that is annular and provides for an appendage to fit through the hollow of the applicator 118. In one of the preferred embodiments the applicator 118 is a simple cylindrical or annular structure. In the preferred application the applicator 118 can be used as a cast cover that has a circumference or a diameter or a length greater than the cast and therefore can provide for the application of the cast cover over the cast without undo effort. The applicator 118 can include an annular structure that is a shallow cylinder that can be being as wide, equal to or less wide than the sealing pad 2. The applicator 118 can lie within or be within or lie outside of the sealing pad 2. In the preferred embodiment the applicator 118 lies within the inner circumference of the sealing pad 2 and expands that sealing pad 2 and the skin covering material 3 to allow the sealing pad 2 and the skin covering to fit over the body part that can include an appendage that can be associated with zero or one or more than one nostril or nares like device to include a cast or monitor or feedback or measuring or delivery device. The applicator 118 can be composed of a material or structure that can expand, contract or remain the same size. The applicator 118 can be formed from a substance or coated by a substance or be combination of substances that can have a coefficient of friction that is equal to, less than or more than the sealing pad 2 or the skin covering material 3 and or can have any combination of these element.

The application device can include substances that reduce friction that include materials that include Teflon, oils ultrahard carbon film, near-frictionless carbon (NFC), MoS2, smooth diamond and diamond-like carbon films, or natural diamond and highly polished metals to include polished steel, a substance with a friction close to the sealing pad 2 or the skin covering which can include a substance that is the same as the sealing pad 2 or skin covering material 3 or a substance with an increased friction relative to the sealing pad 2 or skin covering material 3 that can include a rubber, roughened surfaces or vertically aligned polymer microfibers that can include being each less than a micron in diameter and 20 microns high. Another method to assist in efficient application of the sealing pad 2 and skin covering material 3 onto and off of the applicator 118 can include to have zero, one or more than one form of projections or invaginations on the applicator 118 or the sealing pad 2 fixation device 11, or the skin covering material. Another method to assist in efficient application of the sealing pad 2, fixation device 11, and skin covering material 3 onto and off of the applicator 118 can include to have zero, one or more than one transitional materials to reside between the applicator 118 and the sealing pad 2 or skin covering material 3 fixation device 11 or any combination of these elements. The removal of the sealing pad 2 and skin covering material 3 form the applicator 118 can include mechanical methods to include sliding, pulling 116, rolling, pushing, wiggling, zipping, snipping, twisting, unhooking, unbuttoning and popping the sealing pad 2, fixation device 11, and skin covering material 3 or the applicator 118 or any combination of these elements apart relative to each other. In another embodiment the applicator 118 can be composed such that it has a fastening device 115 that can be unfastened that can include a mirror geometric or random shape that can be unfastened by means to include mechanical means to include sliding, pulling, rolling, pushing, wiggling, zipping, snipping, twisting, unhooking, unbuttoning and popping the sealing pad 2, fixation device 11, and skin covering material 3 or the applicator 118 or any combination of these elements.

In the preferred embodiment the applicator 118 can include a plastic annular cylinder that is of greater diameter than the sealing pad 2, fixation device 11, and skin covering material 3 such that these elements are stretched to a diameter fitting comfortably over the applicator 118. The applicator 118 is annular and has a fastening device 115. The applicator 118 has a diameter greater than the diameter of the cast cover or the appendage over which the sealing pad 2, fixation device 11, and skin covering material 3 and applicator 118 must fit. The sealing pad 2, fixation device 11, and skin covering material 3. The sealing pad 2, fixation device 11, and skin covering material 3 can be fitted over the cast cover and the appendage and put into a position such that the sealing pad 2, fixation device 11, and skin covering material 3 and applicator 118 are proximal to the cast and reside over the skin proximal to the cast. Once in position the fastening device 115 of the applicator 118 which is a mirrored geometric configuration is pulled apart and the applicator 118 is gradually removed leaving the sealing pad 2, fixation device 11, and skin covering material 3 or any combination of these elements in position against the user's skin 1 and creating a watertight or airtight seal. The applicator 118 is removed. The applicator 118 can be used once, more than once making it reusable or the sealing pad 2, fixation device 11, and skin covering material 3 or any combination of these elements can be placed onto the skin without an applicator 118. In another configuration the applicator 118 can reside within a fold of the sealing pad 2, fixation device 11, or skin covering material 3 or any combination of these elements.

Figure 52:
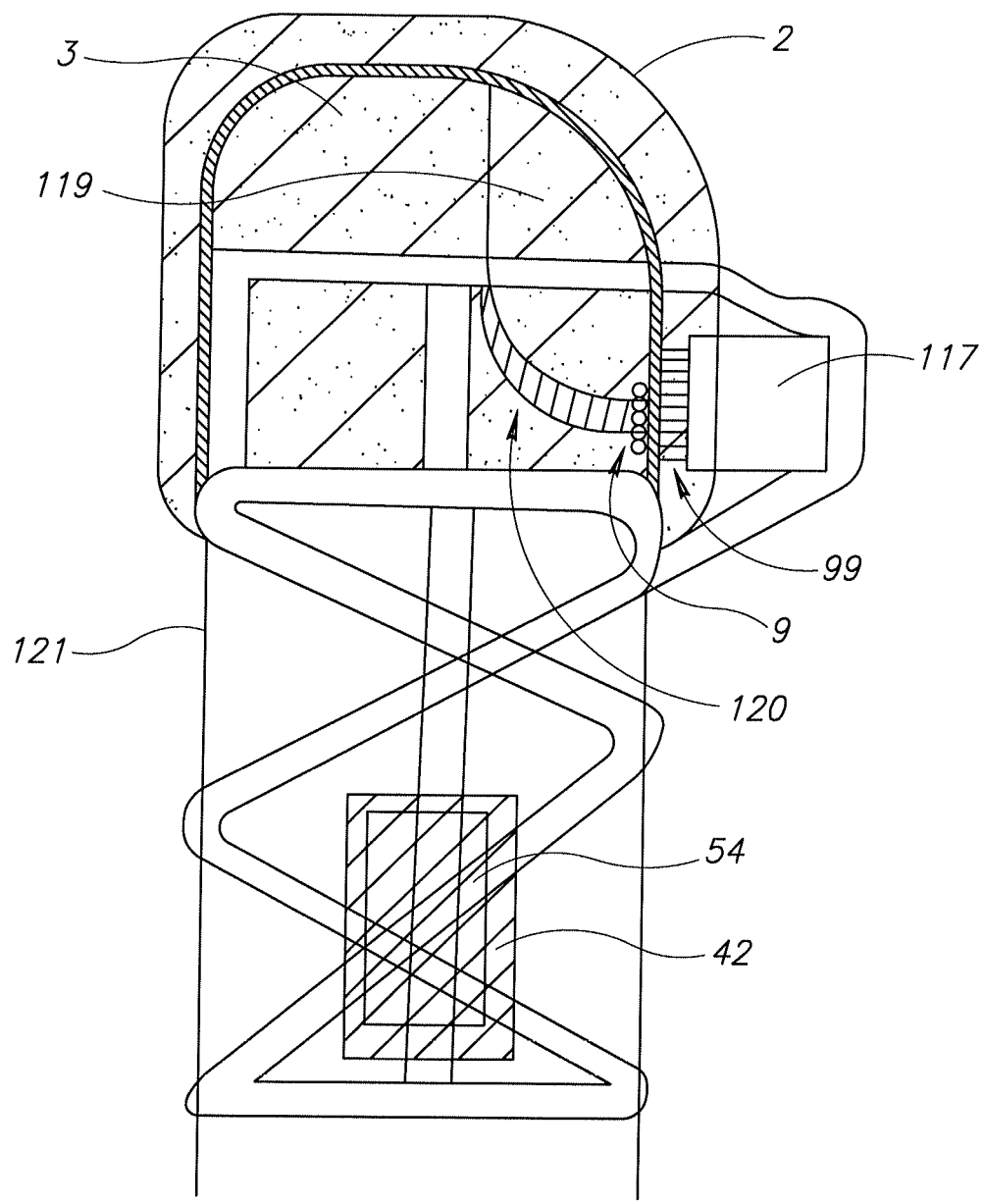
FIG. 52 is a sagittal view of a device to deliver medication through the skin to a subdermal or subcutaneous structure.

FIG. 52 is a sagittal view of a device to deliver medication through the skin to a sub dermal or subcutaneous structure. In one embodiment the sealing pad 2, fixation device, anchoring device, reservoir, or skin covering material 3 or any combination of these elements can contain a medication delivery device that has indicator and measuring device 54 or feedback device 42 to regulate to include the energy and the medication or any combination of these elements. In the preferred embodiment the sealing pad 2 is attached to an appendage which can include a body part to include a finger or toe 121. In the preferred embodiment the nail 119 of the finger or toe has a fungal infection that resides in the nail 119 and in the growth plate of the nail 119 known as the matrix 120. To treat the nail 119 and remove the fungus it is postulated that the matrix 120 must be eradicated of the infection. In the preferred embodiment the gel sealing pad 2 rests on the matrix 120.

An energy delivery or activating device 117 to deliver the delivered substance or energy 9 to include chemical, electromagnetic or kinetic or Brownian energy or a substance to include a solid or liquid or gel or gas, which can be held in place by the sealing pad 2, fixation device, anchoring device, reservoir, or skin covering material 3 or any combination of these elements and the device can reside with these elements or between these elements and the skin or nail 119 bed or external to the nail and skin and these elements. The device can utilize a treatment to include a chemical reaction, an energy source to include chemical energy, electromagnetic energy, kinetic or Brownian energy. An indicator and measuring device 54 and a feedback device 42 can be used to assess the energy delivery and the biological effects of the delivery of the chemical reaction or energy reaction on the biological system. In one embodiment energy alone can be used to alter the biology, which can include treating the infection, sterilizing, reducing aging effects, or promoting biological or physiological wellness. In another embodiment the delivered substance or energy 9 which can be a solid, liquid, gel or gas can be applied to the skin which can be superficial or in a cavity to include the peritoneal lining or the fascia or the adventia or serosa of an organ or body structure or orifice to include the mucosa or a membrane or can be placed deep to the skin or mucosa or membrane. In one embodiment this can create a chemical reaction and the sealing pad 2 can control the environment between the sealing pad 2 and the skin which overlies the body structure to include the epidermis, mucosa or a membrane or the adventia or serosa of an organ or fascia or a nail 119. In another embodiment an energy source can be used alone or an energy source and the delivered substance or energy 9 which can be a solid, liquid, gel or gas can be used together to alter biological or physiological function to include treating the infection, sterilizing, reducing aging effects, or promoting biological or physiological wellness. In the preferred embodiment the substance can include micro-particles or inclusion bodies that contain a substance that can penetrate the skin using and energy source to include ultrasound.

Figure 53:
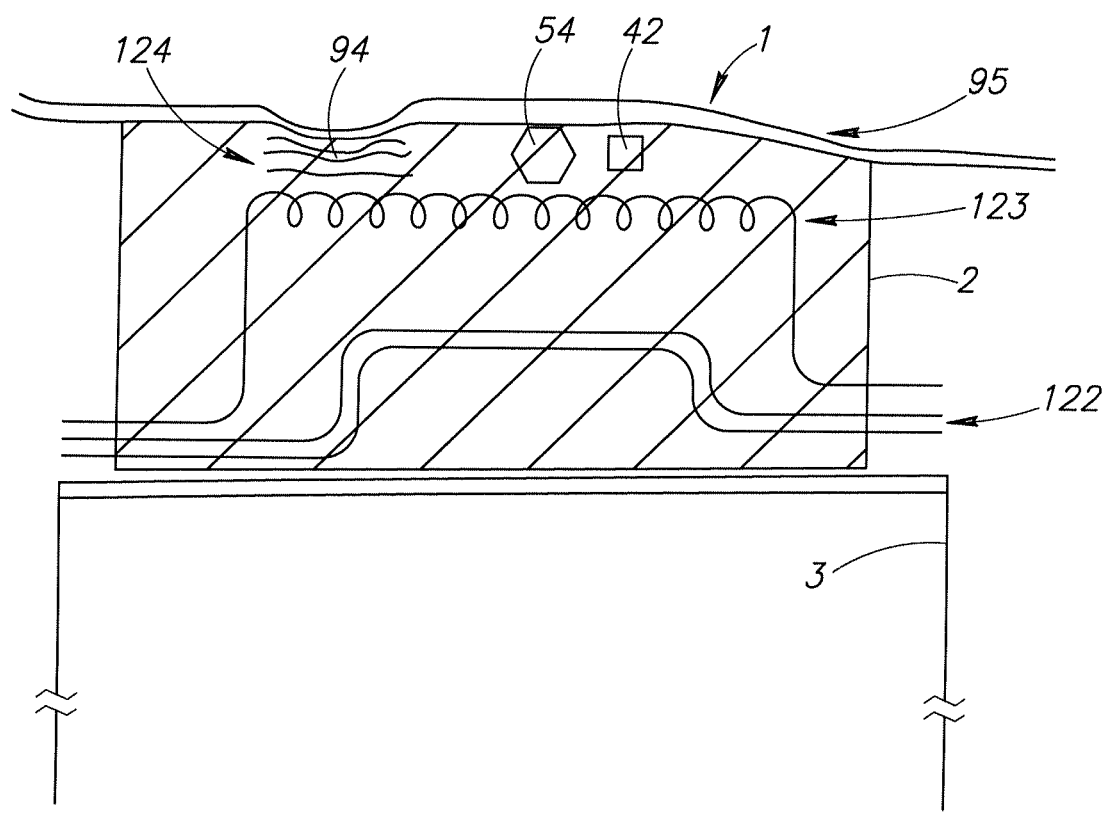
FIG. 53 is a sagittal view of a gel sealing pad 2 with a method for altering its physical properties 124 to include the hardness and softness 94 and thickness 95 of the sealing pad 2.

FIG. 53 is a sagittal view a gel sealing pad 2 with a method for altering its physical properties 124 to include the hardness and softness 94 and thickness 95 of the sealing pad 2. In one embodiment the sealing pad 2, fixation device 11, anchoring device 35 or skin covering material 3 or any combination of these elements can be composed a material to include a gel or solid that has the ability to alter its physical properties 124 to include its hardness and softness 94, its thickness 95 or length or width, its coefficient of friction, or its repair capabilities, or any combination of the physical properties 124. In one embodiment the sealing pad 2, fixation device 11, anchoring device 35 and skin covering material 3 the indicator and measuring device 54 or feedback device 42 or any combination of these elements can be composed a material to include a gel or solid that has the ability to alter physical properties 124 to include its hardness or softness 94 or thickness 95 coefficient of friction or length and width or any combination of the physical properties 124 using a method or device to include a heating or cooling device 122, or a reservoir 41, or can have impregnated materials that can be a solid or liquid or gel or gas and can be formed from a material to include an elastomer to include a thermoplastic elastomer, gel, rubber, latex, and metals polymer and alloy materials to include temperature-responsive polymers which are materials which undergo changes upon temperature changes, smart metals to include Nitenol and shape memory alloys and non-metal shape memory polymers in which large deformation can be induced and recovered through temperature changes or stress changes and martensitic phase changes, piezoelectric materials that produce a voltage when forces or stress are applied resulting in structure altering shape to include bend, expand or contract when said voltage is applied, shape memory alloys and shape memory polymers which can have large deformations which can be induced and recovered through temperature changes or stress changes (pseudoelasticity), magnetostrictive materials which can change in shape under the influence of a magnetic field and can exhibit a change in their magnetization under the influence of mechanical stress, magnetic shape memory alloys which are materials that change their shape in response to a significant change in a magnetic field, pH-sensitive polymers which are materials that change in volume and shape when the pH of the surrounding environment changes, halochromic materials which can change their color as a result of changing acidity which can also be used as indicators to include condoms which can include a sensor to detect a breach in the condom integrity or intubation devices to include a sensor to detect whether gastric reflux or aspiration has occurred or wound covers that can include detect infectious agents that change the pH of the wound to include bacteria, fungi, viruses and other infectious pathogens, chromogenic systems which can change color in response to electrical, optical or thermal changes which can include electrochromic materials, which change their color or opacity on the application of a voltage to include liquid crystal displays, thermochromic materials change in color depending on their temperature, and photochromic materials, which change color in response to light, ferrofluids, photomechanical materials change shape under exposure to light, self-healing materials 125 have the intrinsic ability to repair damage due to normal usage, thus expanding the material's lifetime, dielectric elastomers (DEs) are smart material systems which produce large strains under the influence of an external electric field, magnetocaloric materials are compounds that undergo a reversible change in temperature upon exposure to a changing magnetic field, Thermoelectric materials are used to build devices that convert temperature differences into electricity and the reverse or other electromagnetic sensitive materials that can alter their physical properties when exposed to electromagnetic energy including ultraviolet and infrared sources or chemical reaction energy, kinetic energy including vibration or chemical reactions including chemical bonding methods; and nonotechnology. In one embodiment to include a device for intubation, cast cover, wound cover, environment cover, urination collection and disposal, sexual stimulation, sexual and erectile function and orgasm and gratification, fecal and body waste disposal, eyewear and goggles, breathing masks and intubation devices and masks, nasal and ear devices to include olfactory and auditory devices, surgical cavity and body organ protection and isolation, isolation chambers, and infection treatment and aging treatment as well as other physiologic and biologic functions that are assisted by an effective seal which can be airtight and watertight or not airtight and not watertight which are composed of a gel sealing pad 2 and a skin covering material 3 in which the gel sealing pad 2 or the gel sealing pad and skin covering material 3 incorporate a method for altering their physical properties to include altering the hardness and softness 94 and thickness 95 of the sealing pad 2 in response to the compression or pressure or the airtight and watertight seal required produced on or upon the local skin, mucosal tissue or membranes and orifice lining skin. In one embodiment this embodiment the sealing pad 2 composed of a thermoplastic polymer, a magneto-sensitive material, or an electromagnetic sensitive material that can include a gel. Indicator and measuring device 54 and feedback device 42 can be positioned on or in or near or distant to the sealing pad 2 or skin covering material 3 or fixation device 11 or the anchoring device 35 or any combination of these elements. In the presence of a physiologic or biologic stimulus or event that can include gastric reflux, aspiration, a decreased airtight or watertight seal, adverse pressure on the local mucosa or skin of the internal cavity or the external skin or adverse positioning or pressure on the larynx, the indicator and measuring device 54 can feedback a need to alter the physical property of the sealing pad 2 in the preferred embodiment but can include sealing pad 2, fixation device 11, anchoring device 35 and skin covering material 3 or any combination of these elements. In one embodiment a feedback device 42 can be present but does not have to be present and which can automatically produce or initiate and can also turn off or vary or modulate a stimulus that can include a heating or cooling device 122, an electromagnetic device 123, or a chemical device or any combination of these elements. In the preferred embodiment a heating or electromagnetic device 123 can be can be positioned on or in or near or distant to the sealing pad 2 but can include the sealing pad 2, skin covering material 3, fixation device 11, anchoring device 35, the indicator and measuring device 54 or feedback device 42 or any combination of these elements such that the sealing pad 2 which can include a thermosensitive gel, or thermoplastic elastomer can have its physical properties 124 altered which can include the gel sealing pad 2 which is within the oral or pharyngeal cavity can have its physical properties 124 altered which can include the gel sealing pad becoming softer or harder or thicker or thinner or longer or shortened in response to the physiology or biology needs of the user. The alteration of the physical characteristics can also be manually controlled by the user or the non-user in or upon whom the sealing pad 2 is employed.

Figure 54:
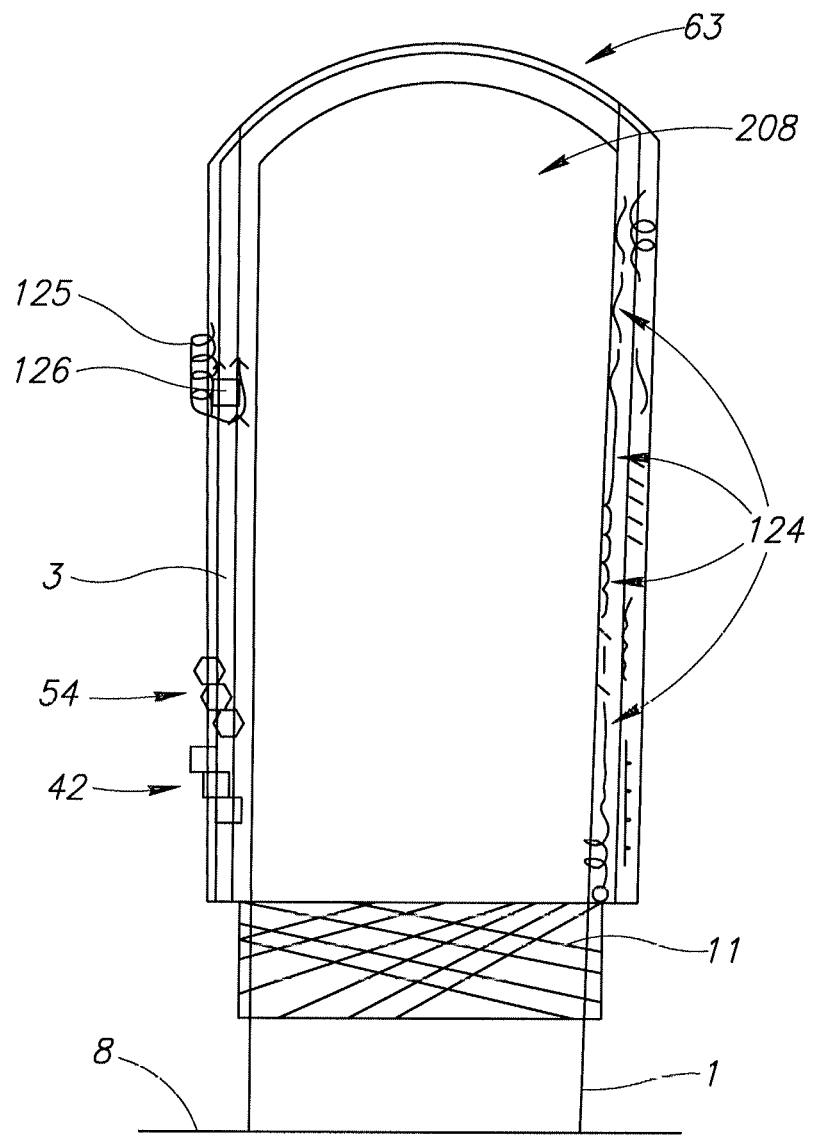
FIG. 54 is a frontal view of condom 63 that can alter its physical characteristics.

FIG. 54 is a frontal view of condom that can alter its physical characteristics to include sealing pad 2, skin covering material 3, fixation device 11, anchoring device 35, indicator and measuring device 54 and feedback device 42 can be composed of materials that can be a solid or liquid or gel or gas that can be formed from zero or at least one or more materials to include materials that alter their physical properties 124 to include temperature-responsive polymers which are materials which undergo changes upon temperature changes, smart metals to include Nitenol and shape memory alloys and non-metal shape memory polymers in which large deformation can be induced and recovered through temperature changes or stress changes and martensitic phase changes, piezoelectric materials that produce a voltage when forces or stress are applied resulting in structure altering shape to include bend, expand or contract when said voltage is applied, shape memory alloys and shape memory polymers which can have large deformations which can be induced and recovered through temperature changes or stress changes (pseudoelasticity), magnetostrictive materials which can change in shape under the influence of a magnetic field and can exhibit a change in their magnetization under the influence of mechanical stress, magnetic shape memory alloys which are materials that change their shape in response to a significant change in a magnetic field, pH-sensitive polymers which are materials that change in volume and shape when the pH of the surrounding environment changes, halochromic materials which can change their color as a result of changing acidity which can also be used as indicators to include condoms which can include a sensor to detect a breach 126 in the condom integrity or intubation devices to include a sensor to detect whether gastric reflux or aspiration has occurred or wound covers that can include detect infectious agents that change the pH of the wound to include bacteria, fungi, viruses and other infectious pathogens, chromogenic systems which can change color in response to electrical, optical or thermal changes which can include electrochromic materials, which change their color or opacity on the application of a voltage to include liquid crystal displays, thermochromic materials change in color depending on their temperature, and photochromic materials, which change color in response to light, ferrofluids, photomechanical materials change shape under exposure to light, self-healing materials 125 have the intrinsic ability to repair damage due to normal usage, thus expanding the material's lifetime, dielectric elastomers (DEs) are smart material systems which produce large strains under the influence of an external electric field, magnetocaloric materials are compounds that undergo a reversible change in temperature upon exposure to a changing magnetic field.

Thermoelectric materials are used to build devices that convert temperature differences into electricity and the reverse. In another embodiment the condom 63 that covers the penis 208 can include be impregnated with or lies within reservoir which contain a substance that can include a solid, liquid or gel or gas that can exhibit self-healing characteristics. In another embodiment a substance can be released from the condom or sealing pad 2 that can include a contraceptive substances which when exposed to a change in its environment to include its pH which differs in vaginal fluid compared to seminal fluid. In the preferred embodiment the condom 63 which covers the penis 208 contains materials that can alter their physical properties 124 and can alter the materials physical characteristics to at least partially repair or seal a breach. Other embodiments include the skin covering material 3 or sealing pad 2 or anchoring device or fixation device 11 altering physical characteristics to alter sensory and material sensations or properties to include changing temperature, physical contours and producing electrical stimulation in response to internal or external stimuli.

Figure 55:
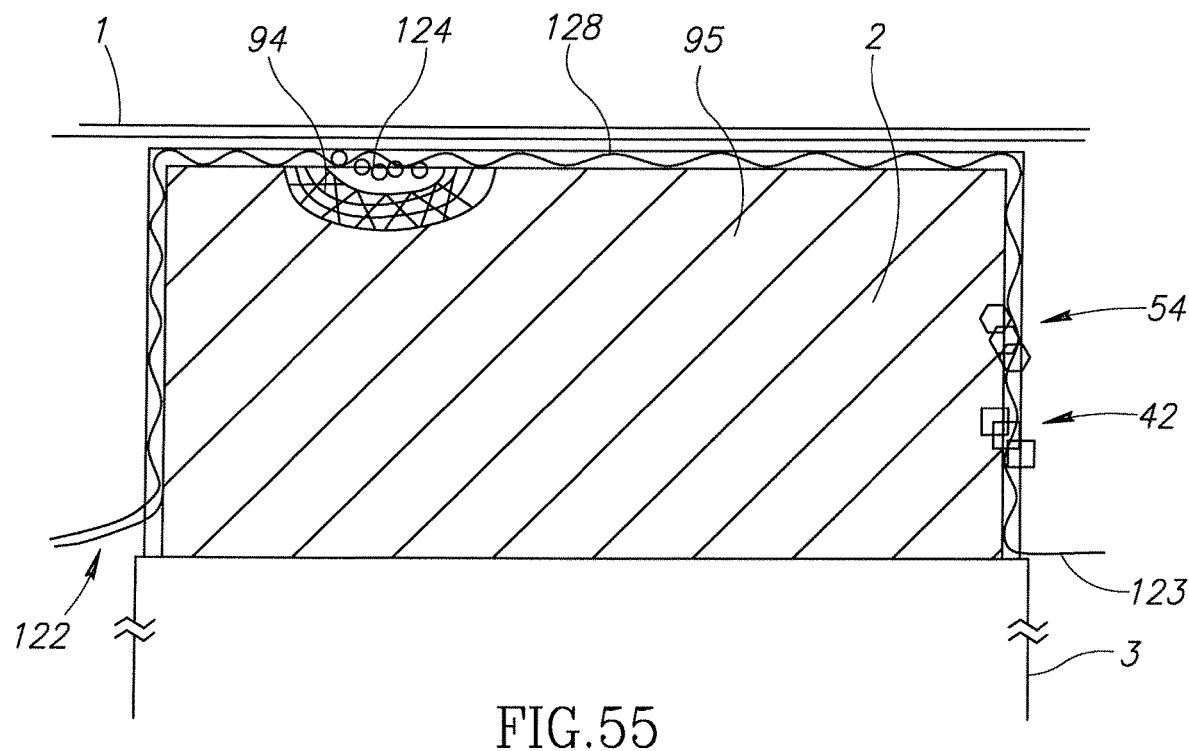
FIG. 55 is a sagittal depiction of an exoskeleton that can be composed a material to include a gel or solid that has the ability to alter its physical properties.

FIG. 55 is a sagittal depiction of an exoskeleton 128 that can be composed a material to include a gel or solid that has the ability to alter its physical properties 124 to include its hardness and softness 94, its thickness 95 or length or width, its coefficient of friction, or its repair capabilities, or any combination of these physical properties 124. In one embodiment the sealing pad 2, fixation device 11, anchoring device 35 and skin covering material 3 the indicator and measuring device 54 or feedback device 42 or any combination of these elements can incorporate and exoskeleton 128 that can be composed a material to include a gel or solid or liquid or gas that has the ability to alter its hardness or softness 94 or thickness 95 or any combination of these physical properties 124 using a method or device to include a heating or cooling device 122, or a reservoir 41, or can have impregnated materials that can be a solid or liquid or gel or gas and can be formed from a material to include an elastomer to include a thermoplastic elastomer, gel, rubber, latex, and metals polymer and alloy materials to include temperature-responsive polymers which are materials which undergo changes upon temperature changes, smart metals to include Nitenol and shape memory alloys and non-metal shape memory polymers in which large deformation can be induced and recovered through temperature changes or stress changes and martensitic phase changes, piezoelectric materials that produce a voltage when forces or stress are applied resulting in structure altering shape to include bend, expand or contract when said voltage is applied, shape memory alloys and shape memory polymers which can have large deformations which can be induced and recovered through temperature changes or stress changes (pseudoelasticity), magnetostrictive materials which can change in shape under the influence of a magnetic field and can exhibit a change in their magnetization under the influence of mechanical stress, magnetic shape memory alloys which are materials that change their shape in response to a significant change in a magnetic field, pH-sensitive polymers which are materials that change in volume and shape when the pH of the surrounding environment changes, halochromic materials which can change their color as a result of changing acidity which can also be used as indicators to include condoms which can include a sensor to detect a breach in the condom integrity or intubation devices to include a sensor to detect whether gastric reflux or aspiration has occurred or wound covers that can include detect infectious agents that change the pH of the wound to include bacteria, fungi, viruses and other infectious pathogens, chromogenic systems which can change color in response to electrical, optical or thermal changes which can include electrochromic materials, which change their color or opacity on the application of a voltage to include liquid crystal displays, thermochromic materials change in color depending on their temperature, and photochromic materials, which change color in response to light, ferrofluids, photomechanical materials change shape under exposure to light.

Self-healing materials have the intrinsic ability to repair damage due to normal usage, thus expanding the material's lifetime, dielectric elastomers (DEs) are smart material systems which produce large strains under the influence of an external electric field, magnetocaloric materials are compounds that undergo a reversible change in temperature upon exposure to a changing magnetic field. Thermoelectric materials are used to build devices that convert temperature differences into electricity and the reverse or other electromagnetic sensitive materials that can alter their physical properties 124 when exposed to electromagnetic energy including ultraviolet and infrared sources or kinetic energy including vibration or chemical reactions including chemical bonding methods; and nonotechnology. In the preferred embodiment the exoskeleton 128 can be incorporated with an intubation device is composed of a gel sealing pad 2 and a skin covering material 3 in which the gel sealing pad 2 or the gel sealing pad 2 and skin covering material 3 incorporate an exoskeleton 128 for altering their physical properties 124 to include altering the hardness and softness 94 and thickness 95 or coefficient of friction of the sealing pad 2 or skin covering material 3 in response to the compression or pressure or the airtight and watertight seal required produced on or upon the local mucosal tissue and orifice lining skin. The exoskeleton 128 can be composed of a thermoplastic polymer, a magneto-sensitive material, or an electromagnetic sensitive material that can include a gel.

Indicator and measuring device 54 and feedback device 42 can be positioned on or in or near or distant to the exoskeleton 128 or sealing pad 2 or skin covering material 3 or fixation device 11 or the anchoring device 35 or any combination of these elements. In the presence of a physiologic or biologic stimulus or event that can include gastric reflux, aspiration, a decreased airtight or watertight seal, adverse pressure on the local mucosa or skin of the internal cavity or the external skin or adverse positioning or pressure on the larynx, the indicator and measuring device 54 can feedback a need to alter the physical property of the exoskeleton 128 or the sealing pad 2 in the preferred embodiment but can include the exoskeleton 128, sealing pad 2, fixation device 11, anchoring device 35 and skin covering material 3 or any combination of these elements. In one embodiment a feedback device 42 can be present but does not have to be present and which can automatically produce or initiate and can also turn off or vary or modulate a stimulus that can include a heating or cooling device 122, an electromagnetic device 123, or a chemical device or any combination of these elements. In the preferred embodiment the exoskeleton 128 can include a heating or cooling device 122 or electromagnetic device 123 that can be can be positioned on or in or just near the surface of the sealing pad 2 but can include the sealing pad 2, skin covering material 3, fixation device 11, anchoring device 35, the indicator and measuring device 54 or feedback device 42 or any combination of these elements such that the sealing pad 2 which can include a thermosensitive metal, polymer, plastic. gel, or thermoplastic elastomer that can have its physical properties 124 altered which can include influencing the gel sealing pad 2 which is within the oral or pharyngeal cavity can have its physical properties 124 altered which can include the gel sealing pad 2 becoming more or less slippery, softer or harder or thicker or thinner or longer or shortened in response to the physiology or biology needs of the user. The alteration of the physical characteristics can be manually controlled by the user upon whom the sealing pad 2 is being employed or the non-user upon whom the sealing pad 2 is not being employed or any combination or numbers of users and non-users.

Zero or one or more endoskeleton 129 or exoskeleton 128 can be used with the sealing pad 2, skin covering material 3, fixation device 11, anchoring device 35 and the indicator and measuring device 54 or feedback device 42 or any combination of these elements. The exoskeleton 128 can include integrating a heating or cooling device 122 or an electromagnetic device 123 or a chemical reaction to altering the characteristics of the exoskeleton 128. These devices can be controlled or modulated locally by the indicator and measuring device 54 and feedback device 42 or by an external source or external controlling individual.

Figure 56:
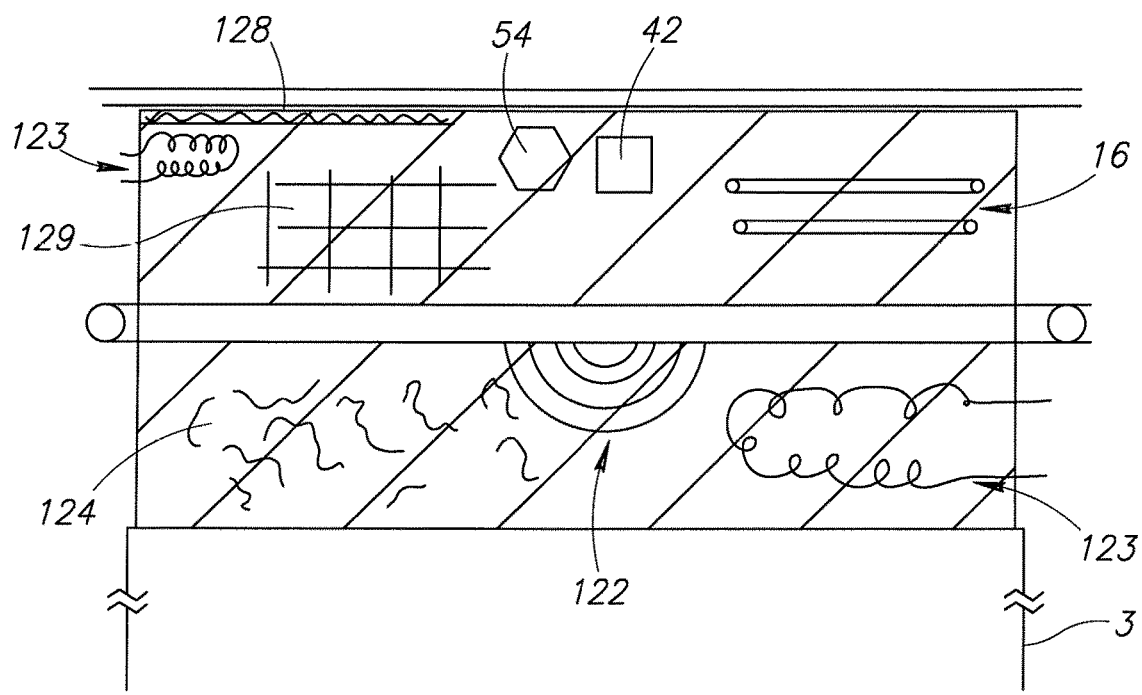
FIG. 56 is a sagittal depiction of an endoskeleton that can be composed a material to include a gel or solid that has the ability to alter its physical properties 124.

FIG. 56 is a sagittal depiction of an endoskeleton 129 that can be composed a material to include a gel or solid that has the ability to alter its physical properties to include its hardness and softness, its thickness or length or width, its coefficient of friction, or its repair capabilities, or any combination of these properties. In one embodiment the sealing pad 2, fixation device 11, anchoring device 35 and skin covering material 3 the indicator and measuring device 54 or feedback device 42 or any combination of these elements can incorporate an endoskeleton 129 that can be composed a material to include a gel or solid or liquid or gas that has the ability to alter its hardness or softness or thickness or any combination of these properties using a method or device to include a heating or cooling device 122, or a reservoir 41, or can have impregnated materials that can be a solid or liquid or gel or gas and can be formed from a material to include an elastomer to include a thermoplastic elastomer, gel, rubber, latex, and metals polymer and alloy materials to include temperature-responsive polymers which are materials which undergo changes upon temperature changes, smart metals to include Nitenol and shape memory alloys and non-metal shape memory polymers in which large deformation can be induced and recovered through temperature changes or stress changes and martensitic phase changes, piezoelectric materials that produce a voltage when forces or stress are applied resulting in structure altering shape to include bend, expand or contract when said voltage is applied, shape memory alloys and shape memory polymers which can have large deformations which can be induced and recovered through temperature changes or stress changes (pseudoelasticity), magnetostrictive materials which can change in shape under the influence of a magnetic field and can exhibit a change in their magnetization under the influence of mechanical stress, magnetic shape memory alloys which are materials that change their shape in response to a significant change in a magnetic field, pH-sensitive polymers which are materials that change in volume and shape when the pH of the surrounding environment changes, halochromic materials which can change their color as a result of changing acidity which can also be used as indicators to include condoms which can include a sensor to detect a breach in the condom integrity or intubation devices to include a sensor to detect whether gastric reflux or aspiration has occurred or wound covers that can include detect infectious agents that change the pH of the wound to include bacteria, fungi, viruses and other infectious pathogens, chromogenic systems which can change color in response to electrical, optical or thermal changes which can include electrochromic materials, which change their color or opacity on the application of a voltage to include liquid crystal displays, thermochromic materials change in color depending on their temperature, and photochromic materials, which change color in response to light, ferrofluids, photomechanical materials change shape under exposure to light.

Self-healing materials have the intrinsic ability to repair damage due to normal usage, thus expanding the material's lifetime, dielectric elastomers (DEs) are smart material systems which produce large strains under the influence of an external electric field, magnetocaloric materials are compounds that undergo a reversible change in temperature upon exposure to a changing magnetic field, Thermoelectric materials are used to build devices that convert temperature differences into electricity and the reverse or other electromagnetic sensitive materials that can alter their physical properties when exposed to electromagnetic energy including ultraviolet and infrared sources or kinetic energy including vibration or chemical reactions including chemical bonding methods; and nonotechnology. In the preferred embodiment the endoskeleton 129 can be incorporated with an intubation device is composed of a gel sealing pad 2 and a skin covering material 3 in which the gel sealing pad 2 or the gel sealing pad 2 and skin covering material 3 incorporate an endoskeleton 129 for altering their physical properties to include altering the hardness and softness and thickness or coefficient of friction of the sealing pad 2 or skin covering material 3 in response to the compression or pressure or the airtight and watertight seal required produced on or upon the local mucosal tissue and orifice lining skin. The endoskeleton 129 can be composed of a thermoplastic polymer, a magneto-sensitive material, or an electromagnetic sensitive material that can include a gel.

Indicator and measuring device 54 and feedback device 42 can be positioned on or in or near or distant to the endoskeleton 129 or sealing pad 2 or skin covering material 3 or fixation device 11 or the anchoring device 35 or any combination of these elements. In the presence of a physiologic or biologic stimulus or event that can include gastric reflux, aspiration, a decreased airtight or watertight seal, adverse pressure on the local mucosa or skin of the internal cavity or the external skin or adverse positioning or pressure on the larynx, the indicator and measuring device 54 can feedback a need to alter the physical property of the endoskeleton 129 or the sealing pad 2 in the preferred embodiment but can include the endoskeleton 129, sealing pad 2, fixation device 11, anchoring device 35 and skin covering material 3 or any combination of these elements. In one embodiment a feedback device 42 can be present but does not have to be present and which can automatically produce or initiate and can also turn off or vary or modulate a stimulus that can include a heating or cooling device 122, an electromagnetic device 123, or a chemical device or any combination of these elements. In the preferred embodiment the endoskeleton 129 can include a heating or electromagnetic device 123 that can be can be positioned on or in or just near the surface of the sealing pad 2 but can include the sealing pad 2, skin covering material 3, fixation device 11, anchoring device 35, the indicator and measuring device 54 or feedback device 42 or any combination of these elements such that the sealing pad 2 which can include a thermosensitive metal, polymer, plastic. gel, or thermoplastic elastomer that can have its physical properties altered which can include influencing the gel sealing pad 2 which is within the oral or pharyngeal cavity can have its physical properties altered which can include the gel sealing pad 2 becoming more or less slippery, softer or harder or thicker or thinner or longer or shortened in response to the physiology or biology needs of the user. The alteration of the physical characteristics can be manually controlled by the user upon whom the sealing pad 2 is being employed or the non-user upon whom the sealing pad 2 is not being employed or any combination or numbers of users and non-users. Zero or one or more endoskeleton 129 or exoskeleton 128 can be used with the sealing pad 2, skin covering material 3, fixation device 11, anchoring device 35 and the indicator and measuring device 54 or feedback device 42 or any combination of these elements.

Figure 57:
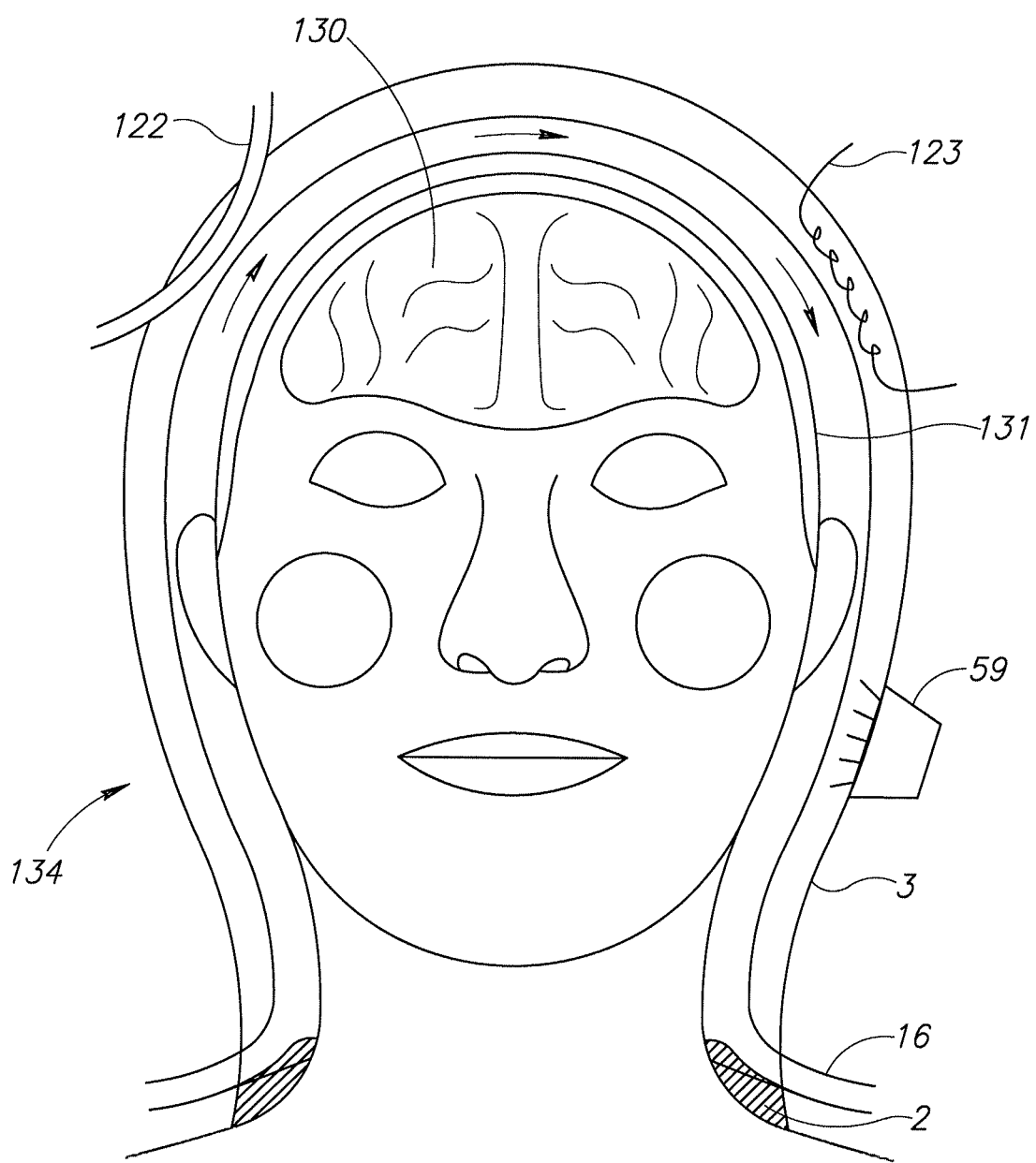
FIG. 57 is a head heating or cooling device that can be worn over the head whose use is to treat body conditions to include brain or biologic or physiologic conditions.
Figure 58:
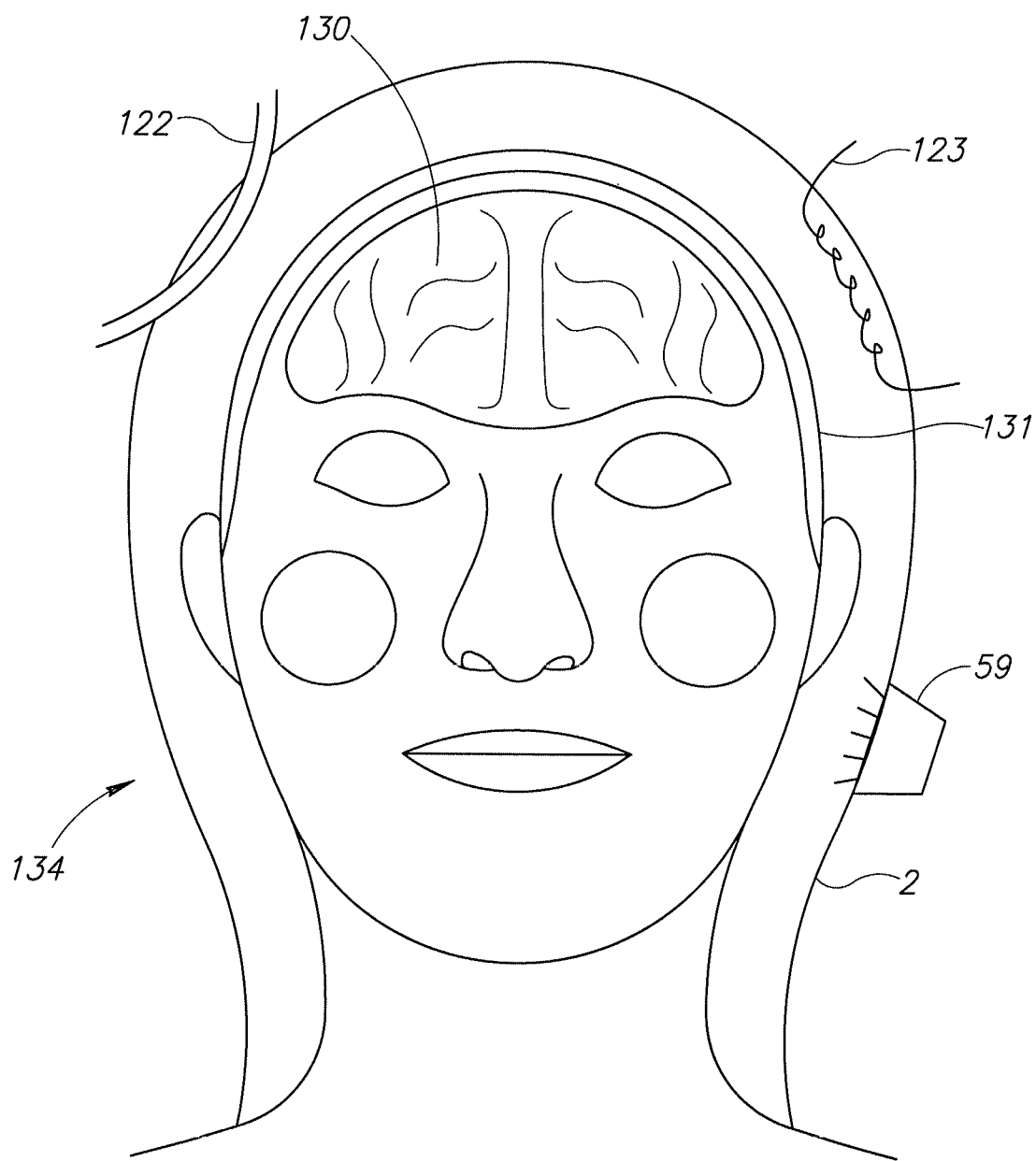
FIG. 58 is a head heating or cooling device that can be worn over the head whose use is to treat body conditions to include brain or biologic or physiologic conditions.

FIG. 57 is a cooling or heating device that has one or more than one compartment that in the preferred embodiment is a head cooling or heating device 134 that in this depiction contains more than one compartment. FIG. 58 is a head cooling or heating device 134 that has one or more than one compartment and in this depiction contains one compartment. One embodiment can include a cooling device that can be worn over the head or other body parts which in the preferred embodiment is worn over the head and neck region whose use is to treat body part to include brain 130 or biologic or physiologic conditions that can include overheating during warm weather, heat stroke, febrile seizures, muscle cramping, hair loss, heart disease and respiratory disease and renal diseases; and psychiatric disorders to include anger or rage or anxiety, suicide, depression, schizophrenia, memory and mania and other biological and psychiatric conditions thought to be caused or felt to be caused or exacerbated by excess body or brain 130 heating, conditions that would benefit from body or brain 130 cooling or slow body or brain 130 metabolism to include ischemic stroke, seizures, brain 130 tumor growth. In one embodiment the cooling device can be composed of a sealing pad 2, skin covering material 3, fixation device 11, anchoring device 35 and indicator and measuring device 54 or feedback device 42 or any combination of these elements. Incorporated into this device is a cooling device that can include a solid of liquid or gas or gel material that can be used to interface with the sealing pad 2 which can be airtight and water tight but does not have to be airtight or watertight.

Methods of cooling can include conduction which can include direct transfer of heat through cooling devices to include cooling tubes, channels, or conduit 16 that can contain water, Freon, chemical reactions, thermoelectric cooling with heating and cooling device 122, or vapor compression cooling; or convection which can include fans, blowers impellers, and evaporation which can include refrigeration and fan and air-conditioning like devices. In one embodiment the cooling head cap is composed of a sealing pad 2 that can include a gel or a non-gel that can form an airtight or watertight seal with at least a portion of the user's head or neck to form an isolation chamber. In the preferred embodiment the seal is a gel seal. In method A the isolation chamber is created such that there can be a liquid or gel or a gas or solid or combination of these elements that passes between the user's skin 1 which can include the scalp 131, face or neck and torso and serves as a means of removing heat or transferring heat away from the user's brain 130. In one embodiments some orifices or some given body part can be kept separate from the isolation chamber and these body parts can include a body that can include the user's mouth and nose and ears or torso such that these body parts can be sequestered from the remainder of the isolation chamber by additional sealing pad 2 or isolation chambers.

There can be zero or one or more than one isolation chamber used for the head cooling device. There can be one or more than one isolating chambers that affect and effect cooling. In another embodiment sealing pads or 2 isolation chambers can be used to isolate body parts that contains indicator and measuring device 54 or feedback device 42 or surgical areas of intervention and in which the material that can include solids, liquids and gels and gases between the user's skin and the cooling device is isolated and sequestered from the actual cooling portion of the head cooling device. In Method B another embodiment the gel sealing pad 2 can contain methods or transferring heat away from the body that can include conduction, convection or evaporation. Method A and Method B can be used alone or in combination. Indicator and measuring device 54 and feedback device 42 can be used to monitor and feedback control of physiologic and biologic functions to regulate core body and brain 130 temperature. The theory behind this invention is that there are some brain functions to include febrile seizure and ischemic stroke that can benefit by reducing oxygen and metabolic requirements of the brain more than other body parts. In another embodiment warming and cooling devices can be used together.

In another embodiment the head warming device that can be worn over the head whose use is to treat the body or body part to include brain 130 or biologic or physiologic conditions that can include overheating during cold weather, hypothermia, hair loss, and psychiatric disorders to include depression, memory and other biological and psychiatric conditions thought to be caused or felt to be caused or exacerbated by excessive body or brain 130 cooling, conditions that would benefit from body or brain 130 heating or more rapid body or brain 130 metabolism to include warming from hypothermia, brain 130 tumor growth to include during chemotherapy. In one embodiment the heating device can be composed of a sealing pad 2, skin covering material 3, fixation device 11, anchoring device 35 and indicator and measuring device 54 or feedback device 42 or any combination of these elements. Incorporated into this device is a heating device that can include a solid of liquid or gas or gel material that can be used to interface with the sealing pad 2 which can be airtight and water tight but does not have to be airtight or watertight. Methods of warming can include conduction which can include direct transfer of heat through heating devices to include heating conduit 16 that can contain water, thermoelectric heating, or radiator-like warming devices; radiant or radiation heat or electromagnetic or chemical or kinetic or Brownian heating or convection which can include heated substances through fans, blowers. Conduit 16 can be used in either compartment or inner chamber 132 or outer chamber 133 to carry materials to include solid, liquid, gels and gases. In one embodiment the heating head cap is composed of a sealing pad 2 that can include a gel or a non-gel that can form an airtight or watertight seal with at least a portion of the user's head or neck to form an isolation chamber. In the preferred embodiment the seal is a gel seal.

In method A the isolation chamber is created such that there can be a liquid or gel or a gas or solid or combination of these elements that passes between the user's skin 1 which can include the scalp 131, face or neck and torso and serves as a means of adding heat or transferring heat toward the user's brain 130. In one embodiments some orifices or some given body parts can be kept separate from the isolation chamber and these body parts can include a body that can include the user's mouth and nose and ears or torso such that these body parts can be sequestered from the remainder of the isolation chamber by additional sealing pad 2 or isolation chambers. There can be zero or one or more than one isolation chamber used for the head warming device. There can be one or more than one isolating chambers that affect and effect cooling. In another embodiment sealing pad 2 or isolation chambers can be used to isolate body parts that contains indicator and measuring device 54 or feedback device 42 or surgical areas of intervention and in which the material that can include solids, liquids and gels and gases between the user's skin and the cooling device is isolated and sequestered from the actual cooling portion of the head cooling device. In Method B another embodiment the gel sealing pad can contain methods or transferring heat toward the body that can include conduction, convection or radiation, radiant heat. Method A and Method B can be used alone or in combination.

Indicator and measuring device 54 and feedback device 42 can be used to monitor and feedback control of physiologic and biologic functions to regulate core body and brain temperature. The theory behind the cooling invention is that there are some brain functions to include febrile seizure and ischemic stroke that can benefit by reducing oxygen and metabolic requirements of the brain more than other body parts. The theory behind the warming invention is that there are some brain functions to include hypothermia, depression and tumor sensitivity during chemotherapy that can benefit by increasing oxygen and metabolic requirements of the brain more than other body parts. Heating and cooling of the brain 130 may have changing benefits depending on tissue and brain 130 sensitivity during treatments to include tumor treatment and psychiatric conditions.

The heating and cooling body part devices can be utilized on just the head or on the head and neck region for greatest effect on the brain 130 and body but these devices are not isolated to the head and neck and can be used on other body parts to include the torso, appendages and internal organs using the sealing pad 2, skin covering material 3, fixation device 11, anchoring device 35 and indicator and measuring device 54 or feedback device 42 or any combination of these elements described herein. These heating and cooling devices can be used to include treatment for treat peripheral vascular disease, Raynaud's disease, diabetes, and neuropathies and can be used to treat and provide symptom relief for sensory discomfort. These devices can be used for providing pleasure and can be used on appendages to include the penile and vaginal and anal regions for sexual pleasure and to improve sexual function to include erectile function, orgasm, and sexual pleasure and stimulation and can be combined with other devices to include vibration and ultrasonic devices and substances that can invoke sensory responses. These devices can be used for relieving pain and discomfort and can be used on appendages to include the arms and legs and anal regions and can be combined with other devices to include vibration and ultrasonic devices and substances that can invoke sensory responses. The heating and cooling device can utilize and include the use of radiant or electromagnetic, kinetic or Brownian, or chemical energy or any combination of these energies to achieve the desired outcome.

An external device can be used to supplement treatment and effect the head cap for heating or cooling. Inner chamber 132 and outer chamber 133 can be zero, one or more than one and the channel or conduit dominated versus the non-conduit or channel dominated forms of healing can be varied and interchanged relative to their positions on the head and relative to their positions on the user's skin 1 to include specific parts of the brain 130 can be heated or cooled more than other parts. These similar variations can be used with other parts of the body in addition to the brain 130 and scalp 131. The heating or cooling units can include a skin covering material 3, sealing pad 2 or fixation device 11 or anchoring device 35 or any combination of these elements which in one of the preferred embodiments can include a single compartment model that is a gel sealing pad which contains feedback device 42, indicator and measuring device 54, and heating and cooling devices and energy delivery devices which are external or internal to the sealing pad 2.

Figure 59:
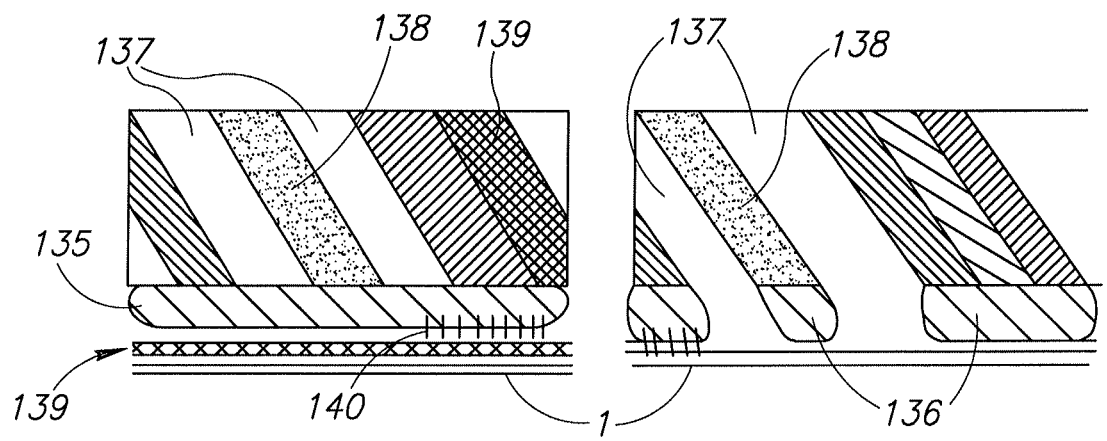
FIG. 59 is a sagittal depiction of a cast 138 that has a gel undercoat 136 or gel roll 135 between the cast 138 and the user's skin 1.

FIG. 59 is a sagittal depiction of a cast 138 that has a gel undercoat 136 or gel roll 135 between the cast 138 and the user's skin 1. In one embodiment a gel can lie between the cast 138, which can include and can be composed of fiberglass, polymers, plastics, metals and metal alloys, microfiber 140, and plaster and clay or earthen materials. Traditionally a cloth or cotton material is interpositioned between the cast 138 and the skin to absorb moisture and prevent abrasion of the user's skin 1. In one embodiment the material between the skin and the cast 138 can be a gel that provides properties to include osmosis, air circulation, and the ability to wick water away from the skin or any combination of these properties. In one embodiment to accomplish osmosis, breathability or ability to wick or any combination of these properties the gel can include the gel being ultra-thin, containing pores or holes, being designed as a weave which can include an open weave, being combined with a fabric that can assist in the needed properties that can include natural fibers to include cotton or synthetic fibers that can emulate cotton to include or a fabric to include Cupro; or microfiber 140 or combination of these materials. In another embodiment the material, which can be used as the lining material interposed between the cast 138 and the skin can include or a fabric to include cotton, Cupro or microfiber 140 or combination of these materials. In another embodiment a gel can be interposed between a fabric to include the Cupro or microfiber 140 or cotton layer or combination of these materials and the cast 138. In another embodiment a gel can be interposed between a fabric to include Cupro or microfiber 140 or cotton or combination of these materials and the skin. In another embodiment the gel can be woven with or a fabric to include cotton or Cupro or microfiber 140 or combination of these materials. In another embodiment the interposed material can be bound to the cast 138 and can include a gel or a fabric to include cotton or Cupro or microfiber or to a combination of these materials and the purpose of this is to create a more waterproof cast 138 that is breathable and less abrasive and wick water more effectively. For initially placing the case onto the skin an resorbable material 139 can be but does not need to be used and the absorbable material can include fabric-like materials that can include resorbable material 139 that can include rice paper, resorbable scaffolds including nontechnology to include Electrospun Fabrics, Salt-Leaching Porous Films, resorbable polymers including polylactide acid and polyglycolides or combinations of these materials. In the preferred embodiment the cast 138 can be made of a water-proof material that can include fiberglass that contains air gap 137 for breathability and has a gel undercoat 136 integrated in the cast or a layer of gel roll-like material lining or process as a lining between the cast 138 and the user's skin 1. In one embodiment the gel lining can be continuous or discontinuous. In another embodiment the cast 138 can include being constructed as a weave or mesh or lattice or fence-like configuration such that air resides between the cast 138. To create this lattice in one embodiment the cast 138 can be composed of a resporbable material 139 that lies in the locations where the air gap 137 will ultimately reside. Once the cast 138 is placed onto the body part the resorbable material 139 can be resorbed by methods to include resorption by water, a chemical reaction, an energetic reaction to include electromagnetic, chemical and kinetic and Brownian energy. In the preferred embodiment the resorbed material 139 can be a lactate or rice like material that can be used with a fiberglass cast 138 with a continuous or discontinuous lining of gel roll 135 or gel undercoat 136 that when exposed to water, the resorbable material 139 resorbs away or melts or dissolves away, leaving the fiberglass cast 138 present and air gap 137 present between the cast 138. This can be performed so the airspaces are vertical or horizontal or a combination of vertical and horizontal relative to the body part. Fabric used can include manmade and natural fabric and fibers. Resorbable materials can include manmade and natural fabric and fibers that can include protein, sugar and carbohydrates, fats and any combination of these molecules which can be at least partially resorbed. In another embodiment the cast material can be composed of manmade and natural fabric and fibers that can include protein, sugar and carbohydrates, fats and any combination of these molecules which can be at least partially not resorbed.

Figure 60:
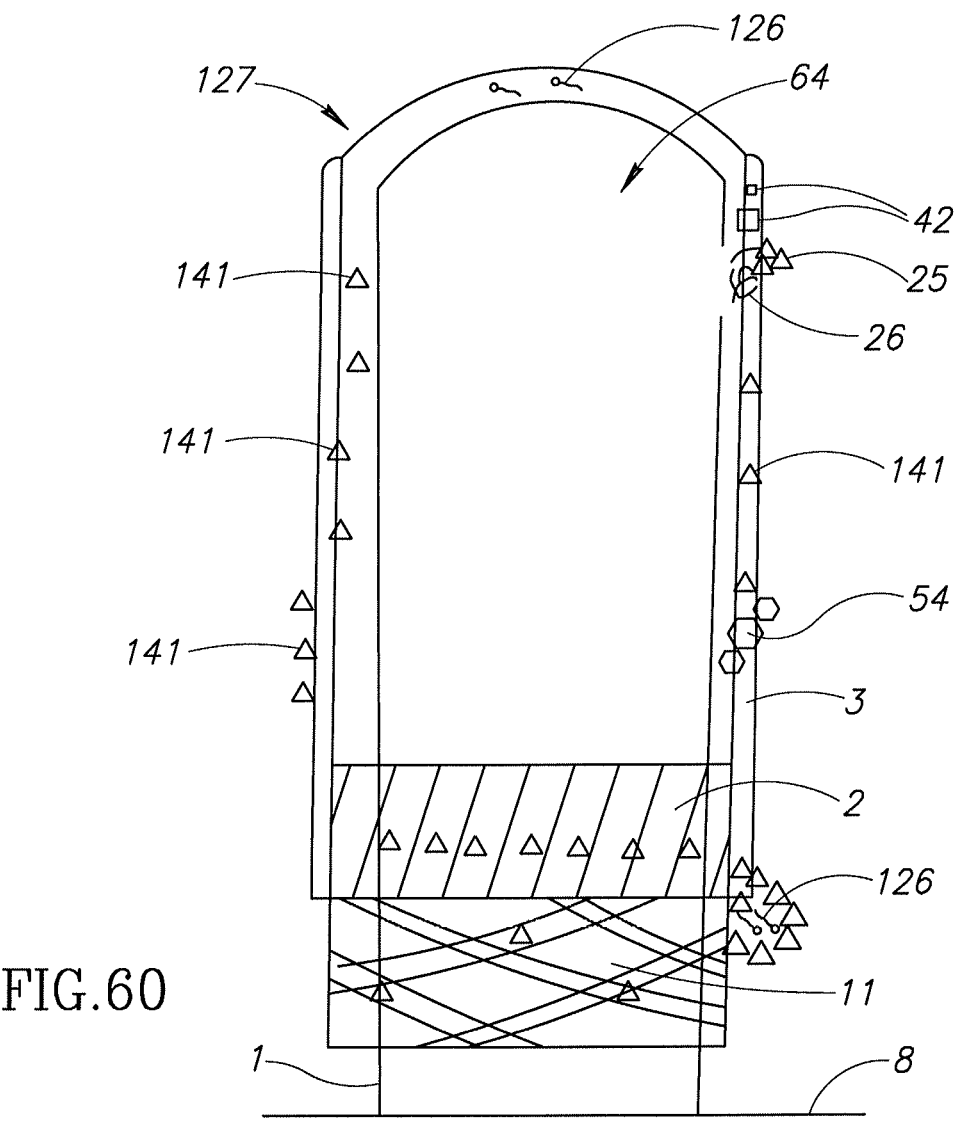
FIG. 60 is a sagittal depiction of a skin covering material 3 which can include being used as a contraceptive or condom or condom-like or infection prevention device that can be used by both a male or female condom that has a state-changing material 141.

FIG. 60 is a sagittal depiction of a skin covering material 3 which can include being used as a contraceptive or condom or condom-like or infection prevention device that can be used by both a male or female condom. In one embodiment the condom, condom-like device, the contraceptive or the infection-prevention device can include a skin covering material 3 which can include including a skin covering material 3, a sealing pad 2, a fixation device 11 or an anchoring device 35 or any combination of these elements that can be being able to be repaired at least partially or fully by a method to include patching, plugging, annealing, neutralizing or closing the breach in the condom or skin covering material 3 function. The breach can include a hole, a tear, a rent or a leak. In the preferred embodiment the condom device can include having a substance or substances that can be a solid a liquid, a gel or a gas which can reside in a location in association with the condom to include residing freely in, coating, loosely bonding, tightly bonding, lining, or impregnating the condom including a skin covering material 3, sealing pad 2 or fixation device 11 or anchoring device 35 or any combination of these elements. The substance can be located on the inside of or on the outside of or within or integrated into the condom or skin covering material 3, or sealing pad 2 or fixation device 11 or the anchoring device 35 or can be any combination of these locations. In another embodiment the condom can contain reservoir 41 within the condom. In the preferred embodiment the condom can patch the breach or leak by the condom containing a substance that can the substance altering its physical properties and state which can include the substance changing its state from a liquid or gel into a denser gel or a solid state.

The stimulus for the state change can include a condition or trigger that includes a change in pH, a change in the concentration of fructose, a change in the concentration of sperm, or other changes in the chemical or electromagnetic or kinetic or Brownian energy of the environment or field. In one embodiment the substance can include a liquid or semi-gel that is triggered by an alkaline environment to become a dense gel or a semi-solid material. In this embodiment when the substance, which lies between the condom and the users' skin or is bonded or impregnated into the condom, is exposed to semen or seminal fluid which has an alkaline pH liquid substance, which lies between the condom and the users' skin or is bonded or impregnated into the condom, undergoes a state and transforms from a liquid to a gel. Other embodiments can include the substance residing at the base of the condom such that if semen leaks along or outside of the base or opening of the condom near the user's torso then the substance will be activated. In this embodiment if the semen or seminal fluid can insinuate themselves between the sealing pad 2 or the skin covering material 3 of the male condom and the user's skin then the substance will be activated to transition from a liquid to a gel. In this embodiment the state-changing material 141 can reside or be associated with residing or being associated with the sealing pad 2 or skin covering material 3 or a combination of these elements. When the semen or seminal fluid leaks from the base and comes in contact with the state-changing material 141 then the liquid transforms into a gel and swells to obstruct the leaking region of the base sealing the condom and preventing any additional emission of semen out of the condom. The condom can have a state-changing material 141.

In another embodiment if the condom or skin cover develops a leak or hole or breach 126 then state-changing material 141 will seal after ejaculation when the semen and seminal fluid is released and comes in contact with the state-changing material 141. In another embodiment a female condom can contain the state-changing material 141 between the user and the condom which can include containing a skin covering material 3 or sealing pad 2 or fixation device 11 or anchoring device 35 or any combination of these elements. If semen or seminal fluid leak between the user's skin and the condom then the condom develops a leak or hole or breach then the state-changing material 141 will seal after ejaculation when the semen and seminal fluid is released and comes in contact with the state-changing material 141 which can be located be located between the user's skin and condom, within the condom on the outside of the user's skin and condom and any combination of these locations. Other embodiments of the condom can include the state-changing material 141 residing in multiple locations relative to the user and the condom and relative to the portions of the condom and relative to the components of the condom.

Embodiments can include condom which can assist with contraception and disease or infection prevention not by altering its physical property of the condom or serving as a chemical patch if a condom or condom like device develops leaks or breaks or has a breach. Other embodiments can include the leak in the condom may at least partially persist but the effects of the leak are reduces or are neutralized or treated when the state-changing material 141 intermingles with either semen or seminal fluid or vaginal fluid or bodily fluids or any combination of these fluids. In another embodiment to assist with contraception other medications or substances can be utilized with the condom that can include a solid, a liquid, a gel or a gas that can be used for contraception or disease or infection prevention. In one embodiment a condom can contain or be impregnated 40 with or be lined with or contains reservoir 41 that can have a contraceptive that can include Contraceptol™, contraceptive jelly, Maraviroc, sold under the brand names of Selzentry and Celsentri, a new class of HIV drugs called CCR5 blockers, which prevents the virus from getting into the cells it infects. In another embodiment, the condom can contain an indicator as discussed in FIG. 31, which can be composed of halochromic materials which can change their color as a result of changing acidity or electrochromic materials that can change with changes in electrical charges. In another embodiment at least a portion of the condom can be composed of an indicator-like material that can change color to include to halochromic materials which can change their color as a result of changing acidity or electrochromic materials that can change with changes in electrical charges. In one embodiment these materials can be located on the inside or outside or within the condom or skin covering. One embodiment can include a male condom where the indicator material or indicator can be located on the inside of the condom and the indicator is sensitive to an acid. Since semen are alkaline if there is no leakage the condom will not change its indicator or condom which is composed at least partially of an indicator then the reference state that can include color or other sensory stimuli to include visual cue, shape, or contour or temperature, will not change its normal reference. In the preferred embodiment if the acid, or fructose or other uniquely vaginal biological substances of the vaginal and female space enters the inner space between the condom and the male user's skin then the indicator on the inside of the condom will change its reference signal which in the preferred embodiment means the indicator or condom will change color or contour indicating a leak or breach in the condom.

Other embodiments can include indicating leakage of male unique biological material into the female space to include semen and seminal fluid. Other embodiments can include the use of self-sealing materials which can form at least a portion of the condom or skin covering material or sealing pad as described in FIG. 54 and can be utilized be used in combination with state-changing material 141. Other applications for self-sealing bags can be used in biological applications to include urinary, ostomy, fecal, blood or other bodily materials or self-sealing seals or skin covering materials can include goggles and other applications described herein.

Figure 61:
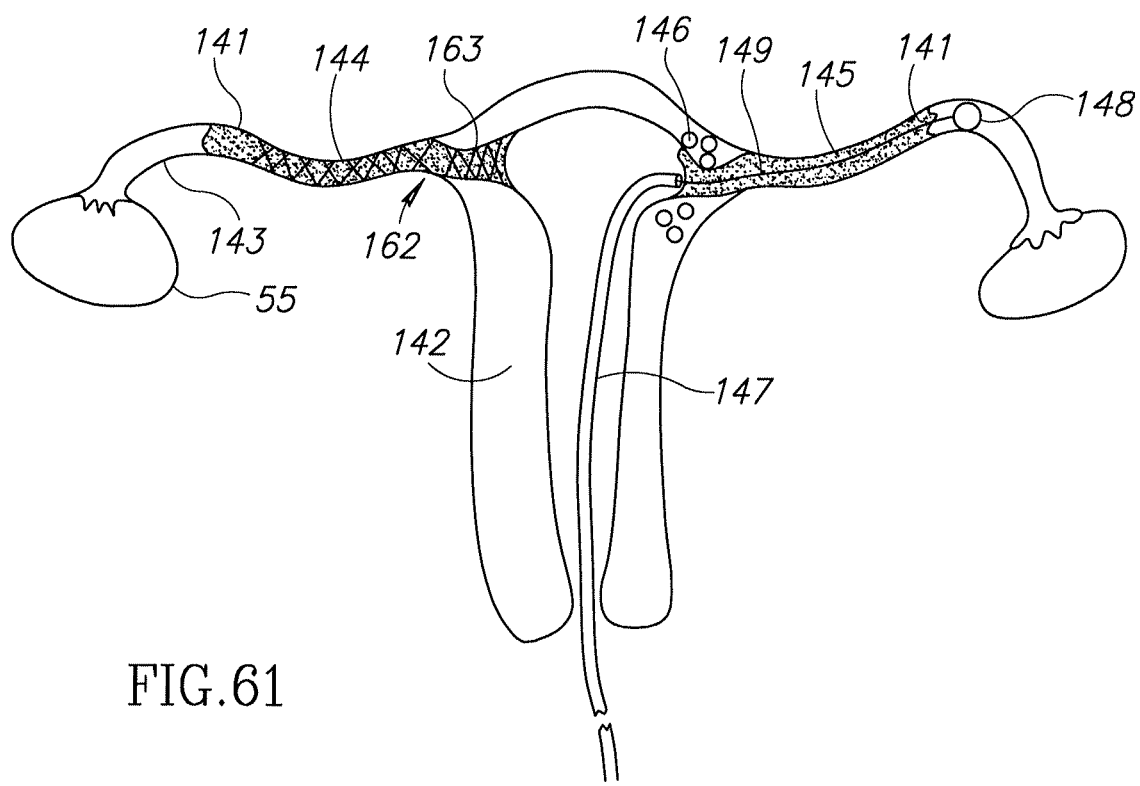
FIG. 61 is a frontal view of an occlusive device that utilizes a substance that can undergo a state-changing material 141 and can be used in a living organism to include a female reproductive system to occlude the fallopian tube 143.

FIG. 61 is a frontal view of an occlusive device that utilizes a substance that can undergo a state-changing material 141 and can be used in a living organism to include but not restricted to a female reproductive system to occlude the fallopian tube 143. Other embodiments can include but are not restricted to the male reproductive system to occlude but not restricted to the male spermatic tubes. Seminiferous tubules, and testicular structures; a vascular structure to include but not restricted to an artery, vein, vascular malformation to include but not restricted to a laceration or tear or rupture of a vessel, a hemangioma, a venous AVM; an aneurysm, an arterial or venous or mixed arterial and venous malformation or a varix; an outpouching or a ganglion of a joint; a burn or wound, a bone defect to include but not restricted to a fracture in the temporal bone or in the cribiform plate; a finger nail or toe nail; an ear structure to include but not restricted to a tympanic membrane, or a nasal structure to include but not restricted to a nasal septum. Currently, tubal ligation of the fallopian tube 143 can be performed by legating or clipping the fallopian tube 143 or by catheterizing the fallopian tube 143, which is invasive and requires surgery or placing a device into the fallopian tube 143 which is often unsuccessful because of the difficulty that doctors have in cannulating deeply into both fallopian tubes 143. One of the methods for visualizing the fallopian tube 143 is performing a hystero-salpingogram, which is a method by which a catheter is place into the uterus 142 and at the junction 162 of the uterus 142 and the fallopian tube 143 there is an entry or opening 163 or ostium or os, where the fallopian tube 143 begins. A catheter 147 is then placed at the fallopian tube 143 opening 163 or os and then contrast is injected. The contrast enters the fallopian tube 143 and visualized the inner tube-like portion of the fallopian tube 143. Injecting a material into the fallopian tube 143 is simpler than placing a wire 149 or introducer or catheter guide, which is simpler than placing a tube or catheter 147 or cannula, and all three are simpler than placing a device into the fallopian tube 143, which is the current method of non-invasive tubal occlusion.

The preferred embodiment can include but is not restricted to placing a catheter 147 at the opening 163 of the fallopian tube 143 at the uterine and fallopian tube 143 junction 162. In the preferred embodiment zero, or one or more wire 149 or wire-like introducer can be introduced into the fallopian tube 143 to include but not restricted to a fiberoptic cable, a metal, a memory metal, a thermal reactive material, electromagnetic-reactive material, pH sensitive material, chemical sensitive material or other biocompatible material to include but not restricted to a fibers including but not restricted to microfibers, man-made fibers or natural fibers, resins, polymers or plastic can be introduced into the fallopian tube 143 and can serve as but are not restricted to a scaffold 144 that can include a resorbable or non-resorbable scaffold 144 or extrusion or removal or stimulating device to include but not a thermal reactive, electromagnetic-reactive, pH reactive, or chemical reactive device. One embodiment can include semi-permanent occlusion and include but are not restricted to cements and materials that can be reversed when exposed to the proper adjuvant which can include but is not restricted to chemical solvents, pH, or energies to include but not restricted to chemical, electromagnetic and kinetic or Brownian energy. One embodiment can include but is not restricted to having a bulbous distal portion 148 that can but is not restricted to occlude the distal fallopian tube 143 to prevent egress of materials out of the tube. One embodiment can include but is not restricted to the bulbous distal portion 148 being a permanent structure to include a flange-like device or a spring like structure that can at least partially occlude the tube, or a reservoir 41 that can be inflated and deflated that can be filled with a solid, a liquid, a gel or a gas. The string or wire-like structure that fits inside of the fallopian tube 143 can include but is not restricted to a wire- or string like device that can hang into the uterus 142 for removal of the fallopian tube 143 occlusive agent.

The wire or optical cable or device can utilize an electromagnetic energy or kinetic or Brownian energy to include but not restricted to heat or cold or a chemical reaction to alter the state of the substance to include but not restricted to the liquid changing to a gel or solid or the gel changing to a solid or the reverse process to include but not restricted to where a solid or harder gel becomes a gel or a liquid.

Currently, materials are available that undergo state changes to include but not restricted from metamorphosize from a liquid to a gel or solid or a gel to a solid. Methods for creating this transformation include but are not restricted to altering the pH as occurs with a liquid contraceptive where the liquid is placed into the vagina which has an acidic pH of 3.8 to 4.5 and when in contact with semen which are alkaline with a pH of 7.2 to 7.8; or materials that alter from liquid-gels and become solid such as dental crowns which are made of biocompatible materials and cements that are UV or heat fixing or tooth coating and sealant treatments which are plastics resins which when exposed to electromagnetic or kinetic energy alter to a solid form or hydrogels that can be formed to include but not restricted to being formed by injecting the hydrogel or can be formed and fixed by mixing one or more materials which when in contact change state such as but not restricted to hydrophilic polymers, incorporating chitosan derivatives complexed with polyvinylpyrrolidone (PVP). Once the catheter is placed into the opening of the fallopian tube 143 an occlusive agent can be placed or injected into the fallopian tube 143 that can include but is not restricted to a state changing material that can include but is not restricted to a material that changes state using a chemical reaction such as a pH change, a thermoplastic and sensitive material, an electromagnetic plastic and sensitive material, hydrogel and other mixed chemical components and resins or a biological sensitive material. In another embodiment more permanent materials can be injected to include but not restricted to silicon, UV sensitive dental cement and sealants, glues to include but not restricted to cyanoacrylate and other acrylic resins, which rapidly polymerize.

One of the limitations of current non-invasive fallopian tube 143 occlusion methods is the inability to fully catheterize the fallopian tube 143s. Methods for improved catheterization can include but are not restricted to the use of muscle relaxing and paralyzing agents to be used at a site to include but not restricted to the entry of the fallopian tube 143, in the uterus 142 and in the fallopian tube 143 and substances to perform this function can include but are not restricted to solids, liquids, gel or gases that can be effective, topically, injected or introduced into the tissue or local blood flow or delivered in other biological methods to include but not restricted to combined delivery or activation of at least one or more substances or forms of energy to include but not restricted to kinetic or electromagnetic or chemical energy or reactions. One embodiment can include chemicals 146 to relax or reduce spasm at the opening of the fallopian tube 143 to include but not restricted to Botx or Botox-like or derivative chemicals, curare and Curari-like substances, paralytic-type agents to include but not restricted to neuromuscular blockers that include but are not restricted to competitive nondepolaring agents that compete for acetylcholine that include but are not restricted to curarizing agents that resemble curare alkaloids that include but are not restricted to pancuronium, atracurium; neuromuscular blocking agents to include but not restricted to gallamine, vercuronium, metocurine; noncompetitive nondepolaring agents to include but not restricted to succinylcholine; spasmolytics and sarcoplasmic reticulim agents to include but not restricted to methocarbamol, guaifenesin, diazepam, dantrolene and other nerologic and muscle and neuromuscular relaxing. In another embodiment a scaffold 144 or triggering agent can be instilled into the fallopian tube 143 or the wire-like device can be but not restricted to being composed of coated with, or can be an introducer of a material to include but is not restricted to a catheter that can have but not restricted to end holes 152 and side hole or can be coated with or composed of reactive substances with the state-changing material 141 or can introduce the state-changing material 141. In another embodiment a scaffold 144 can be introduced that can be but is not restricted to a primary state-changing material 141 or a secondary substance or deliver a secondary substance or energy source that can alter its state when in contact with the state-changing material 141. The scaffold 144 can include but is not restricted to a carbohydrate or cellulose scaffold, a protein or a fat or a mineral or a scaffold that can be a combination of substances and can but is not restricted to react with an energy source or another substance. In one embodiment the state-changing material 141 that fills the fallopian tube 143 can extend into the uterine 142 cavity and can be shaped by a direct method of visualization with fiber optics near the junction 162, or ostium, or opening 163, of the uterine 142 and fallopian tube 143.

In another embodiment as a primary means of occluding the fallopian tube 143 or a secondary means of occluding the fallopian tube 143 to include but not restricted to if the opening or the fallopian tube 143 cannot be cannulated then the state-changing material 141, the scaffold 144 or a combination of one or more of these substances and supportive platform 234 can be injected or placed at the entry and junction 162 of the uterus 142 and the fallopian tube 143 to block the fallopian tube opening. Other more permanent agents can also be used to block the junction 162 of the uterus 142 and the fallopian tube 143 to block the fallopian tube opening to include but not restricted to cements, glues, sclerosants, and sealants. In one embodiment the fallopian tube and the opening and junction of the uterus and the fallopian tube can be blocked together with a combination of a fallopian tube material that is continuous with a cap like covering of the fallopian tube opening and the uterine and fallopian tube junction.

Figure 62:
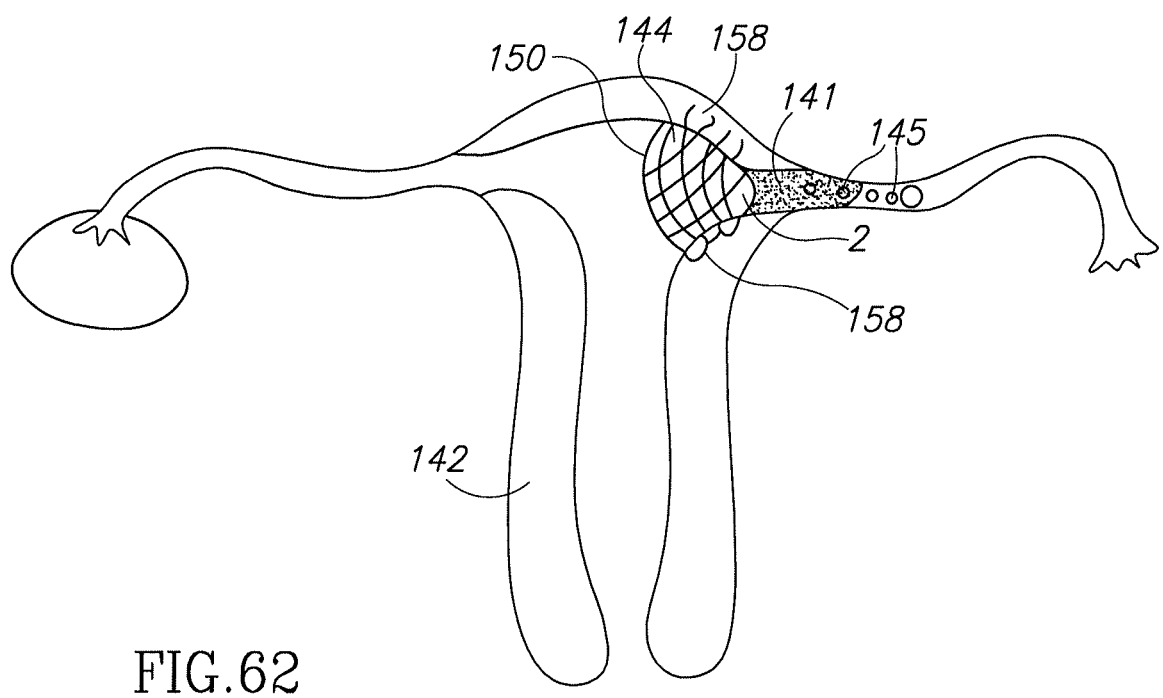
FIG. 62 is a frontal view of a cap 150-like device and method to occlude the female reproductive system at the opening 163 of the uterus 142 and the fallopian tube 143 and a method to the keep in place a scaffold 144 or the state-changing material 141 or a sealing pad 2 or a more permanent agent or a cement or other sclerosing agent 145, or a device can be held in place.

FIG. 62 is a frontal view of a cap 150-like device and method to occlude the female reproductive system at the opening 163 of the uterus 142 and the fallopian tube 143 and a method to the keep in place a scaffold 144 or the state-changing material 141 or a sealing pad 2 or a more permanent agent or a cement or other sclerosing agent 145, or a device can be held in place to include but is not restricted to affixing devices 158 by sewing, hooking or grappling or stapling or pinning the scaffold 144 or cap 150 like device. The device that is referred to herein as a cap 150 that can include a shape that can include but is not restricted to a shape that is formed or emulates and molds to the shape of the uterine 142 fallopian tube 143 junction 162, a rounded shape, or a shape or device that resiliently or non-resiliently deforms to the shape of the uterus 142 at and near the fallopian tube 143 and uterine 142 junction 162. One embodiment can include a shape that is created by performing and imaging scan that can include but is not restricted to a CT scan, MRI scan, or Ultrasound 3-d scan that can reproduce the shape of the uterine 142 and fallopian tube 143 junction 162 and can be produced for each individual to form fit that specific individual. In another embodiment a general shape can be used that can be specifically be molded to the specific individual during the placement of said cap 150. The cap 150 can be composed of a material or a combination of materials to include but not restricted to man-made or natural materials to include but not restricted to metals, plastics, polymers, silicon, resins, gelatinous elastomers, shape memory materials, thermoplastic and electorplastic shape altering materials, state changing materials, scaffold 144, fabrics, wood products, microfibers, and other solids, liquids and gases and gels or combinations thereof. In another embodiment said cap 150 can be a general scaffold 144, which can serve as a general endoskeleton or exoskeleton upon which or into which the occlusal or occluding substance placed. In the preferred embodiment the occlusal or occluding substance can include but is not restricted to a state-changing material 141 or a more permanent material or occluding agent. The occlusal or occluding substance can be used in combination with the scaffold 144, the cap 150-like device in combination or separately or any combination of these. In another embodiment the occlusal or occluding substance can be used in combination with the scaffold 144, the cap 150-like device in combination or separately or any combination of these can be used with a surgery that can include performing a procedure that can include one or more surgical flaps or redundant folds that can hold the occlusal or occluding substance, the scaffold 144, the cap 150-like device or any combination of these in place. The devices and substances describes herein can include but is not restricted to being radio-opaque so as to be visible by electromagnetic X-ray or non-ferromagnetic material to include but not be restricted to be able to be used in an MRI scanner.

In the preferred embodiment the cap-like device will be molded to fit each individual using a planning CT or MRI or Ultrasound scanner. The fallopian cap 150 like device will be composed at least in part of a resilient gel sealing pad 2 that will be of variable elasticity so that it can be anchored into the myometrium with sutures or staples or grappling affixing devices 158. IN one embodiment a state-changing material 141 or a cement or occlusive material can be placed distal to the cap 150 in the fallopian tube 143. The cap will be placed at the junction 162 or the uterus 142 and the fallopian tube 143 to block the fallopian tube 143 opening 163. In a preferred embodiment the state-changing material 141 can be use with an elastomeric cap 150 or scaffold 144. and can be integral or integrated or can be separate.

In another embodiment these processes can be used in combination or in combination with current methods for invasive or non-invasive occlusion. In another embodiment these methods can be used to close other ostia or openings or tubes to include but not restricted to the seminal vesicles, seminiferous tubules, or the biologic sperm delivery components.

Figure 63:
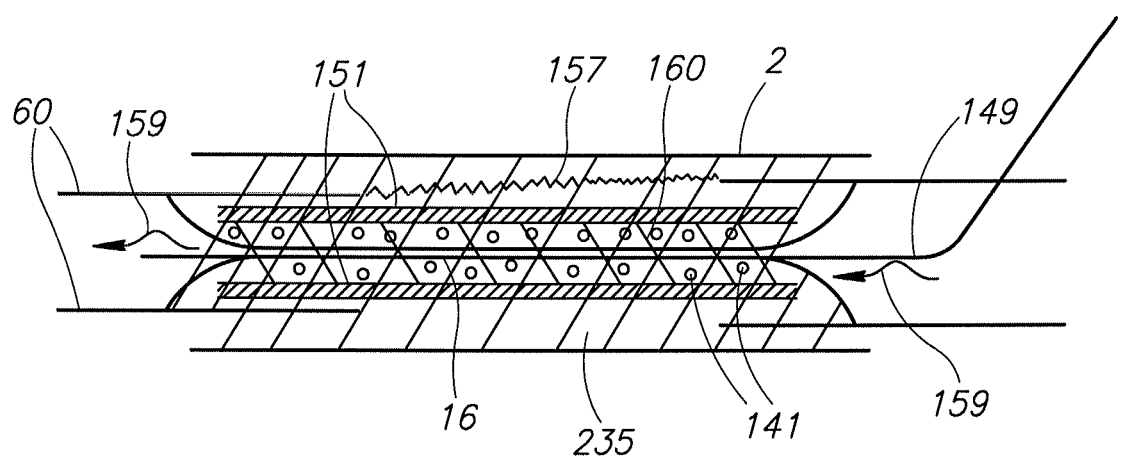
FIG. 63 is a sagittal view of a vessel substitute or stent 151-like device that can comprise a scaffold support 235 that can include a scaffold that can be non-resorbable or at least partially resorbable.

FIG. 63 is a sagittal view of a vessel substitute or stent 151-like device that can comprise a scaffold support 235 that can include a scaffold that can be non-resorbable or at least partially resorbable. The vessel substitute or stent 151-like device can be used to treat but not restricted to be used to treat a situation where blood flow needs to be controlled over a segment of a blood vessel 60 to include but not restricted to a vascular laceration to include but not restricted to an artery or a vein. The blood vessel 60 substitute or stent 151-like device can be composed of to include but not restricted to a solid a liquid or a gel or a gas which can include but not restricted to a carbohydrate or cellulose, a protein or amino acid, a fat, a mineral or a combination of these materials that when exposed to a second substance can be resorbed and can create but is not restricted to creating a conduit 16. The scaffold support 235 can include a catheter 147 or wire 149 that can be used to include but not restricted to include being used as an anchor, a delivery device that can include but is not restricted to a substance or energy to modulate the scaffold support 235 and can include but is not restricted to occluding or open a conduit 16. The catheter 147 can include but is not restricted to containing a valve 89 that can control the flow by wirelessly controlling the diameter of the catheter from external to include but not restricted to compression of the catheter or internally to include but not restricted to valve 89. In one embodiment the scaffold support 235 or catheter 147 and wire 149 or any combination of these can put in the location of the damaged blood vessel 60. One embodiment can include the placement of a state-changing material 141 into or onto the blood vessel 60 substitute or stent 151-like device. The state-changing material 141 can vary in its solid, gel or liquid nature and can include the ability to regulate the channel that allows blood to flow 159 through the blood vessel 60 substitute or stent 151-like device. The blood vessel 60 substitute or stent 151-like device can include an external conduit that can connect to an inner lumen or channel or conduit 16 such that the external conduit can deliver a substance to include but not restricted to a solid or liquid or gel or gas which in the preferred embodiment would deliver an oxygen carrying liquid. In another embodiment the placement of a state-changing material 141 into or onto the blood vessel 60 substitute or stent 151-like device can create an external cast which can include but is not restricted to a gel seal 2 or a state-changing material 141 or clot 160 or a combination of these elements which can form around the blood vessel 60 which can include but is not restricted to bonding, attaching or insinuating into the local tissue to tamponate the blood. This blood vessel 60 substitute or stent 151-like device can include being used with the cast and wound cover described within this patent.

Figure 64A:
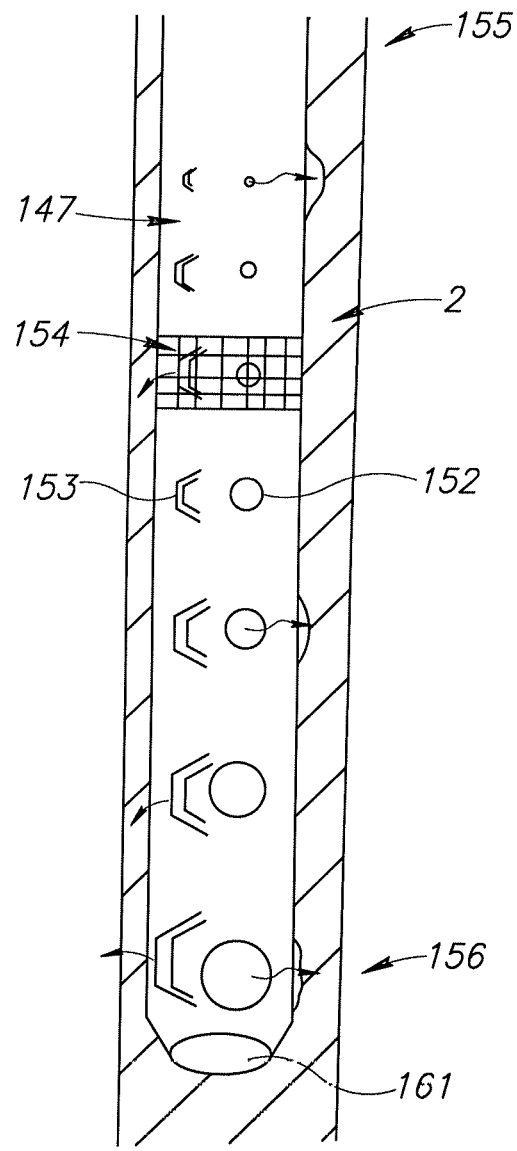
FIGS. 64A and 64B are sagittal views of a multi-hole 152, 153 catheter 147 with side holes 152 that can vary in size and shape that can be used to deliver substances in a differential fashion. In one embodiment the side holes 152 are smaller at the proximal end 155 of the catheter 147 than at the distal end 156 of the catheter 147.
Figure 64B:
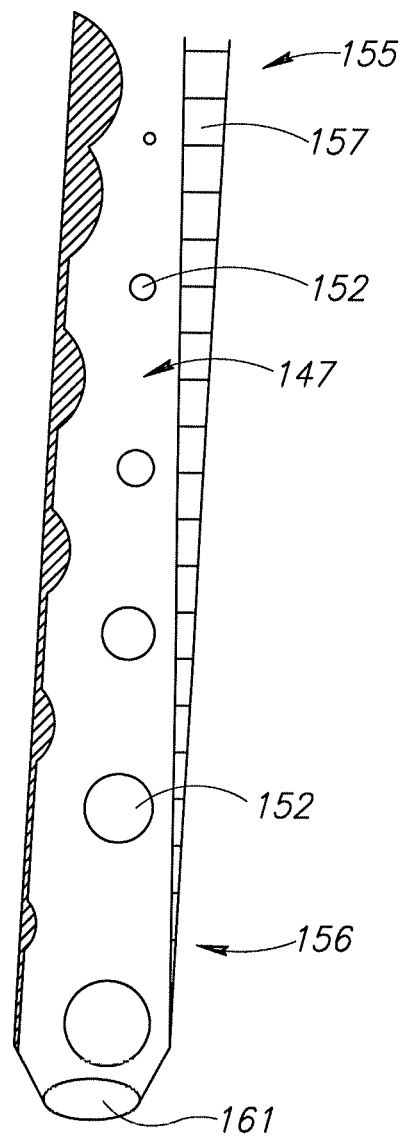

FIGS. 64A and 64B are sagittal views of a multi-hole catheter 147 with side holes 152 that can vary in size and shape that can be used to deliver substances in a differential fashion. In one embodiment the side holes 152 are smaller at the proximal end 155 of the catheter 147 than at the distal end 156 of the catheter 147. The side holes 152 can include but are not restricted to a geometric and a non-geometric pattern. In the preferred embodiment the geometric pattern of the openings can include but are not restricted to circles or ellipses or slits 153 or any combination of geometric patterns. In the non-geometric patterns the openings can include but are not restricted to random patterns that change are similar or variable in shape and size from proximal end 155 to distal end 156.

The rate of enlargement of the side holes 152 can be based to include but not restricted to the length of portion of the tube or conduit or channel or catheter 147 where a substance that can include a solid or liquid or gas or solid is to be delivered; the delivery pressure within the catheter 147 and the external pressure surrounding the catheter 147. The catheter 147 can be used to include but not restricted to use in an environment in which the catheter 147 is surrounded by a gel or semi-gel or semi-solid or solid scaffold that can or needs to be dissolved. An environment in which the catheter 147 is encased or embedded in a gel or semi-gel or semi-solid or solid which can include but is not restricted to a thrombus or blood clot within a blood vessel 60 or tube or catheter 147 or a man-made occlusion of a blood vessel 60 or a catheter 147 or tube to include but not restricted to a gel or semi-gel or semi-solid or solid.

If a tube or catheter 147 resides in a blood vessel 60 that is thrombosed or surrounded by a gel or semi-gel or semi-solid or solid then the fluid that enters said catheter 147 with the end hole 161 and the more distal side holes 152 encased will experience a tendency to have the intra-luminal fluid exit or escape from the tube or catheter 147 more easily at proximal end 155 than at distal end 156 especially if all the side holes 152 are of the same size. This tendency of the intra-luminal fluid to exit at proximal end 155 will increase dramatically if not exponentially once the material encasing the side holes 152 at proximal end 155 begins to dissolve. In one embodiment to counter the tendency of intra-luminal fluid to exit from the catheter 147 at proximal end 155 the side holes 152 can be created to include but not restricted to the side holes 152 at the proximal end 155 being made smaller than the side holes 152 at the distal end. Another embodiment can include but is not restricted to where the side holes 152 at the proximal end 155 can include a shape to include but not restricted to a slit 153 where the resistance in the slit 153 to the fluid exiting from the proximal end 155 of the tube or catheter 147 is greater than the slit 153 at the distal end of the tube or catheter 147. Another embodiment can include but is not restricted to a material that can include but is not restricted to a material that covers or coats the tube or catheter 147 such that the side holes 152 or slit 153 or exit points of the catheter 147 creates greater resistance in the side holes 152 or slits 153 or exit points at the more proximal end 155. One embodiment can include but is not restricted to side holes 152 that are covered by an osmotic material 154 that has greater resistance proximally than distally. In one embodiment this can include but is not restricted to the osmotic material 154 being thicker proximally than distally. In another embodiment the catheter 147 can be made form a state-changing material that has the side holes 152 constricted in size or become closed or coated or covered by a material, once the flow through the side holes 152 increases. Since side holes 152 at the proximal end 155 as a rule will experience greater flow sooner than the side holes 152 at the distal end 156, as a result the exit points at the proximal end 155 will constrict or coat or close sooner than the sides holes 152 at the distal end 156 and thus the side holes 152 at the proximal end 155 will experience a greater pressure resistance than the side holes 152 at the distal end 156 or the end hole 161.

Another embodiment can include but is not restricted to the inner lumen of the tube or catheter 147 being constructed such that the inner luminal diameter 157 varies over the length of the catheter 147 especially at its distal aspect. In the preferred embodiment the inner luminal diameter 157 at the site of the occlusion will be narrower at or near the proximal end 155 of side holes 152 than at or near the distal end 156 of side holes 152 or end hole 161. This will result in the intra-luminal fluid pooling more in the distal portion of catheter 147 than the proximal portion of the catheter 147 or tube. If the fluid is injected in a non-continuous manner then the side holes 152 at the distal end and the distal external encased material should experience a longer temporal exposure to the fluid injected into the catheter 147. Another embodiment can include the tube or catheter 147 having but is not restricted to any combination or variable side holes 152 size, shape, coating and osmotic material 154 and inner luminal diameter 157.

Figure 65A:
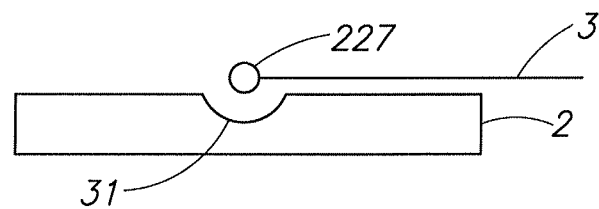
FIGS. 65A, 65B, and 65C are sagittal views of a method for folding a sealing pad to create an airtight and watertight seal with the user's skin using a cast covering skin covering material
Figure 65B:
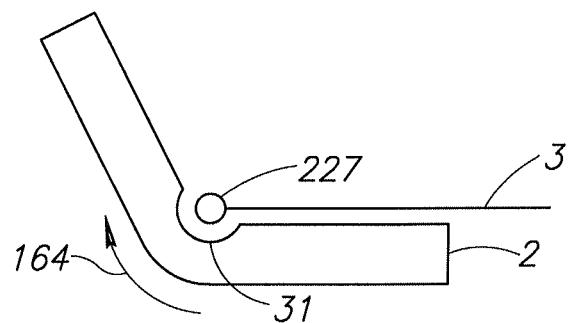
Figure 65C:
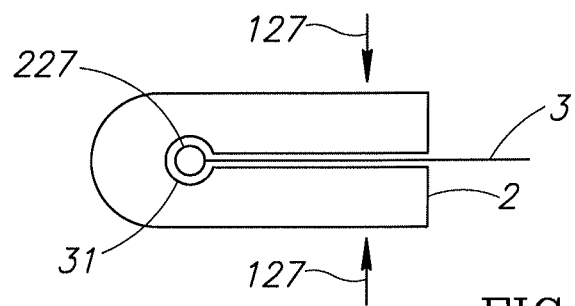
Figure 65D:
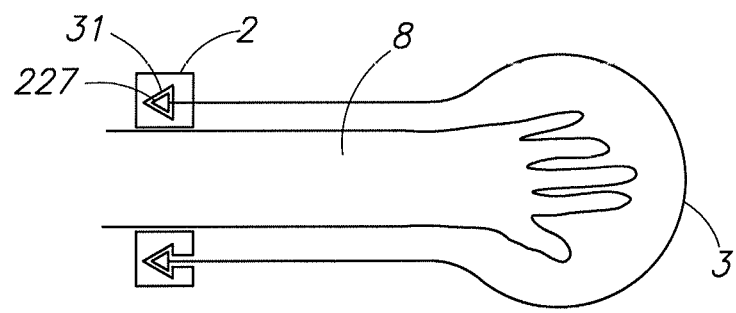
FIG. 65D is an embodiment of the cast cover in its final positioning with the sealing pad and the skin covering in place.

FIGS. 65A, 65B, and 65C are sagittal views of a method for making a folded 164 sealing pad 2 to create an airtight and watertight seal with the user's skin 1 using a cast covering skin covering material 3. In the preferred embodiment of the cast cover 3 is composed of a waterproof skin covering material 3 and an annular gel sealing pad 2 which is tacky and elastic can be formed so that when it is in its resting or relaxed state it is approximately the same circumference or very slightly less circumference than the user's appendage. The gel sealing pad 2 will have the ability to stretch to many times it's resting and will be resiliently deformable such that the sealing pad 2 will return to its resting circumference. This will allow the sealing pad 2 to easily fit over the appendage or a structure or device associated with the appendage to include but not restricted to a cast, a wound cover, a central intravenous or arterial catheter in a manner that the skin of the appendage or the structure or device associated with the appendage is not damaged. The sealing pad 2 can be placed over the distal aspect of the appendage, which for example may be the fingers of the hand and arm. One place comfortably over the distal aspect of the appendage the sealing pad 2 can be positioned over the appendage and the structure or device, which can include but is not restricted to a cast, until the sealing pad 2 are proximal to the cast and rest comfortably on the proximal skin with the sealing pad 2 lying flat against the skin. Once the sealing pad 2 is in place a waterproof skin covering material 3 can be placed into position. If the sealing pad 2 is to be used for a distal arm cast then there will be an open end of the waterproof skin covering material 3 and a closed end. The open end will be place over the fingers first and positioned in a similar manner such that it rests in the middle aspect of flat sealing such that the distal half portion of the sealing pad 2 is covered by the waterproof skin covering material 3 while the proximal half portion of the sealing pad 2 is not covered by the waterproof skin covering. Next the distal half portion of the sealing pad 2 is folded 164 over the proximal half portion. This creates a sealing pad 2 with a C shape such that the distal half of the sealing pad 2 forms a watertight seal with the skin; the waterproof skin covering material 3 is wedged between the proximal and distal halves of the sealing pad 2 in a manner that the sealing pad 2 forms a waterproof seal with the skin covering material 3 on side of the skin covering material 3 that is both interior and exterior or closest and farthest to the skin. The proximal half portion of the sealing pad 2 is now external to the distal half portion and rests on the distal half of the sealing pad 2 and creates a gentle compression on the distal half of the sealing pad 2 that is creating and airtight and watertight seal and this gentle compression further assists with creating the airtight and watertight seal. In the preferred embodiment the open end of the skin covering material 3 will be wider than the remainder of the skin covering material 3 and will serve as a bulbous end portion 227 that can serve as a male end or protuberance or bulbous insinuator. The sealing pad 2 can have a groove or invagination 31. When the sealing pad 2 is folded 164 over the skin covering's male bulbous end portion 227 will insinuate itself into the invagination 31 or groove of the sealing pad 2 and create a lock and key like mechanism for the sealing pad 2 and the skin covering material 3. The sealing pad 2 can include but is not restricted to being folded 164 more than or less than in half. The locking mechanism can include but is not restricted to multiple shapes to include geometric shapes that are more or are less resistant to tugging or disengaging. The skin covering can have more than one opening especially when the skin covering is place such that it is important for the middle portion of the body part or appendage to be covered but a proximal and distal portion of the body part is to remain uncovered. One example of this can include a PIC line that is placed in the antecubital region near the elbow and the shoulders are uncovered and it is desirable to have the hands uncovered so that the hands can be without a covering to be used freely. Waterproof can mean airtight and watertight. Although the sealing pad 2 in the preferred embodiment is singular and flat and is folded 164 over only one, less than or more than one folding or folded forms of the sealing pad 2 can be used and more than one sealing pad 2 can be used. The skin covering can have bulbous end portion 227 or can be flat or have invagination 31. The sealing pad 2 can have bulbous end portion 227 or can be flat or have invagination 31. The sealing pad 2 can have a different radius that varies from distal to proximal. FIG. 65D is an embodiment of the cast cover in its final positioning with the sealing pad 2 and the skin covering cast cover 3 in place and creating an airtight and watertight seal with the body part 8, including a limb, or an arm.

FIGS. 66A-D are fixation methods and devices, that can include overlapping strands. FIGS. 66A and 66B show a lattice or web or integral or interconnected strands and FIGS. 66C and 66D show a weave that can be used with a condom catheter. The first method and structure can include strands that can be overlapping or non-overlapping and which in the preferred embodiment can include a gel material that can include a tackifying material or an adhesive or which can be naturally tacky or: a fabric-like material that can include a microfiber with a high coefficient of friction and increased drag on the user's skin 1 when a force 165 is exerted on the material, such as pulling. When the force 165 is exerted on the fixation device 11, the portions of the fixation in contact with the user's skin exert an increased coefficient of friction or drag that can increase or accumulate the more the fixation device 11 is pulled upon. This embodiment is based at least in part on an increase in the surface area of the high-coefficient material that is in contact with the user's skin 1. A second method and structure and embodiment of the fixation 11 can include a fixation device 11 that is in the shape of a weave 168 that can resemble the weave of a Chinese Finger Puzzle. The weave 168 when exposed to a force 165, such as a pulling force, will tighten in some areas and not in other areas. The weave 168 when exposed to a force 165 will tighten and narrow the diameter of the fixation device and constrict or narrow 167 around the body part 8. The fixation device 11 can be formed from a high coefficient of friction material that at least a portion of the fixation device 11 can include a gel that can include a tackifying material or an adhesive or which can be naturally tacky; or a fabric-like material that can include a microfiber with a high coefficient of friction and increased drag on the skin. The fixation device 11 can be associated with a sealing pad 2 and a skin covering material 3. At least a component of the sealing pad 2 and the skin covering material can be composed of a gel or a microfiber. These embodiments represent both a method and a device.

Figure 67A:
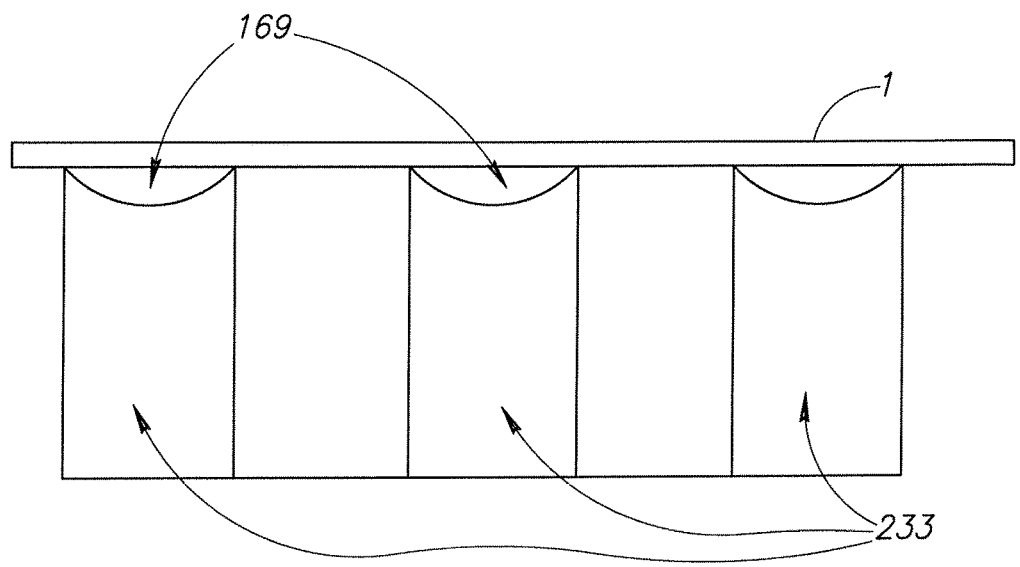
FIGS. 67A and 67B are sagittal views of an embodiment of a method and a device to increase the coefficient of friction in the sealing pad 2.
Figure 67B:
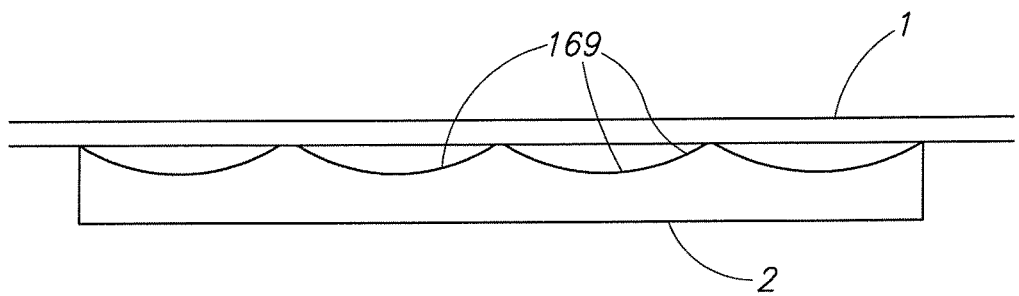

FIGS. 67A and 67B are sagittal views of an embodiment of a method and a device to increase the coefficient of friction in the sealing pad 2 which can include both the gel and the microfiber portions of the sealing pad 2 with ends that contact the user's skin 1 that are with a concave or wave or meniscoid-like configuration 169. FIG. 67A depicts the cross-sectional view of gel sealing pad 2 protrusion 233 or microfibers in which the configuration increases the capillary action or suction between the skin and the gel sealing pad or microfbers. FIG. 67B depicts a sealing pad 2 with a concave or wave or meniscoid-like configuration 169 that contact the user's skin 1 that can be included within a portion of the gel sealing pad 2. This configuration increases the capillary action or suction between the user's skin 1 and the sealing pad 2.

The invention claimed is:
1. An apparatus, comprising:
   a fixation device defining a longitudinal open tube adapted to removably receive a penis, the fixation device comprised of a web of compliant and resiliently deformable annular gelatinous elastomer interconnected strands suitable to anchor the fixation device to the penis, the fixation device further defining spaces between the strands, wherein the fixation device exhibits resistance to being pulled off the penis upon an application of a force to pull the anchored fixation device off the penis, wherein at least one of the strands of the fixation device is more resistant to being pulled off from the penis than at least some of the remaining strands of the fixation device, and wherein at least one of the strands of the fixation device deforms differently than at least some other ones of the strands of the fixation device upon the application of the force;

an annular and circumferential watertight sealing pad extending from the fixation device within which the longitudinal open tube is continued;

a watertight skin covering extending from the sealing pad and defining a condom catheter that distally terminates the longitudinal open tube; and a conduit provided through the condom catheter allowing egress of fluid.

2. An apparatus in accordance with claim 1, wherein each strand stretches in response to the pulling force exerted longitudinally on the fixation device.

3. An apparatus in accordance with claim 1, wherein the strands together stretch in response to the pulling force exerted longitudinally on the fixation device.

4. An apparatus in accordance with claim 1, wherein the strands comprise variable hardnesses.

5. An apparatus in accordance with claim 1, wherein the strands comprise variable elasticities.

6. An apparatus in accordance with claim 1, comprising:
an annular and circumferential bulbous component distally provided on the sealing pad.

7. An apparatus in accordance with claim 1, wherein the skin covering defines a bag.

8. An apparatus in accordance with claim 1, comprising:
a further conduit provided with the condom catheter allowing ingress of one or more of a solid, liquid and gas.

9. An apparatus in accordance with claim 1, wherein at least one of the strands of the fixation device is associated with a coefficient of friction relative to the penis and the coefficient of friction changes upon the application of the force.

10. An apparatus in accordance with claim 1, wherein a surface area of at least some of the strands of the fixation device increases upon the application of the force and a surface area of at least some other ones of the strands of the fixation device attenuates upon an application of the force.

11. An apparatus in accordance with claim 1, wherein the fixation device detaches from the penis upon the force becoming great enough to damage the penis.

12. An apparatus in accordance with claim 1, wherein the fixation device applies a further force to a shaft of the penis upon the application of the force.

13. An apparatus in accordance with claim 12, wherein the further force is in a perpendicular plane relative to the penis.

14. An apparatus in accordance with claim 1, wherein the fixation device is resistant to being pulled off to the application of the force to pull the anchored fixation device off the penis at least partially due to tackiness of the gelatinous elastomer interconnected strands.

15. An apparatus in accordance with claim 1, wherein at least one of the strands of the fixation device is associated with a drag relative to the penis and the drag changes upon the application of the force.

* * * * *